United States Patent
Fleming et al.

(10) Patent No.: US 8,268,822 B2
(45) Date of Patent: *Sep. 18, 2012

(54) 2-(AMINO-SUBSTITUTED)-4-ARYL PYRIMIDINES AND RELATED COMPOUNDS USEFUL FOR TREATING INFLAMMATORY DISEASES

(75) Inventors: Paul E. Fleming, Weston, MA (US); Zhan Shi, Concord, MA (US); Brendan Shaowu Chen, Sudbury, MA (US); Jane F. Schmidt, San Francisco, CA (US); John C. Reader, Linton (GB); Neal D. Hone, Brighton (GB); Jeffrey P. Ciavarri, Reading, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,139

(22) Filed: Apr. 26, 2010

(65) Prior Publication Data

US 2011/0071134 A1    Mar. 24, 2011

Related U.S. Application Data

(63) Continuation of application No. 11/032,299, filed on Jan. 10, 2005, now Pat. No. 7,732,444.

(60) Provisional application No. 60/534,898, filed on Jan. 8, 2004.

(51) Int. Cl.
C07D 239/42 (2006.01)
C07D 401/12 (2006.01)
A61K 31/506 (2006.01)

(52) U.S. Cl. ............ 514/235.8; 514/252.14; 514/275; 544/122; 544/295; 544/330; 544/331; 544/332

(58) Field of Classification Search ............. 544/122, 544/295, 330, 331, 332; 514/235.8, 252.14, 514/275

See application file for complete search history.

(56) References Cited

U.S. PATENT DOCUMENTS

| | | |
|---|---|---|
| 6,335,340 B1 | 1/2002 | Gallagher et al. |
| 6,417,185 B1 | 7/2002 | Goff et al. |
| 6,492,516 B1 | 12/2002 | Liverton et al. |
| 6,541,505 B1 | 4/2003 | Dankulich et al. |
| 6,693,108 B2 | 2/2004 | Green et al. |
| 7,037,918 B2 | 5/2006 | Nuss et al. |
| 7,045,519 B2 | 5/2006 | Nuss et al. |
| 7,169,798 B2 | 1/2007 | Green et al. |
| 7,732,444 B2 * | 6/2010 | Fleming et al. ............ 514/235.8 |
| 2002/0156087 A1 | 10/2002 | Nuss |
| 2003/0109538 A1 | 6/2003 | Carter et al. |
| 2003/0130289 A1 | 7/2003 | Nuss et al. |
| 2003/0144303 A1 | 7/2003 | Hawley et al. |
| 2003/0149051 A1 | 8/2003 | Green et al. |
| 2005/0004151 A1 | 1/2005 | Yang et al. |
| 2005/0026967 A1 | 2/2005 | Green et al. |
| 2005/0256121 A1 | 11/2005 | Jefferson et al. |
| 2006/0009453 A1 | 1/2006 | Geuns-Meyer et al. |
| 2006/0089369 A1 | 4/2006 | Nuss et al. |
| 2006/0160817 A1 | 7/2006 | Martinborough et al. |
| 2006/0178388 A1 | 8/2006 | Wrobleski et al. |
| 2006/0293342 A1 | 12/2006 | Chen et al. |
| 2007/0185133 A1 | 8/2007 | Smith et al. |
| 2007/0225286 A1 | 9/2007 | Ren et al. |

FOREIGN PATENT DOCUMENTS

| | | |
|---|---|---|
| EP | 1 816 128 A1 | 8/2007 |
| JP | 39-5040 | 4/1964 |
| WO | WO 99/41253 A1 | 8/1999 |
| WO | WO 01/00214 A1 | 1/2001 |
| WO | WO 02/079197 A1 | 10/2002 |
| WO | WO 02/096886 A1 | 12/2002 |
| WO | WO 03/087057 A1 | 10/2003 |
| WO | WO 03/106451 A1 | 12/2003 |
| WO | WO 2004/067516 A1 | 8/2004 |
| WO | WO 2004/096797 A1 | 11/2004 |

OTHER PUBLICATIONS

Casanova et al., PubMed Abstract (Rev Neurol. 28(9):909-15) May 1999.*
Hayashi et al., Protein Kinase C theta: A key player in T cell life and death, Pharmacological Research 55, pp. 537-544, 2007.*
Zimmermann, Jurg, et al., "Phenylamino-pyrimidine (PAP) derivatives: a new class of potent and selective inhibitors of protein kinase C (PKC)," Arch. Pharm. Pharm. Med. Chem., vol. 329 (1996) pp. 371-376.
International Search Report issued in PCT Application No. PCT/US05/000663, which corresponds to U.S. Appl. No. 11/032,299.
"4-Pyrimidinecarboxamide, 6-(4-methoxyphenyl)-2-[(2-phenylethyl)amino]-(CA Index Name)," CAS Registry No. 552284-37-4, entered Jul. 22, 2003.
"2-Pyrimidinamine, 4-(4-methoxyphenyl)-N-[2-(2-pyridinyl)ethyl]-(CA Index Name)," CAS Registry No. 667895-75-2, entered Mar. 26, 2004.
"1H-Indole-3-ethanamine, N-[4-(4-methoxyphenyl)-2-pyrimidinyl]-(CA Index Name)," CAS Registry No. 682790-41-6, entered May 18, 2004.
"2-Pyrimidinamine, 4-(4-methoxyphenyl)-N-(2-phenylethyl)-(CA Index Name)," CAS Registry No. 682792-99-0, entered May 18, 2004.

(Continued)

Primary Examiner — Deepak Rao
(74) Attorney, Agent, or Firm — Millennium Pharmaceuticals, Inc.

(57) ABSTRACT

A heterocyclic inhibitor having the formula I, with the variables defined herein, which is useful for treating inflammatory and other physiological disorders in which PKC-theta isoform plays a role:

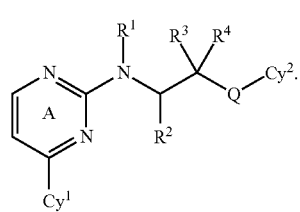

11 Claims, No Drawings

OTHER PUBLICATIONS

"2-Pyrimidinamine, N-[2-(2,4-dichlorophenyl)ethyl]-4-(4-methoxyphenyl)-(CA Index Name)," CAS Registry No. 682793-00-6, entered May 18, 2004.

"2-Pyrimidinamine, N-[2-(4-fluorophenyl)ethyl]-4-(4-methoxyphenyl)-(CA Index Name)," CAS Registry No. 682793-39-1, entered May 18, 2004.

"2-Pyrimidinamine, N-[2-(3,4-dimethoxyphenyl)ethyl]-4-(4-methoxyphenyl)-(CA Index Name)," CAS Registry No. 682793-40-4, entered May 18, 2004.

"1H-Indole-3-ethanamine, N-[4-(2,4-dimethoxyphenyl)-2-pyrimidinyl]-(CA Index Name)," CAS Registry No. 682795-07-9, entered May 18, 2004.

"2-Pyrimidinamine, 4-(2,4-dimethoxyphenyl)-N-(2-phenylethyl)-(CA Index Name)," CAS Registry No. 682795-16-0, entered May 18, 2004.

"2-Pyrimidinamine, 4-(2,4-dimethoxyphenyl)-N-[2-(2-pyridinyl)ethyl]-(CA Index Name)," CAS Registry No. 682795-19-3, entered May 18, 2004.

"2-Pyrimidinamine, 4-(2,4-dimethoxyphenyl)-N-[2-(3,4-dimethoxyphenyl)ethyl]-(CA Index Name)," CAS Registry No. 682795-24-0, entered May 18, 2004.

"2-Pyrimidinamine, 4-(2,4-dimethoxyphenyl)-N-[2-(4-fluorophenyl)ethyl]-(CA Index Name)," CAS Registry No. 682795-85-3, entered May 18, 2004.

"2-Pyrimidinamine, N-[2-(2,4-dichlorophenyl)ethyl]-4-(2,4-dimethoxyphenyl)-(CA Index Name)," CAS Registry No. 682797-30-4, entered May 18, 2004.

"2-Pyrimidinamine, N-[2-(3,4-dimethoxyphenyl)ethyl]-4-(4-methoxyphenyl)-6-(trifluoromethyl)-(CA Index Name)," CAS Registry No. 686725-15-5, entered May 28, 2004.

"2-Pyrimidinamine, 4-(3-methoxyphenyl)-N-(2-phenylethyl)-6-(trifluoromethyl)-(CA Index Name)," CAS Registry No. 686725-36-0, entered May 28, 2004.

"2-Pyrimidinamine, N-[2-(3,4-dimethoxyphenyl)ethyl]-4-(3-methoxyphenyl)-6-(trifluoromethyl)-(CA Index Name)," CAS Registry No. 686725-37-1, entered May 28, 2004.

"2-Pyrimidinamine, 4-(3,4-dimethoxyphenyl)-N-(2-phenylethyl)-6-(trifluoromethyl)-(CA Index Name)," CAS Registry No. 686725-47-3, entered May 28, 2004.

"2-Pyrimidinamine, 4-(3,4-dimethoxyphenyl)-N-[2-(3,4-dimethoxyphenyl)ethyl]-6-(trifluoromethyl)-(CA Index Name)," CAS Registry No. 686725-48-4, entered May 28, 2004.

"2-Pyrimidinamine, 4-(4-methoxyphenyl)-N-(2-phenylethyl)-6-(trifluoromethyl)-(CA Index Name)," CAS Registry No. 725695-31-8, entered Aug. 12, 2004.

* cited by examiner

2-(AMINO-SUBSTITUTED)-4-ARYL PYRIMIDINES AND RELATED COMPOUNDS USEFUL FOR TREATING INFLAMMATORY DISEASES

PRIORITY INFORMATION

The present application is a Continuation of U.S. application Ser. No. 11/032,299, filed Jan. 10, 2005 now U.S. Pat. No. 7,732,444, which claims priority to U.S. Provisional Application No. 60/534,898, filed Jan. 8, 2004, the entire contents of which are hereby incorporated by reference.

BACKGROUND OF THE INVENTION

The protein kinase C family is a group of serine/threonine kinases that is comprised of twelve related isoenzymes. These kinases are expressed in a wide range of tissues and cell types. The PKC-theta isoform of protein kinase C is selectively expressed in T lymphocytes and plays an important role in the T cell antigen receptor (TCR)-triggered activation of mature T cells, and the subsequent release of cytokines such as IL-2 and T cell proliferation (Isakov and Altman, *Annu. Rev. Immunol.*, 2002, 20, 761-94).

It has been well established that T cells play an important role in regulating the immune response (Powrie and Coffman, *Immunology Today*, 1993, 14, 270). The activation of T cells is often the initiating event in a variety of immunological disorders. It is believed that following activation of the TCR, there is an influx of calcium that is required for T cell activation. Upon activation, T cells produce cytokines, including IL-2, leading to cell proliferation, differentiation, and effector function. Clinical studies with inhibitors of IL-2 have shown that interference with T cell activation and proliferation effectively suppresses immune response in vivo (Waldmann, *Immunology Today*, 1993, 14, 264). Accordingly, agents that inhibit T lymphocyte activation and subsequent cytokine production are therapeutically useful for selectively suppressing the immune response in a patient in need of such immunosuppression and therefore are useful in treating immunological disorders such as autoimmune and inflammatory diseases.

Additionally, PKC-theta activation has been shown to play a role in insulin resistance in skeletal muscle and therefore inhibitors of PKC-theta may also be useful for treating type II diabetes (M. E. Griffen et al., *Diabetes*, 1999, 48, 1270). PKC-theta activation has also been implicated in leukemia and thus inhibitors of PKC-theta may be useful for the treatment of leukemia (Villalba and Altman, *Current Cancer Targets*, 2002, 2, 125).

There remains a need to develop effective therapeutic agents for the majority of the diseases and disorders associated with activation of PKC-theta. Accordingly, it would be beneficial to provide safe and effective compounds that are useful as inhibitors of PKC-theta and thus in the treatment of disorders and diseases associated with activation of PKC-theta.

SUMMARY OF THE INVENTION

This invention provides compounds that inhibit PKC-theta. Also provided are methods for the treatment of PKC-theta associated disorders, including inflammatory diseases, such as rheumatoid arthritis. The compounds of this invention are represented by formula I:

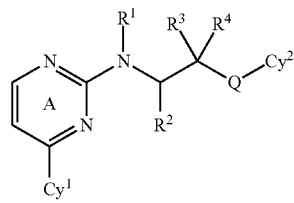

or a pharmaceutically acceptable salt thereof, wherein $R^1$, $R^2$, $R^3$, $R^4$, Q, $Cy^1$, and $Cy^2$ are described generally and in subsets herein.

In another embodiment of the present invention a pharmaceutical composition is provided which comprises a pharmaceutically acceptable carrier or diluent and a compound as disclosed herein. The pharmaceutical compositions can be used in therapy, for example, to treat a subject with inflammatory and allergic disorders and diseases including, but not limited to asthma, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis, urticaria, rheumatoid arthritis, osteoarthritis, inflammatory bowel disease e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis, disorders of the skin [e.g., psoriasis, erythema, pruritis, and acne], multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease), stroke, cardiac ischemia, mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases, sarcoidosis, vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

In another embodiment, the present invention provides a method of inhibiting PKC theta activity in (a) a subject; or (b) a biological sample; which method comprises administering to said subject, or contacting said biological sample with compounds as described herein, or a pharmaceutically acceptable salt or composition thereof.

Another embodiment of the present invention method is a method of treating a subject with a PKC-theta mediated condition or disease, e.g., a subject with asthma. The method comprises the step of administering to the subject an effective amount of a PKC-theta inhibitor disclosed herein.

Yet another embodiment of the present invention is the use of one of the disclosed PKC-theta inhibitors for the manufacture of a medicament for treating a subject with a PKC-theta mediated condition or disease. The medicament comprises an effective amount of the PKC-theta inhibitor.

DESCRIPTION OF THE INVENTION

I. General Description of Compounds of the Invention

The present invention relates to a compound of formula I:

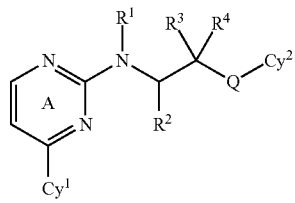

or a pharmaceutically acceptable salt thereof, wherein:

$R^1$ and $R^2$ are each independently H, $C_{1-3}$ alkyl or $C_{3-5}$cycloalkyl;

$R^3$ is H or F;

$R^4$ is H, F, $-OR^A$, $-C(O)R^A$, $-C(O)OR^A$ or $-N(R^A)_2$; or $R^3$ and $R^4$ together with the carbon atom to which they are attached form a carbonyl group; wherein each occurrence of $R^A$ is independently H, $C_{1-3}$alkyl or $C_{3-5}$cycloalkyl;

Ring A is optionally substituted with 1 or 2 independent occurrences of $R^5$, wherein each $R^5$ is independently selected from halo, $C_{1-4}$ aliphatic, $-CN$, $-OR^B$, $-SR^C$, $-N(R^B)_2$, $-NR^BC(O)R^B$, $-NR^BC(O)N(R^B)_2$, $-NR^BCO_2R^C$, $-CO_2R^B$, $-C(O)R^B$, $-C(O)N(R^B)_2$, $-OC(O)N(R^B)_2$, $-S(O)_2R^C$, $-SO_2N(R^B)_2$, $-S(O)R^C$, $-NR^BSO_2N(R^B)_2$, $-NR^BSO_2R^C$, or $C_{1-4}$aliphatic optionally substituted with halo, $-CN$, $-OR^B$, $-SR^C$, $-N(R^B)_2$, $-NR^BC(O)R^B$, $-NR^BC(O)N(R^B)_2$, $-NR^BCO_2R^C$, $-CO_2R^B$, $-C(O)R^B$, $-C(O)N(R^B)_2$, $-OC(O)N(R^B)_2$, $-S(O)_2R^C$, $-SO_2N(R^B)_2$, $-S(O)R^C$, $-NR^BSO_2N(R^B)_2$, or $-NR^BSO_2R^C$, wherein each occurrence of $R^B$ is independently H or $C_{1-4}$aliphatic; or two $R^B$ on the same nitrogen atom taken together with the nitrogen atom form a 5-8 membered aromatic or non-aromatic ring having in addition to the nitrogen atom 0-2 ring heteroatoms selected from N, O or S; and each occurrence of $R^C$ is independently $C_{1-4}$ aliphatic;

$Cy^1$ is selected from:

a) a 6-membered aryl or heteroaryl ring substituted by one occurrence of W at the meta or para position of the ring; or b) a 5-membered heteroaryl ring substituted by one occurrence of W;

wherein $Cy^1$ is optionally further substituted by one to three independent occurrences of $R^6$, wherein each occurrence of $R^6$ is independently selected from -halo, $C_{1-8}$ aliphatic, $-CN$, $-OR^B$, $-SR^D$, $-N(R^E)_2$, $-NR^EC(O)R^D$, $-NR^EC(O)N(R^E)_2$, $-NR^ECO_2R^D$, $-CO_2R^B$, $-C(O)R^B$, $-C(O)N(R^E)_2$, $-OC(O)N(R^E)_2$, $-S(O)_2R^D$, $-SO_2N(R^E)_2$, $-S(O)R^D$, $-NR^ESO_2N(R^E)_2$, $-NR^ESO_2R^D$, $-C(=NH)-N(R^E)_2$, or $C_{1-8}$ aliphatic optionally substituted with halo, $-CN$, $-OR^B$, $-SR^D$, $-N(R^E)_2$, $-NR^EC(O)R^B$, $-NR^EC(O)N(R^E)_2$, $-NR^ECO_2R^D$, $-CO_2R^B$, $-C(O)R^B$, $-C(O)N(R^E)_2$, $-OC(O)N(R^E)_2$, $-S(O)_2R^D$, $-SO_2N(R^E)_2$, $-S(O)R^D$, $-NR^ESO_2N(R^E)_2$, $-NR^ESO_2R^D$, or $-C(=NH)-N(R^E)_2$, wherein each occurrence of $R^D$ is $C_{1-6}$ aliphatic and each occurrence of $R^E$ is independently H, $C_{1-6}$ aliphatic, $-C(=O)R^B$, $-C(O)OR^B$ or $-SO_2R^B$; or two $R^E$ on the same nitrogen atom taken together with the nitrogen atom form a 5-8 membered aromatic or non-aromatic ring having in addition to the nitrogen atom 0-2 ring heteroatoms selected from N, O or S;

W is $-R^8$, $V-R^8$, $L_1-R^7$, $V-L_1-R^7$, $L_1-V-R^8$, or $L_1-V-L_2-R^7$; wherein:

$L_1$ and $L_2$ are each independently an optionally substituted $C_{1-6}$ alkylene chain;

V is $-CH_2-$, $-O-$, $-S-$, $-S(O)-$, $-S(O)_2-$, $-C(O)-$, $-CO_2-$, $-NR^E-$, $-NR^EC(O)-$, $-NR^ECO_2-$, $-NR^ESO_2-$, $-C(O)N(R^B)-$, $-SO_2N(R^B)-$, $-NR^EC(O)N(R^B)-$ or $-OC(O)-$;

$R^7$ is H, halo, $-OH$, $-N(R^F)_2$, $-CN$, $-OR^G$, $-C(O)R^G$, $-CO_2H$, $-CO_2R^G$, $-SR^G$, $-S(O)R^G$, $-S(O)_2R^G$, $-N(R^E)C(O)R^G$, $-N(R^E)CO_2R^G$, $-N(R^E)SO_2R^G$, $-C(O)N(R^F)_2$, $-SO_2N(R^F)_2$, $-N(R^E)C(O)N(R^F)_2$, $-OC(O)R^F$ or an optionally substituted group selected from $C_{1-10}$ aliphatic, $C_{6-10}$aryl, 3-14 membered heterocyclyl or 5-14 membered heteroaryl, wherein each occurrence of $R^F$ is independently H, $C_{1-6}$ aliphatic, $C_{6-10}$aryl, 3-14 membered heterocyclyl, 5-14 membered heteroaryl, $-C(=O)R^B$, $-C(O)OR^B$ or $-SO_2R^B$; or two $R^F$ on the same nitrogen atom taken together with the nitrogen atom form an optionally substituted 5-8 membered aromatic or non-aromatic ring having in addition to the nitrogen atom 0-2 ring heteroatoms selected from N, O or S; and each occurrence of $R^G$ is $C_{1-6}$ aliphatic, $C_{6-10}$aryl, 3-14 membered heterocyclyl, or 5-14 membered heteroaryl;

$R^8$ is an optionally substituted group selected from $C_{1-10}$ aliphatic, $C_{6-10}$ aryl, 3-14 membered heterocyclyl or 5-14 membered heteroaryl;

Q is a bond, $CH_2$ or $C(=O)$;

$Cy^2$ is a $C_{6-10}$ aryl, a 5-10 membered heteroaryl, or a 5-10 membered heterocyclyl ring, wherein each ring is optionally substituted by one to three independent occurrences of $R^9$ and one occurrence of $R^{10}$, wherein each occurrence of $R^9$ is independently selected from $C_{1-4}$aliphatic, $-N(R^B)_2$, halo, $NO_2$, $-CN$, $-OR^B$, $-C(O)R^A$, $-CO_2R^A$, $-SR^C$, $-S(O)R^C$, $-S(O)_2R^C$, $-OS(O)_2R^C$, $N(R^B)C(O)R^A$, $-N(R^B)CO_2R^A$, $-N(R^B)SO_2R^A$, $-C(O)N(R^B)_2$, $-SO_2N(R^B)_2$, $-N(R^B)C(O)N(R^B)_2$, $-OC(O)R^A$, or $C_{1-4}$ aliphatic optionally substituted by $-N(R^B)_2$, halo, $NO_2$, $-CN$, $-OR^B$, $-C(O)R^A$, $-CO_2R^A$, $-SR^C$, $-S(O)R^C$, $-OS(O)_2R^C$, $-S(O)_2R^C$, $-N(R^B)C(O)R^A$, $-N(R^B)CO_2R^A$, $-N(R^B)SO_2R^A$, $-C(O)N(R^B)_2$, $-SO_2N(R^B)_2$, $-N(R^B)C(O)N(R^B)_2$, or $-OC(O)R^A$, and $R^{10}$ is selected from phenyl, or a 5-6 membered heterocyclyl or heteroaryl ring.

In certain embodiments, compounds of formula I are subject to one or more, or all of, the following limitations:

1) when $Cy^1$ is phenyl substituted in the meta position with W then:

a) when W is $-OMe$, $R^1$, $R^2$, $R^3$, and $R^4$ are each hydrogen, and Q is a bond, then when ring A is further substituted with $R^5$, $R^5$ is a group other than $-CF_3$ or $-C(O)N(R^B)_2$; and b) when W is $-OMe$, $R^1$, $R^2$, $R^3$, and $R^4$ are each hydrogen, and Q is $-CH_2-$, then $Cy^2$ is other than 1H-benzimidazol-1-yl;

2) when $Cy^1$ is phenyl substituted in the para position with W, and $R^1$, $R^2$, $R^3$, and $R^4$ are each hydrogen then:

a) when Q is a bond, W is other than:

i) $-CONH_2$;

ii) $-CONHR^8$, where $R^8$ is an optionally substituted group selected from phenyl, -alkylphenyl, alkyl, or -alkylheterocycle;

iii) $-CF_3$;

iv) $-SO_2Me$;

v) $-NH_2$;

vi) -tBu;

vii) —CO$_2$H when Cy$^2$ is morpholine;
viii) —O(phenyl) when Cy$^2$ is indole; and
ix) —OMe;
b) when Q is —CH$_2$—, W is other than:
i) —CONH$_2$, when Cy$^2$ is optionally substituted imidazole or benzimidazole;
ii) —CONHR$^8$, where R$^8$ is an optionally substituted group selected from phenyl, -alkylphenyl, or -alkylheterocycle;
iii) —CF$_3$;
iv) —SO$_2$Me;
v) —OH, where Cy$^2$ is a 5-10 membered heterocyclyl ring;
vi) tBu, when Cy$^2$ is a 5-10 membered heterocyclyl ring; and
vii) —OMe; and 3) when Cy$^1$ is a 5-membered heteroaryl ring then:
a) when Cy$^1$ is isoxazole, R$^1$, R$^2$, R$^3$, and R$^4$ are each hydrogen, Q is a bond, and W is p-fluoro-phenyl, then Cy$^2$ is a group other than pyridyl or N-pyrrolidinyl;
b) when Cy$^1$ is triazolyl, R$^1$, R$^2$, R$^3$, and R$^4$ are each hydrogen, Q is a bond, and W is —(CH$_2$)$_2$N(cyclopentyl)C(O)CH$_2$(naphthyl), then Cy$^2$ is a group other than N-piperidinyl;
c) when Cy$^1$ is imidazolyl, R$^1$, R$^2$, R$^3$, and R$^4$ are each hydrogen, Q is a bond, and W is meta-CF$_3$-phenyl, then R$^6$ is a group other than C(O)OCH$_2$CH$_3$; and
d) when Cy$^1$ is imidazol-5-yl and W is para-fluoro-phenyl, then R$^6$ is a group other than cyclohexyl.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic", "cycloalkyl", or "cycloalkenyl"). For example, suitable aliphatic groups include substituted or unsubstituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-20, 1-15, 1-12, 1-10, 1-8, 1-6, 1-4, or 1-3 carbon atoms.

The terms "cycloaliphatic", "carbocycle", "carbocyclyl", "carbocyclo", or "carbocyclic", used alone or as part of a larger moiety, refer to a saturated or partially unsaturated cyclic aliphatic ring system having from 3 to about 14 members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic", "haloalkyl", "haloalkenyl" and "haloalkoxy" refer to an aliphatic, alkyl, alkenyl or alkoxy group, as the case may be, substituted with one or more halogen atoms. As used herein, the term "halogen" or "halo" means F, Cl, Br, or I. Unless otherwise indicated, the terms "alkyl", "alkenyl", and "alkoxy" include haloalkyl, haloalkenyl and haloalkoxy groups, including, in particular, those with 1-5 fluorine atoms. By way of example, the terms "C$_{1-3}$ aliphatic" and "C$_{1-3}$ alkyl" include within their scope trifluoromethyl and pentafluoroethyl groups.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to a C$_6$ to C$_{14}$ aromatic moiety comprising one to three aromatic rings, which are optionally substituted. Preferably, the aryl group is a C$_{6-10}$ aryl group. Aryl groups include, without limitation, phenyl, naphthyl, and anthracenyl. The term "aryl", as used herein, also includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is C$_{6-10}$ aryl(C$_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group.

An alkylene chain also can be optionally replaced by a functional group. An alkylene chain is "replaced" by a functional group when an internal methylene unit is replaced with the functional group. Examples of suitable "replacing functional groups" are described in the specification and claims herein.

The term "substituted", as used herein, means that one or more hydrogens of the designated moiety are replaced, provided that the substitution results in a stable or chemically feasible compound. A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O) R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)$_2$; —OC(O)N(R°)$_2$; —OC(O)R°; —C(O)N(OR°)R°; —C(NOR°) R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(═NH)—N(R°)$_2$; —P(O)$_2$R°; —PO(R°)$_2$; —OPO(R°)$_2$; —(CH$_2$)$_{0-2}$NHC(O)R°; phenyl (Ph) optionally substituted with R°; —O(Ph) optionally substituted with R°; —(CH$_2$)$_{1-2}$(Ph), optionally substituted with R°; or —CH═CH(Ph), optionally substituted with R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with their intervening atom(s) form an optionally substituted 3-12 membered saturated, partially unsaturated, or fully unsaturated monocyclic or bicyclic ring having 0-4 heteroatoms independently selected from nitrogen, oxygen, or sulfur.

In addition to the substituents defined above and herein, suitable substituents on the aliphatic group of R° also include and are generally selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with their intervening atom(s) form an optionally substituted 3-12 membered saturated, partially unsaturated, or fully unsaturated monocyclic or bicyclic ring having 0-4 heteroatoms independently selected from nitrogen, oxygen, or sulfur.

In addition to the substituents defined above and herein, optional substituents on the aliphatic group or the phenyl ring of R$^+$ also include and are generally selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

As detailed above, in some embodiments, two independent occurrences of R$^°$ (or R$^+$, or any other variable similarly defined in the specification and claims herein), are taken together with their intervening atom(s) to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R$^°$ (or R$^+$, or any other variable similarly defined in the specification and claims herein), are taken together with their intervening atom(s) include, but are not limited to the following: a) two independent occurrences of R$^°$ (or R$^+$, or any other variable similarly defined in the specification or claims herein) that are bound to the same atom and are taken together with that atom to form a ring, for example, N(R$^°$)$_2$, where both occurrences of R$^°$ are taken together with the nitrogen atom to form a piperidin-1-yl, piperazin-1-yl, or morpholin-4-yl group; and b) two independent occurrences of R$^°$ (or R$^+$, or any other variable similarly defined in the specification or claims herein) that are bound to different atoms and are taken together with both of those atoms to form a ring, for example where a phenyl group is substituted with two occurrences of OR$^°$

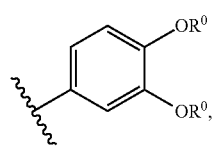

these two occurrences of R$^°$ are taken together with the oxygen atoms to which they are bound to form a fused 6-membered oxygen containing ring:

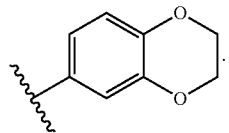

It will be appreciated that a variety of other rings (e.g., also spiro, and bridged rings) can be formed when two independent occurrences of R$^°$ (or R$^+$, or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention.

3. Description of Exemplary Compounds

As described generally above for compounds of Formula I, R$^1$ and R$^2$ are each independently H, C$_{1-3}$ alkyl or C$_{3-5}$ cycloalkyl, R$^3$ is H or F, and R$^4$ is H, F, —OR$^4$, —C(O)R$^4$, —C(O)OR$^4$ or —N(R$^4$)$_2$; or R$^3$ and R$^4$ together with the carbon atom to which they are attached form a carbonyl group; wherein each occurrence of R$^4$ is independently H, C$_{1-3}$alkyl or C$_{3-5}$cycloalkyl. In certain exemplary embodiments, R$^1$ is H, —CH$_3$, or cyclopropyl. In other embodiments R$^1$ is H. In still other embodiments, R$^2$ is H or C$_1$-C$_3$alkyl. In other embodiments, R$^2$ is H, methyl, ethyl, propyl, or cyclopropyl. In yet other embodiments, R$^3$ is H and R$^4$ is H, methyl, or OH. In still other embodiments, both R$^3$ and R$^4$ are H. In yet other embodiments, R$^3$ and R$^4$ taken together with their intervening carbon form a carbonyl group. In still other embodiments, R$^1$, R$^2$, R$^3$, and R$^4$ are all hydrogen.

As described generally above, Q is a bond, CH$_2$ or C(=O). In certain embodiments, Q is a bond.

As described generally above, Cy$^2$ is a C$_{6-10}$ aryl, a 5-10 membered heteroaryl, or a 5-10 membered heterocyclyl ring, wherein each ring is optionally substituted by one to three independent occurrences of R$^9$ and one occurrence of R$^{10}$. In some embodiments, Cy$^2$ is a C$_{6-10}$aryl or a 5-10-membered heteroaryl ring. In other embodiments, Ring Cy$^2$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, tetrazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, benzo[1,3]dioxolyl, benzo[1,3]dioxinyl, quinolinyl, isoquinolinyl, quinazolinyl, quinoxalinyl, [1,8]naphthyridinyl, naphthyl, 1,3-dihydrobenzoimidazol-2-on-1-yl, 2-oxo-2,3-dihydrobenzooxazolyl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, indazolyl, 3-1H-benzimidazol-2-one, tetrahydrofuranyl, morpholinyl, thiomorpholinyl, pyrrolidinyl, piperazinyl, or piperidinyl. In yet other embodiments, $Cy^2$ is phenyl, pyridyl, naphthyl, thienyl, 2-oxo-2,3-dihydrobenzooxazolyl, benzo[1,3]dioxolyl, benzo[1,3]dioxinyl, indolyl, tetrazole, piperidinyl, piperazinyl, or morpholinyl. In still other embodiments, $Cy^2$ is phenyl or pyridyl. In yet other embodiments, $Cy^2$ is phenyl.

As described generally above, $Cy^2$ is optionally substituted by one to three independent occurrences of $R^9$ and one occurrence of $R^{10}$, wherein each occurrence of $R^9$ is independently selected from $C_{1-4}$aliphatic, —$N(R^B)_2$, halo, $NO_2$, —CN, —$OR^B$, —$C(O)R^A$, —$CO_2R^A$, —$SR^C$, —$S(O)R^C$, —$S(O)_2R^C$, —$OS(O)_2R^C$—, $N(R^B)C(O)R^A$, —$N(R^B)CO_2R^A$, —$N(R^B)SO_2R^A$, —$C(O)N(R^B)_2$, —$SO_2N(R^B)_2$, —$N(R^B)C(O)N(R^B)_2$, —$OC(O)R^A$, or $C_{1-4}$ aliphatic optionally substituted by —$N(R^B)_2$, halo, $NO_2$, —CN, —$OR^B$, —$C(O)R^A$, —$CO_2R^A$, —$SR^C$, —$S(O)R^C$, —$OS(O)_2R^C$, —$S(O)_2R^C$, —$N(R^B)C(O)R^A$, —$N(R^B)CO_2R^A$, —$N(R^B)SO_2R^A$, —$C(O)N(R^B)_2$, —$SO_2N(R^B)_2$, —$N(R^B)C(O)N(R^B)_2$, or —$OC(O)R^A$, and $R^{10}$ is selected from phenyl, or a 5-6 membered heterocyclyl or heteroaryl ring.

In certain exemplary embodiments, $Cy^2$ is unsubstituted, or is substituted by one, two, or three occurrences of $R^9$, wherein each occurrence of $R^9$ is independently selected from —$OR^B$, —$N(R^B)C(O)R^A$, —$N(R^B)_2$, halo, $C_{1-4}$aliphatic optionally substituted by halo, $NO_2$, —$OS(O)_2R^C$, —$S(O)R^C$, —$N(R^B)SO_2R^A$, or —$S(O)_2N(R^B)_2$. In still other embodiments, $Cy^2$ is unsubstituted, or is substituted by one, two, or three occurrences of $R^9$, wherein each occurrence of $R^9$ is independently selected from of —$OR^B$, —$N(R^B)C(O)R^A$, —$N(R^B)_2$, halo, —$N(R^B)SO_2R^A$, —$S(O)_2N(R^B)_2$, or $C_{1-4}$aliphatic optionally substituted by halo. In yet other embodiments, $Cy^2$ is unsubstituted, or is substituted by one, two, or three occurrences of $R^9$, wherein each occurrence of $R^9$ is independently selected from F, Cl, Br, —$OR^B$, —$NR^BC(O)R^A$, —$N(R^B)SO_2R^A$, —$S(O)_2N(R^B)_2$, or $C_{1-4}$aliphatic optionally substituted by halo. In still other embodiments, $Cy^2$ is unsubstituted, or is substituted by one, two, or three occurrences of $R^9$, wherein each occurrence of $R^9$ is independently selected from F, Cl, Br, —OH, —$NHC(O)CH_3$, —$NHSO_2CH_3$, —OMe, methyl, ethyl, n-propyl, isopropyl, t-butyl, $CF_3$, or —$S(O)_2NH_2$. In yet other embodiments, $Cy^2$ is unsubstituted, or is substituted by one, two, or three occurrences of $R^9$, wherein each occurrence of $R^9$ is independently selected from F, Cl, Br, —OH, —OMe, or methyl. In yet other embodiments, each occurrence of $R^9$ is independently halo or —OH.

Generally, ring A is optionally substituted with 1 or 2 independent occurrences of $R^5$, wherein each $R^5$ is independently selected from halo, $C_{1-4}$ aliphatic, —CN, —$OR^B$, —$SR^C$, —$N(R^B)_2$, —$NR^BC(O)R^B$, —$NR^BC(O)N(R^B)_2$, —$NR^BCO_2R^C$, —$CO_2R^B$, —$C(O)R^B$, —$C(O)N(R^B)_2$, —$OC(O)N(R^B)_2$, —$S(O)_2R^C$, —$SO_2N(R^B)_2$, —$S(O)R^C$, —$NR^BSO_2N(R^B)_2$, —$NR^BSO_2R^C$, or $C_{1-4}$aliphatic optionally substituted with halo, —CN, —$OR^B$, —$SR^C$, —$N(R^B)_2$, —$NR^BC(O)R^B$, —$NR^BC(O)N(R^B)_2$, —$NR^BCO_2R^C$, —$CO_2R^B$, —$C(O)R^B$, —$C(O)N(R^B)_2$, —$OC(O)N(R^B)_2$, $S(O)_2R^C$, —$SO_2N(R^B)_2$, —$S(O)R^C$, —$NR^BSO_2N(R^B)_2$, or —$NR^BSO_2R^C$, wherein each occurrence of $R^B$ is independently H or $C_{1-4}$ aliphatic; or two $R^B$ on the same nitrogen atom taken together with the nitrogen atom form a 5-8 membered aromatic or non-aromatic ring having in addition to the nitrogen atom 0-2 ring heteroatoms selected from N, O or S; and each occurrence of $R^C$ is independently $C_{1-4}$ aliphatic. In certain embodiments, $R^5$ on ring A, when present, is selected from halo or optionally substituted $C_{1-4}$ aliphatic. In other embodiments, $R^5$ on ring A, when present, is selected from F, Cl, Br, or methyl. In certain other embodiments, ring A is not substituted with $R^5$.

As described generally above, $Cy^1$ is selected from a 6-membered aryl or heteroaryl ring substituted by one occurrence of W at the meta or para position of the ring, or a 5-membered heteroaryl ring substituted by one occurrence of W, wherein $Cy^1$ is optionally further substituted by one to three independent occurrences of $R^6$.

In certain embodiments, $Cy^1$ is selected from phenyl, pyridyl, pyrimidinyl, pyrazinyl, pyridazinyl, triazinyl, triazolyl, imidazolyl, pyrazolyl, pyrrolyl, thiazolyl, isothiazolyl, thienyl, thiadiazolyl, thiadiazolyl, isoxazolyl, oxazolyl, furanyl, or oxadiazolyl. In certain other embodiments, $Cy^1$ is phenyl, pyridyl, pyrimidinyl, or thienyl. In yet other embodiments, $Cy^1$ is phenyl, pyrid-3-yl, or thien-2-yl. In still other embodiments, $Cy^1$ is phenyl.

As described above, $Cy^1$ is substituted by one occurrence of W, wherein W is —$R^8$, —V—$R^8$, -$L_1$-$R^7$, —V-$L_1$-$R^7$, -$L_1$-V—$R^8$, or -$L_1$-V-$L_2$-$R^7$; wherein:
  $L_1$ and $L_2$ are each independently an optionally substituted $C_{1-6}$ alkylene chain;
  V is —$CH_2$—, —O—, —S—, —S(O)—, —$S(O)_2$—, —C(O)—, —$CO_2$—, —$NR^E$—$NR^EC(O)$—, —$NR^ECO_2$—, —$NR^ESO_2$—, —$C(O)N(R^B)$—, —$SO_2N(R^B)$—, —$NR^EC(O)N(R^B)$— or —OC(O)—;
  $R^7$ is H, halo, —OH, —$N(R^F)_2$, —CN, —$OR^G$, —$C(O)R^G$, —$CO_2H$, —$CO_2R^G$, —$SR^G$, —$S(O)R^G$, —$S(O)_2R^G$, —$N(R^E)C(O)R^G$, —$N(R^E)CO_2R^G$, —$N(R^E)SO_2R^G$, —$C(O)N(R^F)_2$, —$SO_2N(R^F)_2$, —$N(R^E)C(O)N(R^F)_2$, —$OC(O)R^F$ or an optionally substituted group selected from $C_{1-10}$ aliphatic, $C_{6-10}$aryl, 3-14 membered heterocyclyl or 5-14 membered heteroaryl, wherein each occurrence of $R^F$ is independently H, $C_{1-6}$ aliphatic, $C_{6-10}$aryl, 3-14 membered heterocyclyl, 5-14 membered heteroaryl, —C(=O)$R^B$, —C(O)$OR^B$ of —$SO_2R^B$; or two $R^F$ on the same nitrogen atom taken together with the nitrogen atom form an optionally substituted 5-8 membered aromatic or non-aromatic ring having in addition to the nitrogen atom 0-2 ring heteroatoms selected from N, O or S; and each occurrence of $R^G$ is $C_{1-6}$ aliphatic, $C_{6-10}$aryl, 3-14 membered heterocyclyl, or 5-14 membered heteroaryl; and
  $R^8$ is an optionally substituted group selected from $C_{1-10}$ aliphatic, $C_{6-10}$ aryl, 3-14-membered heterocyclyl or 5-14 membered heteroaryl.

In certain embodiments, each independent occurrence of $L_1$ and $L_2$ is an optionally substituted $C_1$-$C_4$alkylene chain. In some embodiments, $L_1$ is —$(CH_2)_n$, where n is 1-4, and wherein one hydrogen atom on any methylene unit is optionally substituted, and $L_2$ is —$(CH_2)_m$, where m is 1-4, and wherein one hydrogen atom on any methylene unit is optionally substituted. In other embodiments, $L_1$ is —$(CH_2)_n$, where n is 1-2, and wherein one hydrogen atom on any methylene unit is optionally substituted with $C_{1-3}$alkyl, —OH, —$O(C_{1-3}alkyl)$, —COOH, or —$COO(C_{1-3}alkyl)$, and $L_2$ is —$(CH_2)_m$, where m is 1-3, and wherein one hydrogen atom on any methylene unit is optionally substituted with $C_{1-3}$alkyl, —OH, —$O(C_{1-3}alkyl)$, —COOH, or —$COO(C_{1-3}alkyl)$. In other embodiments, $L_1$ is —$CH(CH_3)(CH_2)_n$, where n is 0-3.

In still other embodiments, L₁ is —CH(OH)(CH₂)ₙ—, where n is 0-3. In yet other embodiments, L₂ is —(CH₂)ₘCH-COOH—, where m is 1 or 2.

In certain embodiments, V is —O—, —NR$^E$—, —NR$^E$C(O)—, —NR$^E$ CO₂—, —NR$^E$SO₂—, —C(O)N(R$^B$)—, —CO₂—, or —SO₂N(R$^B$)—, where R$^B$ is independently H or C$_{1-4}$ aliphatic and R$^E$ is independently H, C$_{1-6}$ aliphatic, —C(=O)R$^B$, —C(O)OR$^B$ or —SO₂R$^B$; or two R$^E$ on the same nitrogen atom taken together with the nitrogen atom form a 5-8 membered aromatic or non-aromatic ring having in addition to the nitrogen atom 0-2 ring heteroatoms selected from N, O or S. In yet other embodiments, V is —O—, —NR$^E$—, C(O)N(R$^B$)—, or —NR$^E$C(O)—. In still other embodiments, V is —NR$^E$—.

In some embodiments, R$^7$ is —N(R$^F$)₂, —OR$^G$, —N(R$^E$)C(O)R$^G$, —N(R$^E$)CO₂R$^G$, —N(R$^E$)SO₂R$^G$, —C(O)N(R$^F$)₂, —SO₂N(R$^F$)₂, an optionally substituted 5- or 6-membered aryl or heteroaryl group, or an optionally substituted 3-8-membered monocyclic or bicyclic heterocyclyl group. In other embodiments, R$^7$ is selected from —NH₂, —NH(C$_{1-5}$alkyl), —N(C$_{1-5}$alkyl)₂, —NHCO₂(C$_{1-6}$alkyl), —NHCO(C$_{1-6}$alkyl), —NHCO(optionally substituted phenyl), —NHSO₂(C$_{1-6}$alkyl), or an optionally substituted group selected from C$_{1-6}$alkyl, phenyl, pyridyl, piperidinyl, piperazinyl, pyrrolidinyl, or azetidinyl, wherein the C$_{1-5}$alkyl group is optionally substituted and is linear, cyclic, or branched.

In some embodiments, R$^8$ is an optionally substituted group selected from C$_{1-6}$alkyl, phenyl, pyridyl, piperidinyl, piperazinyl, pyrrolidinyl, or azetidinyl.

It will be appreciated that in some embodiments, R$^7$ and R$^8$ are optionally substituted at one or more carbon atoms with 1, 2, or 3 independent occurrences of R$^{11}$, and at one or more substitutable nitrogen atoms with R$^{12}$, wherein each occurrence of R$^{11}$ is independently selected from optionally substituted C$_{1-6}$aliphatic, optionally substituted 6-10-membered aryl, optionally substituted 5-10-membered heteroaryl, —N(R$^B$)₂, =O, halo, NO₂, —CN, —OR$^B$, —C(O)R$^A$, —CO₂R$^A$, —SR$^C$, —S(O)R$^C$, —S(O)₂R$^C$, —OS(O)₂R$^C$—, N(R$^B$)C(O)R$^A$, —N(R$^B$)CO₂R$^A$, —N(R$^B$)SO₂R$^A$, —C(O)N(R$^B$)₂, —SO₂N(R$^B$)₂, —N(R$^B$)C(O)N(R$^B$)₂, or —OC(O)R$^A$, and each occurrence of R$^{12}$ is independently selected from H, optionally substituted C$_{1-6}$ aliphatic, optionally substituted 6-10-membered aryl, optionally substituted 5-10-membered heteroaryl, —C(=O)R$^B$, —C(O)OR$^B$ or —SO₂R$^B$.

In certain other embodiments, W is -L₁-V-L₂-R$^7$, wherein L₁ is —CHR$^{13}$—, where R$^{13}$ is C$_{1-3}$alkyl, OH, or OMe, V is NR$^E$, L₂ is —(CH₂)ₙ—, where n is 1-3, and R$^7$ is —N(R$^F$)₂, NR$^E$COOR$^G$, NR$^E$COR$^G$, NR$^E$SO₂R$^G$, an optionally substituted 5-6-membered aryl or heteroaryl group, or an optionally substituted 3-8-membered heterocyclyl group. In still other embodiments, R$^7$ is —N(R$^F$)₂, NR$^E$COOR$^G$, NR$^E$COR$^G$, NR$^E$SO₂R$^G$, or an optionally substituted group selected from phenyl, pyridyl, piperidinyl, piperazinyl, pyrrolidinyl, morpholinyl, or azetidinyl. In yet other embodiments, R$^7$ is —N(R$^F$)₂, NHCOOR$^G$, NHCOR$^G$, NHSO₂R$^G$, or an optionally substituted group selected from phenyl, pyridyl, piperidinyl, piperazinyl, or pyrrolidinyl. In certain other embodiments for compounds described directly above, R$^F$ is H or C$_{1-3}$alkyl. R$^G$ is C$_{1-6}$alkyl or a 5-6-membered aryl or heteroaryl group, and R$^E$ is H, C$_{1-3}$alkyl, or SO₂CH₃.

In yet other embodiments W is selected from:

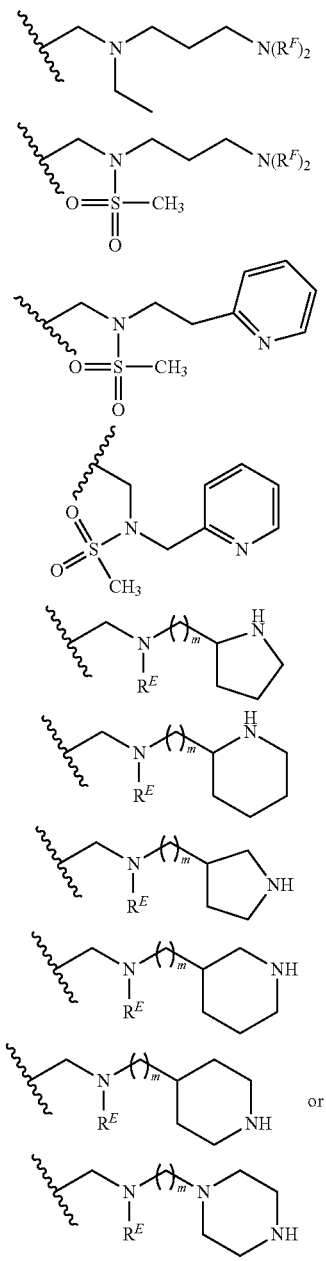

wherein m is 1, 2, or 3, R$^F$ is H or C$_{1-3}$alkyl, and R$^E$ is H, C$_{1-3}$alkyl, or SO₂CH₃, and wherein each of the foregoing pyridyl, pyrrolidinyl, piperidinyl, and piperazinyl groups is optionally substituted at one or more carbon atoms with 1, 2, or 3 independent occurrences of R$^{11}$, and at one or more substitutable nitrogen atoms with R$^{12}$. In certain embodiments, each of the foregoing pyridyl, pyrrolidinyl, piperidinyl, and piperazinyl groups is unsubstituted.

In still other embodiments, W is —V—R$^8$. In one embodiment, V is —NH— and R$^8$ is optionally substituted piperidinyl, azetidinyl, or pyrrolidinyl. In other embodiments, V is —O— or —COO—, and R$^8$ is C$_{1-6}$alkyl. In still other embodiments, V is —CH₂— or SO₂, and R$^8$ is an optionally substituted group selected from:

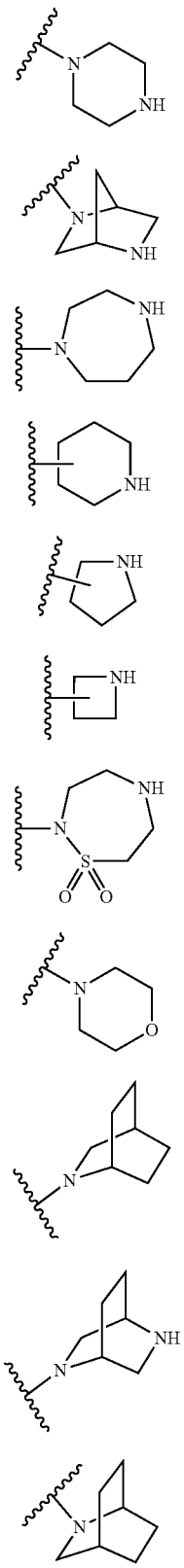

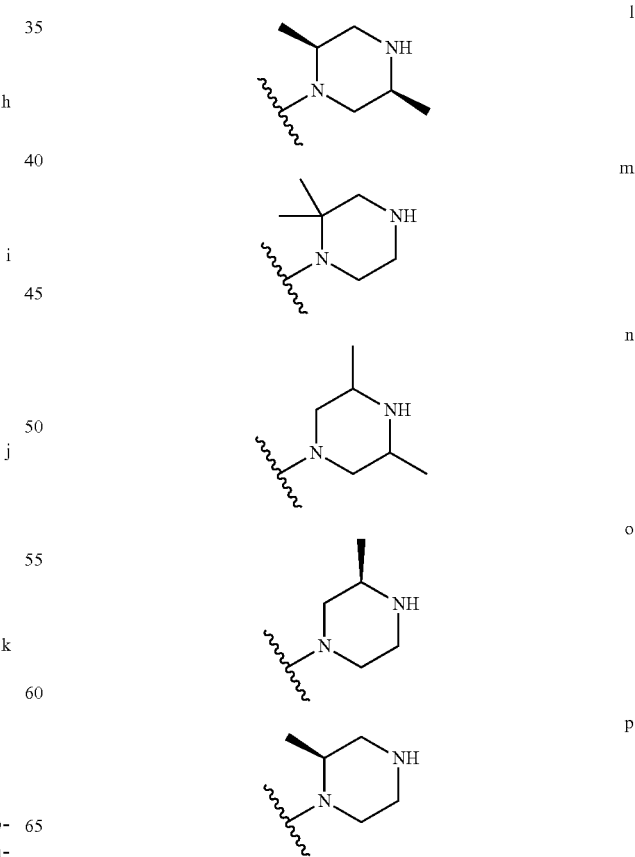

nitrogen atoms with $R^{12}$, wherein each occurrence of $R^{11}$ is independently selected from optionally substituted $C_{1-6}$aliphatic, optionally substituted 6-10-membered aryl, optionally substituted 5-10-membered heteroaryl, —N($R^B$)$_2$, =O, halo, NO$_2$, —CN, —OR$^B$, —C(O)R$^A$, —CO$_2$R$^A$, —SR$^C$, —S(O)R$^C$, —S(O)$_2$R$^C$, —OS(O)$_2$R$^C$—, N($R^B$)C(O)R$^A$, —N($R^B$)CO$_2$R$^A$, —N($R^B$)SO$_2$R$^A$, —C(O)N($R^B$)$_2$, —SO$_2$N($R^B$)$_2$, —N($R^B$)C(O)N($R^B$)$_2$, and —OC(O)R$^A$, and each occurrence of $R^{12}$ is independently selected from H, optionally substituted $C_{1-6}$ aliphatic, optionally substituted 6-10-membered aryl, optionally substituted 5-10-membered heteroaryl, —C(=O)R$^B$, —C(O)OR$^B$ or —SO$_2$R$^B$. In certain embodiments, $R^8$ is unsubstituted. In yet other embodiments, $R^8$ is substituted on one or two carbon atoms with one or two occurrences of $C_{1-4}$alkyl, phenyl, heteroaryl, halo, —COOH, —COO($C_{1-4}$alkyl), —CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), —N($C_{1-4}$alkyl)$_2$, =O, or $C_{1-4}$alkyl substituted with one or two independent occurrences of phenyl, heteroaryl, halo, —COOH, —COO($C_{1-4}$alkyl), —CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), or —N($C_{1-4}$alkyl)$_2$. In still other embodiments, $R_8$ is substituted on one nitrogen atom with —$C_{1-4}$alkyl, or —COO($C_{1-4}$alkyl), —SO$_2$($C_{1-4}$alkyl). In certain embodiments for compounds described directly above, when V is —SO$_2$—, $R^8$ is not ring g. In other embodiments, for compounds described directly above, V is —CH$_2$—.

In yet other embodiments, V is —CH$_2$— and $R^8$ is a group selected from:

wherein each of the foregoing $R^8$ groups is optionally substituted at one or more carbon atoms with 1, 2, or 3 independent occurrences of $R^{11}$, and at one or more substitutable

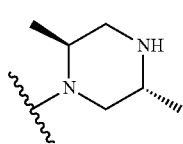

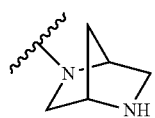

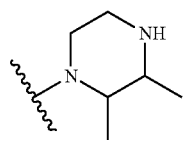

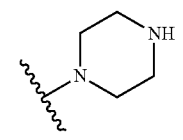

In certain other embodiments W is -L$_1$-V—R$^8$, wherein L$_1$ is —CH$_2$—, V is —NR$^E$— or —NR$^E$CO—, and R$^8$ is an optionally substituted group selected from C$_{1-6}$alkyl, or a 5-6-membered heteroaryl or a 3-7-membered heterocyclyl group. In certain embodiments, R$^8$ is an optionally substituted group selected from C$_{1-6}$alkyl, piperidinyl, pyrrolidinyl, azetidinyl, pyrazinyl, pyridyl, or pyrimidinyl. In still other embodiments, R$^8$ is an optionally substituted group selected from:

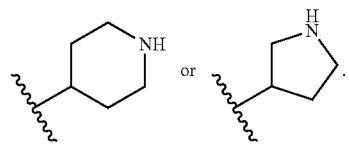

In yet other embodiments W is an optionally substituted group selected from:

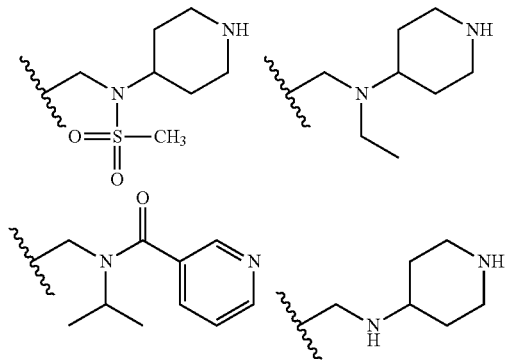

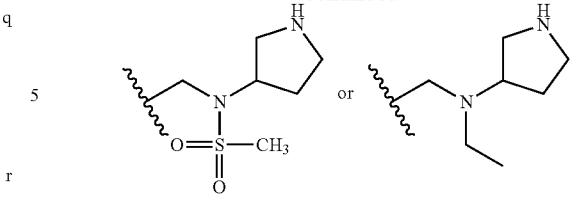

It will be appreciated that for compounds described directly above where W is -L$_1$-V—R$^8$, each of the R$^8$ groups described directly is optionally substituted at one or more carbon atoms with 1, 2, or 3 independent occurrences of R$^{11}$, and at one or more substitutable nitrogen atoms with R$^{12}$, wherein each occurrence of R$^{11}$ is independently selected from optionally substituted C$_{1-6}$aliphatic, optionally substituted 6-10-membered aryl, optionally substituted 5-10-membered heteroaryl, —N(R$^B$)$_2$, =O, halo, NO$_2$, —CN, —OR$^B$, —C(O)R$^A$, —CO$_2$R$^A$, —SR$^C$, —S(O)R$^C$, —S(O)$_2$R$^C$, —OS(O)$_2$R$^C$—, —N(R$^B$)C(O)R$^A$, —N(R$^B$)CO$_2$R$^A$, —N(R$^B$)SO$_2$R$^A$, —C(O)N(R$^B$)$_2$, —SO$_2$N(R$^B$)$_2$, N(R$^B$)C(O)N(R$^B$)$_2$, and —OC(O)R$^A$, and each occurrence of R$^{12}$ is independently selected from H, optionally substituted C$_{1-6}$ aliphatic, optionally substituted 6-10-membered aryl, optionally substituted 5-10-membered heteroaryl, —C(=O)R$^B$, —C(O)OR$^B$ or —SO$_2$R$^B$. In certain embodiments, R$^8$ is unsubstituted. In yet other embodiments, R$^8$ is substituted on one or two carbon atoms with one or two occurrences of C$_{1-4}$alkyl, phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), —N(C$_{1-4}$alkyl)$_2$, =O, or C$_{1-4}$alkyl substituted with one or two independent occurrences of phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —NH(C$_{1-4}$alkyl), or —N(C$_{1-4}$alkyl)$_2$. In still other embodiments, R$_8$ is substituted on one nitrogen atom with —C$_{1-4}$alkyl, or —COO(C$_{1-4}$alkyl), —SO$_2$(C$_{1-4}$alkyl), benzyl, or CH$_2$(heteroaryl). In still other embodiments, R$^8$ is substituted with one or two occurrences of —CF$_3$, halo, C$_{1-3}$alkyl, or COO(C$_{1-3}$alkyl), and is substituted on one nitrogen atom with —C$_{1-4}$alkyl, or —COO(C$_{1-4}$alkyl), —SO$_2$(C$_{1-4}$alkyl), benzyl, or CH$_2$(heteroaryl).

As also described above, Cy$^1$ is optionally further substituted by one to three independent occurrences of R$^6$, wherein each occurrence of R$^6$ is independently selected from -halo, C$_{1-8}$ aliphatic, —CN, —OR$^B$, —SR$^D$, —N(R$^E$)$_2$, —NR$^E$C(O)R$^B$, —NR$^E$C(O)N(R$^E$)$_2$, —NR$^E$CO$_2$R$^D$, —CO$_2$R$^B$, —C(O)R$^B$, —C(O)N(R$^E$)$_2$, —OC(O)N(R$^E$)$_2$, —S(O)$_2$R$^D$, —SO$_2$N(R$^E$)$_2$, —S(O)R$^D$, —NR$^E$SO$_2$N(R$^E$)$_2$, —NR$^E$SO$_2$R$^D$, —C(=NH)—N(R$^E$)$_2$, or C$_{1-8}$ aliphatic optionally substituted with halo, —CN, —OR$^B$, —SR$^D$, —N(R$^E$)$_2$, —NR$^E$C(O)R$^B$, —NR$^E$C(O)N(R$^E$)$_2$, —NR$^E$CO$_2$R$^D$, —CO$_2$R$^B$, —C(O)R$^B$, —C(O)N(R$^E$)$_2$, —OC(O)N(R$^E$)$_2$, —S(O)$_2$R$^D$, —SO$_2$N(R$^E$)$_2$, —S(O)R$^D$, —NR$^E$SO$_2$N(R$^E$)$_2$, —NR$^E$SO$_2$R$^D$, or —C(=NH)—N(R$^E$)$_2$, wherein each occurrence of R$^D$ is C$_{1-6}$ aliphatic and each occurrence of R$^E$ is independently H, C$_{1-6}$ aliphatic, —C(=O)R$^B$, —C(O)OR$^B$ or —SO$_2$R$^B$; or two R$^E$ on the same nitrogen atom taken together with the nitrogen atom form a 5-8 membered aromatic or non-aromatic ring having in addition to the nitrogen atom 0-2 ring heteroatoms selected from N, O or S. In certain embodiments, Cy$^1$ is optionally further substituted with one occurrence of R$^6$, wherein R$^6$ is selected from —OR$^B$, C$_{1-3}$aliphatic, or halo. In yet other embodiments, R$^6$ is selected from —OMe, methyl, ethyl, F, or Cl.

In certain other exemplary embodiments, for compounds of general formula I, Cy$^1$ is optionally substituted phenyl and thus compounds of formula I-A are provided:

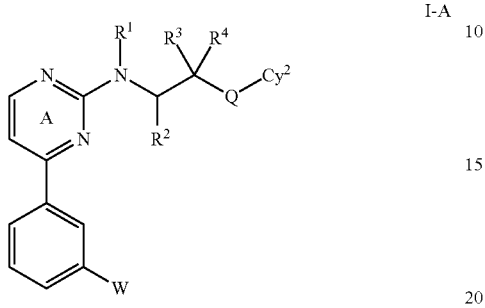

I-A wherein W, R$^1$, R$^2$, R$^3$, R$^4$, Q and Cy$^2$ are defined generally and in subsets above.

In still other embodiments, for compounds of formula I-A, R$^1$, R$^2$, R$^3$, and R$^4$ are all hydrogen, and Q is a bond and compounds of formula I-A-i are provided:

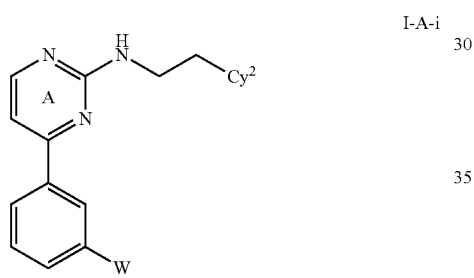

I-A-i wherein W and Cy$^2$ are defined generally and in subsets above.

In certain embodiments, for compounds described directly above, compound variables are selected from one or more, or all of:

a. Cy$^2$ is a C$_{6-10}$aryl or a 5-10-membered heteroaryl ring optionally substituted by one to three independent occurrences of R$^9$ and one occurrence of R$^{10}$, wherein each occurrence of R$^9$ is independently selected from —OR$^B$, —N(R$^B$)C(O)R$^A$, —N(R$^B$)$_2$, halo, C$_{1-4}$aliphatic optionally substituted by halo, NO$_2$, —OS(O)$_2$R$^C$, —S(O)R$^C$, —N(R$^B$)SO$_2$R$^A$, or —S(O)$_2$N(R$^B$)$_2$;

b. ring A is optionally substituted with 1 or 2 independent occurrences of R$^5$, wherein R$^5$ on ring A, when present, is selected from halo or optionally substituted C$_{1-4}$ aliphatic;

c. W is selected from one of:
  i) -L$_1$-V-L$_2$-R$^7$, wherein L$_1$ is —CHR$^{13}$—, where R$^{13}$ is C$_{1-3}$alkyl, OH, or OMe, V is NR$^E$, L$_2$ is —(CH$_2$)$_n$—, where n is 1-3, and R$^7$ is —N(R$^F$)$_2$, NR$^E$COOR$^G$, NR$^E$COR$^G$, NR$^E$SO$_2$R$^G$, an optionally substituted 5-6-membered aryl or heteroaryl group, or an optionally substituted 3-8-membered heterocyclyl group;
  ii) —V—R$^8$, wherein V is —NH— and R$^8$ is optionally substituted group selected from piperidinyl, azetidinyl, or pyrrolidinyl; V is —O— or —COO—, and R$^8$ is C$_{1-6}$alkyl; or V is —CH$_2$— or SO$_2$, and R$^8$ is an optionally substituted group selected from:

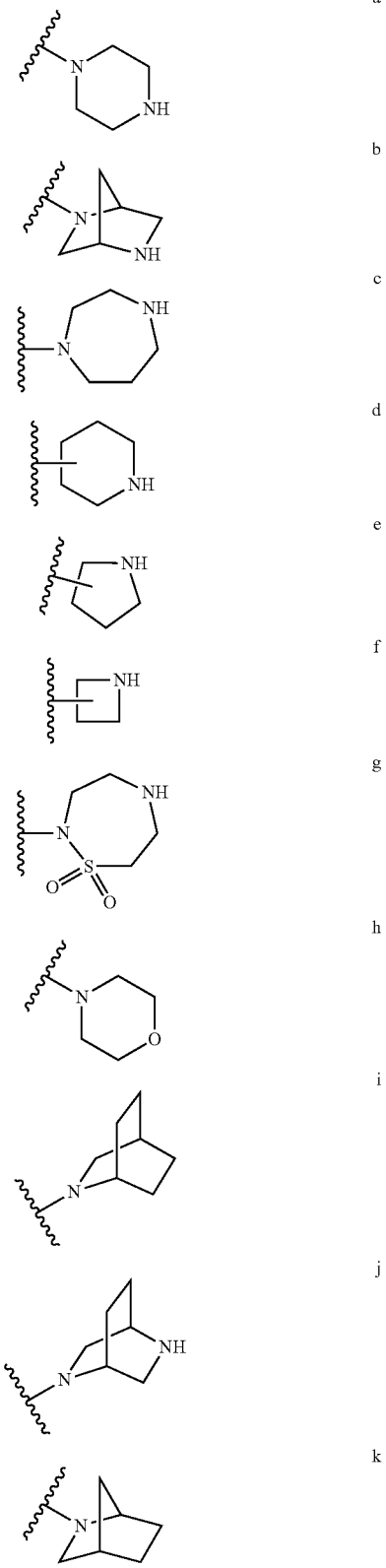

wherein R$^8$ is substituted on one or two carbon atoms with one or two occurrences of C$_{1-4}$alkyl, phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH (heteroaryl), —CN, —NH$_2$, —OH, —O(C$_{1-4}$alkyl), —NH(C$_{1-4}$alkyl), —N(C$_{1-4}$alkyl)$_2$, =O, or C$_{1-4}$alkyl substituted with one or two independent occurrences of phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), or —N(C$_{1-4}$alkyl)$_2$; or iii)-L$_1$-V—R$^8$, wherein L$_1$ is —CH$_2$—, V is —NR$^E$— or —NR$^E$CO—, and R$^8$ is an optionally substituted group selected from C$_{1-6}$alkyl, or a 5-6-membered heteroaryl or a 3-7-membered heterocyclyl group, wherein R$^8$ is unsubstituted, or R$^8$ is substituted on one or two carbon atoms with one or two occurrences of C$_{1-4}$alkyl, phenyl, heteroaryl, halo, —COON, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), —N(C$_{1-4}$alkyl)$_2$, =O, or C$_{1-4}$alkyl substituted with one or two independent occurrences of phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), or —N(C$_{1-4}$alkyl)$_2$, and R$_8$ is optionally substituted on one nitrogen atom with —C$_{1-4}$alkyl, or —COO(C$_{1-4}$alkyl), —SO$_2$(C$_{1-4}$alkyl), benzyl, or CH$_2$(heteroaryl); and d) Cy$^1$ is optionally further substituted by one to three independent occurrences of R$^6$, wherein each occurrence of R$^6$ is independently selected from —OR$^B$, C$_{1-3}$aliphatic, or halo.

In certain other embodiments, for compounds described directly above, compound variables are selected from one or more, or all of:

a. Cy$^2$ is phenyl, pyridyl, naphthyl, thienyl, 2-oxo-2,3-dihydrobenzooxazolyl, benzo[1,3]dioxolyl, benzo[1,3]dioxinyl, indolyl, tetrazole, piperidinyl, piperazinyl, or morpholinyl optionally substituted by one to three independent occurrences of R$^9$ and one occurrence of R$^{10}$, wherein each occurrence of R$^9$ is independently selected from —OR$^B$, —N(R$^B$)C(O)R$^A$, —N(R$^B$)$_2$, halo, C$_{1-4}$aliphatic optionally substituted by halo, NO$_2$, —OS(O)$_2$R$^C$, —S(O)R$^B$, —N(R$^B$)SO$_2$R$^A$, or —S(O)$_2$N(R$^B$)$_2$;

b. ring A is optionally substituted with 1 or 2 independent occurrences of R$^5$, wherein R$^5$ on ring A, when present, is selected from F, Cl, Br, or methyl;

c. W is selected from:

i)

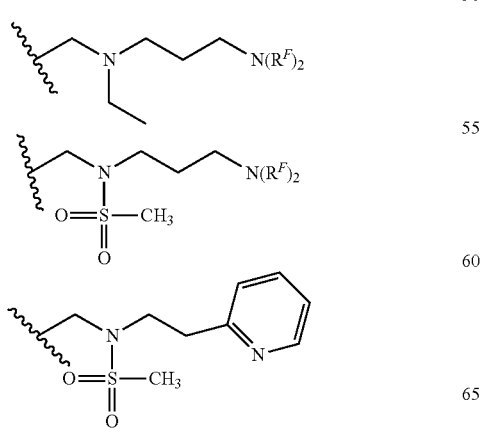

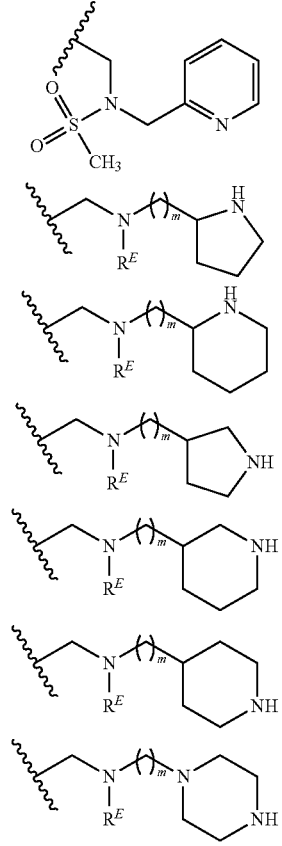

wherein m is 1, 2, or 3, R$^F$ is H or C$_{1-3}$alkyl, and R$^E$ is H, C$_{1-3}$alkyl, or SO$_2$CH$_3$, and wherein each of the foregoing pyridyl, pyrrolidinyl, piperidinyl, and piperazinyl groups is optionally substituted at one or more carbon atoms with 1, 2, or 3 independent occurrences of R$^{11}$, and at one or more substitutable nitrogen atoms with R$^{12}$;

ii) —V—R$^8$, wherein V is —CH$_2$— and R$^8$ is a group selected from:

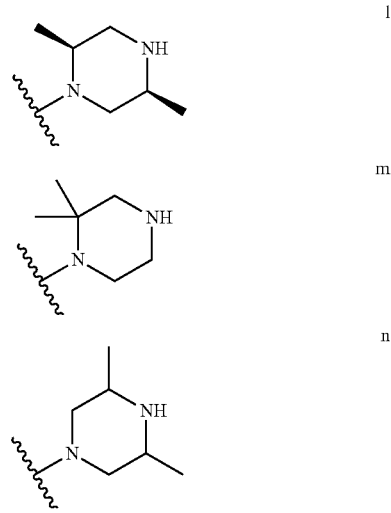

-continued

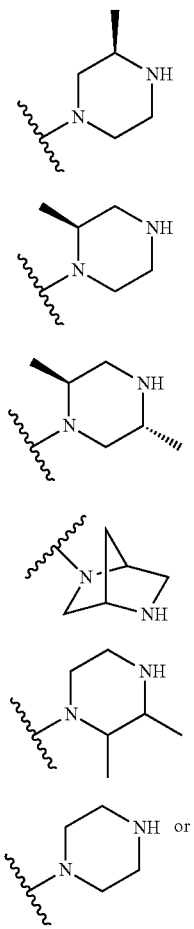

o p q r s t iii)

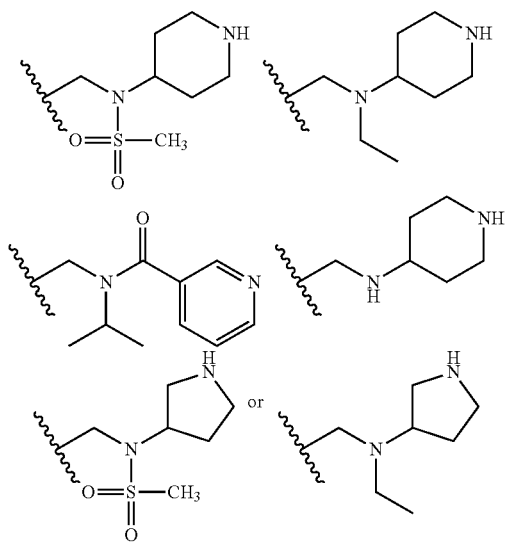

wherein the pyrrolidinyl, piperidinyl, and pyridyl groups are unsubstituted, or are substituted on one or two carbon atoms with one or two occurrences of $C_{1-4}$alkyl, phenyl, heteroaryl, halo, —COOH, —COO($C_{1-4}$alkyl),
—CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), —N($C_{1-4}$alkyl)$_2$, =O, or $C_{1-4}$alkyl substituted with one or two independent occurrences of phenyl, heteroaryl, halo, —COOH, —COO($C_{1-4}$alkyl), —CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), or —N($C_{1-4}$alkyl)$_2$, and are optionally substituted on one nitrogen atom with —$C_{1-4}$alkyl, or —COO($C_{1-4}$alkyl), —SO$_2$($C_{1-4}$alkyl), benzyl, or CH$_2$(heteroaryl); and d) Cy$^1$ is optionally further substituted by one to three independent occurrences of R$^6$, wherein each occurrence of R$^6$ is —OMe, methyl, ethyl, F, or Cl.

In yet other exemplary embodiments, for compounds of general formula I, Cy$^1$ is optionally substituted thienyl and thus compounds of formula I-B are provided:

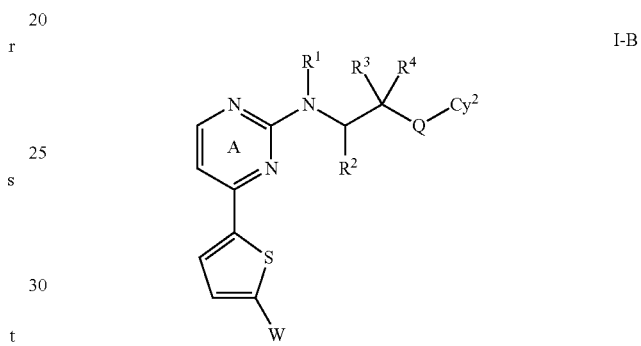

I-B wherein W, R$^1$, R$^2$, R$^3$, R$^4$, Q and Cy$^2$ are defined generally and in subsets above.

In still other embodiments, for compounds of formula I-B, R$^1$, R$^2$, R$^3$, and R$^4$ are all hydrogen, and Q is a bond and compounds of formula I-B-i are provided:

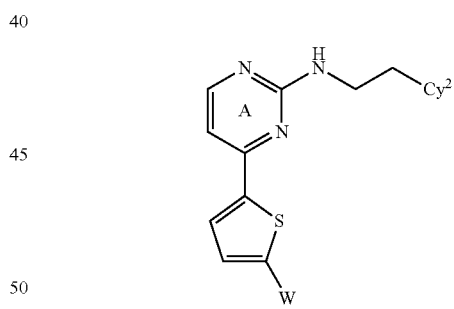

wherein W and Cy$^2$ are defined generally and in subsets above.

In certain embodiments, for compounds described directly above, compound variables are selected from one or more, or all of:

a. Cy$^2$ is a $C_{6-10}$aryl or a 5-10-membered heteroaryl ring optionally substituted by one to three independent occurrences of R$^9$ and one occurrence of R$^{10}$, wherein each occurrence of R$^9$ is independently selected from —OR$^B$, —N(R$^B$)C(O)R$^A$, —N(R$^B$)$_2$, halo, $C_{1-4}$aliphatic optionally substituted by halo, NO$_2$, —OS(O)$_2$R$^C$, —S(O)R$^C$, —N(R$^B$)SO$_2$R$^A$, or —S(O)$_2$N(R$^B$)$_2$;

b. ring A is optionally substituted with 1 or 2 independent occurrences of R$^5$, wherein R$^5$ on ring A, when present, is selected from halo or optionally substituted $C_{1-4}$ aliphatic;

c. W is -L$_1$—V—R$^8$, wherein L$_1$ is —CH$_2$—, V is —NR$^E$— or —NR$^E$CO—, and R$^8$ is an optionally substituted group selected from C$_{1-6}$alkyl, or a 5-6-membered heteroaryl or a 3-7-membered heterocyclyl group, wherein R$^8$ is unsubstituted, or R$^8$ is substituted on one or two carbon atoms with one or two occurrences of C$_{1-4}$alkyl, phenyl, heteroaryl, halo, —COOH, —COO(C$_{1-4}$alkyl), —CONH$_2$, —CONH(C$_{1-4}$ alkyl), —CON(C$_{1-4}$allyl)$_2$, —CONH(heteroaryl), —CN, —NH$_2$, —OH, —O(C$_{1-4}$alkyl), —NH(C$_{1-4}$alkyl), —N(C$_{1-4}$alkyl)$_2$, =O, or C$_{1-4}$allyl substituted with one or two independent occurrences of phenyl, heteroaryl, halo, —COOH, —COO(C$_{1-4}$alkyl), —CONH$_2$, —CONH(C$_{1-4}$ alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), or —N(C$_{1-4}$alkyl)$_2$, and R$_8$ is optionally substituted on one nitrogen atom with —C$_{1-4}$alkyl, or —COO(C$_{1-4}$alkyl), —SO$_2$(C$_{1-4}$alkyl), benzyl, or CH$_2$(heteroaryl); and d. Cy$^1$ is optionally further substituted by one to three independent occurrences of R$^6$, wherein each occurrence of R$^6$ is independently selected from —OR$^B$, C$_{1-3}$aliphatic, or halo.

In certain other embodiments, for compounds described directly above, compound variables are selected from one or more, or all of:

a. Cy$^2$ is phenyl, pyridyl, naphthyl, thienyl, 2-oxo-2,3-dihydrobenzooxazolyl, benzo[1,3]dioxolyl, benzo[1,3]dioxinyl, indolyl, tetrazole, piperidinyl, piperazinyl, or morpholinyl optionally substituted by one to three independent occurrences of R$^9$ and one occurrence of R$^{10}$, wherein each occurrence of R$^9$ is independently selected from —OR$^B$, —N(R$^B$)C(O)R$^A$, —N(R$^B$)$_2$, halo, C$_{1-4}$aliphatic optionally substituted by halo, NO$_2$, —OS(O)$_2$R$^C$, —S(O)R$^C$, —N(R$^B$) SO$_2$R$^A$, or —S(O)$_2$N(R$^B$)$_2$;

b. ring A is optionally substituted with 1 or 2 independent occurrences of R$^5$, wherein R$^5$ on ring A, when present, is selected from F, Cl, Br, or methyl;

c. W is:

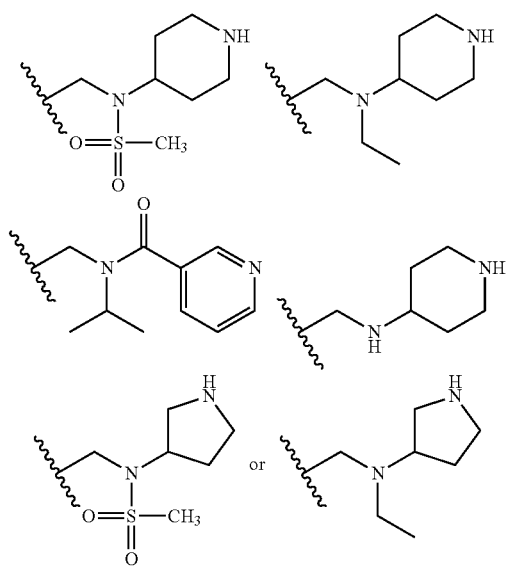

wherein the pyrrolidinyl, piperidinyl, and pyridyl groups are unsubstituted, or are substituted on one or two carbon atoms with one or two occurrences of C$_{1-4}$alkyl, phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), —N(C$_{1-4}$alkyl)$_2$, =O, or C$_{1-4}$alkyl substituted with one or two independent occurrences of phenyl, heteroaryl, halo, —COOH, —COO(C$_{1-4}$alkyl), —CONH$_2$, —CONH(C$_{1-4}$alkyl), —CON(C$_{1-4}$alkyl)$_2$, —CONH(heteroaryl), —CN, —NH$_2$, —OH, —O(C$_{1-4}$alkyl), —NH(C$_{1-4}$alkyl), or —N(C$_{1-4}$alkyl)$_2$, and are optionally substituted on one nitrogen atom with —C$_{1-4}$alkyl, or —COO (C$_{1-4}$alkyl), —SO$_2$(C$_{1-4}$alkyl), benzyl, or CH$_2$(heteroaryl); and d. Cy$^1$ is optionally further substituted by one to three independent occurrences of R$^6$, wherein each occurrence of R$^6$ is —OMe, methyl, ethyl, F, or Cl.

In still other embodiments, compounds of formula I-A-i are provided:

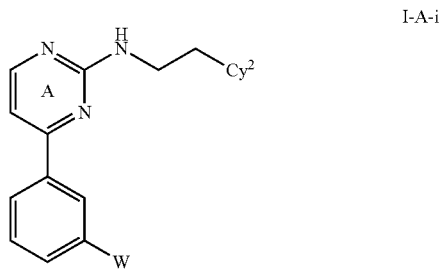

I-A-i wherein a. Cy$^2$ is phenyl optionally substituted by one to three independent occurrences of R$^9$ and one occurrence of R$^{10}$, wherein each occurrence of R$^9$ is independently selected from —OR$^B$, —N(R$^B$)C(O)R$^A$, —N(R$^B$)$_2$, halo, C$_{1-4}$aliphatic optionally substituted by halo, NO$_2$, —OS(O)$_2$R$^C$, —S(O) R$^C$, —N(R$^B$)SO$_2$R$^A$, or —S(O)$_2$N(R$^B$)$_2$;

b. ring A is optionally substituted with 1 or 2 independent occurrences of R$^5$, wherein R$^5$ on ring A, when present, is selected from F, Cl, Br, or methyl;

c. W is selected from:

i)

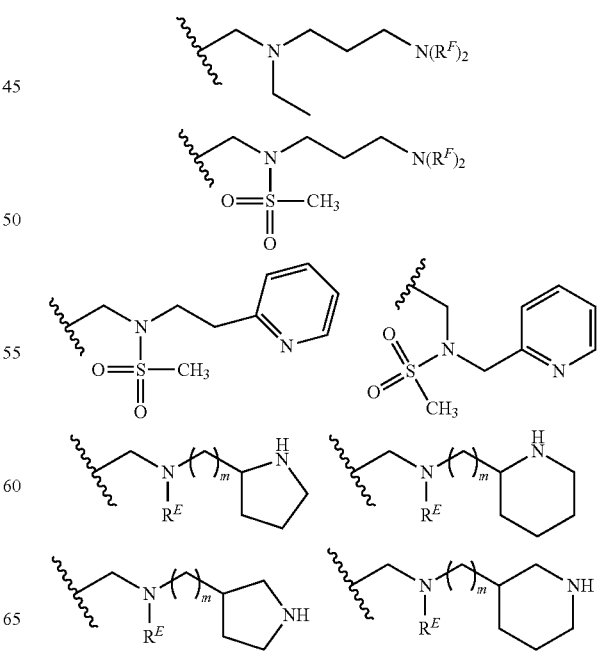

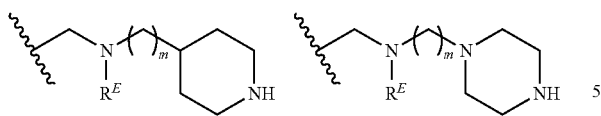

wherein m is 1, 2, or 3, $R^F$ is H or $C_{1-3}$alkyl, and $R^E$ is H, $C_{1-3}$alkyl, or $SO_2CH_3$, and wherein each of the foregoing pyridyl, pyrrolidinyl, piperidinyl, and piperazinyl groups is optionally substituted at one or more carbon atoms with 1, 2, or 3 independent occurrences of $R^{11}$, and at one or more substitutable nitrogen atoms with $R^{12}$;

ii) —V—$R^8$, wherein V is —CH$_2$— and $R^8$ is a group selected from:

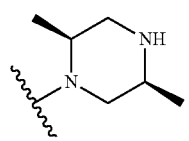 l

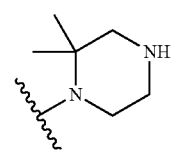 m

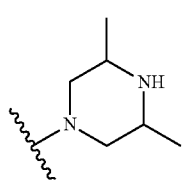 n

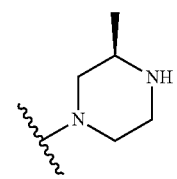 o

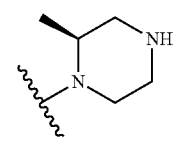 p

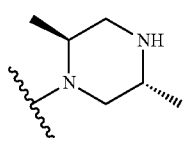 q

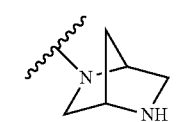 r

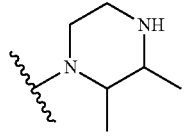 s

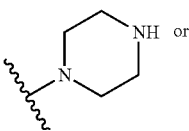 t iii)

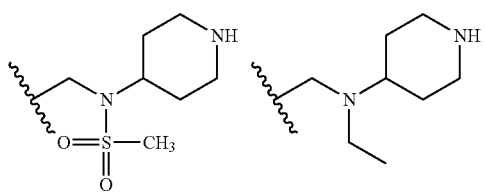

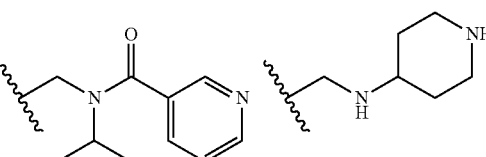

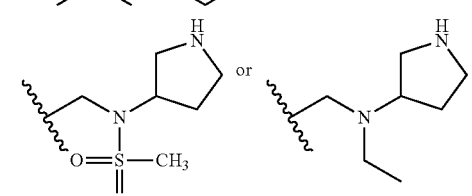 or wherein the pyrrolidinyl, piperidinyl, and pyridyl groups are unsubstituted, or are substituted on one or two carbon atoms with one or two occurrences of $C_{1-4}$alkyl, phenyl, heteroaryl, halo, —COOH, —COO($C_{1-4}$alkyl), —CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), —N($C_{1-4}$alkyl)$_2$, =O, or $C_{1-4}$alkyl substituted with one or two independent occurrences of phenyl, heteroaryl, halo, —COOH, —COO($C_{1-4}$alkyl), —CONH$_2$, —CONH($C_{1-4}$alkyl), —CON($C_{1-4}$alkyl)$_2$, —CONH(heteroaryl), —CN, —NH$_2$, —OH, —O($C_{1-4}$alkyl), —NH($C_{1-4}$alkyl), or —N($C_{1-4}$alkyl)$_2$, and are optionally substituted on one nitrogen atom with —$C_{1-4}$alkyl, or —COO($C_{1-4}$alkyl), —SO$_2$($C_{1-4}$alkyl), benzyl, or CH$_2$(heteroaryl); and d) Cy$^1$ is optionally further substituted by one to three independent occurrences of $R^6$, wherein each occurrence of $R^6$ is —OMe, methyl, ethyl, F, or Cl.

In certain other embodiments, for compounds described directly above, Cy$^2$ is optionally further substituted with one or two occurrences of $R^9$, wherein $R^9$ is halo. In yet other embodiments, ring A is not further substituted by $R^5$. In still other embodiments, Cy$^1$ is optionally further substituted by one occurrence of F or methyl.

The following chemical structures are examples of specific compounds of the invention:
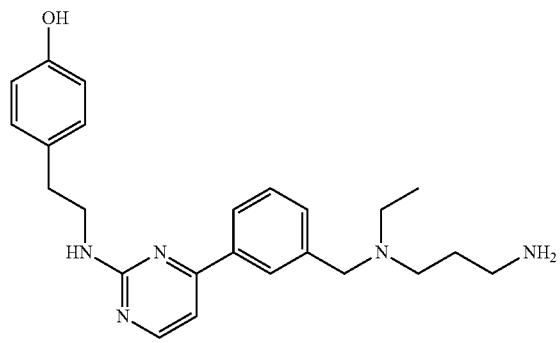
1
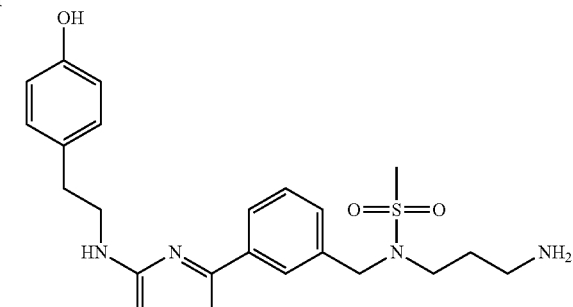
2
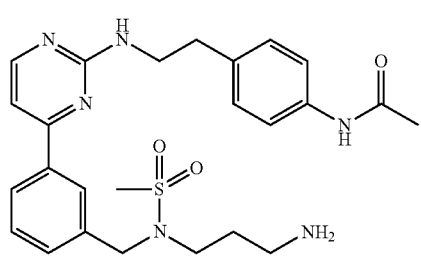
3
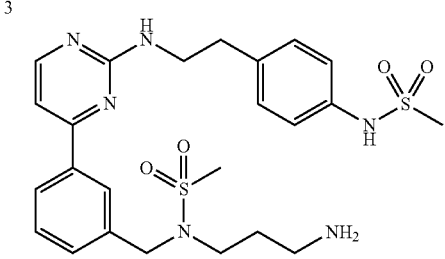
4
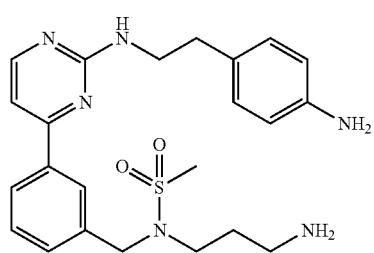
5
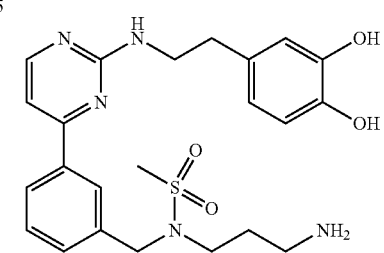
6
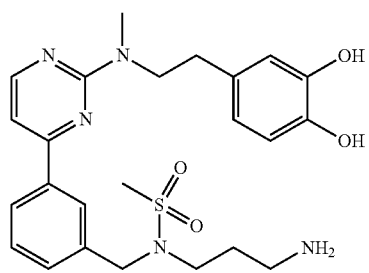
7
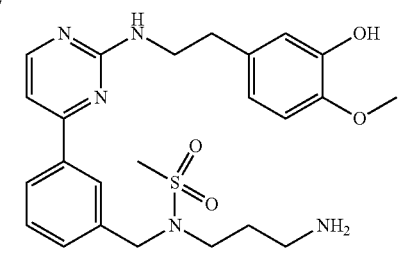
8
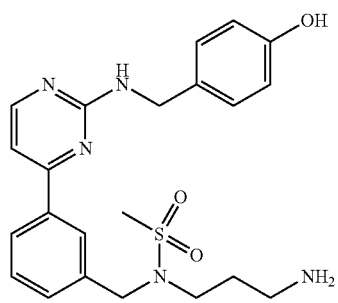
9
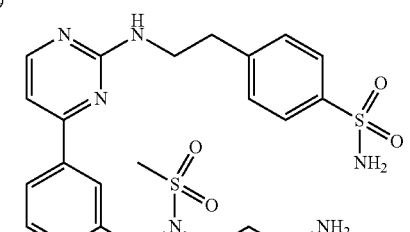
10

-continued
| | |
|---|---|
| 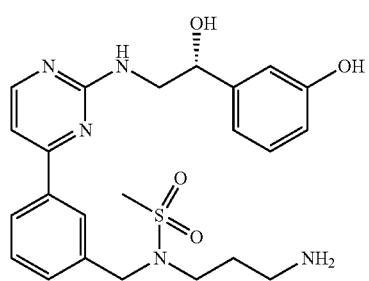 9 | 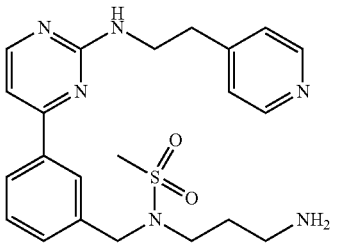 11 |
| 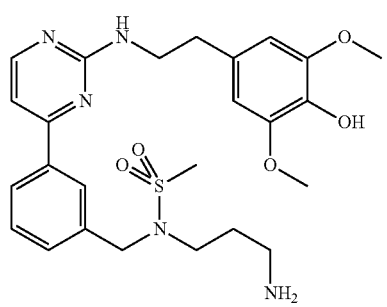 | 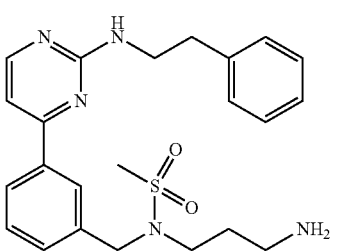 13 |
| 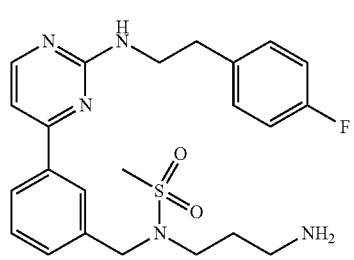 | 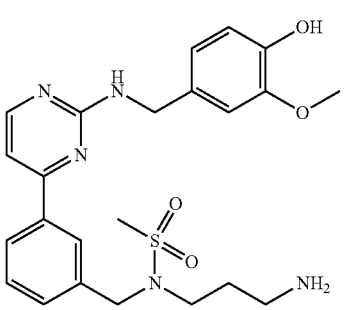 15 |
| 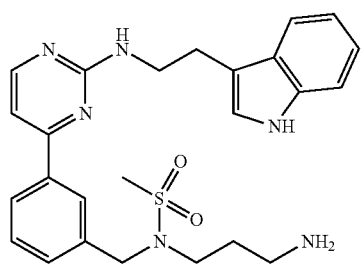 | 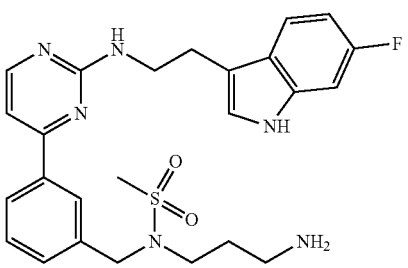 17 |
| 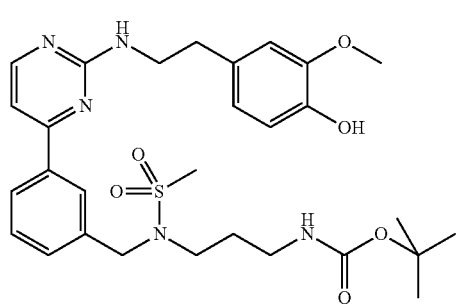 | 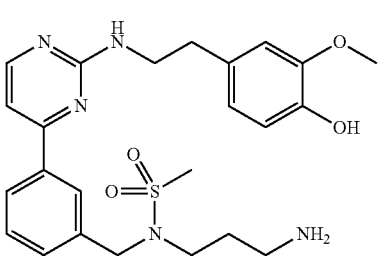 19 |

21 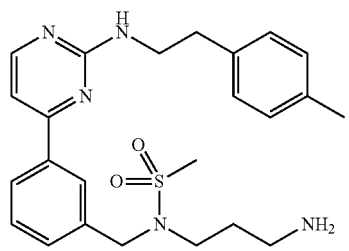
22 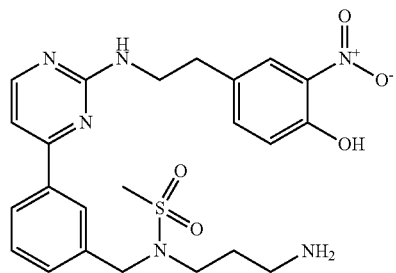
23 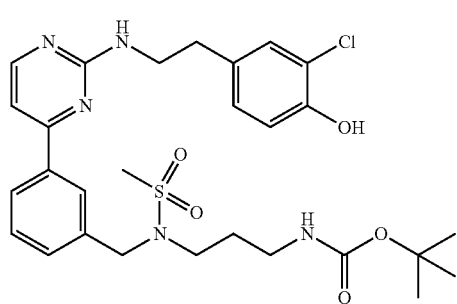
24 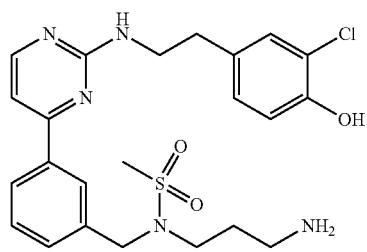
25 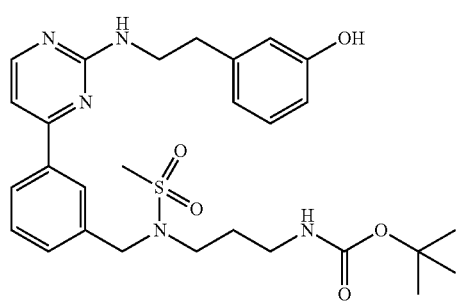
26 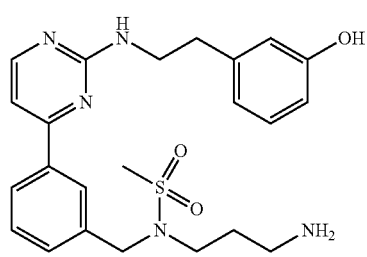
27 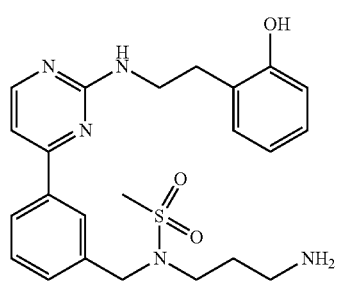
28 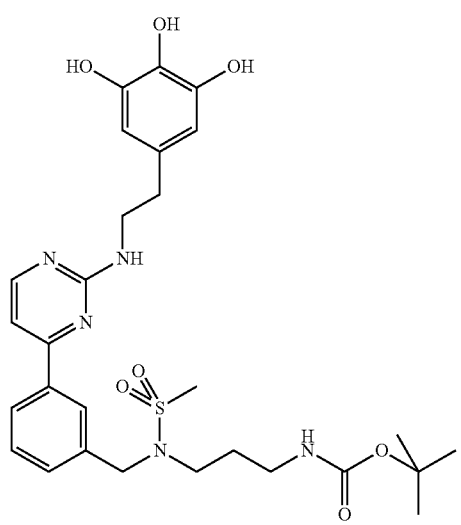

-continued
29
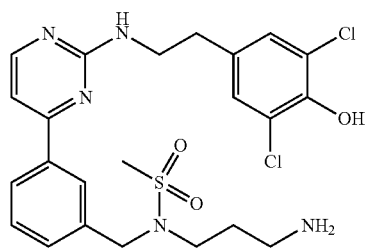
30
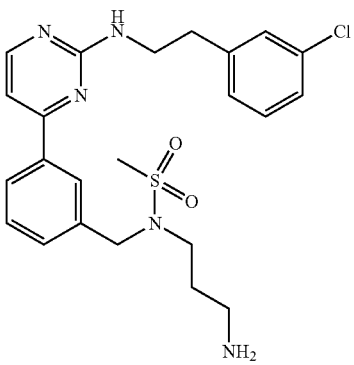
31
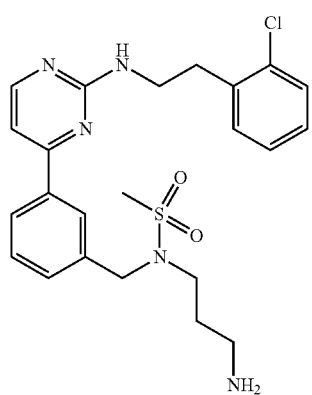
32
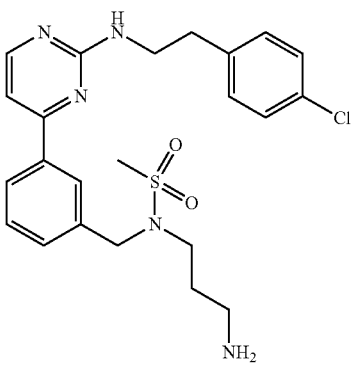
33
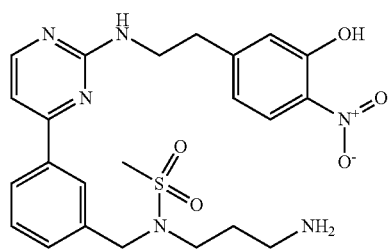
34
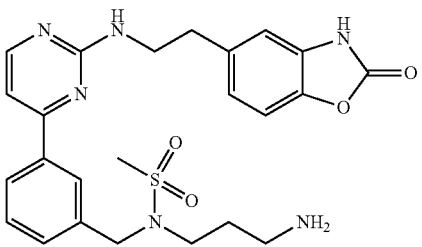
35
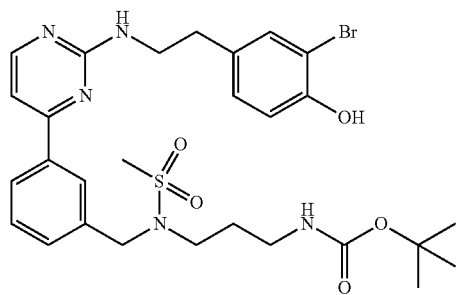
36
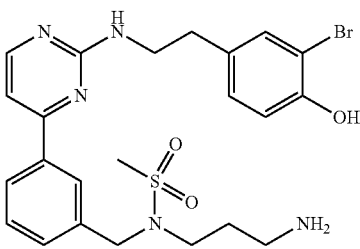
37
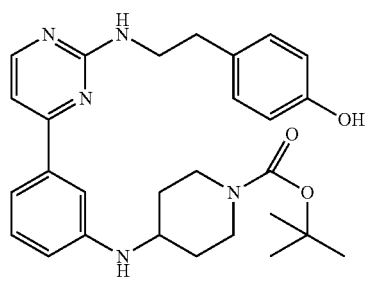
38
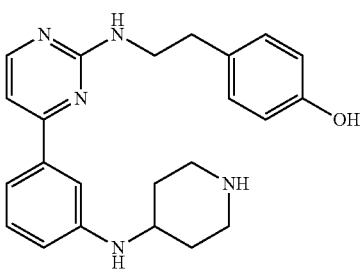

37
| 37 | 38 |
|---|---|
-continued
| | 39 | | 40 |
|---|---|---|---|
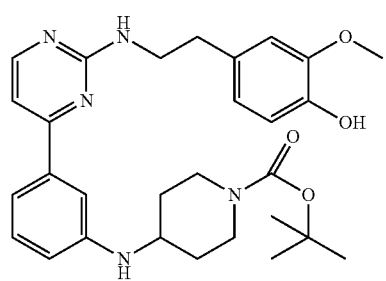
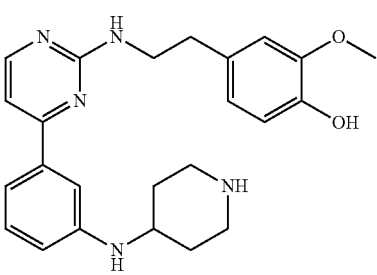
| 41 | 42 |
|---|---|
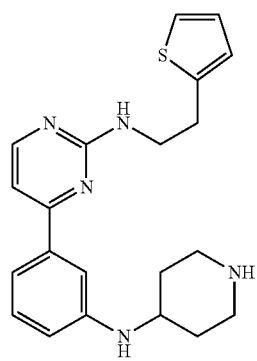
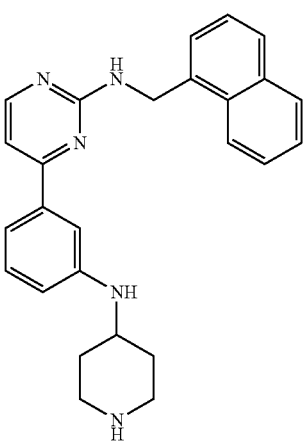
| 43 | 44 |
|---|---|
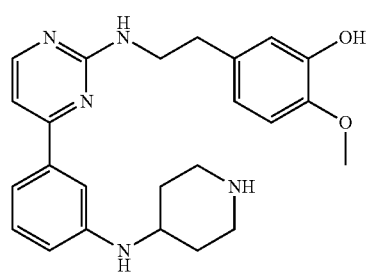
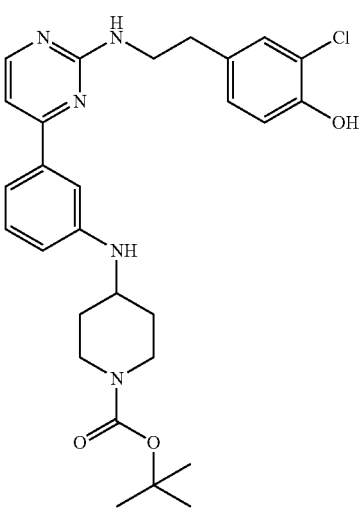
| 45 | 46 |
|---|---|
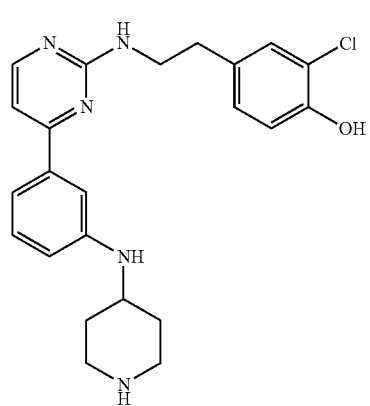
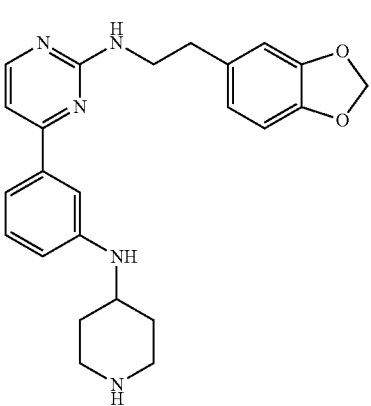

-continued
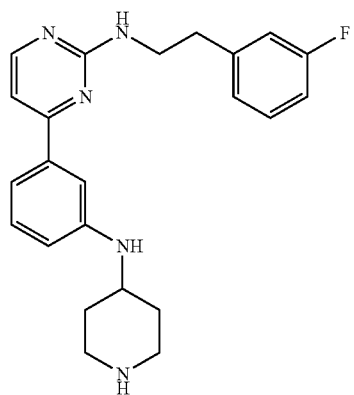
47
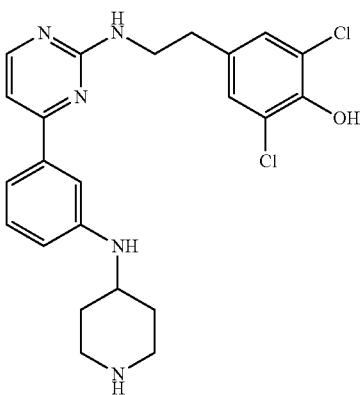
48
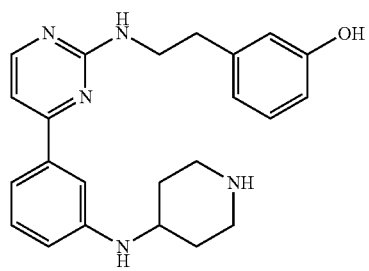
49
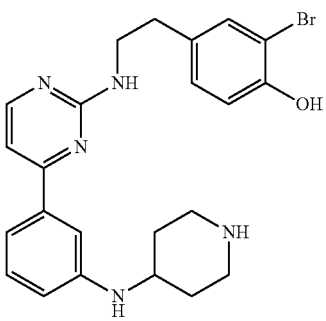
50
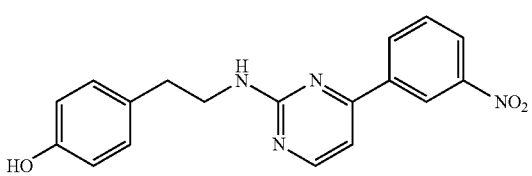
51 52
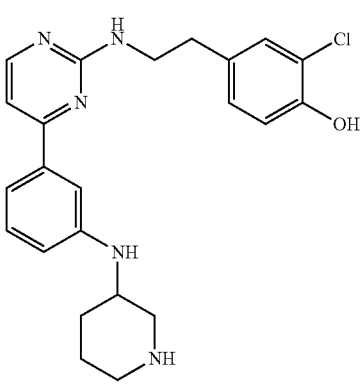
53 54

55
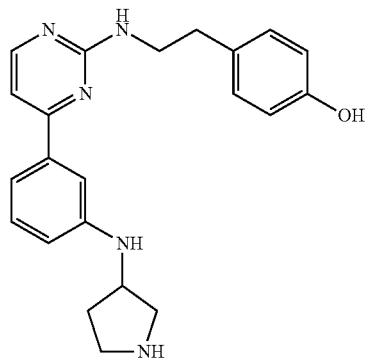
56
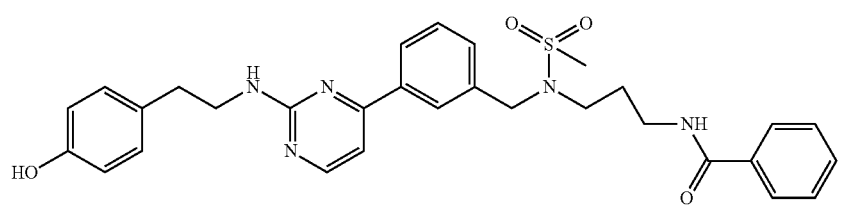
57
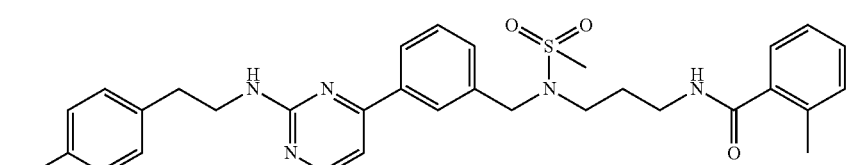
58
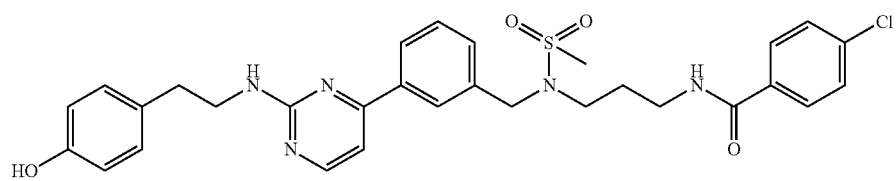
59
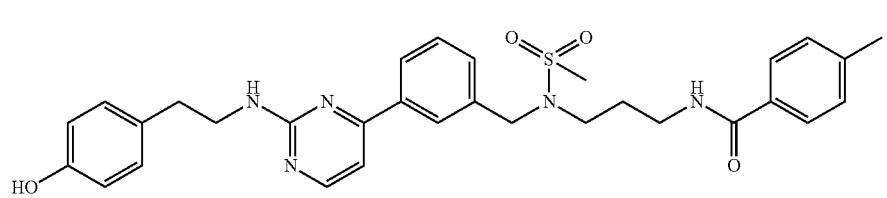
60
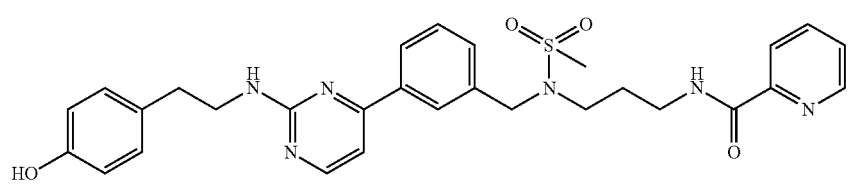
61
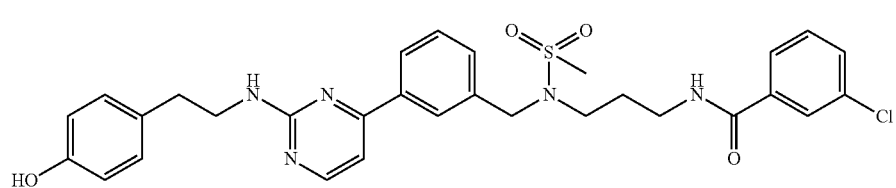

62
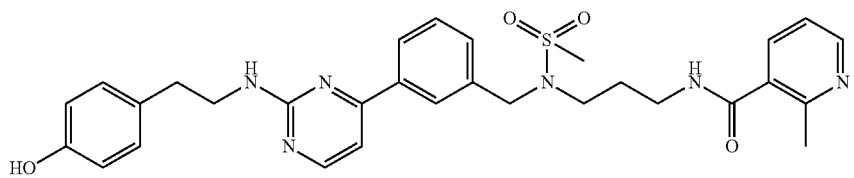
63
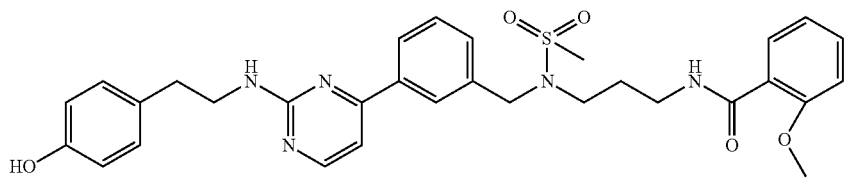
64
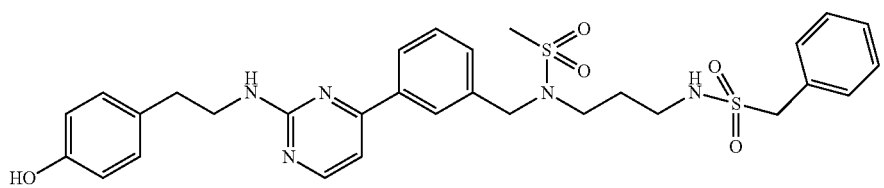
65
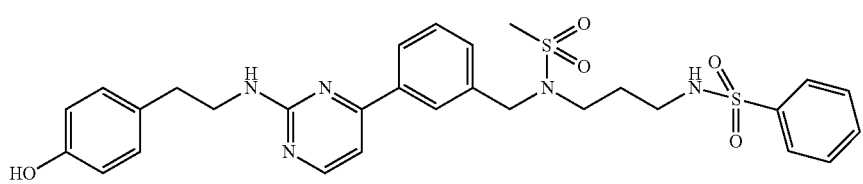
66 67
68 69
70 71
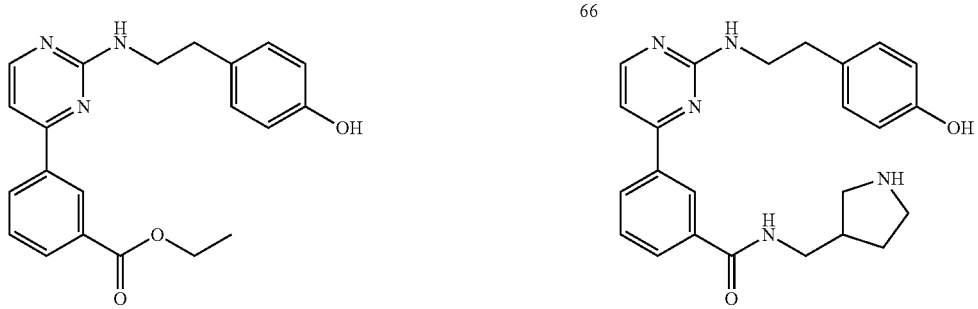
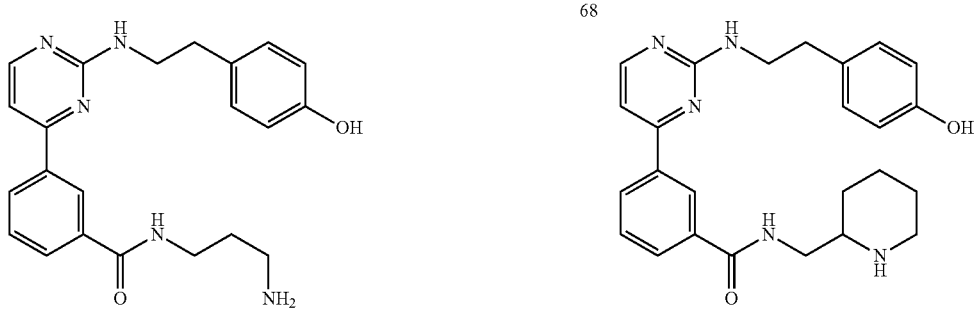
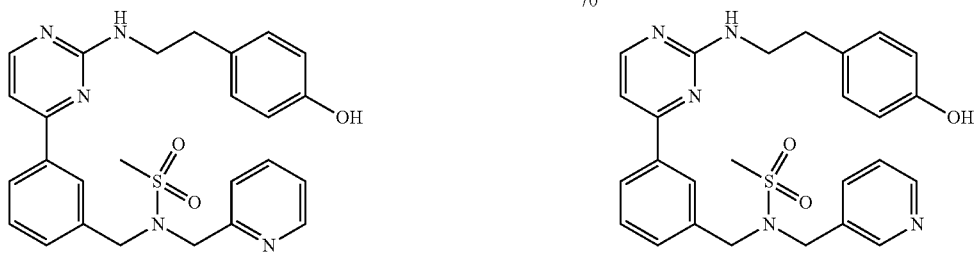

-continued
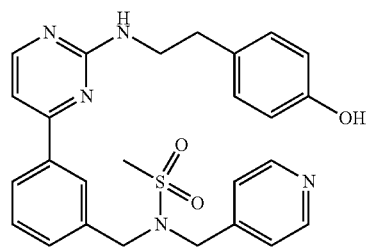
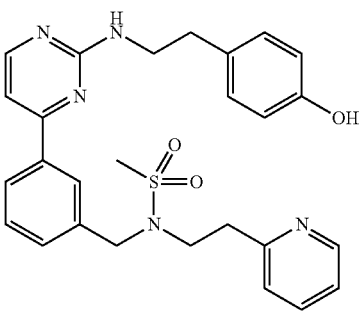
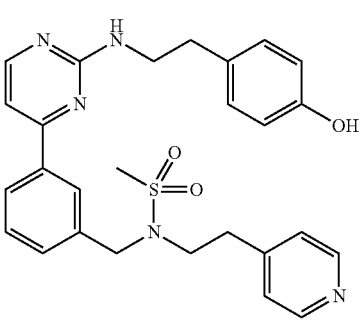
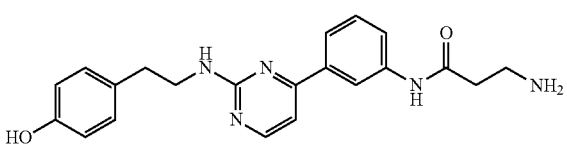
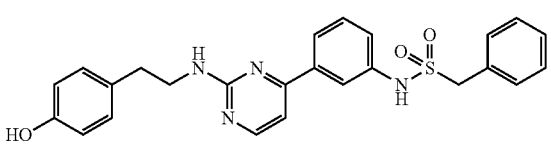
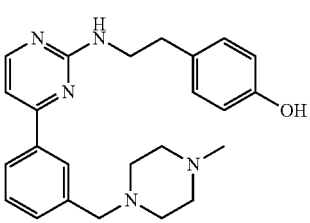
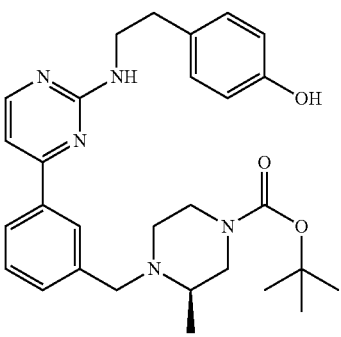

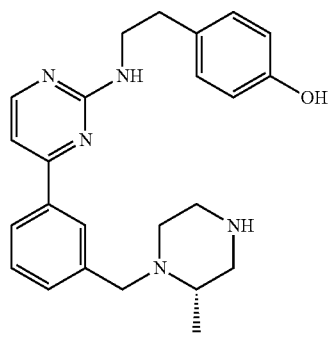
84
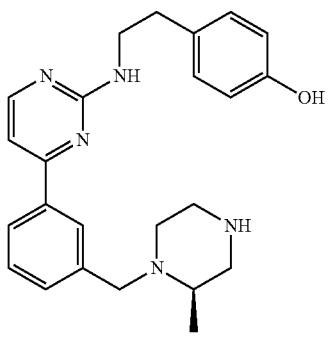
85
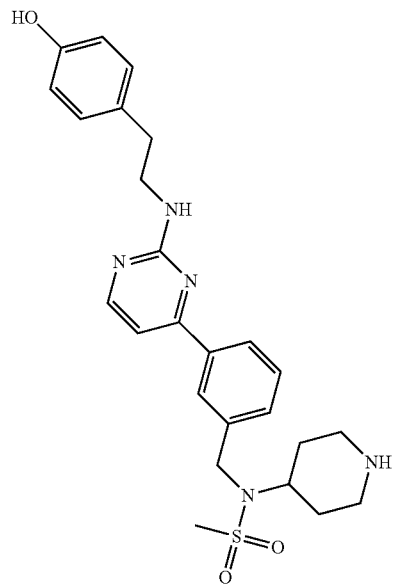
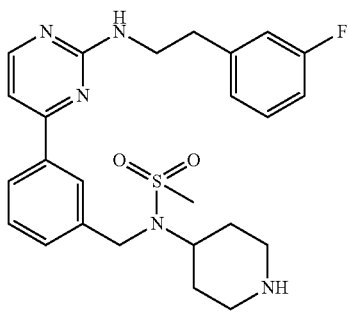
86 87
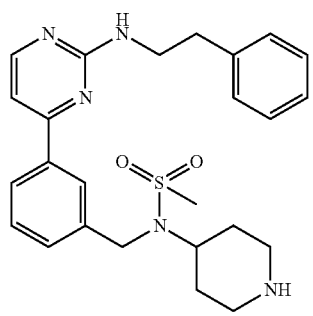
88
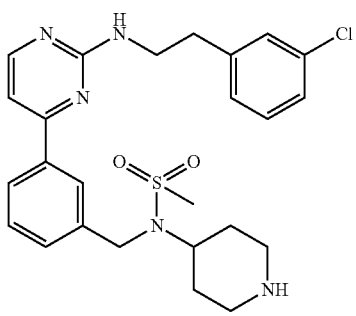
89
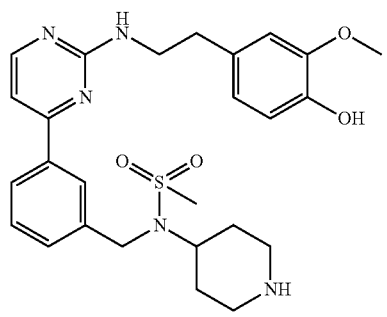
90
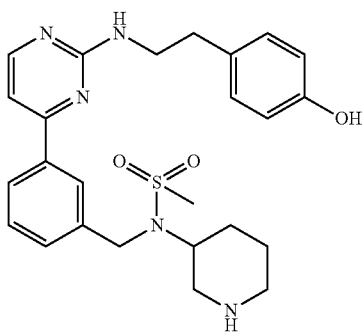
91

-continued
92
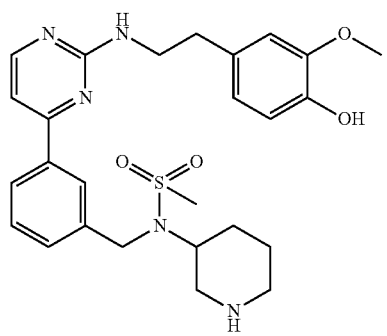
93
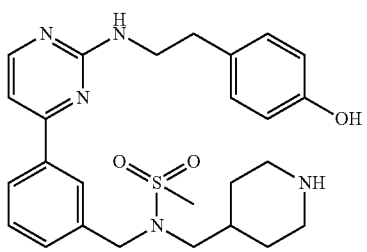
94
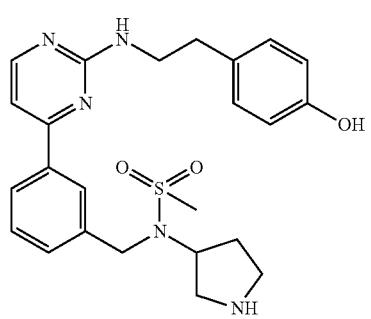
95
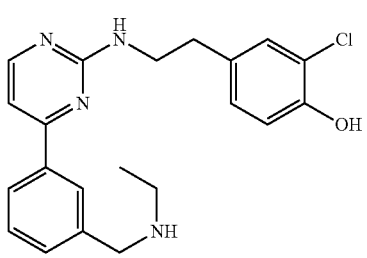
96
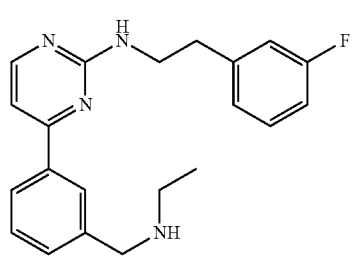
97
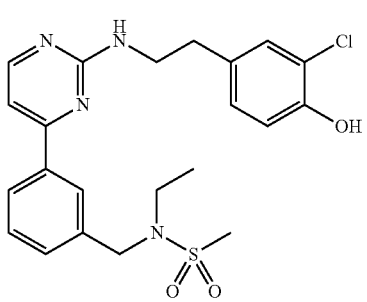
98
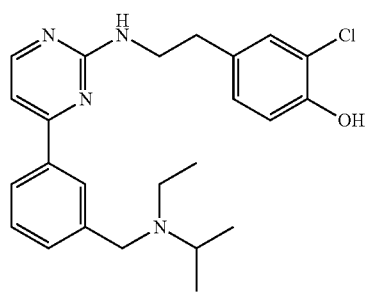
99
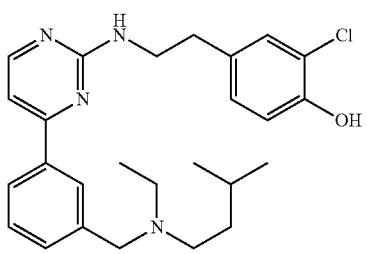
100
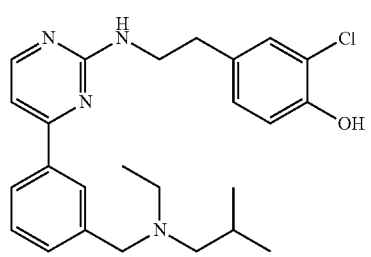
101
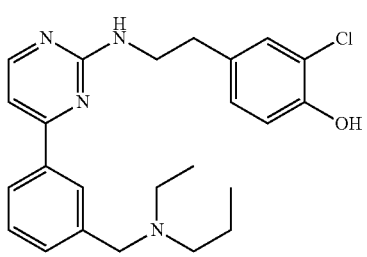

-continued
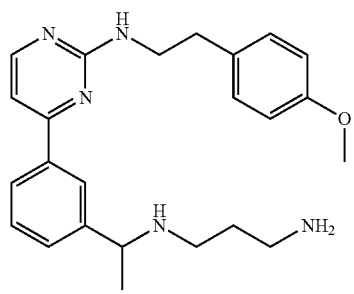 102
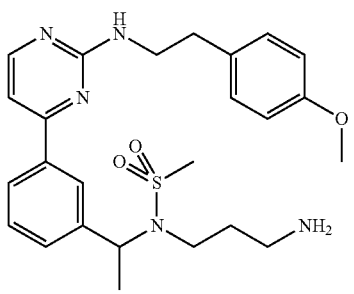 103
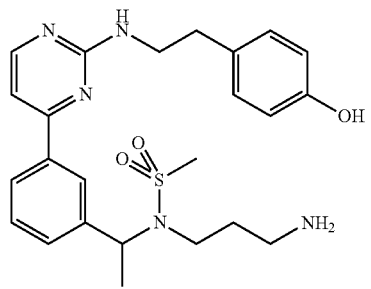 104
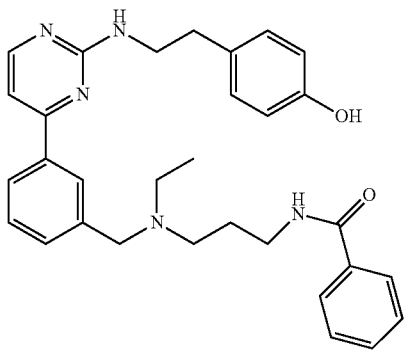 105
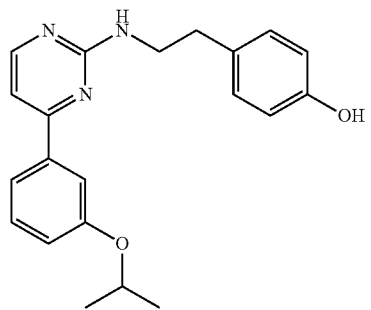 106
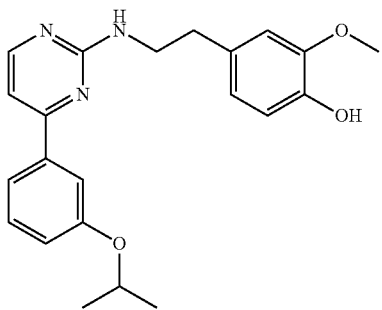 107
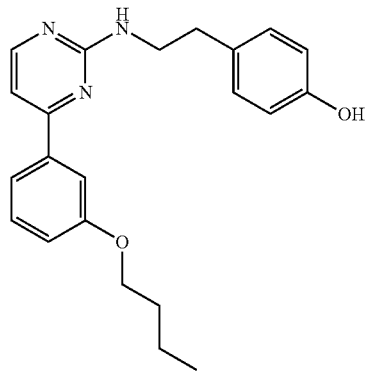 108
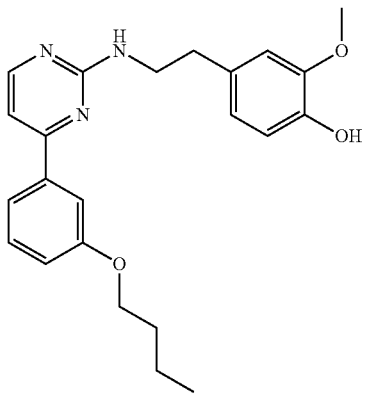 109
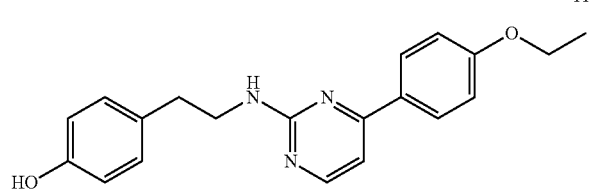 110
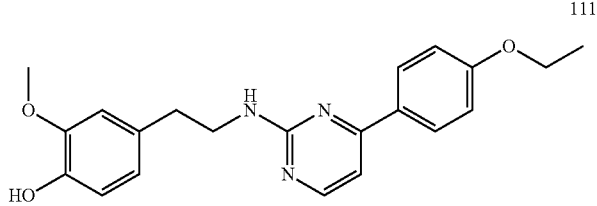 111

-continued
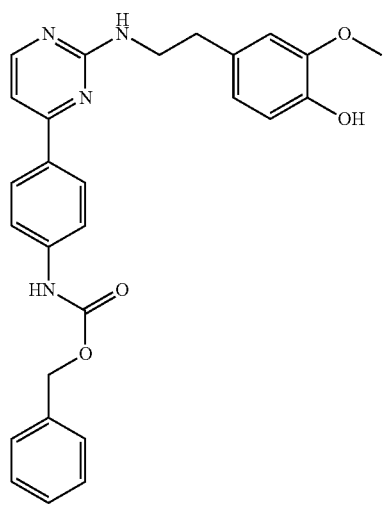
112
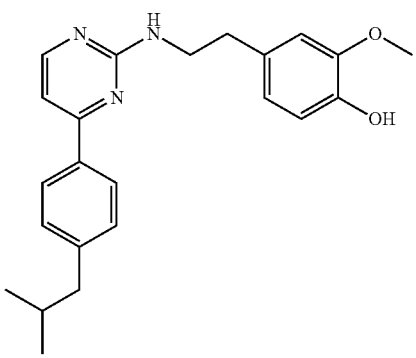
113
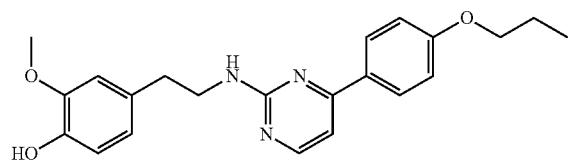
114
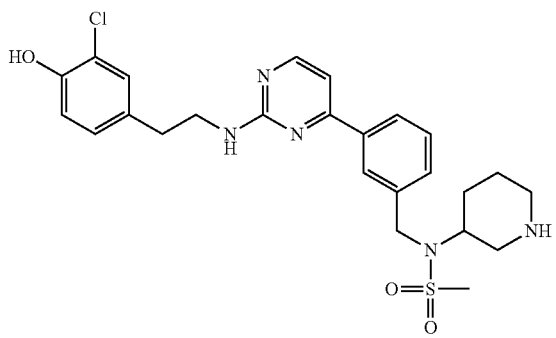
115
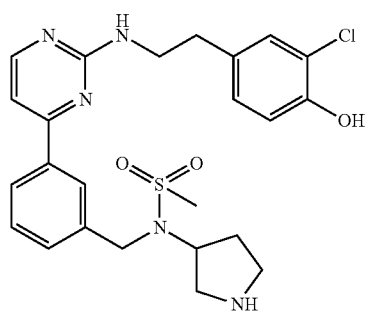
116
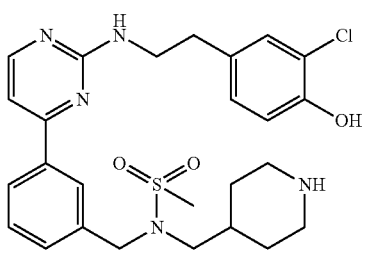
117
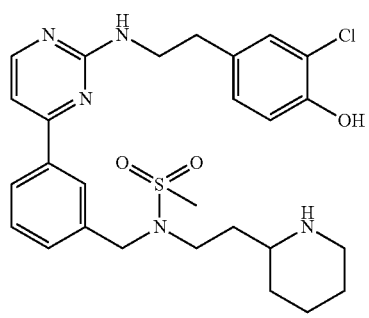
118
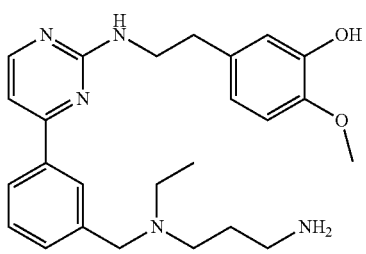
119

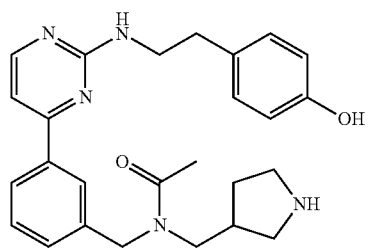
55
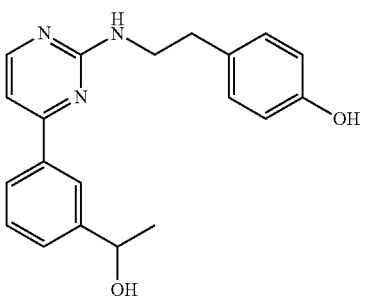
120
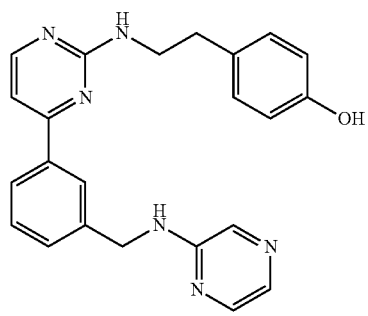
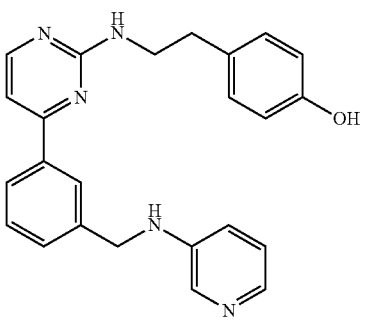
122
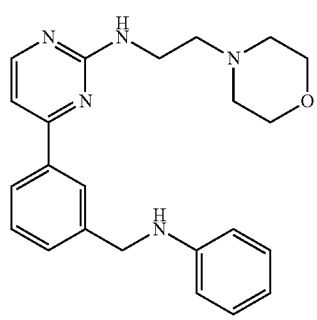
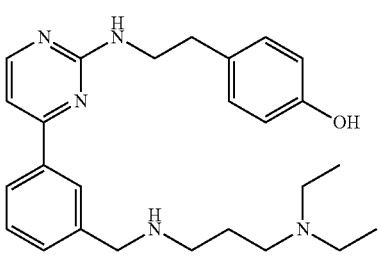
124
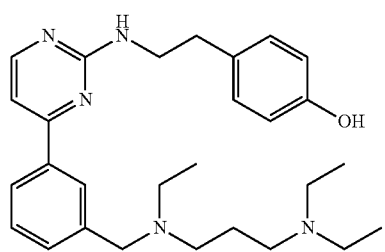
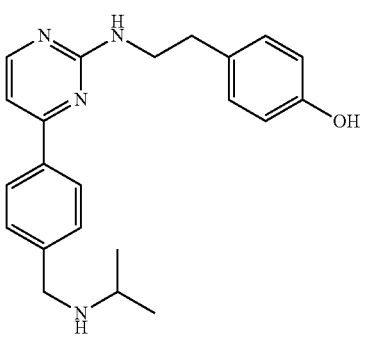
126
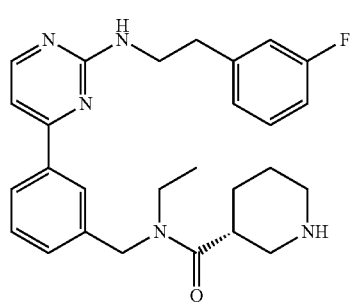
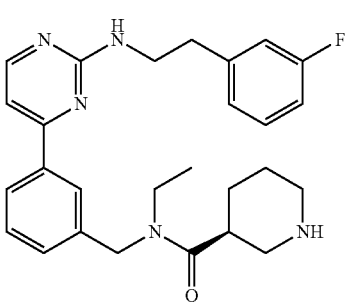
128

130 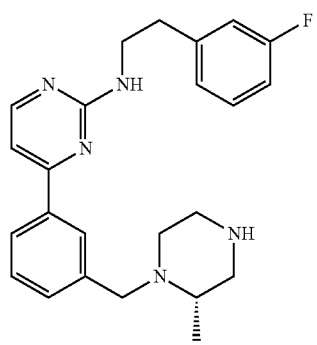
131 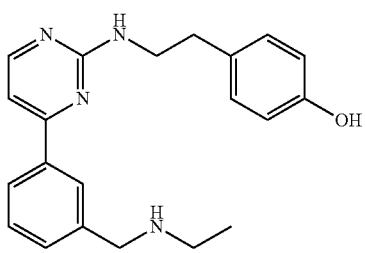
132 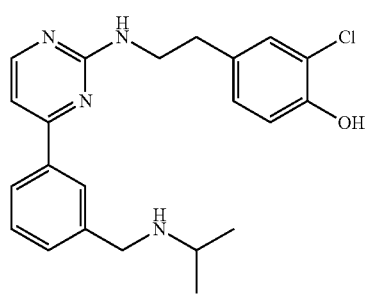
133 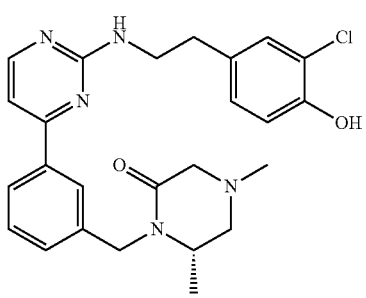
134 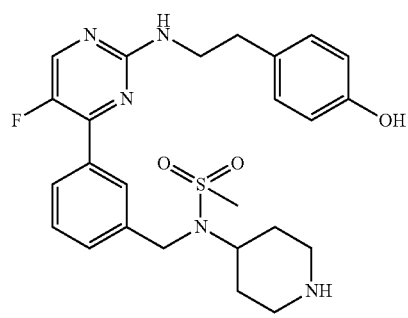
135 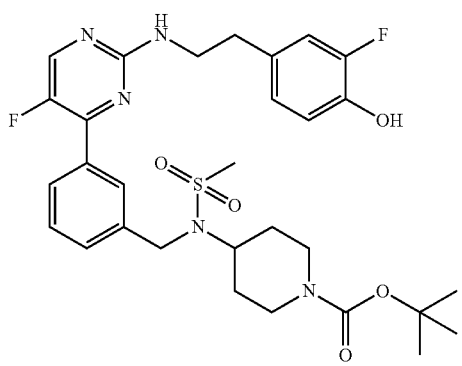
136 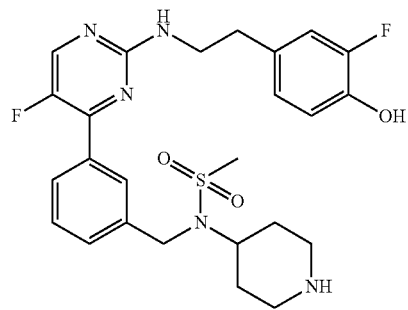
137 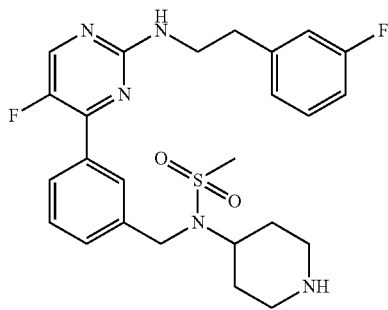
138 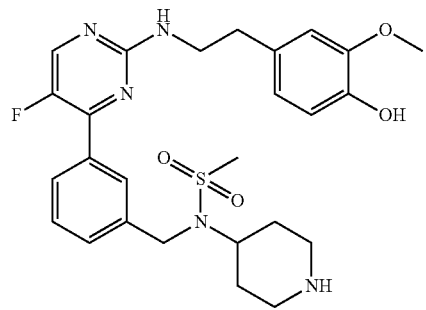
139 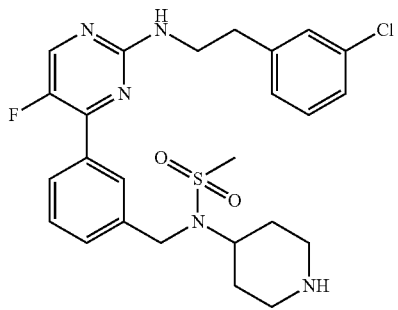

-continued
| 139 | 140 |
|---|---|
| 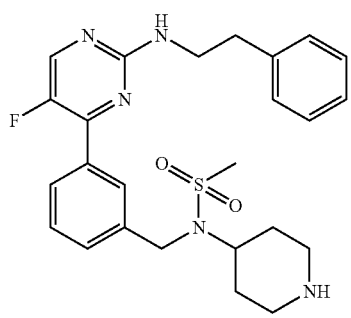 | 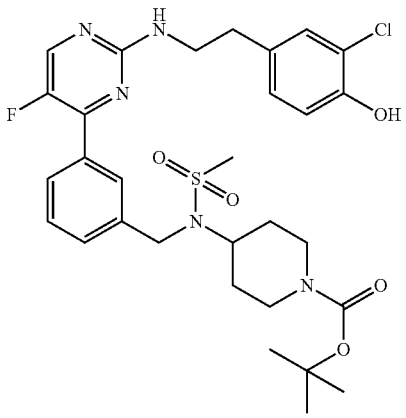 |
| 141 | 142 |
|---|---|
| 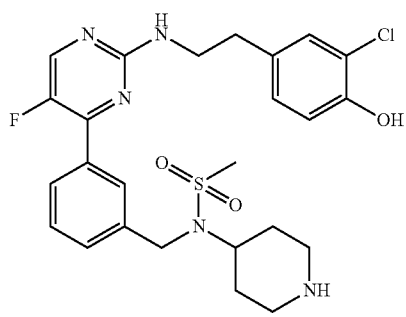 | 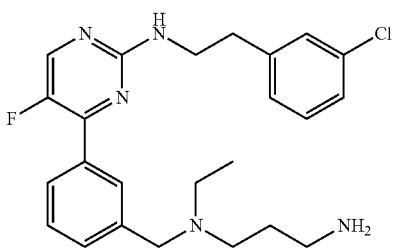 |
143
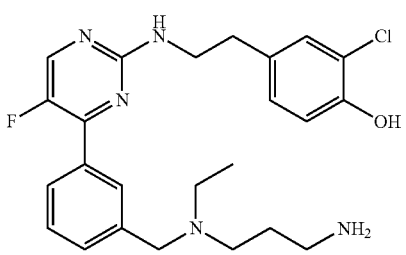
144
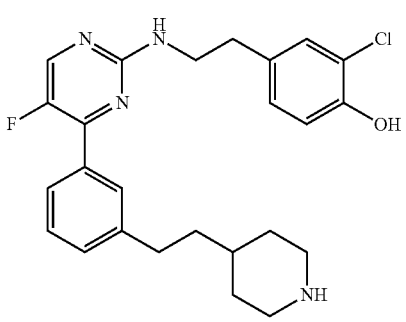

-continued
| 150 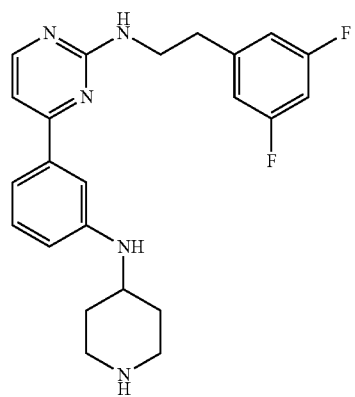 | 151 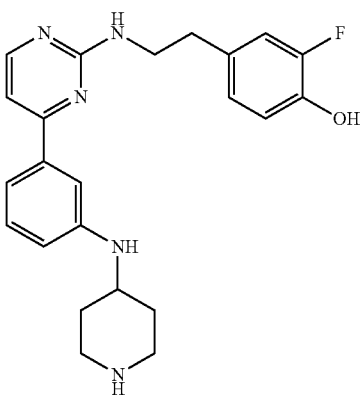 |
| 152 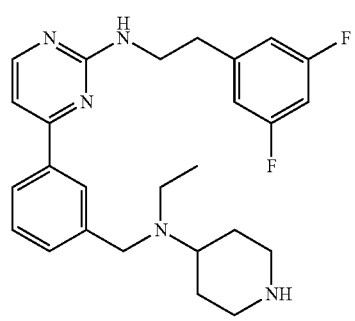 | 153 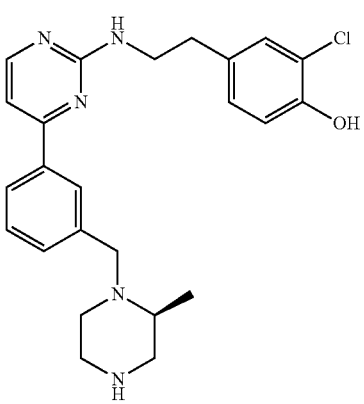 |
| 154 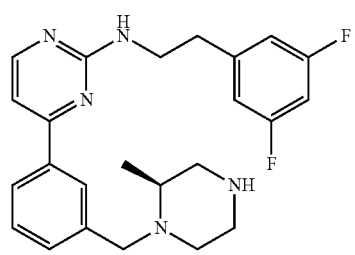 | 155 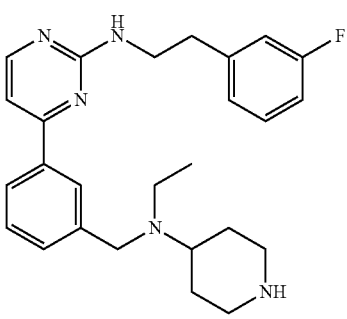 |
| 156 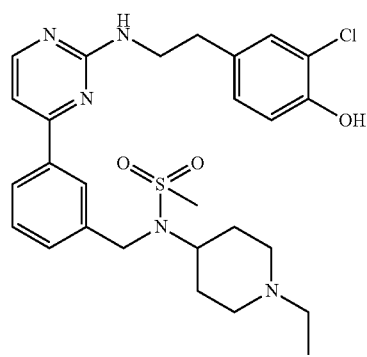 | 157 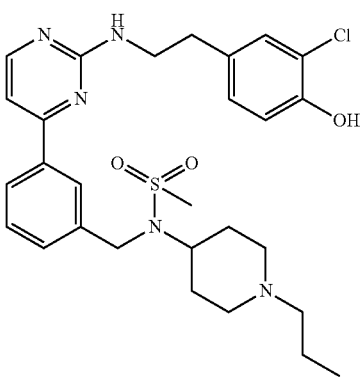 |

-continued
158 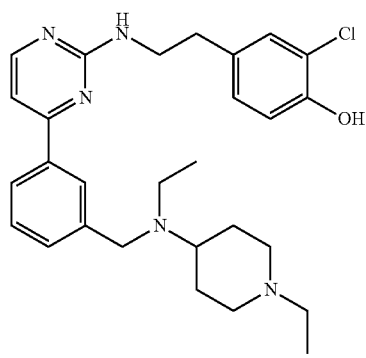
159 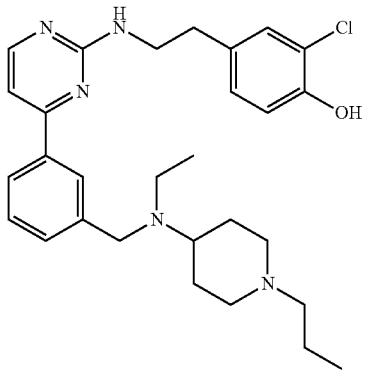
160 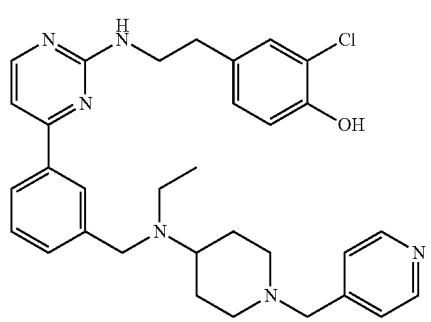
161 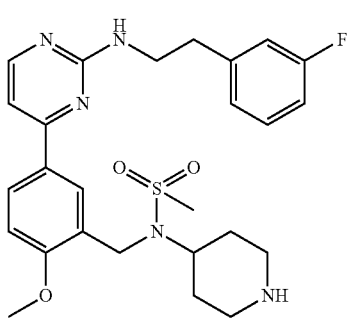
162 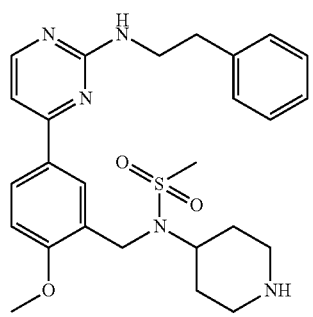
163 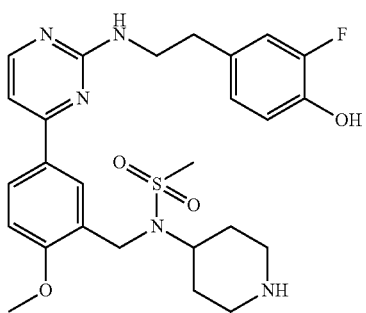
164 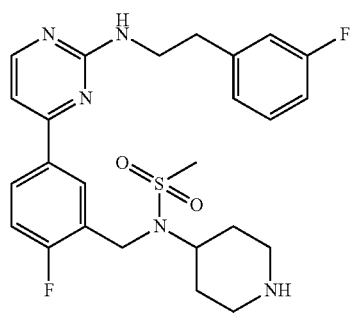
165 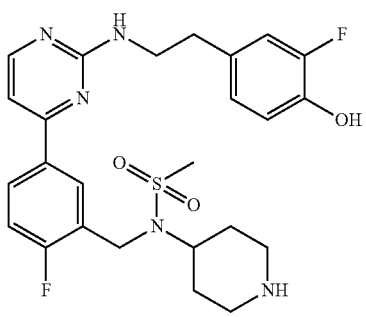

-continued
165 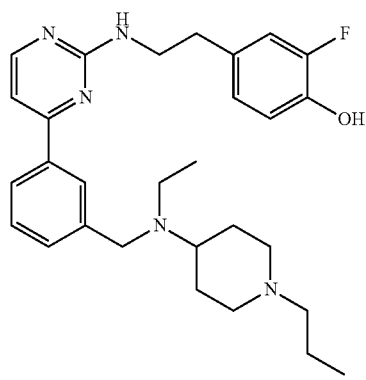 166 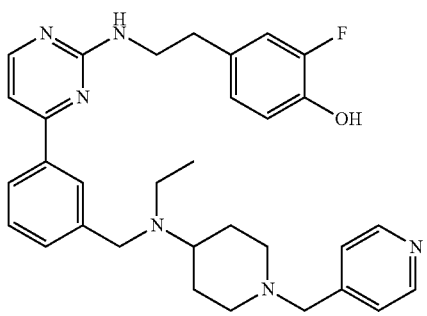
167
168 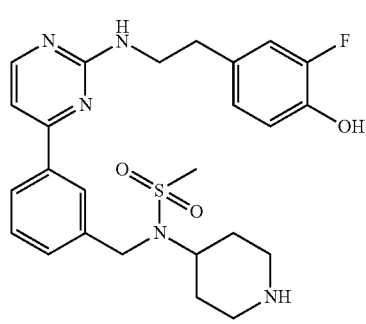 169 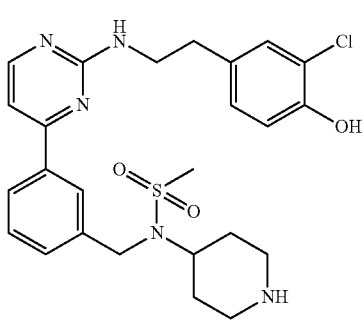
170 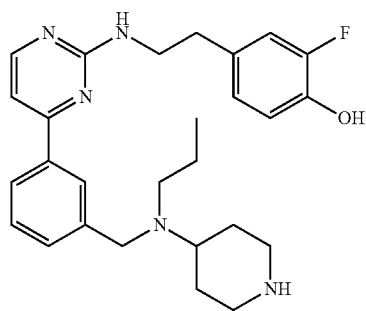 171 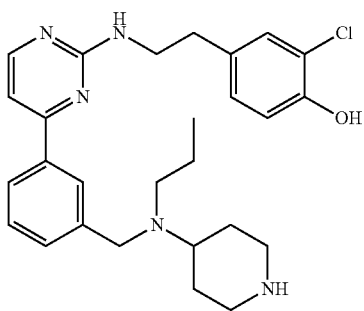
172 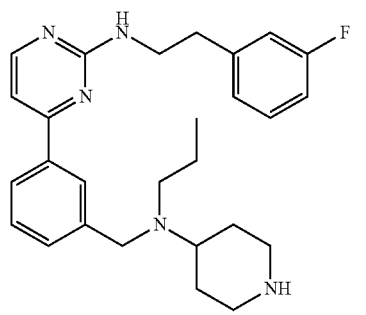 173 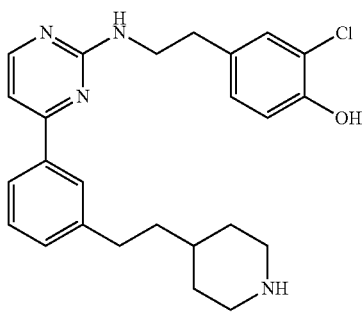
174 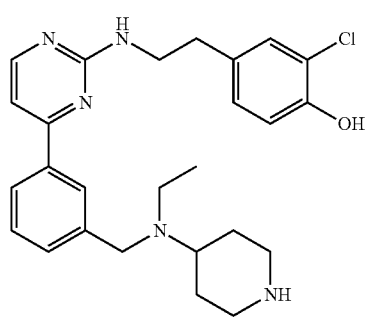 175 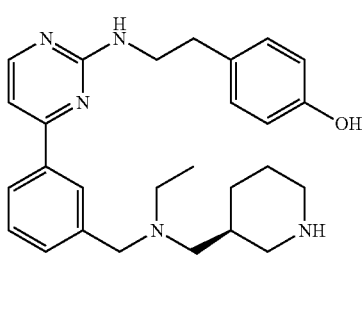

-continued
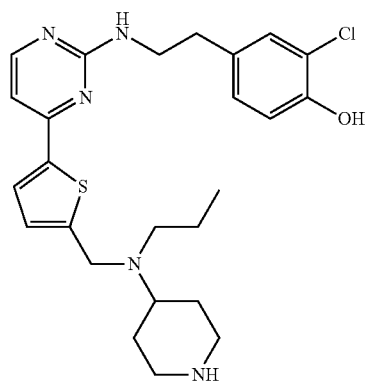
176
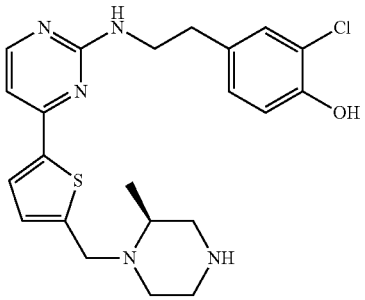
177
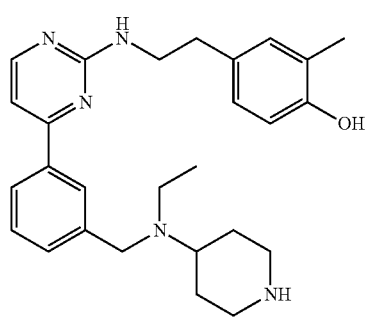
178
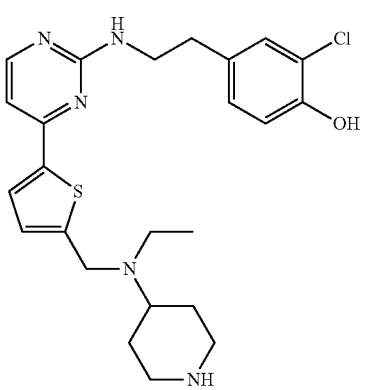
179
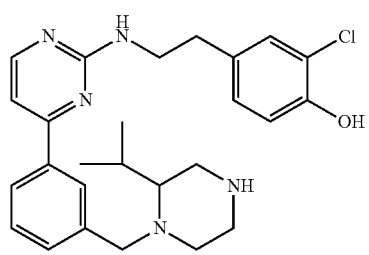
180
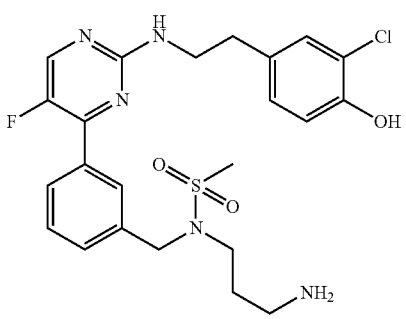
181
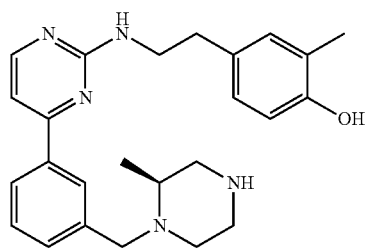
182
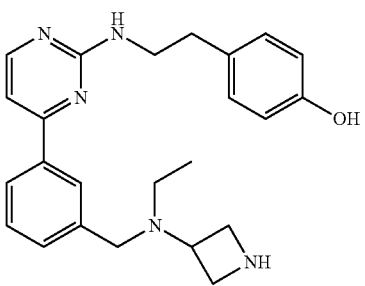
183

184 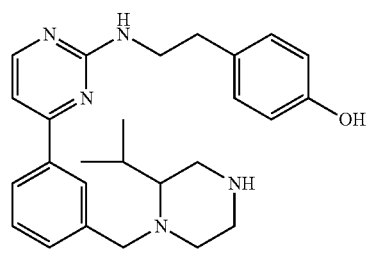
185 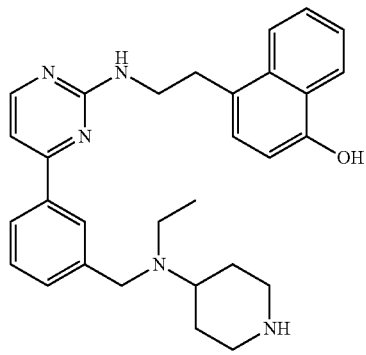
186 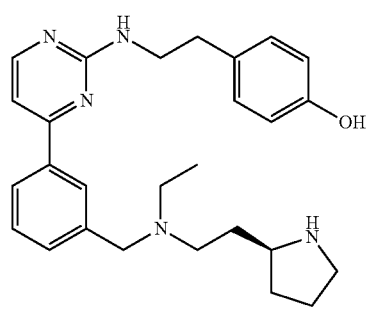
187 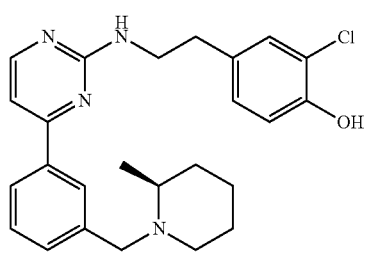
188 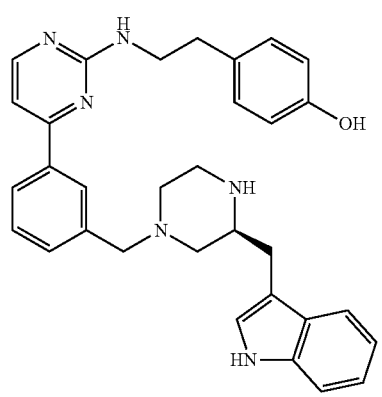
189 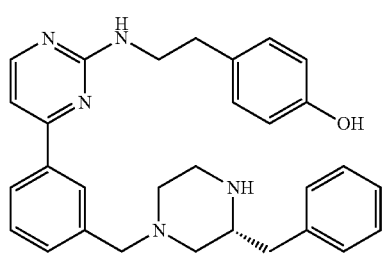
190 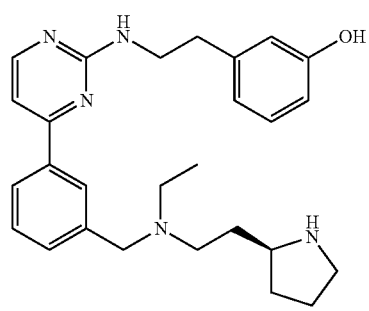
191 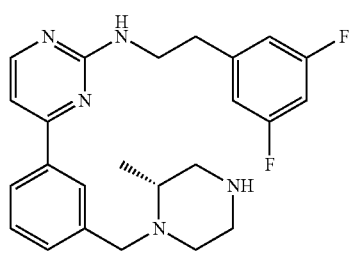
192 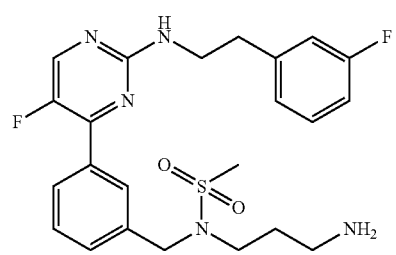
193 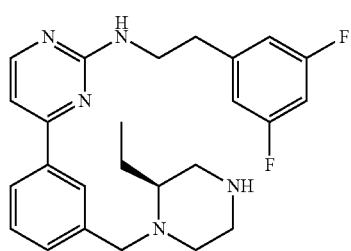

71
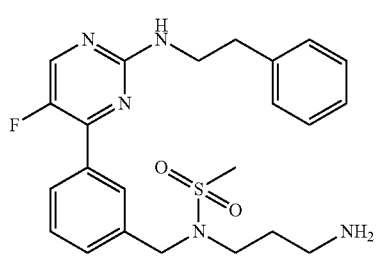
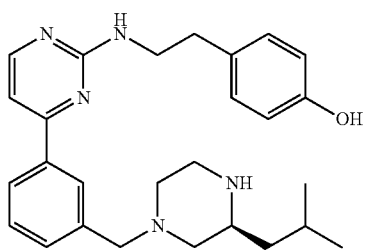
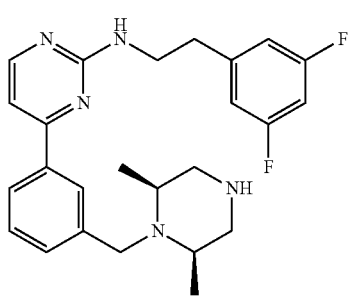
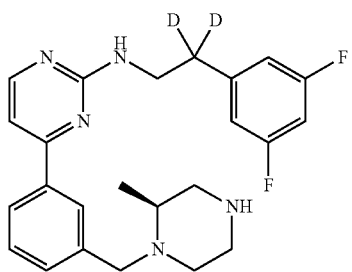
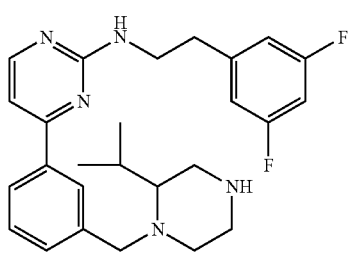
72
-continued
194
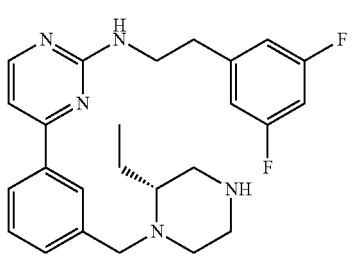
195
196
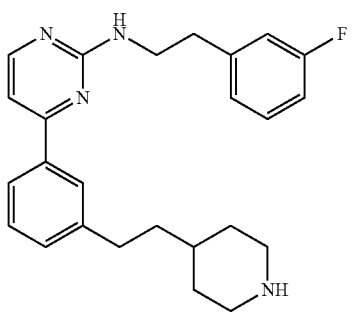
197
198
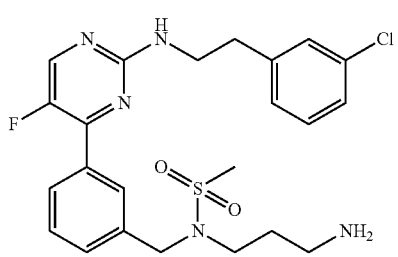
199
200
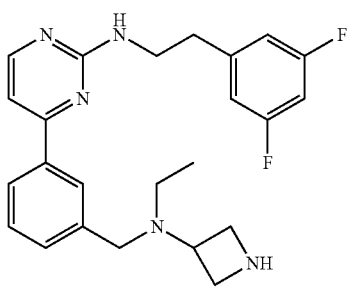
201
202
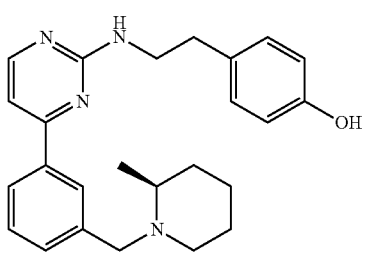
203

-continued
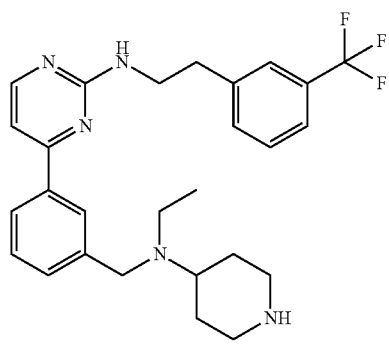
204
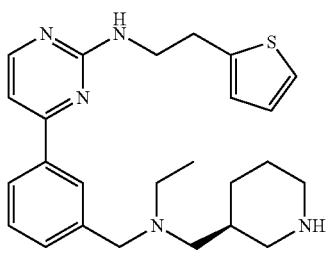
205
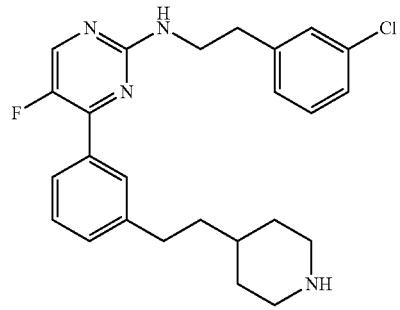
206
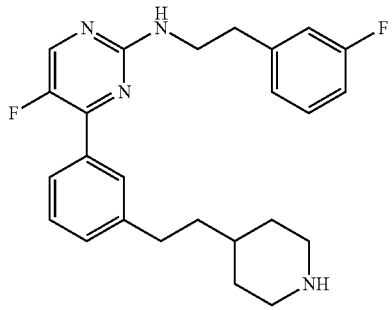
207
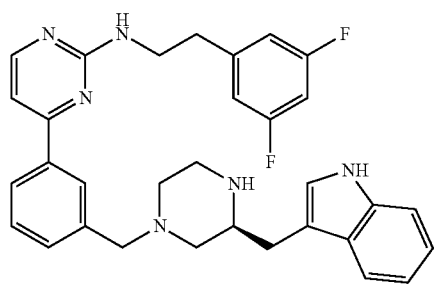
208
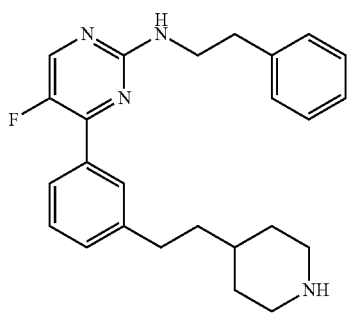
209
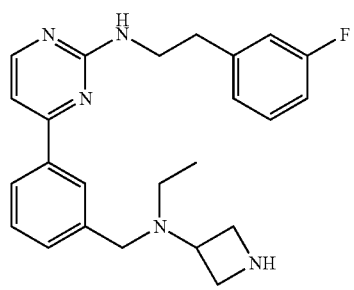
210
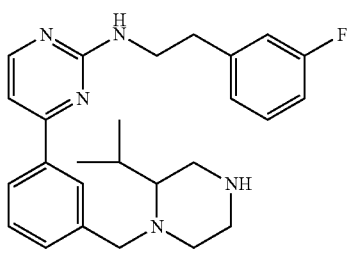
211
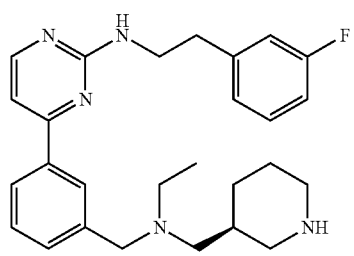
212
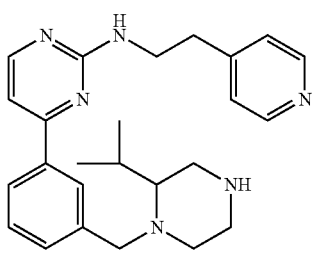
213

-continued
| | |
|---|---|
| 214 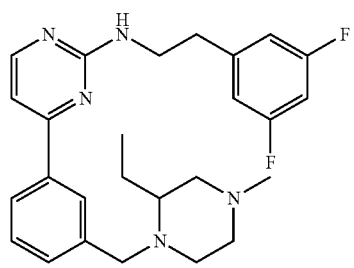 | 215 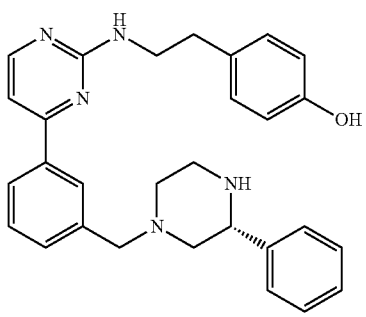 |
| 216 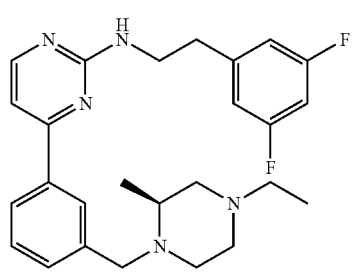 | 217 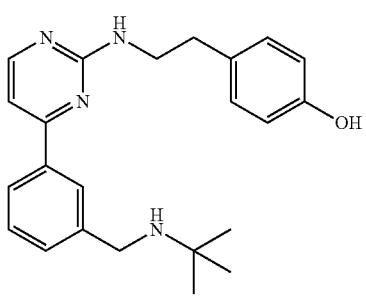 |
| 218 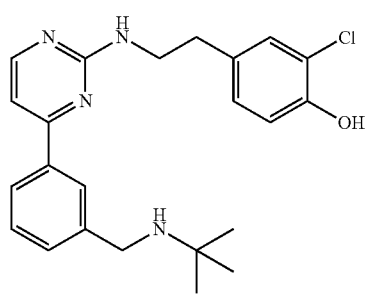 | 219 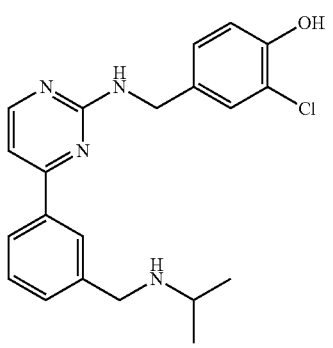 |
| 220 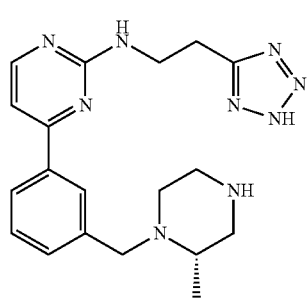 | 221 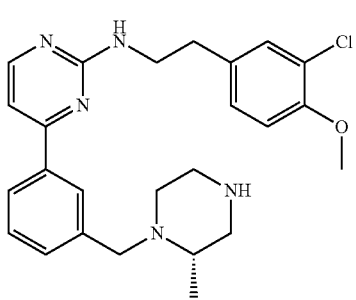 |
| 222 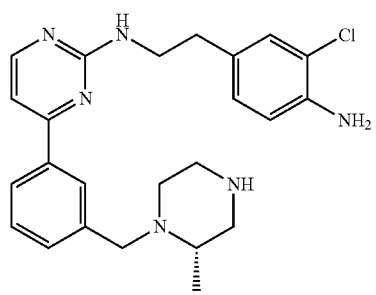 | 223 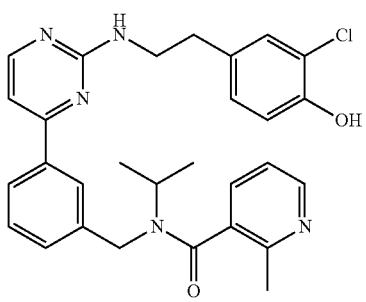 |

-continued
| | |
|---|---|
| 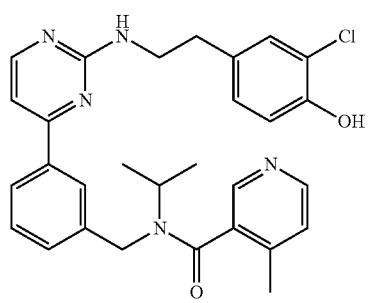 | 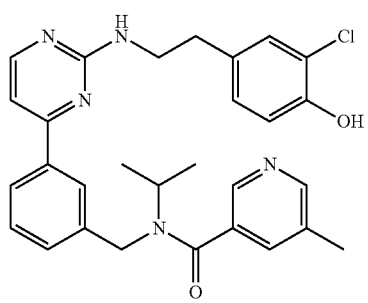 224 225 |
| 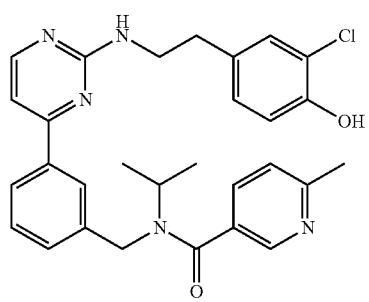 | 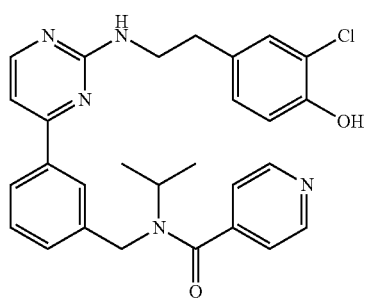 226 227 |
| 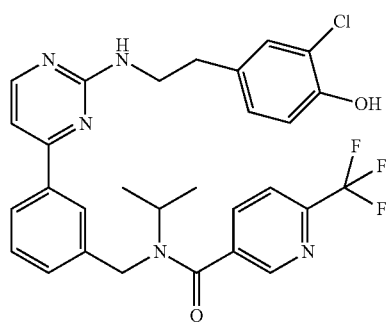 | 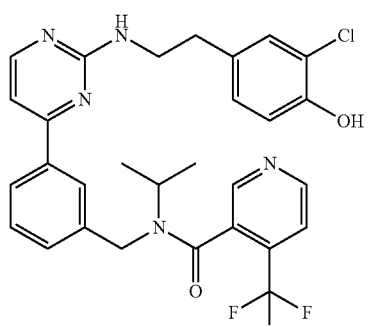 228 229 |
| 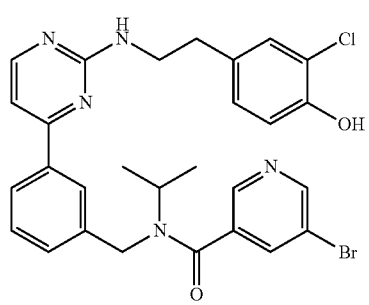 | 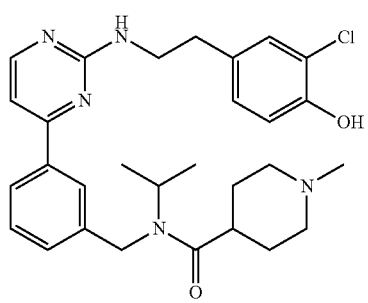 230 231 |
| 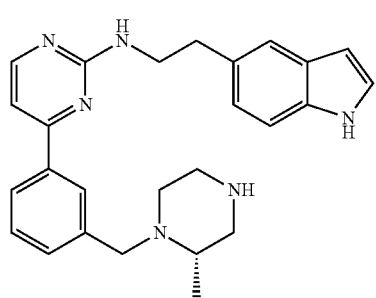 | 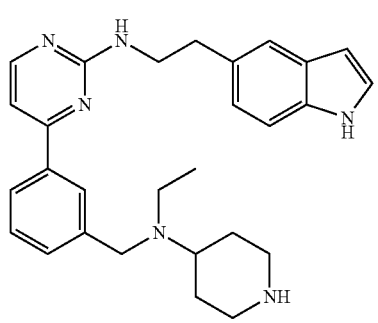 232 233 |

-continued
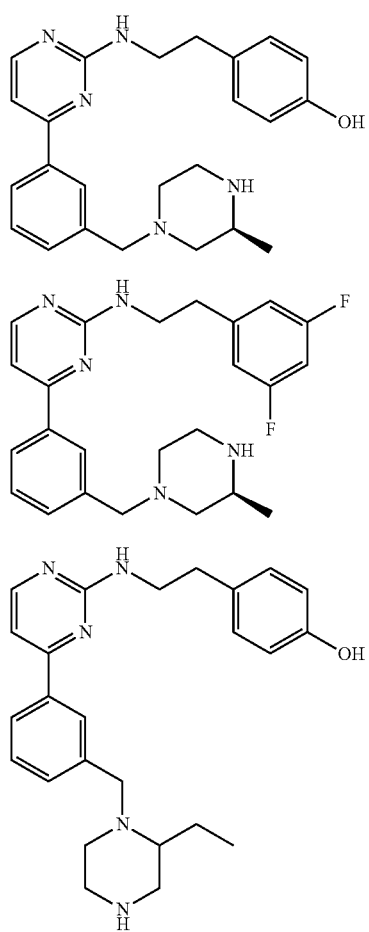
234
235
236
237
238
239
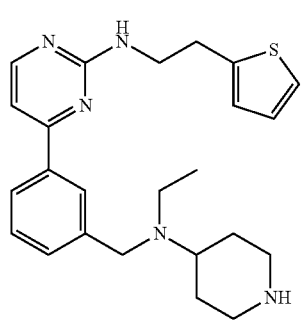
240
241
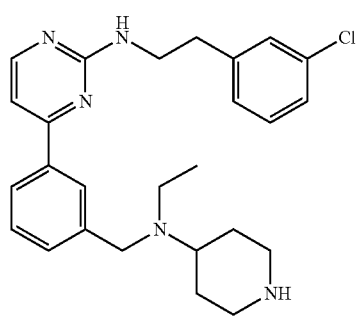
242
243

-continued
| | |
|---|---|
| 244 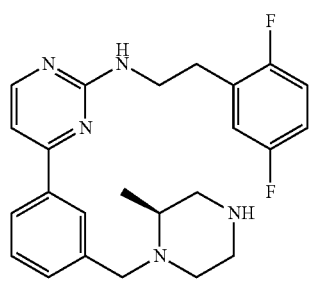 | 245 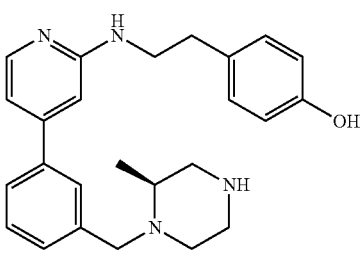 |
| 246 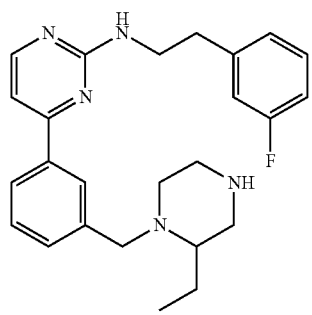 | 247 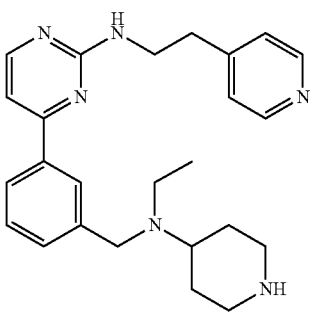 |
| 248 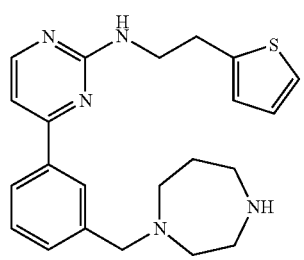 | 249 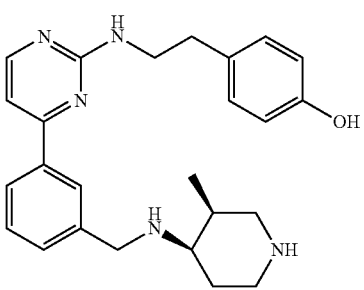 |
| 250 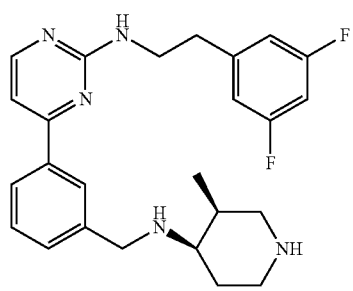 | 251 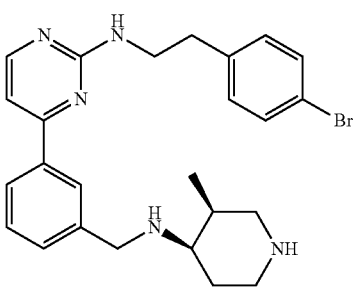 |
| 252 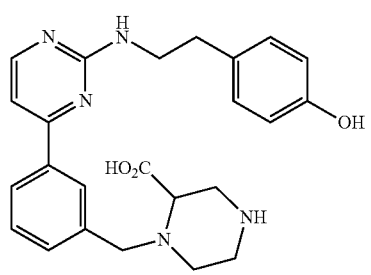 | 253 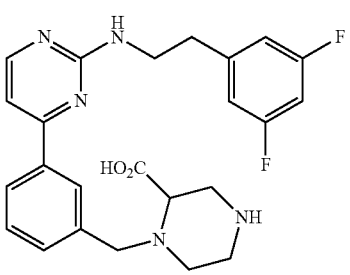 |

-continued
254 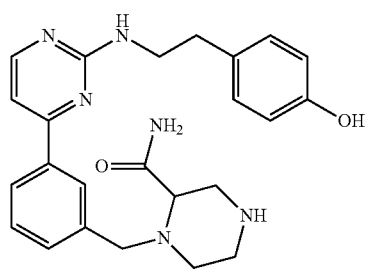
255 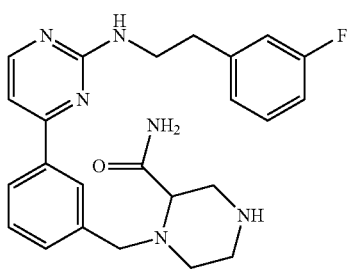
256 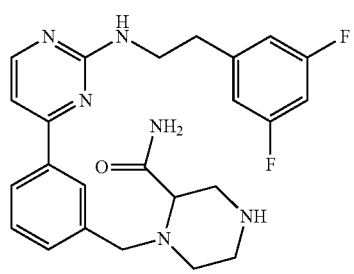
257 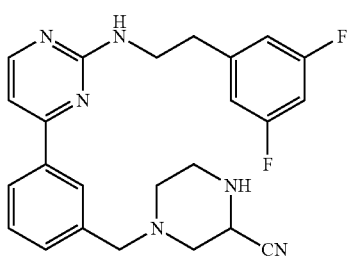
258 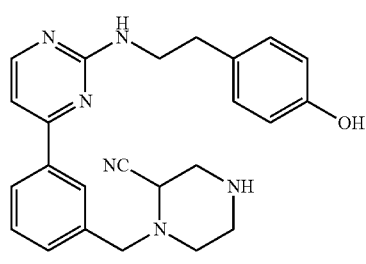
259 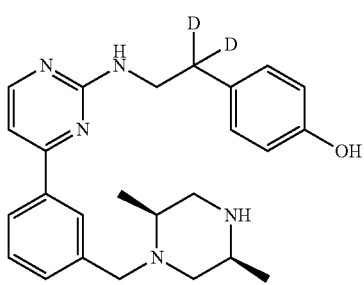
260 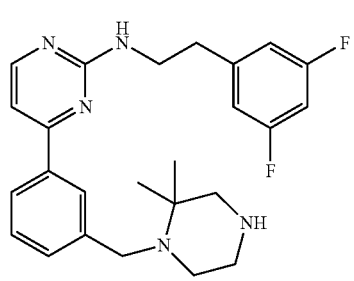
261 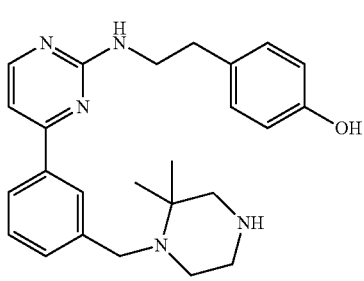
262 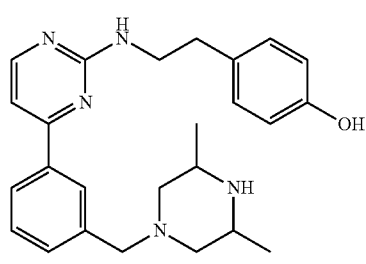
263 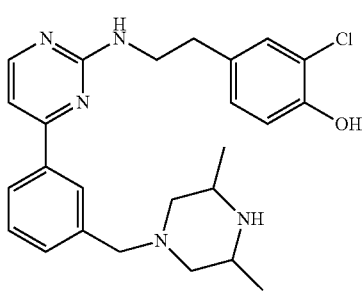

-continued
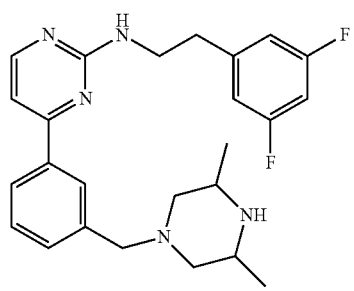
264
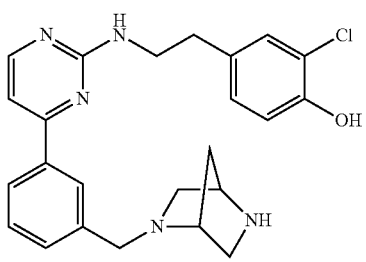
265
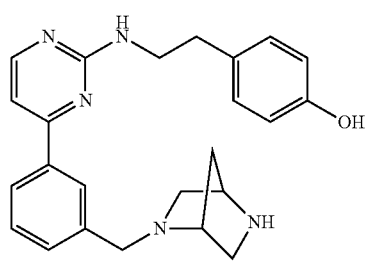
266
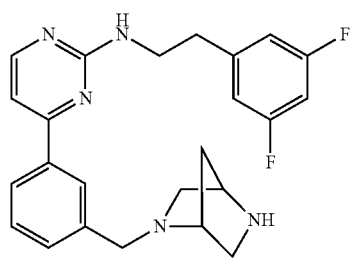
267
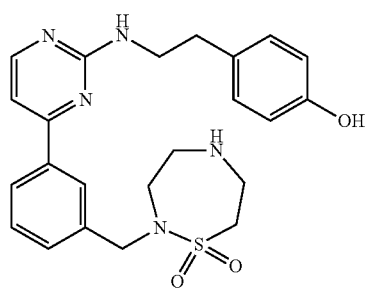
268
269
270
271
272
273
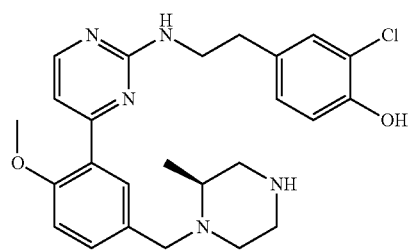
274
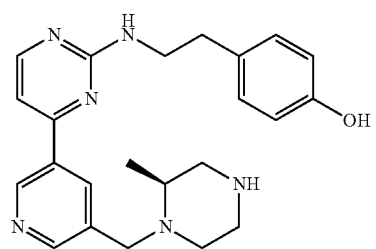
275

-continued
| | |
|---|---|
| 277 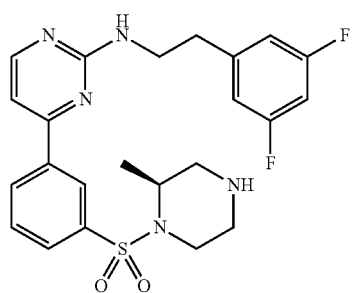 | 278 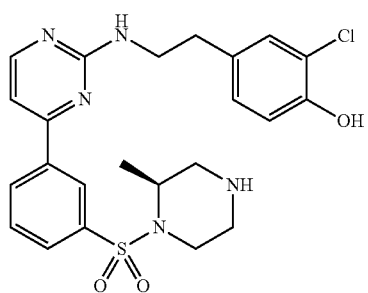 |
| 279 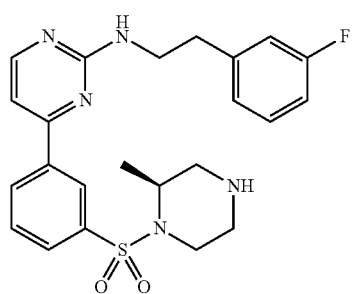 | 280 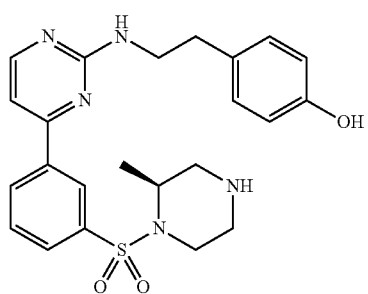 |
| 281 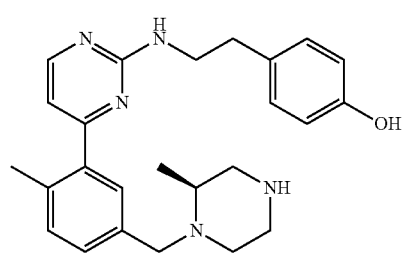 | 282 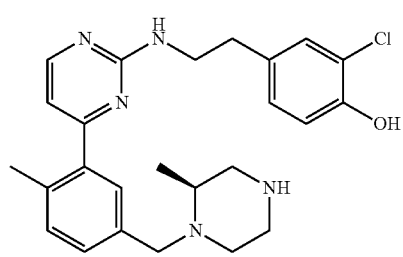 |
| 283 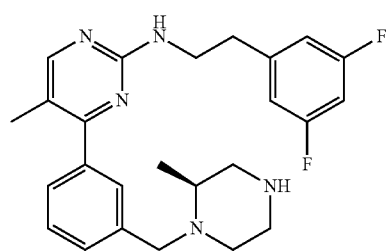 | 284 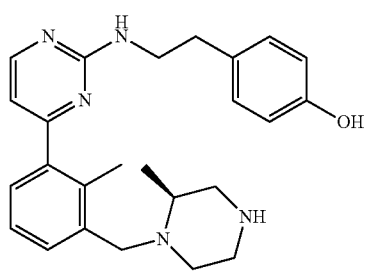 |
| 285 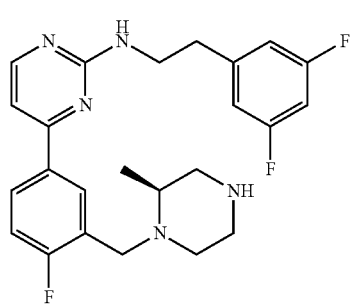 | 286 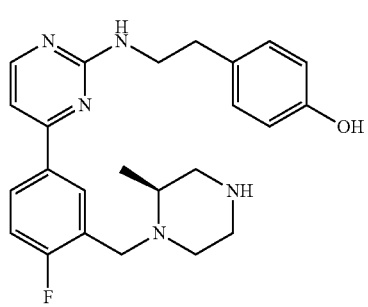 |

-continued
287 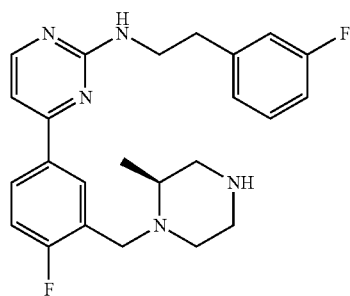
288 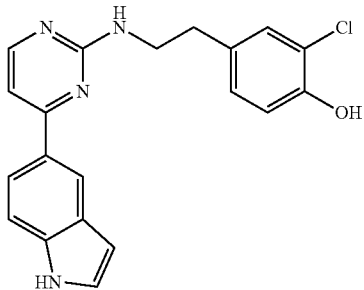
289 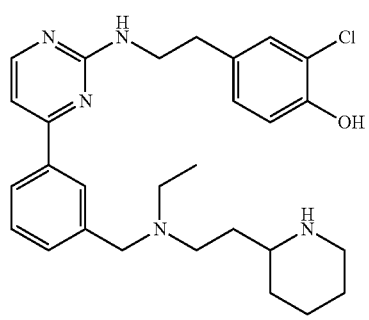
290 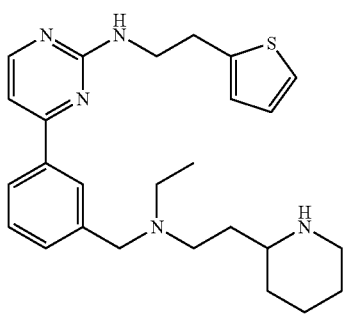
291 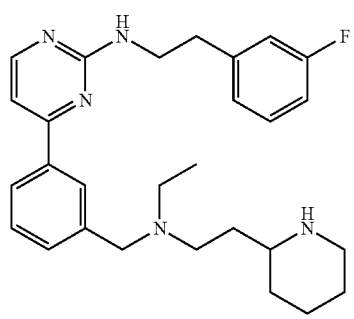
292 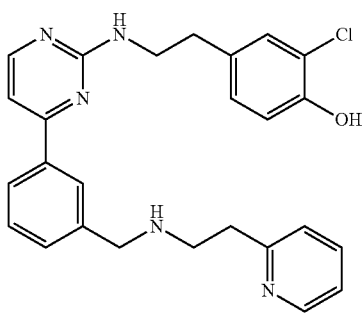
293 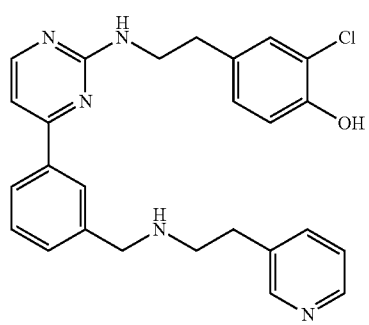
294 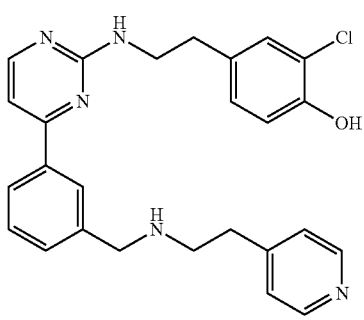
295 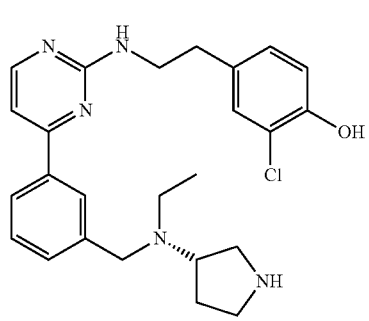
296 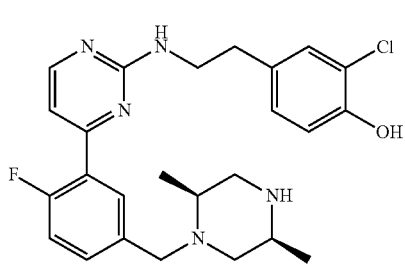

-continued
297 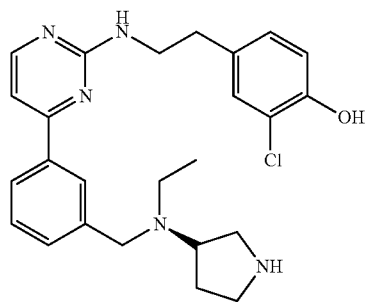
298 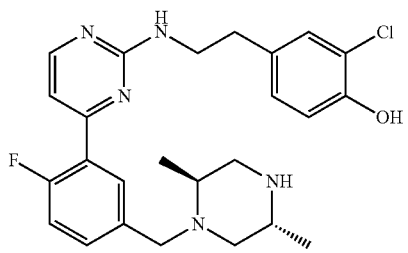
299 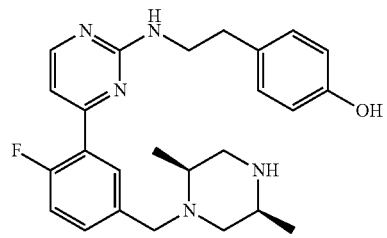
300 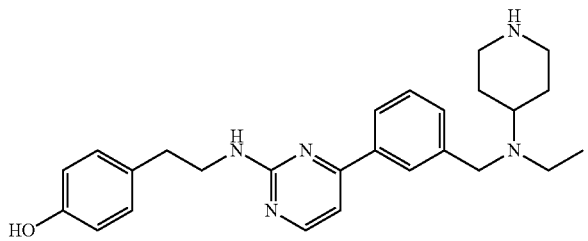
301 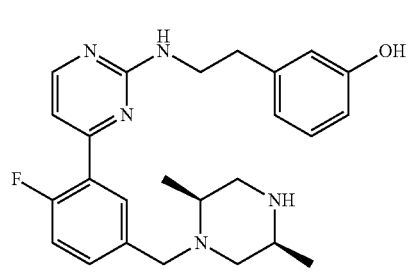
302 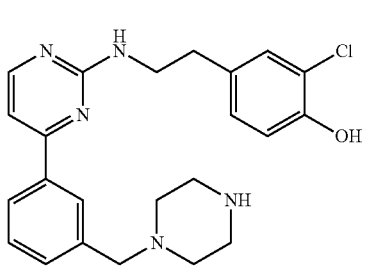
303 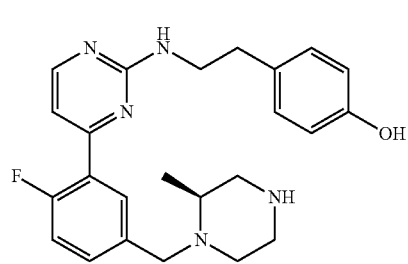
304 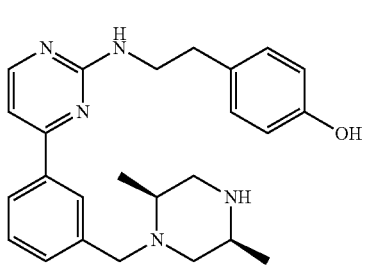
305 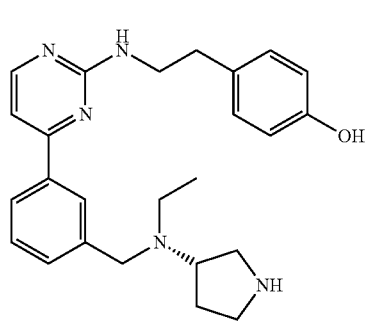
306 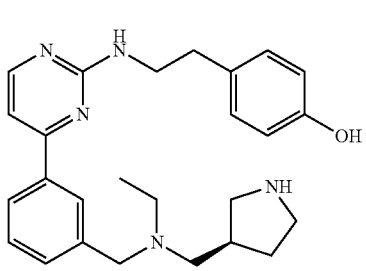

307
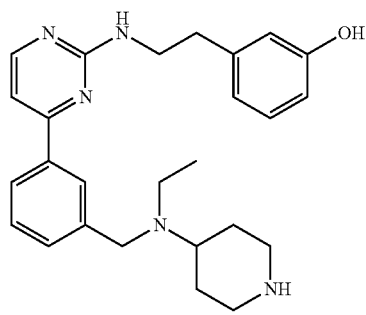
308
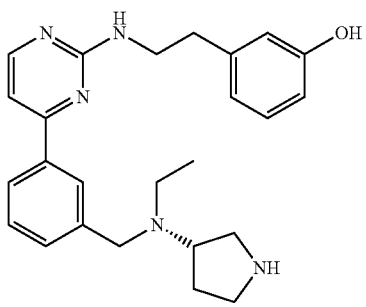
309
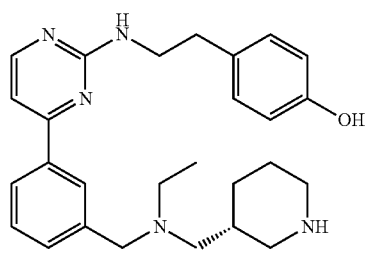
310
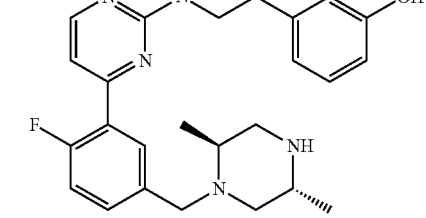
311
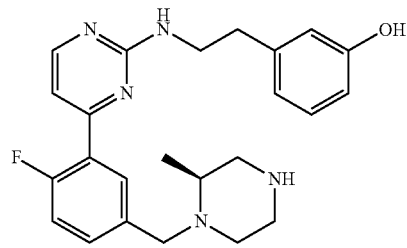
312
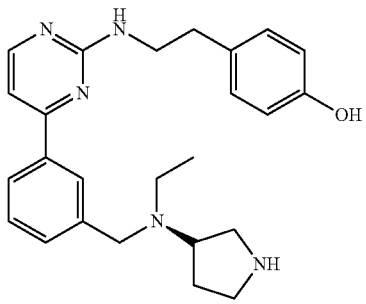
313
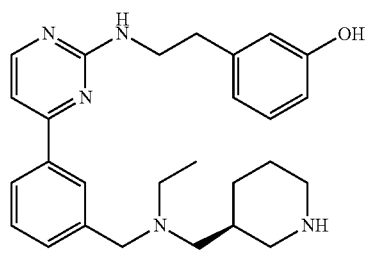
314
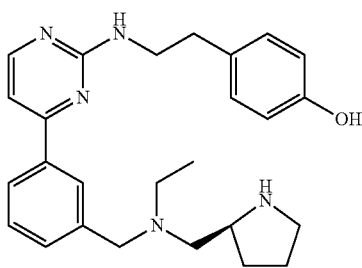
315
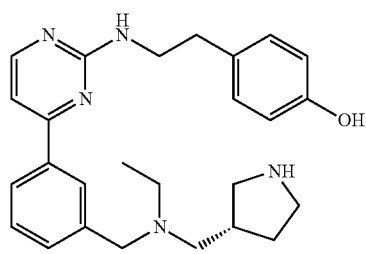
316
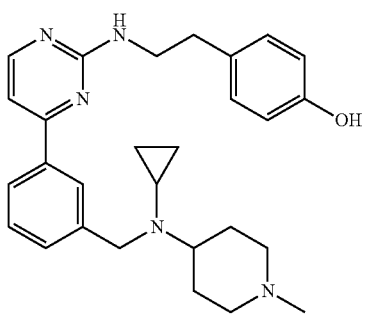

-continued
317 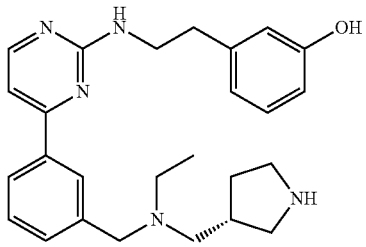
318
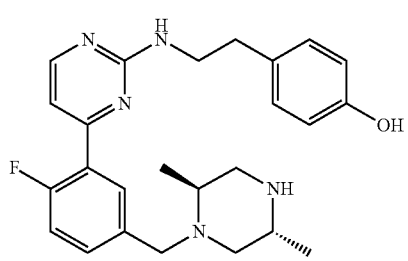
319 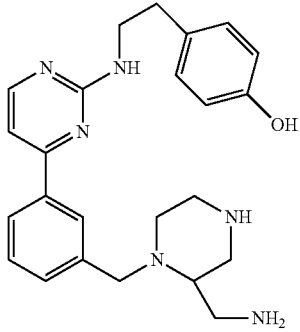
320
321 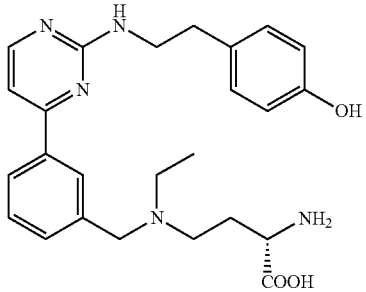
322
323 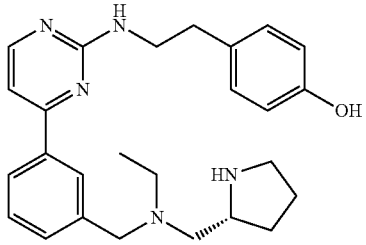
324
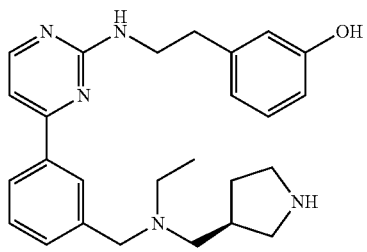
325 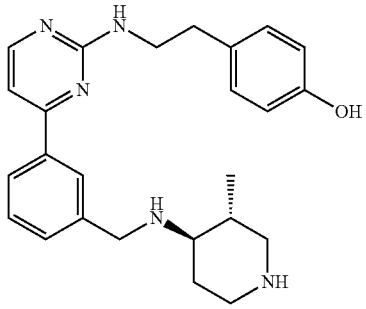
326
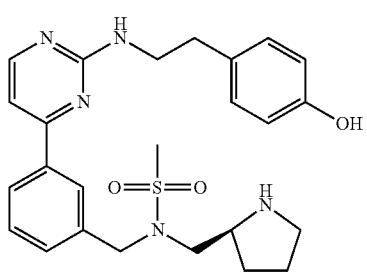

-continued
| | |
|---|---|
| 327 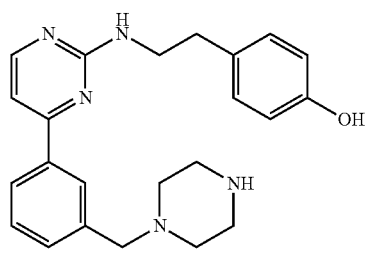 | 328 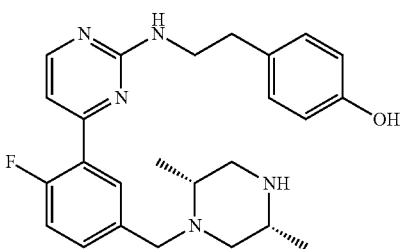 |
| 329 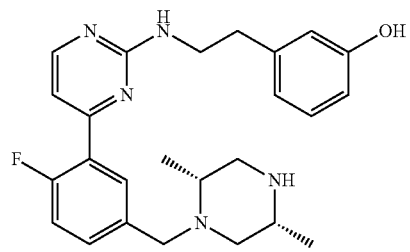 | 330 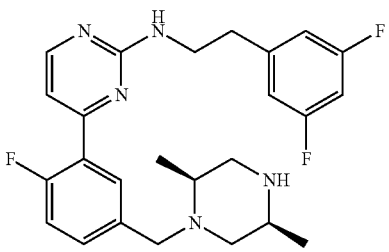 |
| 331 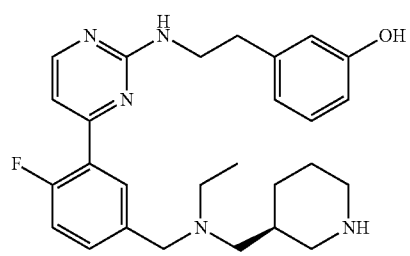 | 332 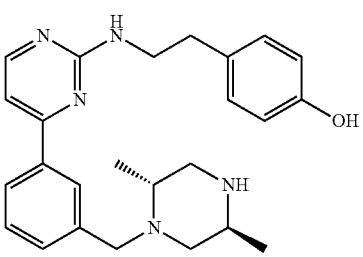 |
| 333 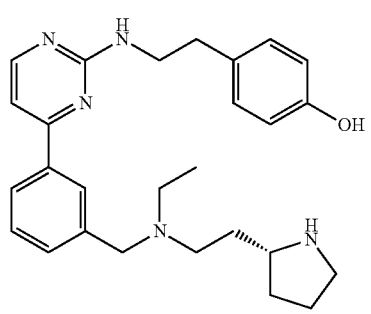 | 334 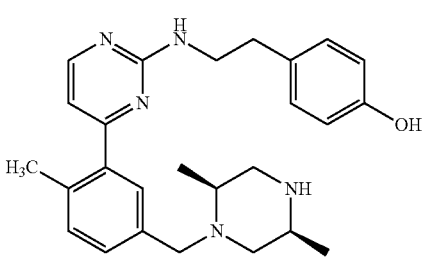 |
| 335 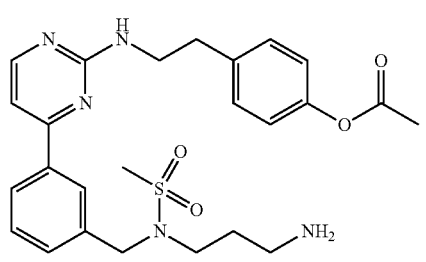 | 336 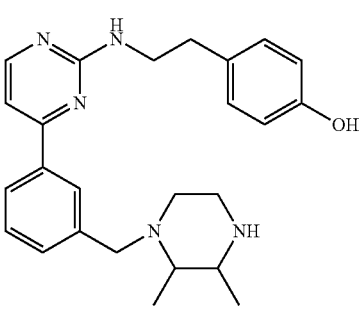 |

337 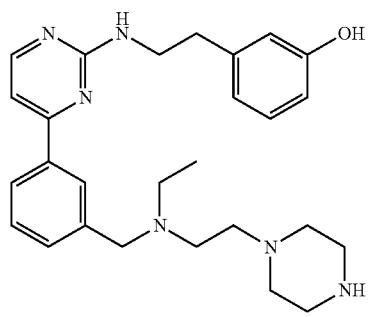
338 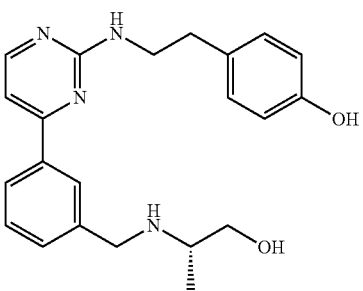
339 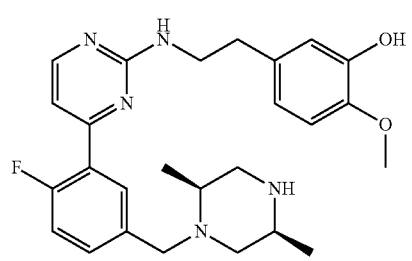
340 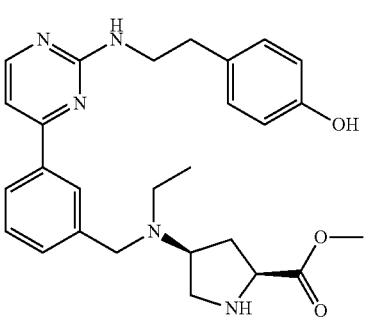
341 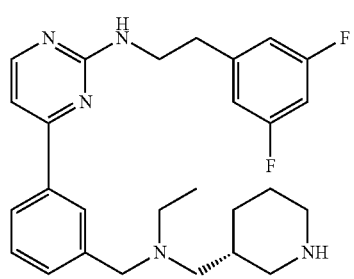
342 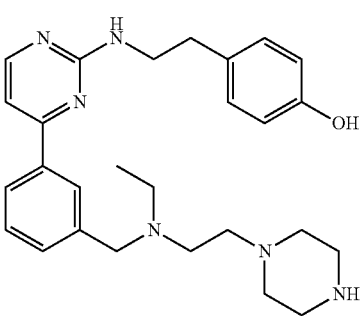
343 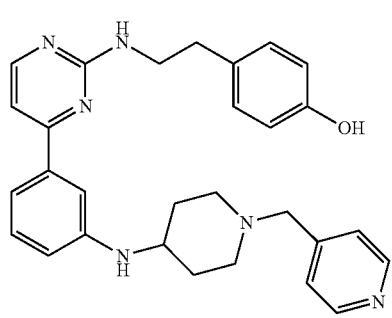
344 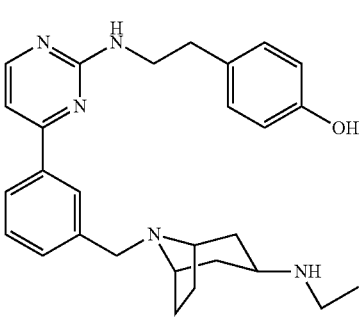
345 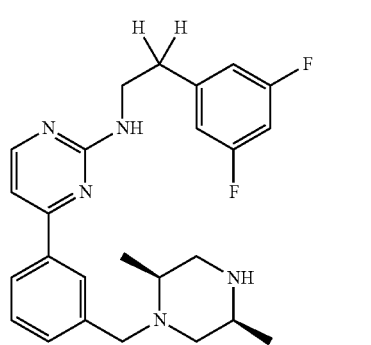
346 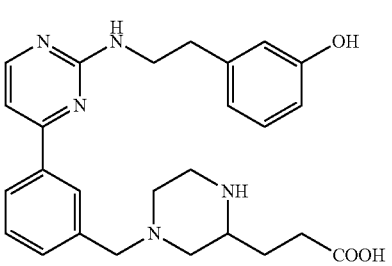

101
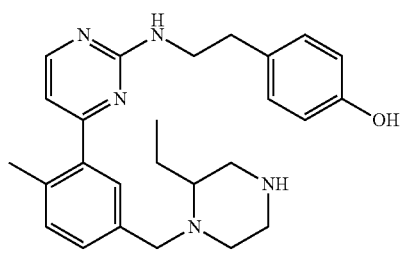
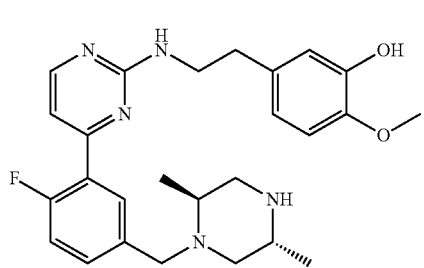
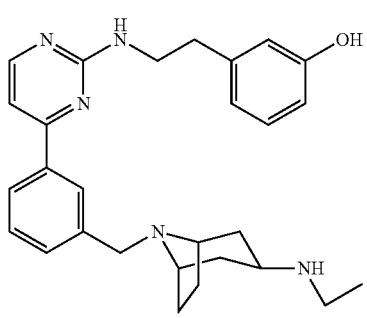
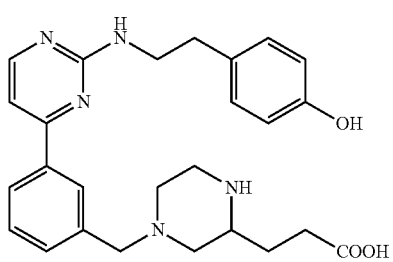
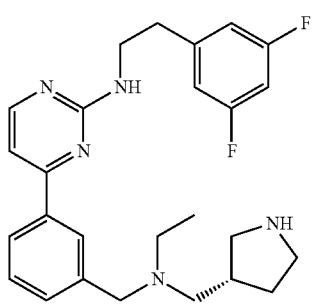
102
-continued
347
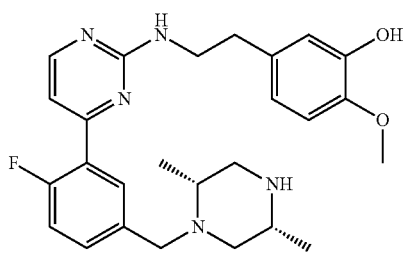
349
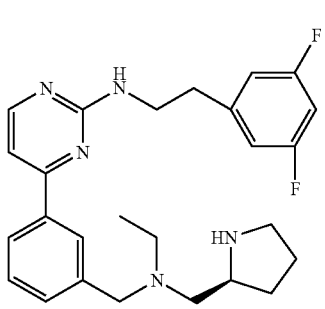
351
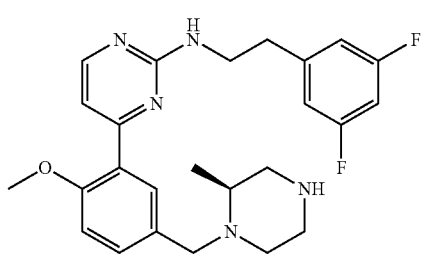
353
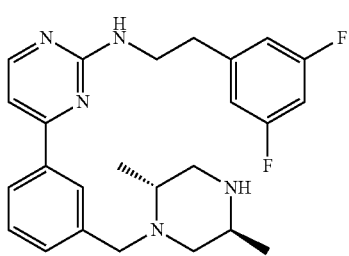
355
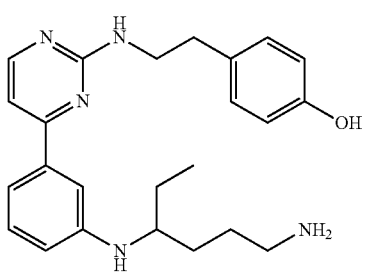
348
350
352
354
356

357
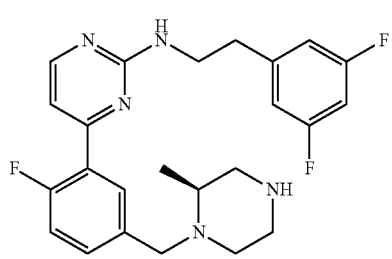
358
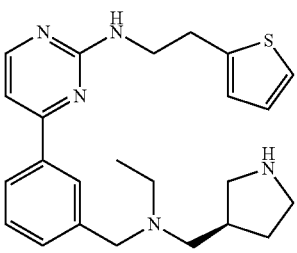
359
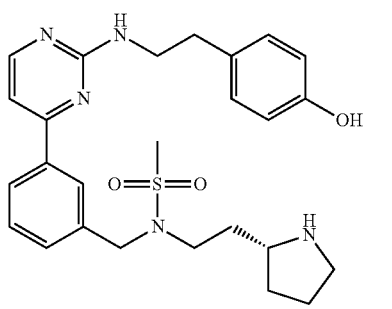
360
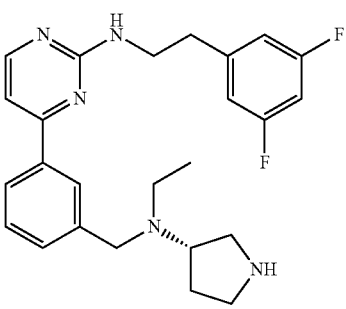
361
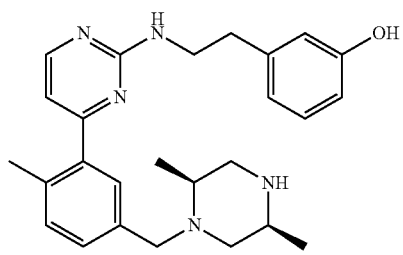
362
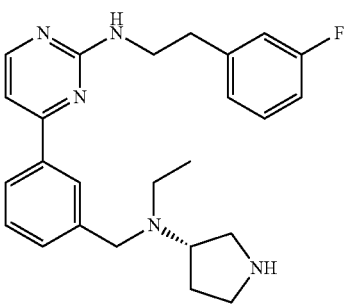
363
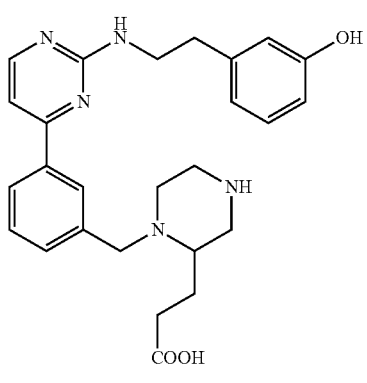
364
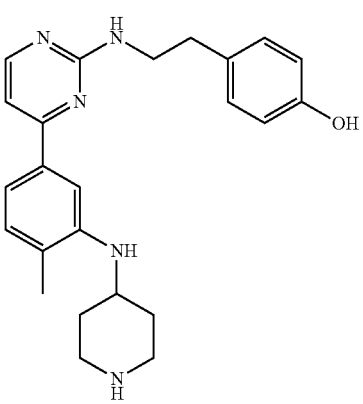
365
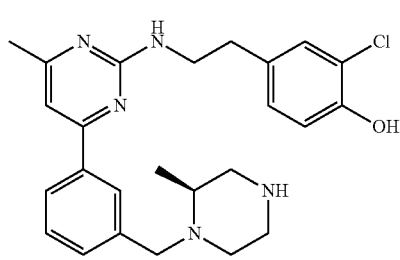
366
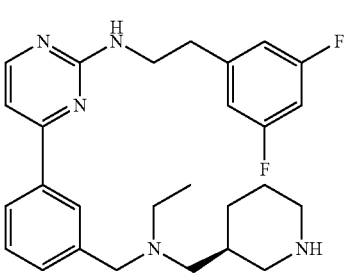

105
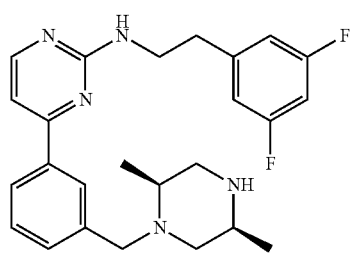
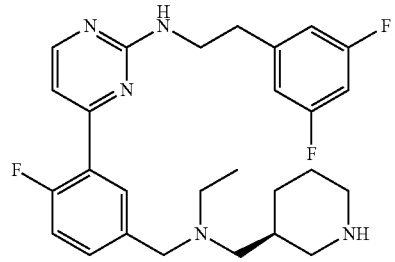
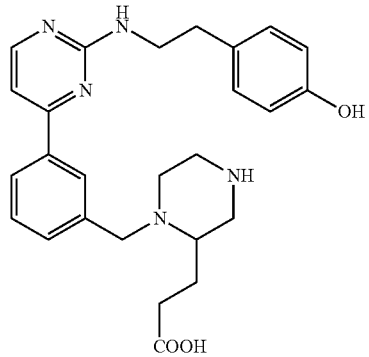
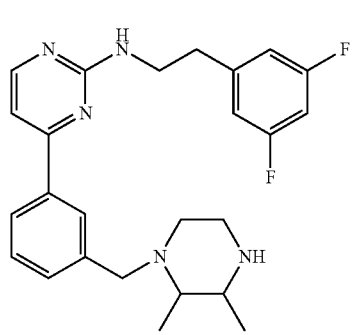
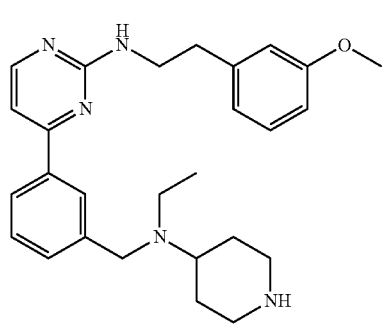
106
-continued
367
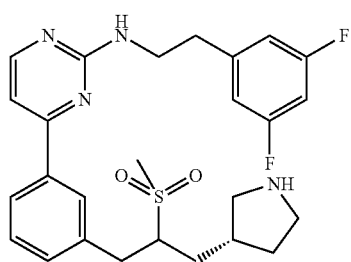
369
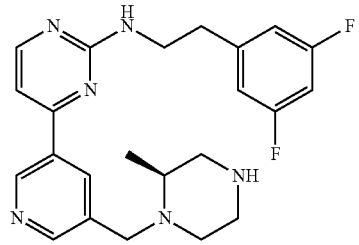
371
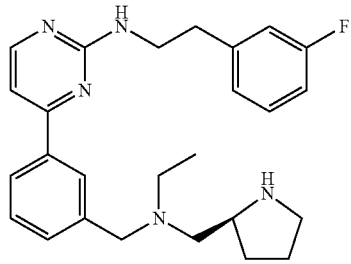
373
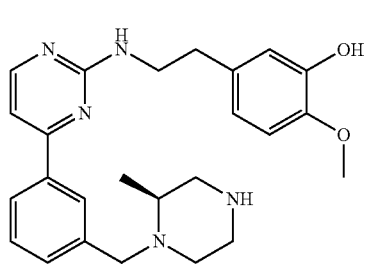
375
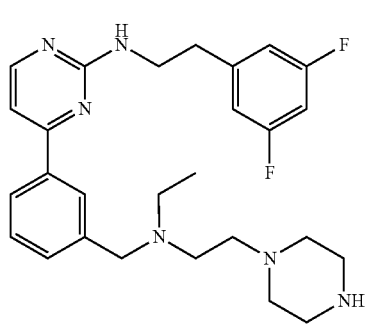
368
370
372
374
376

| 377 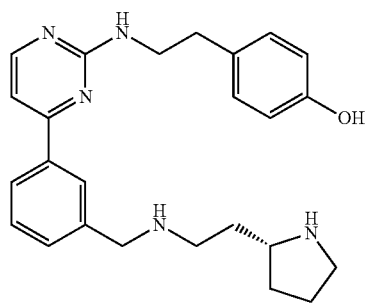 | 378 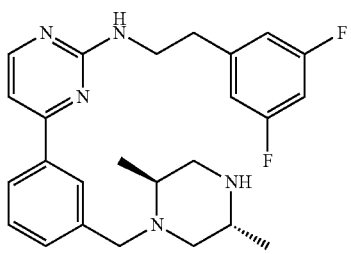 |
| --- | --- |
| 379 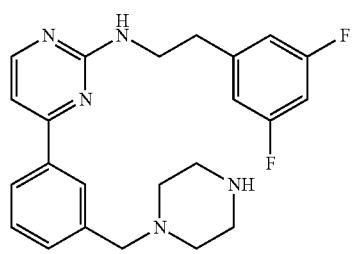 | 380 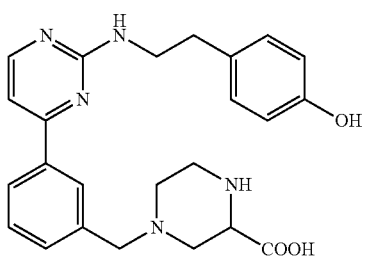 |
| 381 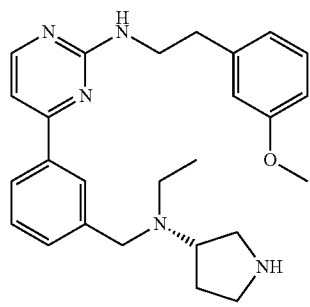 | 382 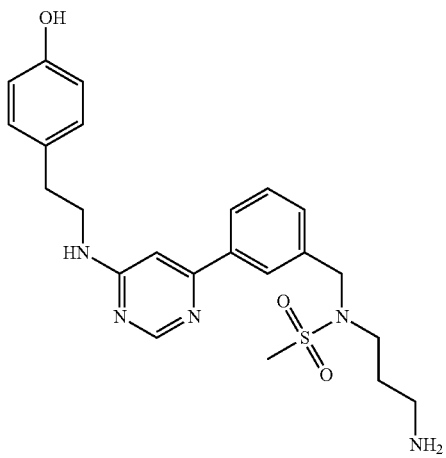 |
| 383 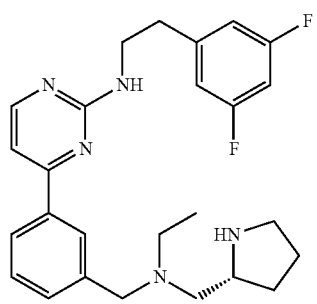 | 384 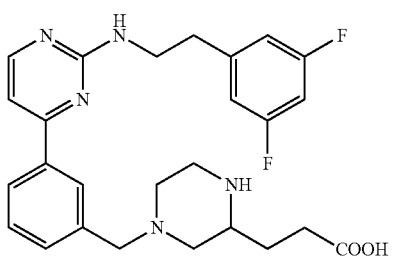 |

-continued
| | |
|---|---|
| 385 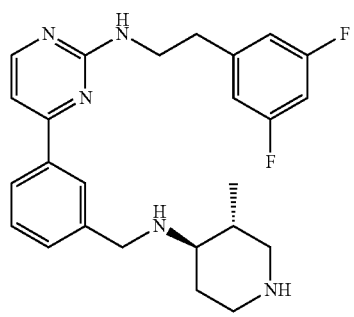 | 386 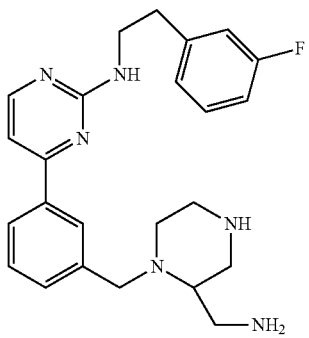 |
| 387 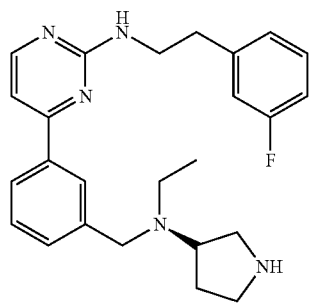 | 388 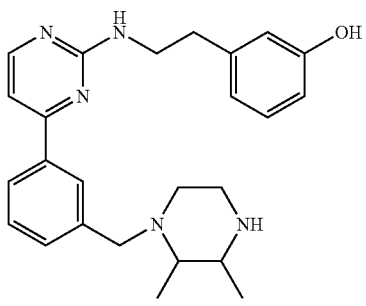 |
| 389 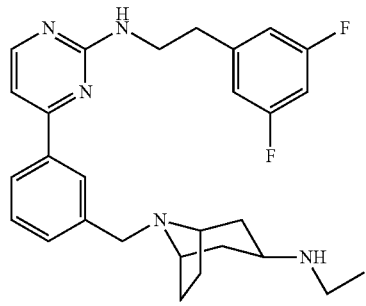 | 390 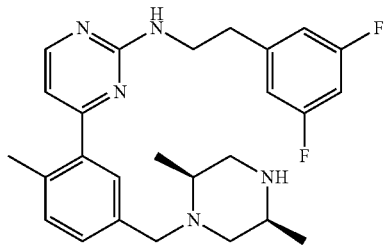 |
| 391 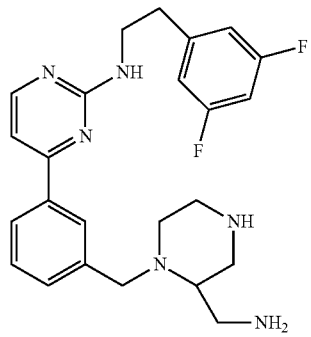 | 392 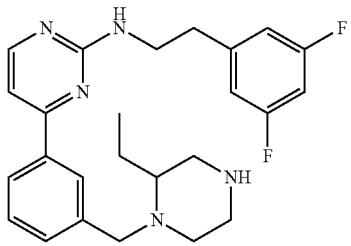 |
| 393 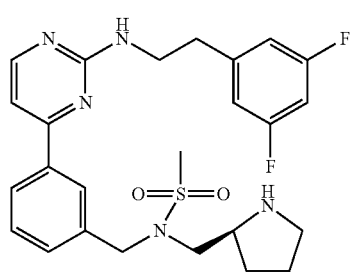 | 394 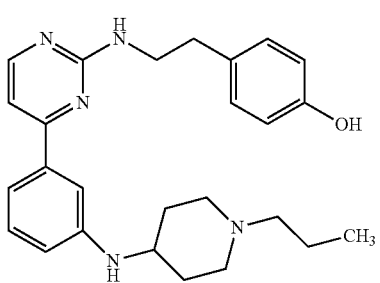 |

-continued
| 111 | 112 |
|---|---|
| 395 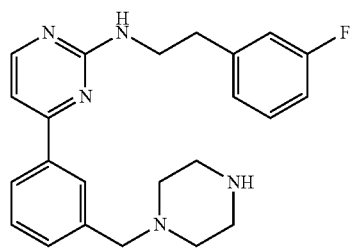 | 396 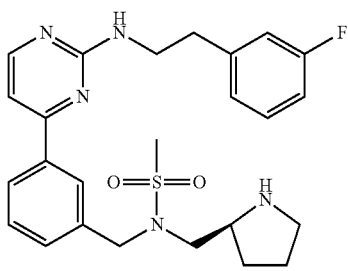 |
| 397 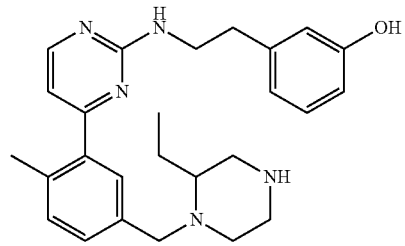 | 398 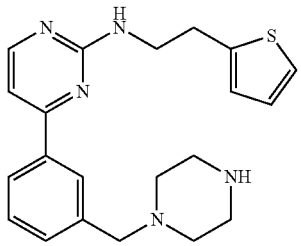 |
| 399 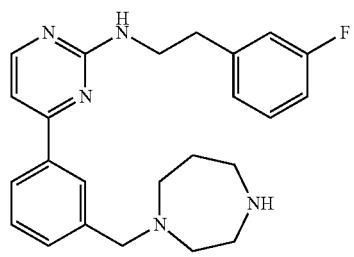 | 400 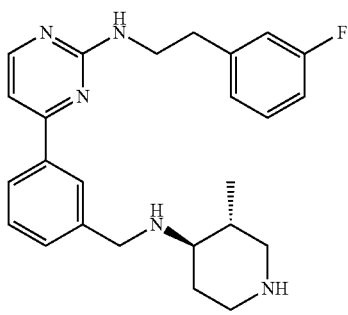 |
| 401 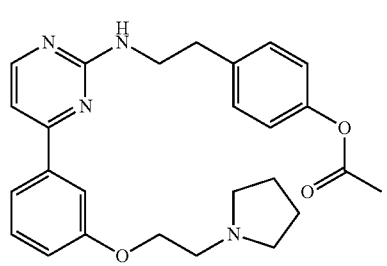 | 402 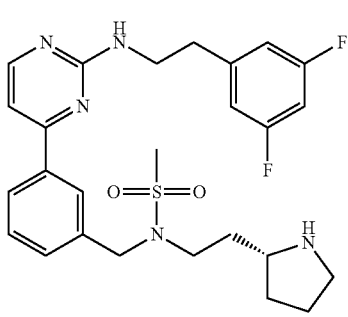 |
| 403 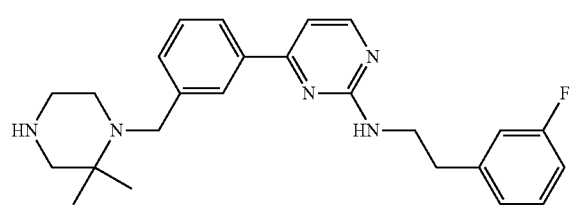 | 404 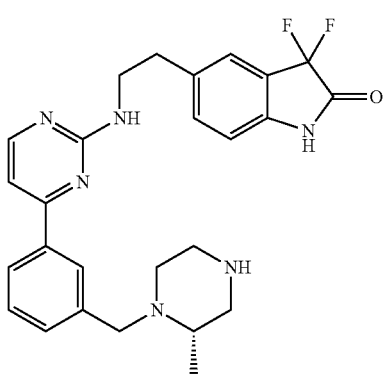 |

-continued
405 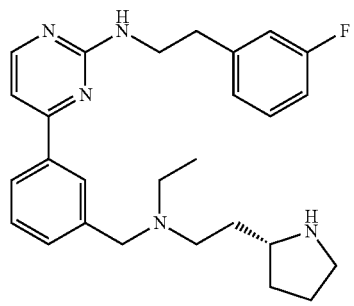
406 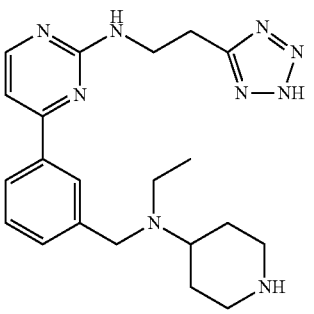
407 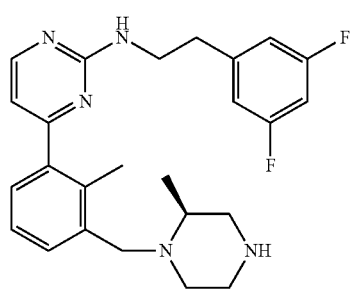
408 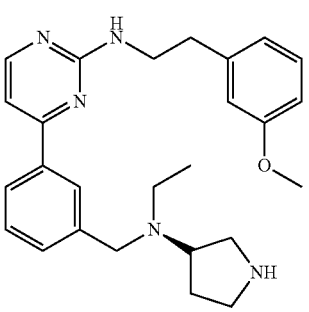
409 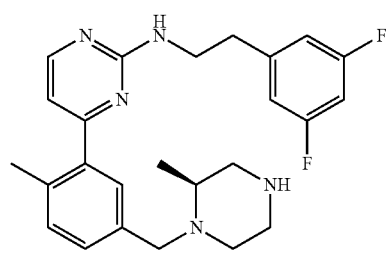
410 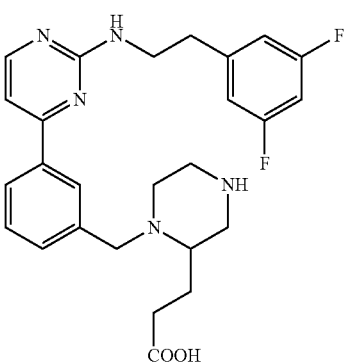
411 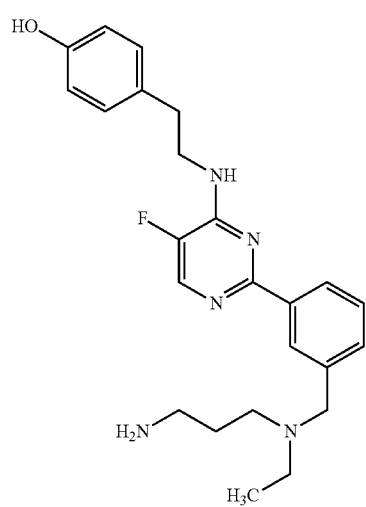
412 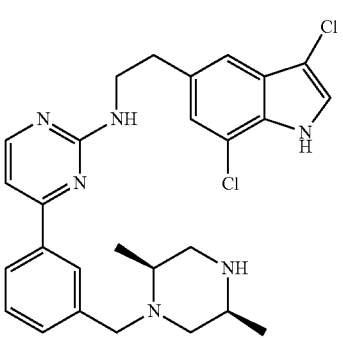

-continued
| 115 | 116 |
413
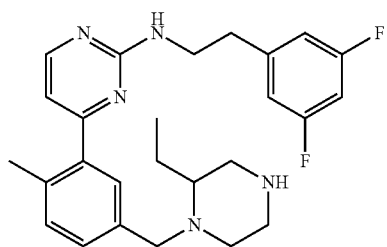
414
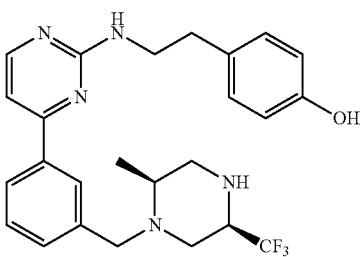
415
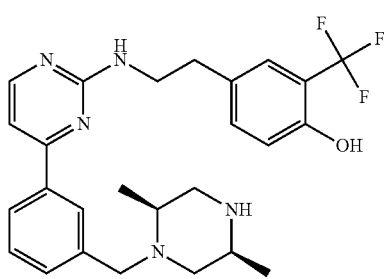
416
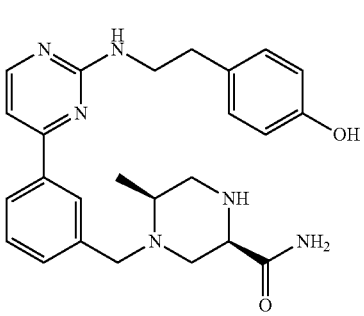
417
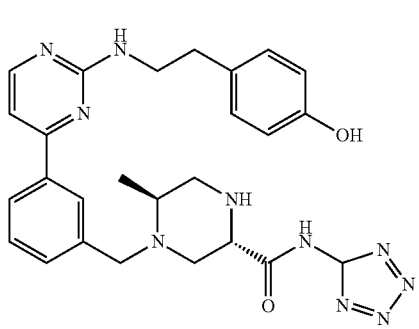
418
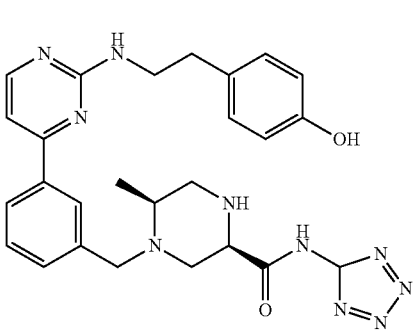
419
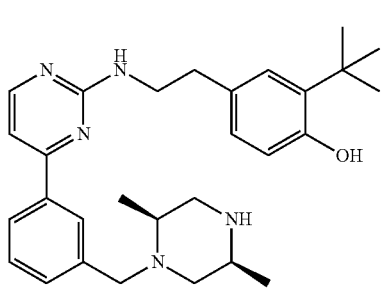
420
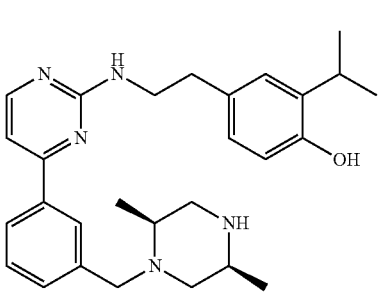
421
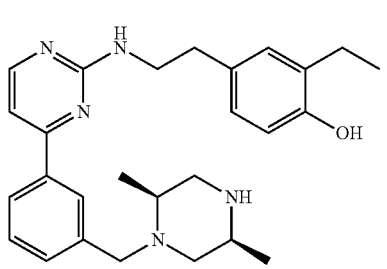
422
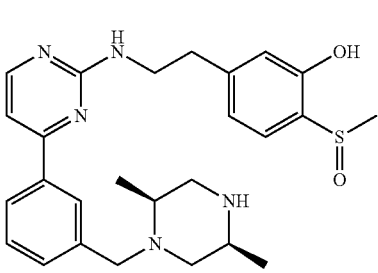

| 117 | 118 |
|---|---|
| 423 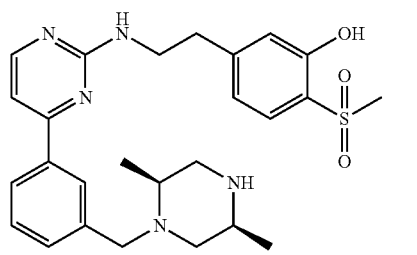 | 424 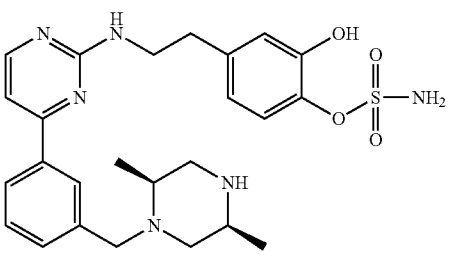 |
| 425 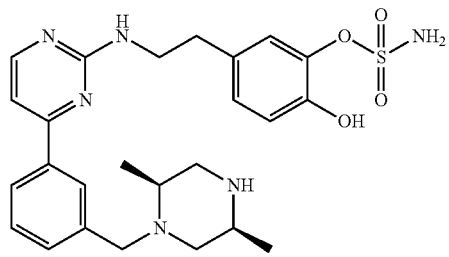 | 426 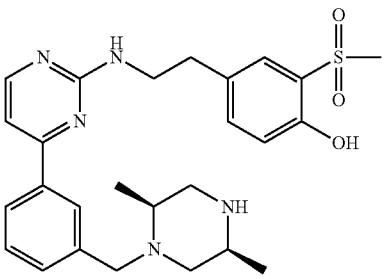 |
| 427 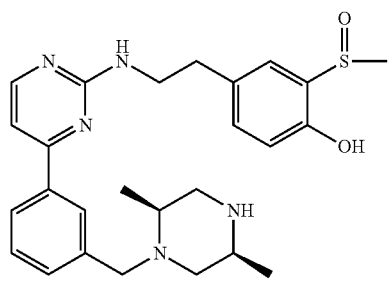 | 428 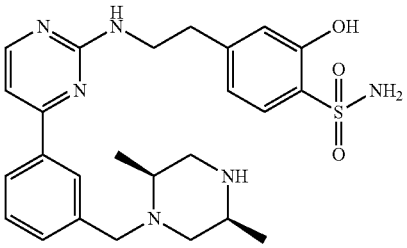 |
| 429 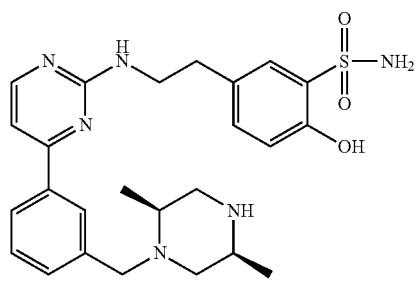 | 430 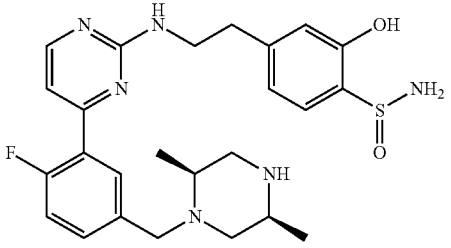 |
| 431 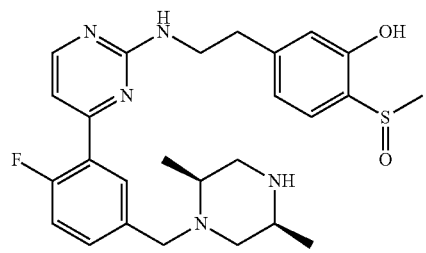 | 432 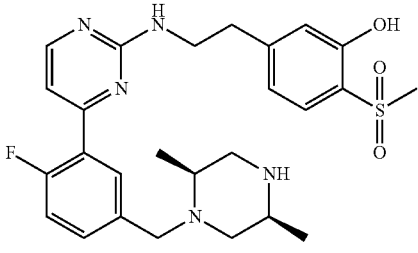 |
| 433 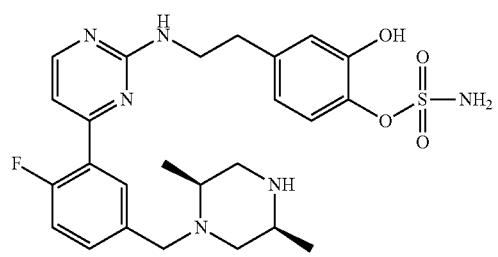 | 434 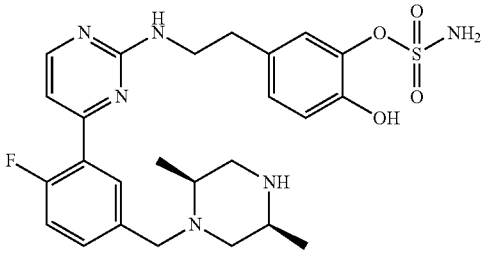 |

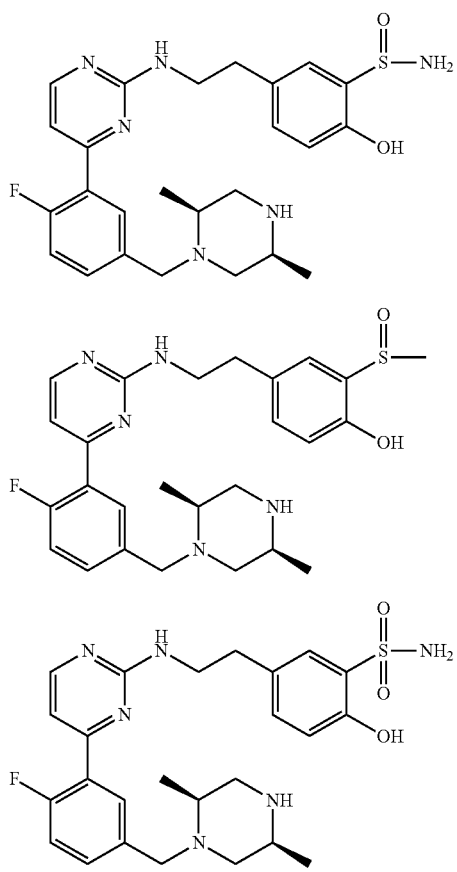

435

437

439

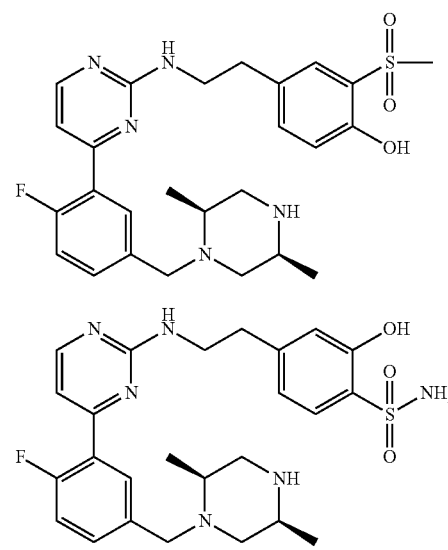

436

438

4. Uses, Formulation and Administration
Pharmaceutically Acceptable Compositions As discussed above, the present invention provides compounds that are useful as inhibitors of PKC-theta, and thus the present compounds are useful for treating or lessening the severity of a variety of acute or chronic inflammatory or autoimmune diseases, conditions, or disorders, including, but not limited to, rheumatoid arthritis (RA), osteoarthritis, multiple sclerosis (MS), inflammatory bowel disease (IBD), psoriasis, organ transplantation, graft vs. host disease, asthma and chronic obstructive pulmonary disease (COPD).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PKC-theta.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of an acute or chronic inflammatory or autoimmune disease or disorder is provided comprising administering an effective amount of a compound, or a pharmaceutically acceptable composition comprising a compound to a subject in need thereof.

In certain embodiments of the present invention an "effective amount" of the compound or pharmaceutically acceptable composition is that amount effective for treating or lessening the severity of an acute or chronic inflammatory or autoimmune disease or disorder. In other embodiments, an "effective amount" of a compound or composition of the invention includes those amounts that antagonize or inhibit PKC-theta. An amount which antagonizes or inhibits PKC-theta is detectable, for example, by any assay capable of determining PKC-theta activity, including the one described below as an illustrative testing method.

In other embodiments, an "effective amount" of a compound can achieve a desired therapeutic and/or prophylactic effect, such as an amount which results in the prevention of or a decrease in the symptoms associated with a disease mediated by the inappropriate activation of PKC-theta and subsequently the inappropriate activation of T cells.

The compounds and compositions, according to the method of the present invention, may be administered using any amount and any route of administration effective for treating or lessening the severity of an acute or chronic inflammatory disease or disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an, oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, t) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of PKC-theta and thus the invention further relates to a method for treating (e.g., palliative, curative, prophylactic) a disease or disorder associated with PKC-theta activation including but not limited to inflammatory diseases, autoimmune diseases, organ and bone marrow transplant rejection and other disorders associated with T cell mediated immune response, including acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus.

When activation of PKC-theta is implicated in a particular disease, condition, or disorder, the disease, condition, or disorder may also be referred to as a "PKC-theta-mediated disease" or disease symptom. Accordingly, in another aspect, the present invention provides a method for treating or lessening the severity of a disease, condition, or disorder where activation of PKC-theta is implicated in the disease state.

In one embodiment, the invention provides a method of treating rheumatoid arthritis, comprising administering an effective amount of a compound of general formula I (and subsets as described above and herein) to a subject in need thereof.

In another embodiment, the invention provides a method of treating multiple sclerosis, comprising administering an effective amount of compounds of general formula I (and subsets thereof as described herein) to a subject in need thereof. The manifestation of MS is variable and the clinical course of MS can be grouped into four categories: relapsing-remitting, primary progressive, secondary progressive and progressive-relapsing. The method of the invention can be used to treat MS which presents with each of the recognized clinical courses. Accordingly, a compound of the invention can be administered to a patient with a progressive course of MS to retard or prevent the progression of neurological impairment. A compound of the invention can also be administered to a subject with relapsing-remitting, secondary progressive or progressive-relapsing MS to inhibit relapse (e.g., an acute attack). For example, a compound of the invention can be administered to a subject with relapsing-remitting MS during the remitting phase of the disease to prevent or delay relapse.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

In some embodiments, the compounds of the invention may be employed alone or in combination with other therapeutic agents, particularly, other inhibitors of PKC-theta isoform. Exemplary of these combination agents include anti-proliferative agents (e.g., methotrexate) and the agents disclosed in U.S. Pat. Application Publication No. US2003/0022898, p 14, para. [0173-0174], which is incorporated herein in its entirety. For example, it is expected that a combination therapy for rheumatoid arthritis would involve one or more inventive compounds with methotrexate. It is understood that other combinations may be undertaken while remaining within the scope of the invention.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting PKC-theta, activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of PKC-theta activity in a biological sample is useful for a variety of purposes that are known to one of skill in the art. Examples of such purposes include, but are not limited to, blood transfusion, organ-transplantation, biological specimen storage, and biological assays.

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where PKC-theta isoform plays a role.

EXAMPLES

The following abbreviations are used in the examples:

| | |
|---|---|
| RT | room temperature |
| NMR | nuclear magnetic resonance spectroscopy |
| LC-MS | liquid chromatography/mass spectrometry |
| HCl | hydrochloric acid |
| sat. NaCl | a saturated solution of sodium chloride |
| NaHCO$_3$ | sodium bicarbonate |
| NaBH$_3$CN | sodium cyanoborohydride |
| NaBH(OAc)$_3$ | sodium triacetoxy borohydride |
| CH$_2$Cl$_2$ | methylene chloride |
| EtOAc | ethyl acetate |
| DMSO | dimethyl sulfoxide |
| THF | tetrahydrofuran |

-continued

| | |
|---|---|
| MeOH | methanol |
| CD₃OD | deuterated methanol |
| CDCl₃ | deuterated chloroform |
| DMSO-d₆ | deuterated dimethyl sulfoxide |
| BOC (Boc or boc) | tertiary butoxy carbonyl |
| EDC | ethyldimethylaminopropyl carbodiimide |
| mL | milliliter |
| mmol | millimole |

A: General Experimental Procedures

Procedure B (Reductive Amination of Aryl Aldehyde):

Dissolve 10 mmol of the appropriate aldehyde in 100 mL of $CH_2Cl_2$. Add 1.1 eq. of an appropriately substituted amine, followed by 1.5 eq. of $NaBH(OAc)_3$. Stir the mixture at room temperature for two hours and work up by partitioning the reaction mixture between $CH_2Cl_2$ and water. Wash the organic layer with water followed by a saturated solution of NaCl. Remove the solvent to give product, which is typically >90% pure and is used without purification.

Scheme 1. Synthesis of aminopyrimidines:

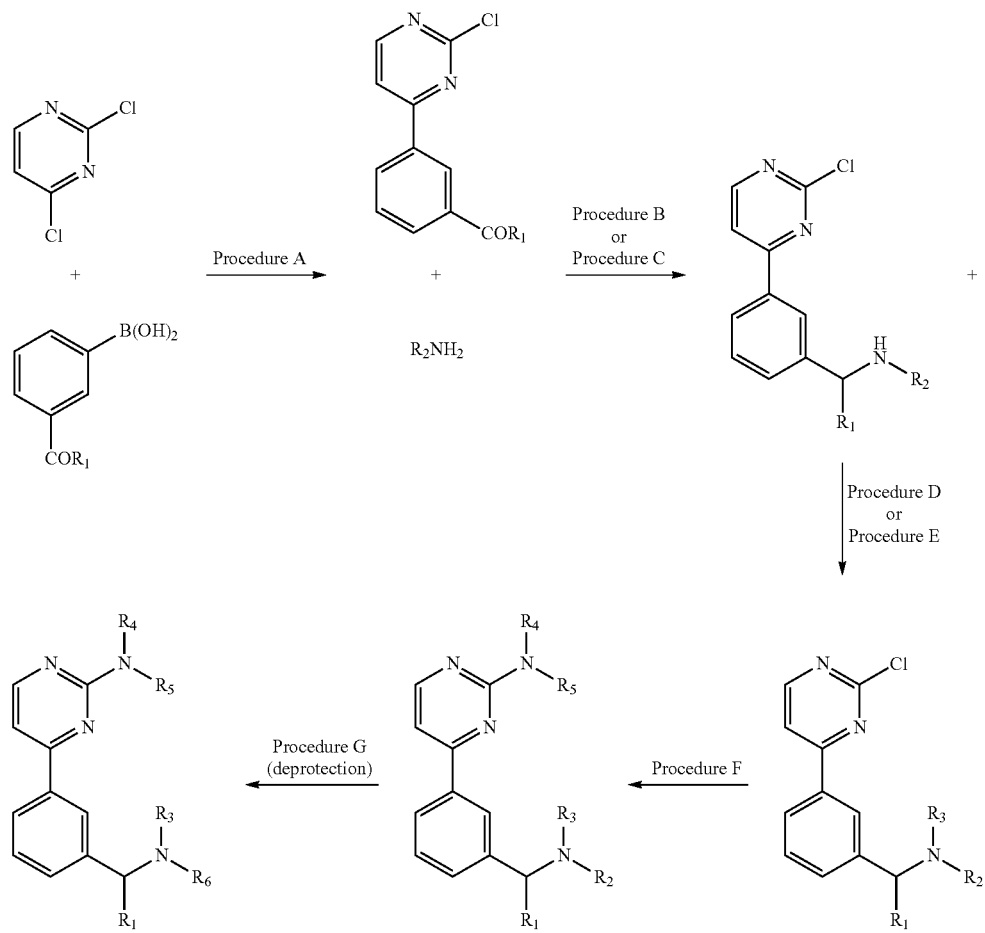

$R_1$ = H, alkyl $R_2$ = alkyl, substituted alkyl $R_3$ = alkyl, substituted alkyl, acyl, sulfonamido, ureido ($R_2$-$R_3$ and $R_3$-$R_6$ can be a cyclic amine) $R_4$ = H, alkyl, substituted alkyl
$R_5$ = H, alkyl, substituted alkyl $R_6$ = alkylamino, substituted alkylamino Procedure A (Suzuki Coupling of 2,4 Dichloropyrimidine with Arylboronic Acid):

Dissolve 2.57 g (17.3 mmol) of 2,4 dichloropyrimidine and 1.2 eq of a 3-substituted phenylboronic acid in 300 mL of THF. Add 2.4 eq. of $K_2CO_3$ and 30 mL of water and flush the flask with nitrogen. Add 1 g of $Pd(PPh_3)_4$ and heat the mixture to 65° C. for 4 hours. Remove the THF by rotary evaporation and partition the residue between ethyl acetate and water. Wash the organic layer with a saturated solution of sodium chloride and remove the solvent. Chromatograph the residue on silica gel, typically using 30% ethyl acetate in hexanes as eluent. Yields are typically 30-70%.

Procedure C (Reductive Amination of Acetophenone):

Dissolve 10 mmol of the appropriate ketone in 100 mL of toluene. Add 1.3 eq of an appropriately substituted amine and heat to reflux for four hours, using a Dean Stark trap to remove water formed in the reaction. Remove the toluene by rotary evaporation and take up the residue in THF. Add $NaBH_4$ (1.4 eq) portionwise and stir at room temperature for 1 hour. Remove the THF by rotary evaporation and partition the residue between ethyl acetate/water. Wash the organic layer with a saturated solution of NaCl and remove the solvent. Chromatograph the residue on silica gel (15% methanol in ethyl acetate) to give the product. Typical yields are 20-30%.

Procedure D (Acylation):

Dissolve the amine in methylene chloride. Add 1.2 eq. of triethylamine followed by 1.2 eq. of sulfonyl chloride or acid chloride. Stir at room temperature for 4 hours. Pour the mixture into a separatory funnel and wash with 1N HCl, saturated NaHCO$_3$, and sat. NaCl. Remove the solvent and chromatograph the residue on silica gel (ethyl acetate as eluent.) Typical yields are >90%.

Procedure D2 (Alternate Acylation):

Dissolve the amine in methylene chloride. Add 4 eq. of diisopropylethylamine followed by 1.1 eq. of carboxylic acid and EDCI. Stir at room temperature overnight. The mixture was washed with water, brine, dried over Na$_2$SO$_4$ and subject to chromatography on silica gel or HPLC purification to afford product.

Procedure E (Reductive Amination):

Dissolve product from procedure B or C in methylene chloride and add 1.4 equivalents of the appropriate aldehyde or ketone. Add 1.5 equivalents of NaBH(OAc)$_3$ and stir at room temperature for two hours. Partition the reaction mixture between ethyl acetate and water. Wash the organic layer with sat. NaHCO$_3$, followed by sat NaCl. Remove the solvent and purify the product by chromatography on silica gel. Typical yields are 70-90%.

Procedure F (Nucleophilic Substitution):

Dissolve the appropriate 2-chloropyrimidine in butanol along with 1.2 equivalents of an appropriate amine. Add 1.5 equivalents of diisopropylethylamine and heat the mixture to 130° C. overnight. Remove the solvent and chromatograph the residue on silica to give product. Typical yields are 70-90%.

Procedure G (BOC Deprotection):

Dissolve the appropriate BOC protected amine (1 mmol) in 20 mL of methylene chloride. Add 10 mL of trifluoroacetic acid and stir at room temperature for 2 hours. Remove the methylene chloride/trifluoroacetic acid by rotary evaporation, add 5 mL of toluene, and again remove the solvent to remove residual trifluoroacetic acid. Dry the sample under vacuum overnight.

Procedure G2 (Alternate BOC Deprotection):

Dissolve the appropriate BOC protected amine (1 mmol) in 10 ml of acetonitrile. Add 5 ml of 4 N HCl-dioxane solution and stir at room temperature for 3 hours. Remove the solvent by rotary evaporation. Dry the sample under vacuum overnight.

Procedure G3 (Cbz Deprotection):

Dissolve the appropriate Cbz protected amine (0.5 mmol) in 3 ml of methanol. Add 3 ml of 6N HCl (aq) solution and stir at room temperature for 30 min. Remove the solvent by rotary evaporation. Dry the sample under vacuum overnight.

Scheme 2. Synthesis of anilino-aminopyrimidines:

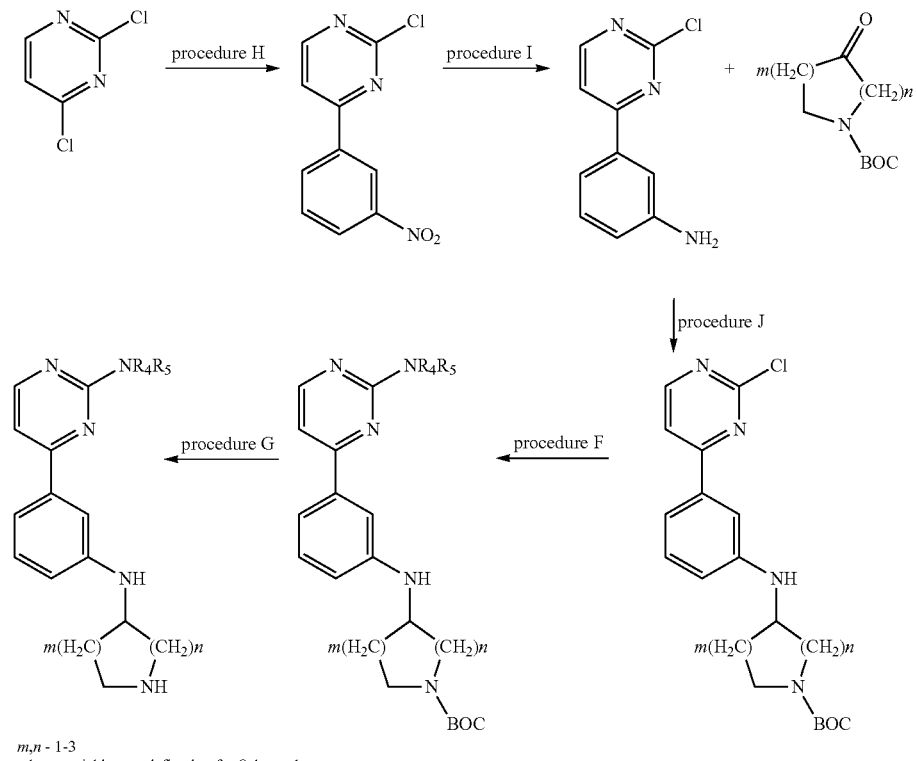

m,n - 1-3
where variables are defined as for Scheme 1

Procedure H (Suzuki Coupling with 3-Nitrophenylboronic Acid):

Dissolve 5.1 g (35 mmol) of 2,4 dichloropyrimidine and 1.2 eq of a 3-nitrophenylboronic acid in 600 mL of THF. Add 2.4 eq. of K$_2$CO$_3$ and 60 mL of water and flush the flask with nitrogen. Add 2 g of Pd(PPh$_3$)$_4$ and heat the mixture to 70° C. for 4 hours. Remove the THF by rotary evaporation and partition the residue between ethyl acetate and water. Wash the organic layer with a saturated solution of sodium chloride and evaporate the solvent to about 100 mL. By this point the product will precipitate and can be isolated by filtration. The solid is washed with 100 mL of diethyl ether and dried under vacuum to give 6 g (83%) of the desired product.

Procedure I (Nitro Group Reduction):

The product from above is suspended in 300 mL of ethanol along with 0.7 g of 10% Pt/C. The flask is evacuated to remove oxygen and hydrogen introduced ($H_2$ atmosphere maintained using a balloon.) The mixture is stirred overnight, by which point the starting nitro compound has gone into solution and been reduced to the aniline. The mixture is filtered through Celite and the solvent evaporated to give a quantitative yield of product.

Procedure J (Reductive Amination with $NaBH_3CN$):

An appropriate amine is dissolved in methanol and an appropriate aldehyde or ketone (1.2 equivalents) is added followed by sodium cyanoborohydride (1.2 equivalents). The pH is adjusted to 6.0 with acetic acid and the mixture stirred overnight. The methanol is removed by rotary evaporation and the residue partitioned between ethyl acetate and water. The organic layer is washed with water followed by saturated NaCl and the solvent removed. The residue is chromatographed on silica to give product. Typical yields are about 60%.

Procedure K (Acylation Using RCOOH/EDC):

The amine is dissolved in pyridine (10 mL/mmol) along with 1.2 equivalents of the appropriate carboxylic acid and 1.2 equivalents of ethyl-dimethylaminopropyl carbodiimide (EDC.) The mixture is stirred at room temperature overnight and the pyridine removed by rotary evaporation. The residue is partitioned between ethyl acetate and water and the organic layer washed with sat. NaCl. Removal of the solvent followed by chromatography on silica gel (1:1 ethyl acetate:hexane eluent) yields product, typically in 60-90% yield.

Procedure L (Cyclization Using Mitsunobu Reaction):

Dissolve the amino alcohol in tetrahydrofuran (THF). Triphenylphosphine (1.3 eq.) and N,N-diisopropylethylamine (1.2 eq.) were added, followed by diisopropyl azodicarboxylate (1.3 eq.). The mixture is stirred at room temperature overnight. Removal of the solvent followed by chromatography on silica gel (2:98 methanol:methylene chloride eluent) yields product.

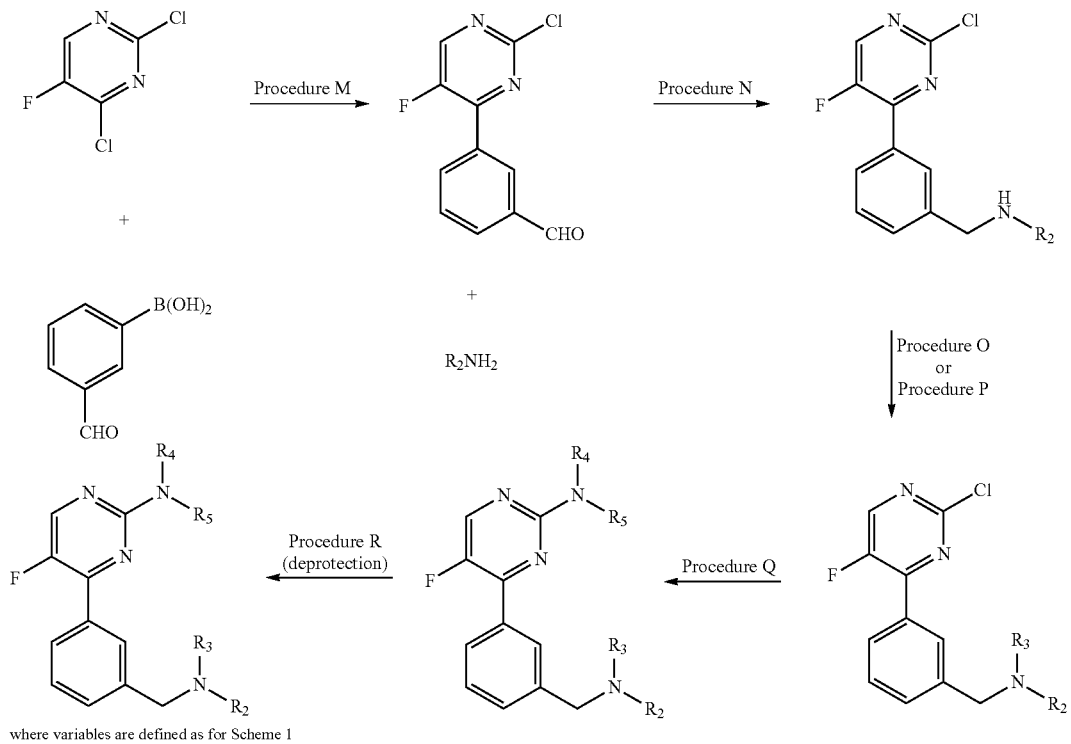

Scheme 3. Synthesis of fluoro-aminopyrimidines where variables are defined as for Scheme 1

Procedure M (Suzuki Coupling of 2,4-Dichloro-5-Fluoropyrimidine and Boronic Acid):

Dissolve 10 g (60 mmol) of 2,4-dichloro-5-fluoropyrimidine and 1.0 eq. of 3-formylbenzeneboronic acid in 250 mL of THF. Add 2.0 eq. of $K_2CO_3$ and 250 mL of water and flush the flask with argon. Add 3.5 g (3.0 mmol) of $Pd(PPh_3)_4$ and heat the mixture to 75° C. for 16 hours. Pour the reaction mixture into a separatory funnel and remove the water layer. Remove the THF by rotary evaporation and add ethyl acetate (ca. 100 mL) to the crude material. The resulting suspension is isolated by vacuum filtration and washed with ethyl acetate (2×50 mL) to provide an off white solid. Yields are typically 50-60%.

Procedure N (Reductive Amination with $NaBH(OAc)_3$):

Dissolve 1.8 g (7.7 mmol) of the aryl aldehyde in 25 mL of THF. Add 1.2 eq. of either 4-amino-1-N-boc-piperidine or N-(3'-aminopropyl) carbamic acid tert-butyl ester and 4 eq. of acetic acid and stir the reaction mixture at rt for 2.5 h. Cool to 0° C. and add 3 eq. of $NaBH(OAc)_3$. Warm the reaction mixture to rt and stir for two hours. Work up by partitioning the reaction mixture between EtOAc and water. Wash the organic layer with a saturated solution of $NaHCO_3$ and brine. Remove the solvent and chromatograph the residue on silica gel (1-5% MeOH/CH$_2$Cl$_2$) to obtain a dark yellow oil. Yields are 55-75% for the piperidine adduct and 66% for the propylamine compound.

Procedure O (Mesylation):

Dissolve 0.6 g (1.4 mmol) of the amine in 6 mL of methylene chloride. Add 2.0 eq. of diisopropyl ethylamine. Cool to 0° C. and add 1.2 eq. of methanesulfonyl chloride dropwise (ca. 1 min) and stir for 5 min. Warm to rt and stir for an additional 1.5 h. Work up by adding a saturated solution of NaHCO$_3$ and extracting with EtOAc. Wash the organic layer with HCl (1 N) followed by NaHCO$_3$ and brine. Remove the solvent to afford a crude dark yellow oil. Recrystallization of the piperidine derivative from butanol provides the desired product as a yellow solid (0.34 g, 50% yield). Purification of the propylamine derivative by chromatography on silica gel (100% EtOAc) affords the desired product as a dark yellow oil (0.97 g, 66%).

matograph the residue on silica gel (1-5% MeOH, CH$_2$Cl$_2$), yields are 48% for the piperidine adduct and 40% for the propylamine compound.

Procedure Q (Nucleophilic Substitution):

Dissolve the appropriate 2-chloropyrimidine in butanol along with 3 equivalents of an appropriate amine. Add 6 equivalents of diisopropylethylamine and heat the mixture to 130° C. overnight. Remove the solvent and chromatograph the residue on silica to give product. Typical yields are 40-80%.

Procedure R (BOC Deprotection):

Dissolve the appropriate BOC protected amine (0.4 mmol) in 3 mL of methylene chloride. Add 1 mL of trifluoroacetic acid and stir at room temperature for 2 hours. Remove the methylene chloride/trifluoroacetic acid by rotary evaporation. Add 5 mL of toluene, and again remove the solvent to remove residual trifluoroacetic acid (repeat 2 more times). Dry the sample under vacuum overnight.

Scheme 4. Synthesis of alkylphenyl substituted fluoroaminopyrimidines

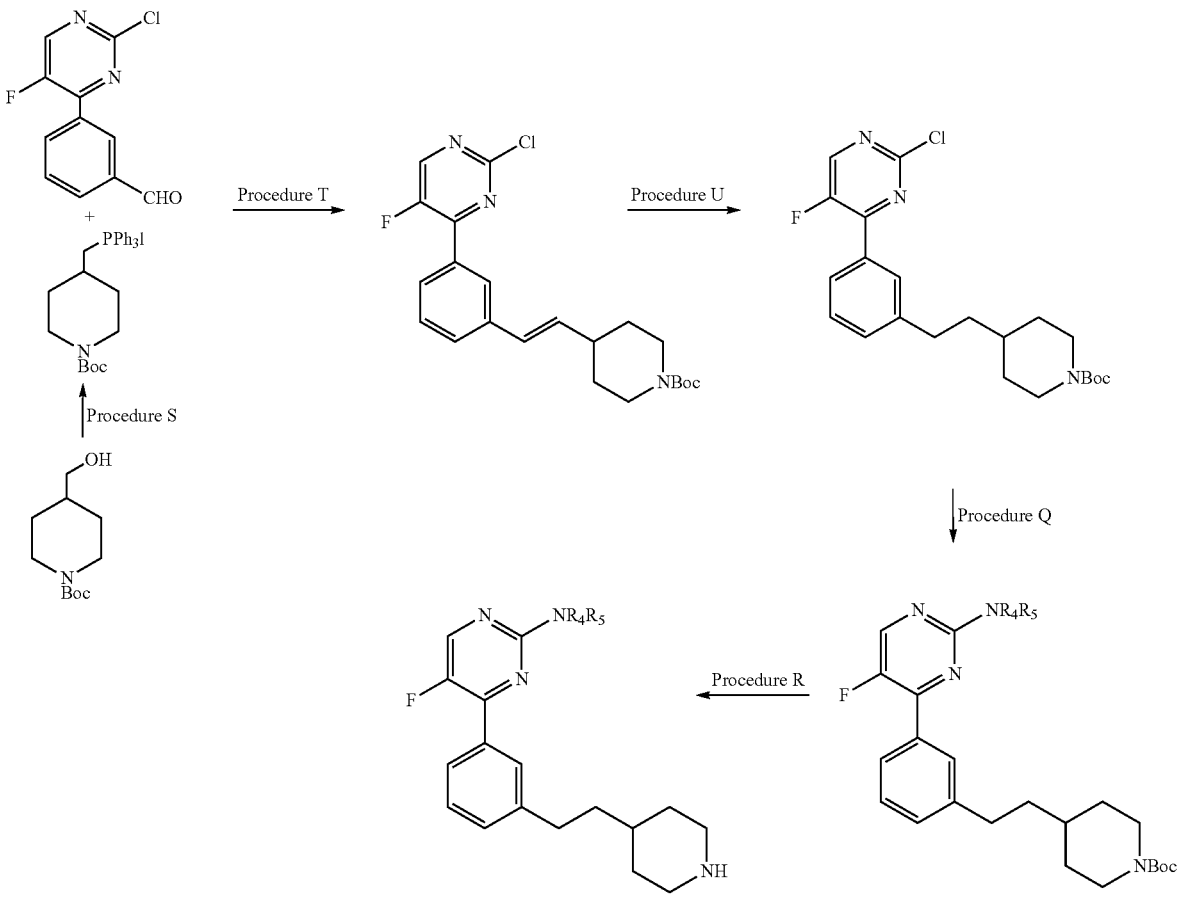

where variable are defined as for Scheme 1.

Procedure P (Reductive Amination):

Dissolve the product from procedure B in CH$_2$Cl$_2$. Add 1.2 eq. of acetaldehyde and 4.0 eq. of acetic acid and stir the reaction mixture at rt for 2.5 h. Cool to 0° C. and add 3 eq. of NaBH(OAc)$_3$. Warm the reaction mixture to rt and stir for two hours. Work up by partitioning the reaction mixture between EtOAc and water. Wash the organic layer with a saturated solution of NaHCO$_3$ and brine. Remove the solvent and chro- Procedure S: Synthesis of the Wittig Salt:

Step 1: Dissolve 28.3 g (112 mmol) of iodine and 30.5 g (116 mmol) of triphenylphosphine in 450 mL of benzene and stir at rt for 5 min. Add 18.1 mL (223 mmol) of pyridine and 20 g (93 mmol) of N-Boc-4-piperidine methanol and reflux the reaction mixture at for 2 h. Cool to rt and filter off the solid precipitate. Remove the solvent by rotary evaporation and add hexanes to precipitate the triphenylphosphine oxide. Filter off the oxide and remove the solvent to afford the desired iodide as a faint yellow oil (100% yield) and use in the next step without further purification.

Step 2: Dissolve the iodide (22.5 g, 69.2 mmol) in acetonitrile (275 mL) and add 2.1 eq. of triphenylphosphine. Reflux the mixture for 18-24 h. Cool to rt and remove the solvent by rotary evaporation. Recrystallize the residue from ethanol/hexanes. Yields are typically 70-80%.

Procedure T (Wittig Reaction):

To a suspension of the Wittig salt (18.9 g, 32.2 mmol) in THF (125 mL) cooled to 0° C. add 34.2 mL (34.2 mmol) of potassium tert-butoxide (1 M in 2-methyl-2-propanol) dropwise (ca. 1 min) and stir the resulting yellow solution for 15 min. Add a solution of the aryl aldehyde (2.53 g, 10.7 mmol) in THF (30 mL) via syringe and warm the resulting purple reaction mixture to rt. After 30 min, quench the reaction with a saturated solution of ammonium chloride and extract with EtOAc. Remove the solvent and chromatograph the residue on silica gel (25% EtOAc/hexanes) to obtain a clear, colorless oil. Yields are typically 55-75%.

Procedure U (Olefin Reduction):

Dissolve 1.3 g (3.1 mmol) of the olefin from Procedure G in methanol and add 5 mol % (0.31 g) of 10% Pt/C. Purge the reaction mixture with argon and affix a balloon of hydrogen. Stir at rt for 2 h. Filter the reaction mixture through celite and wash with methylene chloride. Remove the solvent and chromatograph (10-25% EtOAc/hexanes) the resulting black residue on silica gel to obtain a clear, colorless oil. Yields are typically 85%-95%.

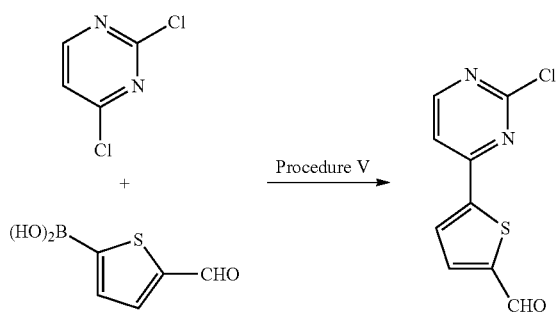

Procedure V: (Suzuki Coupling with Thiophene Boronic Acid):

Dissolve 0.43 g (2.9 mmol) of 2,4 dichloropyrimidine and 1.1 eq of 5-formyl-2-thiopheneboronic acid in 10 mL of THF. Add 2.0 eq. of $K_2CO_3$ and 10 mL of water and flush the flask with nitrogen. Add 0.17 g of $Pd(PPh_3)_4$ and heat the mixture to 75° C. for 12 hours. Remove the water layer and concentrate the TI-IF layer by rotary evaporation. Chromatograph the residue quickly on silica gel, typically using 75% ethyl acetate in hexanes as eluent. Yield: 23%.

B. Synthesis of Exemplary Intermediates and Compounds:

Intermediate 1: 3-(2-Chloro-pyrimidin-4-yl)-benzaldehyde: 2,4 dichloropyrimidine and 3-formyl phenyl boronic acid were coupled following procedure A. The yield was 60%. LC-MS showed the product was >95% pure and had the expected M+H$^+$ of 219. $^1$H NMR (Varian 300 MHz, CDCl$_3$, shifts relative to the solvent peak at 7.24 ppm) δ10.1 (s, 1H) 8.7 (d, 1H) 8.6 (m, 1H) 8.4 (m, 1H) 8.1 (m, 1H) 7.7 (m, 2H).

Intermediate 2: {3-[3-(2-Chloro-pyrimidin-4-yl)-benzylamino]-propyl}-carbamic acid tert-butyl ester: The product from the above reaction and tert-butyl N-(3-aminopropyl) carbamate) were coupled by procedure B. The yield was 85%. LC-MS showed the product had the expected M+H$^+$ of 377.

Intermediate 3: (3-{[3-(2-Chloro-pyrimidin-4-yl)-benzyl]-ethyl-amino}-propyl)-carbamic acid tert-butyl ester: The product from the above reaction was coupled with acetaldehyde by procedure B. The yield was 80%. LC-MS showed the product had the expected M+H$^+$ of 405.

Compound 1: (4-{2-[4-(3-{[(3-Amino-propyl)-ethyl-amino]-methyl}-phenyl)-pyrimidin-2-ylamino]-ethyl}-phenol): Intermediate 3 from above was coupled with tyramine following procedure F. The product was deprotected by procedure G. LC-MS showed the product had the expected M+H$^+$ of 406. $^1$H NMR (Varian 300 MHz, DMSO-d$_6$, shifts relative to the solvent peak at 2.49 ppm) δ 8.5 (s, 1H) 8.4 (d, 1H) 8.2 (s, 1H) 8.1 (m, 3H), 7.9 (d, 1H) 7.6 (m, 1H) 7.4 (s, 1H) 7.0 (d, 2H) 6.6 (d, 2H) 4.4 (s, 2H) 3.6 (m, 2H) 3.5 (s, 1H) 3.1 (m, 4H) 2.8 (m, 4H) 2.1 (m, 2H) 1.3 (m, 3H).

Intermediate 4: (3-{[3-(2-Chloro-pyrimidin-4-yl)-benzyl]-methanesulfonyl-amino}-propyl)-carbamic acid tert-butyl ester. Intermediate 2 from above was treated with methanesulfonyl chloride following procedure D. LC-MS showed the product had the expected M+H$^+$ of 456.

Compound 2: N-(3-Amino-propyl)-N-(3-{2-[2-(4-hydroxy-phenyl)-ethylamino]-pyrimidin-4-yl}-benzyl)-methanesulfonamide: Intermediate 4 from above was coupled with tyramine following procedure F and the resulting product deprotected following procedure G. LC-MS showed the product had the expected M+H$^+$ of 456. $^1$H NMR (Varian 300 MHz, DMSO-d$_6$, shifts relative to the solvent peak at 2.49 ppm) δ 8.5 (d, 1H) 8.1 (m, 2H) 8.0 (s, 2H) 7.6 (m, 2H) 7.4 s, 1H) 7.0 (d, 2H) 6.7 (d, 2H) 4.5 (s, 2H) 3.6 (m, 2H) 3.2 (m, 2H) 3.0 (s, 3H) 2.8 (m, 2H) 2.7 (m, 2H) 1.8 (m, 2H).

Compound 3: N-(4-{2-[4-(3-{[(3-Amino-propyl)-methanesulfonyl-amino]-methyl}-phenyl)-pyrimidin-2-ylamino]-ethyl}-phenyl)-acetamide: Intermediate 4 from above was coupled with N-[4-(2-Amino-ethyl)-phenyl]-acetamide by procedure F and the resulting product deprotected by procedure G to give 3. LC-MS showed the product had the expected M+H$^+$ of 497. $^1$H NMR (Varian 300 MHz, CDCl$_3$-CD$_3$OD, shifts relative to the solvent peak at 7.24 ppm) δ 8.1 (m, 2H) 8.0 (m, 1H) 7.6 (m, 1H) 7.5 (m, 1H) 7.4 (m, 2H) 7.3 (m, 1H) 7.2 (d, 2H) 4.4 (s, 2H) 3.9 (m, 2H) 3.3 (m, 2H) 2.9 (m, 2H) 2.8 (s, 3H) 2.7 (m, 2H) 2.1 (s, 3H) 1.8 (m, 2H).

Compound 4: N-(4-{2-[4-(3-{[(3-Amino-propyl)-methanesulfonyl-amino]-methyl}-phenyl)-pyrimidin-2-ylamino]-ethyl}-phenyl)-methanesulfonamide: intermediate 4 from above was coupled with N-[4-(2-Amino-ethyl)-phenyl]-methanesulfonamide following procedure F and the resulting product deprotected following procedure G to give 4. LC-MS showed the product had the expected M+H$^+$ of 533. $^1$H NMR (Varian 300 MHz, CDCl$_3$-CD$_3$OD, shifts relative to the solvent peak at 7.24 ppm) δ 8.0 (m, 2H) 7.9 (d, 1H) 7.6 (d, 1H) 7.4 (m, 1H) 7.3 (m, 1H) 7.1 (d, 2H) 7.0 (d, 2H) 4.4 (s, 2H) 3.9 (m, 2H), 3.2 (m, 5H) 2.9 (m, 2H) 2.8 (s, 3H) 2.7 (m, 4H) 1.7 (m, 2H).

Compound 5: N-(3-{2-[2-(4-Amino-phenyl)-ethylamino]-pyrimidin-4-yl}-benzyl)-N-(3-amino-propyl)-methanesulfonamide: Intermediate 4 from above was coupled with 4-(2-Amino-ethyl)-phenylamine following procedure F and the resulting product deprotected following procedure G. LC-MS showed the product had the expected M+H$^+$ of 455. CDCl$_3$-CD$_3$OD, shifts relative to the solvent peak at 7.24 ppm) δ 8.1 (m, 2H) 7.9 (d, 1H) 7.5 (d, 1H) 7.4 (m, 1H) 7.2 (m, 3H) 7.1 (d, 2H) 4.4 (s, 2H) 3.7 (m, 2H) 3.2 (m, 4H) 2.9 (m, 2H) 2.8 (s, 3H) 2.6 (m, 2H) 1.6 (m, 2H).

Compound 6: N-(3-Amino-propyl)-N-(3-{2-[2-(3,4-dihydroxy-phenyl)-ethylamino]-pyrimidin-4-yl}-benzyl)-methanesulfonamide: Intermediate 4 from above was coupled with 4-(2-Amino-ethyl)-benzene-1,2-diol following procedure F and the resulting product deprotected following procedure G. LC-MS showed the product had the expected M+H$^+$ of 472. $^1$H NMR (Varian 300 MHz, CDCl$_3$-CD$_3$OD, shifts relative to the solvent peak at 7.24 ppm) δ 8.1 (m, 2H) 8.0 (d, 1H) 7.7 (d, 1H) 7.5 (m, 1H) 7.2 (m, 1H) 6.7 (d, 1H) 6.6 (m, 2H) 4.7 (s, 2H) 3.8 (m, 2H) 3.6 (m, 2H) 2.9 (s, 3H) 2.8 (m, 4H) 1.8 (m, 2H).

Compound 7: N-(3-Amino-propyl)-N-[3-(2-{[2-(3,4-dihydroxy-phenyl)-ethyl]-methyl-amino}-pyrimidin-4-yl)-benzyl]-methanesulfonamide: Intermediate 4 from above was coupled with 4-(2-Methylamino-ethyl)-benzene-1,2-diol following procedure F and the resulting product deprotected following procedure G. LC-MS showed the product had the expected M+H$^+$ of 486. $^1$H NMR (Varian 300 MHz, CDCl$_3$-CD$_3$OD, shifts relative to the solvent peak at 7.24 ppm) δ 8.2 (m, 2H) 8.0 (m, 2H) 7.6 (d, 1H) 7.5 (m, 1H) 6.6 (m, 1H) 6.4 (m, 2H) 4.4 (s, 2H) 4.0 (m, 2H) 3.2 (m, 5H) 2.9 (s, 3H) 2.8 (m, 4H) 1.7 (m, 2H).

Compound 8: N-(3-Amino-propyl)-N-(3-{2-[2-(3-hydroxy-4-methoxy-phenyl)-ethylamino]-pyrimidin-4-yl}-benzyl)-methanesulfonamide: Intermediate 4 from above was coupled with 5-(2-Amino-ethyl)-2-methoxy-phenol following procedure F and the resulting product deprotected following procedure G. LC-MS showed the product had the expected M+H$^+$ of 486. $^1$H NMR (Varian 300 MHz, CDCl$_3$-CD$_3$OD, shifts relative to the solvent peak at 7.24 ppm) δ 8.1 (m, 2H) 8.0 (d, 1H) 7.6 (m, 1H) 7.5 (m, 1H) 7.2 (m, 1H) 6.8 (s, 1H) 6.6 (s, 2H) 4.5 (s, 2H) 3.8 (m, 2H) 3.7 (s, 3H) 3.3 (m, 2H), 2.9 (m, 7H) 1.8 (m, 2H).

Compound 9: N-(3-Amino-propyl)-N-{3-[2-(4-hydroxy-benzylamino)-pyrimidin-4-yl]-benzyl}-methanesulfonamide: Intermediate 4 from above was coupled with 4-aminomethyl-phenol following procedure F and the resulting product deprotected following procedure G. LC-MS showed the product had the expected M+H$^+$ of 442.

Compound 10: 4-{2-[4-(3-{[(3-Amino-propyl)-methanesulfonyl-amino]-methyl}-phenyl)-pyrimidin-2-ylamino]-ethyl}-benzenesulfonamide: Intermediate 4 was coupled with 4-(2-Amino-ethyl)-benzenesulfonamide following procedure F and the resulting product deprotected following procedure G. LC-MS showed the product had the expected M+H$^+$ of 519. $^1$H NMR (Varian 300 MHz, CDCl$_3$-CD$_3$OD, shifts relative to the solvent peak at 7.24 ppm) δ 8.0 (m, 2H) 7.8 (m, 1H) 7.6 (m, 4H) 7.4 (m, 1H) 7.2 (m, 2H) 4.3 (s, 2H) 3.8 (m, 2H) 3.4 (m, 2H) 2.9 (m, 2H) 2.8 (s, 3H) 2.6 (m, 2H) 1.6 (m, 2H).

Compound 11: N-(3-Amino-propyl)-N-(3-{2-[2-hydroxy-2-(3-hydroxy-phenyl)-ethylamino]-pyrimidin-4-yl}-benzyl)-methanesulfonamide: Intermediate 4 was coupled with 3-(2-Amino-1-hydroxy-ethyl)-phenol following procedure F and the resulting product deprotected following procedure G. LC-MS showed the product had the expected M+H$^+$ of 472. $^1$H NMR (Varian 300 MHz, CDCl$_3$-CD$_3$OD, shifts relative to the solvent peak at 7.24 ppm) δ 8.1 (m, 2H) 7.9 (m, 1H) 7.6 (m, 1H) 7.5 (m, 1H) 7.3 (m, 1H) 7.0 (m, 1H) 6.8 (m, 2H) 6.6 (m, 1H) 4.8 (m, 1H) 4.4 (s, 2H) 3.8 (m, 2H) 3.3 (m, 2H) 2.9 (s, 3H) 2.7 (m, 2H) 1.7 (m, 2H).

Compound 12: N-(3-Amino-propyl)-N-{3-[2-(2-pyridin-4-yl-ethylamino)-pyrimidin-4-yl]-benzyl}-methanesulfonamide: Intermediate 4 was coupled with 2-pyridin-4-yl-ethylamine following procedure F and the resulting product deprotected following procedure G. LC-MS showed the product had the expected M+H$^+$ of 441. $^1$H NMR (Varian 300 MHz, CDCl$_3$-CD$_3$OD, shifts relative to the solvent peak at 7.24 ppm) δ 8.6 (m, 2H) 8.3 (m, 1H) 8.1 (m, 3H) 7.9 (m, 1H) 7.6 (m, 1H) 7.5 (m, 1H) 7.3 (m, 1H) 4.4 (m, 2H) 4.0 (m, 2H) 3.3 (m, 2H) 2.9 (m, 4H) 1.8 (m, 2H).

Compound 13: N-(3-Amino-propyl)-N-(3-{2-[2-(4-hydroxy-3,5-dimethoxy-phenyl)-ethylamino]-pyrimidin-4-yl}-benzyl)-methanesulfonamide: Intermediate 4 was coupled with 4-(2-Amino-ethyl)-2,6-dimethoxy-phenol following procedure F and the resulting product deprotected following procedure G. LC-MS showed the product had the expected M+H$^+$ of 516. $^1$H NMR (Varian 300 MHz, CD$_3$OD, shifts relative to the solvent peak at 3.3 ppm) δ 8.26 (d, 1H) 8.21 (s, 1H) 8.12 (d, 1H) 7.68 (d, 1H) 7.58 (d, 1H) 7.33 (d, 1H) 6.53 (s, 2H) 4.50 (s, 2H) 3.76 (s, 6H) 3.37 (m, 2H) 2.97 (s, 3H) 2.9 (m, 2H) 2.81 (m, 2H) 1.70 (m, 2H).

Compound 14: N-(3-Amino-propyl)-N-[3-(2-phenethylamino-pyrimidin-4-yl)-benzyl]methanesulfonamide: Intermediate 4 was coupled to phenethylamine following procedure F and the resulting product deprotected following procedure G. LC-MS showed the product had the expected M+H$^+$ of 440. $^1$H NMR (Varian 300 MHz, CDCl$_3$-CD$_3$OD, shifts relative to the solvent peak at 7.24 ppm) δ 8.1 (m, 3H) 7.7 (m, 1H) 7.5 (m, 2H) 7.2 (m, 5H) 4.5 (d, 2H) 3.8 (m, 2H) 3.6 (m, 1H) 3.3 (m, 3H) 3.0 (m, 2H) 2.9 (s, 3H) 1.8 (m, 2H).

Compound 15: N-(3-Amino-propyl)-N-(3-{2-[2-(4-fluoro-phenyl)-ethylamino]-pyrimidin-4-yl}-benzyl)-methanesulfonamide: Intermediate 4 was coupled with 2-(4-fluoro-phenyl)-ethylamine following procedure F and the resulting product deprotected following procedure G. LC-MS showed the product had the expected M+H$^+$ of 458. $^1$H NMR (Varian 300 MHz, CDCl$_3$-CD$_3$OD, shifts relative to the solvent peak at 7.24 ppm) δ 8.1 (m, 3H) 7.7 (m, 1H) 7.5 (m, 2H) 7.2 (m, 2H) 6.9 (m, 2H) 4.5 (s, 2H) 3.8 (m, 2H) 3.7 (m, 1H) 3.4 (m, 2H) 2.9 (m, 7H) 1.9 (s, 2H).

Compound 16: N-(3-Amino-propyl)-N-{3-[2-(4-hydroxy-3-methoxy-benzylamino)-pyrimidin-4-yl]-benzyl}-methanesulfonamide: Intermediate 4 was coupled with 4-Aminomethyl-2-methoxy-phenol following procedure F and the resulting product deprotected following procedure G. LC-MS showed the product had the expected M+H$^+$ of 472. $^1$H NMR (Varian 300 MHz, CDCl$_3$-CD$_3$OD, shifts relative to the solvent peak at 7.24 ppm) δ 8.2 (m, 3H) 7.6 (m, 2H) 7.3 (m, 2H) 6.8 (m, 2H) 4.4 (s, 2H) 3.8 (s, 2H) 3.7 (m, 2H) 3.4 (s, 3H) 2.9 (s, 3H) 2.8 (m, 2H) 1.7 (m, 2H).

Compound 17: N-(3-Amino-propyl)-N-(3-{2-[2-(1H-indol-3-yl)-ethylamino]-pyrimidin-4-yl}-benzyl)-methanesulfonamide: Intermediate 4 was coupled with 2-(1H-Indol-3-yl)-ethylamine following procedure F and the resulting product deprotected following procedure G. LC-MS showed the product had the expected M+H$^+$ of 479. $^1$H NMR (Varian 300 MHz, CDCl$_3$-CD$_3$OD, shifts relative to the solvent peak at 7.24 ppm) 8.1 (m, 2H) 7.9 (m, 1H) 7.7 (d, 1H) 7.6 (m, 4H) 7.2 (m, 1H) 7.0 (m, 2H) 4.4 (d, 2H) 3.9 (m, 1H) 3.6 (m, 1H) 3.3 (m, 2H) 3.1 (m, 2H) 2.9 (m, 5H) 1.7 (m, 2H).

Compound 18: N-(3-Amino-propyl)-N-(3-{2-[2-(6-fluoro-1H-indol-3-yl)-ethylamino]-pyrimidin-4-yl}-benzyl)-methanesulfonamide: Intermediate 4 was coupled with 2-(6-Fluoro-1H-indol-3-yl)-ethylamine following procedure F and the resulting product deprotected following procedure G. LC-MS showed the product had the expected M+H$^+$ of 497. $^1$H NMR (Varian 300 MHz, CDCl$_3$-CD$_3$OD, shifts relative to the solvent peak at 7.24 ppm) δ 8.1 (m, 2H) 7.8 (d, 1H) 7.5 (m, 4H) 7.3 (m, 1H) 6.8 (m, 2H) 4.4 (d, 2H) 3.9 (m, 1H) 3.6 (m, 2H) 3.3 (m, 2H) 3.1 (m, 1H) 2.8 (m, 5H) 1.7 (m, 2H).

Compound 19: {3-[(3-{2-[2-(4-Hydroxy-3-methoxy-phenyl)-ethylamino]-pyrimidin-4-yl}-benzyl)-methanesulfonyl-amino]-propyl}-carbamic acid tert-butyl ester: Intermediate 4 was coupled to 4-(2-Amino-ethyl)-2-methoxy-phenol following procedure F. LC-MS showed the product had the expected M+H$^+$ of 586. $^1$H NMR (Varian 300 MHz, CDCl$_3$, shifts relative to the solvent peak at 7.24 ppm) δ 8.28 (s, 1H)

8.05 (s, 1H) 7.96 (s, 1H) 7.50 (m, 2H) 7.0 (m, 1H) 6.83 (m, 1H) 6.77 (m, 2H) 5.64 (s, 1H) 4.84 (s, 1H) 4.44 (s, 3H) 4.09 (s, 2H) 3.86 (s, 2H) 3.77 (m, 1H) 3.25 (m, 3H) 3.07 (br s, 2H) 2.90 (m, 2H) 2.85 (S, 3H) 1.60 (m, 2H) 1.39 (s, 9H).

Compound 20: N-(3-Amino-propyl)-N-(3-{2-[2-(4-hydroxy-3-methoxy-phenyl)-ethylamino]-pyrimidin-4-yl}-benzyl)-methanesulfonamide: Compound 19 was deprotected following procedure G. LC-MS showed the product had the expected M+H+ of 486.

Compound 21: N-(3-Amino-propyl)-N-{3-[2-(2-p-tolyl-ethylamino)-pyrimidin-4-yl]-benzyl}-methanesulfonamide: Intermediate 4 was coupled to 2-p-tolyl-ethylamine following procedure F and the resulting product deprotected following procedure G. LC-MS showed the product had the expected M+H+ of 454. $^1$H NMR (Varian 300 MHz, CDCl$_3$, shifts relative to the solvent peak at 7.24 ppm) δ 9.55 (br s, 1H) 8.1 (m, 2H) 7.6 (m, 4H) 7.2 (m, 4H) 4.4 (s, 2H) 3.81 (s, 2H) 3.37 (m, 2H) 2.97 (m, 4H) 2.94 (s, 3H) 2.25 (s, 3H) 1.75 (s, 2H) 1.69 (m, 2H).

Compound 22: N-(3-Amino-propyl)-N-(3-{2-[2-(4-hydroxy-3-nitro-phenyl)-ethylamino]-pyrimidin-4-yl}-benzyl)-methanesulfonamide: Intermediate 4 was coupled to 4-(2-Amino-ethyl)-2-nitro-phenol by procedure F and the resulting product deprotected by procedure G2. LC-MS showed the product had the expected M+H+ of 501. $^1$H NMR (Varian 300 MHz, CD$_3$OD, shifts relative to the solvent peak at 3.30 ppm) δ 8.4 (s, 1H) 8.3 (d, 1H) 8.2 (d, 1H) 8.0 (s, 1H) 7.8 (d, 1H) 7.6 (m, 3H) 7.0 (m, 1H) 4.5 (s, 2H) 4.0 (m, 2H) 3.4 (m, 2H) 3.0 (m, 5H) 2.8 (m, 2H) 1.8 (m, 2H).

Compound 23: {3-[(3-{2-[2-(3-Chloro-4-hydroxy-phenyl)-ethylamino]-pyrimidin-4-yl}-benzyl)-methanesulfonyl-amino]-propyl}-carbamic acid tert-butyl ester: Intermediate 4 was coupled to intermediate 71 following procedure F. LC-MS showed the product had the expected M+H+ of 590. $^1$H NMR (Varian 300 MHz, CDCl$_3$, shifts relative to the solvent peak at 7.24 ppm) δ 8.3 (m, 1H) 8.1 (d, 1H) 8.0 (d, 1H) 7.5 (m, 4H) 7.1 (m, 2H) 6.9 (m, 1H) 4.9 (m, 1H) 4.5 (s, 2H) 3.8 (m, 2H) 3.5 (s, 1H) 3.3 (m, 2H) 3.1 (m, 2H) 2.9 (m, 5H) 1.6 (m, 2H) 1.4 (s, 9H).

Compound 24: N-(3-Amino-propyl)-N-(3-{2-[2-(3-chloro-4-hydroxy-phenyl)-ethylamino]-pyrimidin-4-yl}-benzyl)-methanesulfonamide: Compound 23 was deprotected following procedure G. LC-MS showed the product had the expected M+H+ of 490. $^1$H NMR (Varian 300 MHz, CD$_3$OD, shifts relative to the solvent peak at 3.30 ppm) δ 8.3 (m, 2H) 8.2 (d, 1H) 7.8 (d, 1H) 7.6 (m, 1H) 7.5 (d, 1H) 7.3 (s, 1H) 7.1 (d, 1H) 6.8 (d, 1H) 4.6 (s, 2H) 3.9 (m, 2H) 3.4 (m, 2H) 3.0 (s, 3H) 2.9 (m, 4H) 1.8 (m, 2H).

Compound 25: {3-[(3-{2-[2-(3-Hydroxy-phenyl)-ethylamino]-pyrimidin-4-yl}-benzyl)-methanesulfonyl-amino]-propyl}-carbamic acid tert-butyl ester: Intermediate 4 was coupled with 3-(2-amino-ethyl)-phenol following procedure F. LC-MS showed the product had the expected M+H+ of 556. $^1$H NMR (Varian 300 MHz, CDCl$_3$, shifts relative to the solvent peak at 7.24 ppm) δ 8.3 (m, 2H) 7.9 (d, 1H) 7.5 (m, 2H) 7.2 (m, 1H) 7.0 (d, 1H) 6.8 (m, 3H) 4.9 (s, br, 1H) 4.5 (s, 2H) 3.8 (m, 2H) 3.3 (m, 2H) 3.1 (m, 2H) 2.9 (m, 5H) 1.7 (m, 2H) 1.4 (s, 9H).

Compound 26: N-(3-Amino-propyl)-N-(3-{2-[2-(3-hydroxy-phenyl)-ethylamino]-pyrimidin-4-yl}-benzyl)-methanesulfonamide: Compound 25 was deprotected following procedure G. LC-MS showed the product had the expected M+H+ of 456. $^1$H NMR (Varian 300 MHz, CD$_3$OD, shifts relative to the solvent peak at 3.30 ppm) δ 8.3 (m, 2H) 8.2 (d, 1H) 7.8 (d, 1H) 7.6 (m, 1H) 7.5 (d, 1H) 7.1 (m, 1H) 6.8 (m, 2H) 6.6 (d, 1H) 4.6 (s, 2H) 3.9 (m, 2H) 3.4 (m, 2H) 3.0 (m, 5H) 2.8 (m, 2H) 1.8 (m, 2H).

Compound 27: N-(3-Amino-propyl)-N-(3-{2-[2-(2-hydroxy-phenyl)-ethylamino]-pyrimidin-4-yl}-benzyl)-methanesulfonamide: Intermediate 4 was coupled with 2-(2-amino-ethyl)-phenol following procedure F and the resulting product deprotected following procedure G. LC-MS showed the product had the expected M+H+ of 456. $^1$H NMR (Varian 300 MHz, CD$_3$OD, shifts relative to the solvent peak at 3.30 ppm) δ 8.3 (m, 3H) 7.8 (d, 1H) 7.6 (m, 1H) 7.5 (d, 1H) 7.1 (d, 1H) 7.0 (m, 1H) 6.7 (d, 2H) 4.5 (s, 2H) 3.9 (m, 2H) 3.4 (m, 2H) 3.0 (m, 5H) 2.8 (m, 2H) 1.8 (m, 2H).

Compound 28: {3-[Methanesulfonyl-(3-{2-[2-(3,4,5-trihydroxy-phenyl)-ethylamino]-pyrimidin-4-yl}-benzyl)-amino]-propyl}-carbamic acid tert-butyl ester: Intermediate 4 was coupled with 5-(2-Amino-ethyl)-benzene-1,2,3-triol following procedure F. LC-MS showed the product had the expected M+H+ of 588. $^1$H NMR (Varian 300 MHz, CDCl$_3$, shifts relative to the solvent peak at 7.24 ppm) δ 8.2 (m, 2H) 8.0 (m, 1H) 7.6 (m, 2H) 7.3 (m, 3H) 4.8 (m, 1H) 4.5 (s, 2H) 3.9 (m, 2H) 3.3 (m, 2H) 3.0 (m, 2H) 2.9 (m, 5H) 1.6 (m, 2H) 1.4 (s, 9H).

Compound 29: N-(3-Amino-propyl)-N-(3-{2-[2-(3,5-dichloro-4-hydroxy-phenyl)-ethylamino]-pyrimidin-4-yl}-benzyl)-methanesulfonamide: Intermediate 4 was coupled to 4-(2-Amino-ethyl)-2,6-dichloro-phenol by procedure F and the resulting product was deprotected by procedure G. LC-MS showed the product had the expected M+H+ of 524. $^1$H NMR (Varian 300 MHz, CD$_3$OD, shifts relative to the solvent peak at 3.30 ppm) δ 8.4 (m, 2H) 8.2 (d, 1H) 7.8 (d, 1H) 7.2 (s, 2H) 4.6 (s, 2H) 3.9 (m, 2H) 3.4 (m, 2H) 3.0 (s, 3H) 2.9 (m, 2H) 2.8 (m, 2H) 1.8 (m, 2H).

Compound 30: N-(3-Amino-propyl)-N-(3-{2-[2-(3-chloro-phenyl)-ethylamino]-pyrimidin-4-yl}-benzyl)-methanesulfonamide: Intermediate 4 was coupled to 2-(3-Chloro-phenyl)-ethylamine following procedure F and the resulting product deprotected following procedure G. LC-MS showed the product had the expected M+H+ of 474. $^1$H NMR (Varian 300 MHz, CD$_3$OD, shifts relative to the solvent peak at 3.30 ppm) δ 8.85 (m, 1H) 8.15 (m, 4H) 7.6 (m, 6H) 4.45 (s, 2H) 3.95 (m, 2H) 3.4 (m, 2H) 3.18 (m, 4H) 3.0 (m, 2H) 2.9 (s, 3H) 1.75 (m, 2H).

Compound 31: N-(3-Amino-propyl)-N-(3-{2-[2-(2-chloro-phenyl)-ethylamino]-pyrimidin-4-yl}-benzyl)-methanesulfonamide: Intermediate 4 was coupled to 2-(2-chloro-phenyl)-ethylamine following procedure F and the resulting product deprotected by procedure G. LC-MS showed the product had the expected M+H+ of 474. $^1$H NMR (Varian 300 MHz, CD$_3$OD, shifts relative to the solvent peak at 3.30 ppm) δ 8.8 (m, 1H) 8.18 (m, 4H) 7.6 (m, 6H) 4.45 (s, 2H) 3.95 (m, 2H) 3.4 (m, 2H) 3.18 (m, 4H) 3.0 (m, 2H) 2.9 (s, 3H) 1.75 (m, 2H).

Compound 32: N-(3-Amino-propyl)-N-(3-{2-[2-(4-chloro-phenyl)-ethylamino]-pyrimidin-4-yl}-benzyl)-methanesulfonamide: Intermediate 4 was coupled to 2-(4-chloro-phenyl)-ethylamine following procedure F and the resulting product deprotected following procedure G. LC-MS showed the product had the expected M+H+ of 474. $^1$H NMR (Varian 300 MHz, CD$_3$OD, shifts relative to the solvent peak at 3.30 ppm) δ 8.7 (m, 1H) 8.16 (m, 4H) 7.65 (m, 6H) 4.45 (s, 2H) 3.95 (m, 2H) 3.4 (m, 2H) 3.18 (m, 4H) 3.0 (m, 2H) 2.9 (s, 3H) 1.75 (m, 2H).

Compound 33: N-(3-Amino-propyl)-N-(3-{2-[2-(3-hydroxy-4-nitro-phenyl)-ethylamino]-pyrimidin-4-yl}-benzyl)-methanesulfonamide: Intermediate 4 was coupled with 5-(2-amino-ethyl)-2-nitro-phenol and the resulting product deprotected following procedure G. LC-MS showed the product had the expected M+H+ of 501. $^1$H NMR (Varian 300 MHz, DMSO-d$_6$, shifts relative to the solvent peak at 2.49 ppm) δ 8.4 (d, 1H) 8.1 (m, 2H) 7.8 (m, 4H) 7.6 (s, 1H) 7.3 (m, 1H) 7.1 (s, 1H) 6.9 (d, 1H) 4.4 (s, 2H) 3.7 (m, 2H) 3.6 (s, 1H) 3.2 (m, 2H) 3.0 (s, 3H) 2.9 (m, 2H) 2.7 (m, 2H) 1.7 (m, 2H).

Compound 34: N-(3-Amino-propyl)-N-(3-{2-[2-(2-oxo-2,3-dihydro-benzooxazol-5-yl)-ethylamino]-pyrimidin-4-yl}-benzyl)-methanesulfonamide: Intermediate 4 was coupled to 5-(2-Amino-ethyl)-3H-benzooxazol-2-one following procedure F and the resulting product deprotected following procedure G. LC-MS showed the product had the expected M+H$^+$ of 497. $^1$H NMR (Varian 300 MHz, DMSO-d$_6$, shifts relative to the solvent peak at 2.49 ppm) δ 11.6 (s, 1H) 8.5 (d, 1H) 8.1 (m, 2H) 7.9 (m, 2H) 7.6 (m, 1H) 7.4 (m, 1H) 7.0 (m, 3H) 4.4 (s, 2H) 3.7 (m, 2H) 3.2 (m, 2H) 3.0 (s, 3H) 2.9 (m, 2H) 2.7 (m, 2H) 1.7 (m, 2H).

Compound 35: {3-[(3-{2-[2-(3-Bromo-4-hydroxy-phenyl)-ethylamino]-pyrimidin-4-yl}-benzyl)-methanesulfonyl-amino]-propyl}-carbamic acid tert-butyl ester: Intermediate 4 was coupled to 4-(2-amino-ethyl)-2-bromo-phenol following procedure F. LC-MS showed the product had the expected M+H$^+$ of 634. $^1$H NMR (Varian 300 MHz, CDCl$_3$, shifts relative to the solvent peak at 7.24 ppm) δ 8.3 (m, 1H) 8.1 (m, 1H) 8.0 (d, 1H) 7.5 (m, 3H) 7.4 (s, 1H) 7.1 (m, 2H) 6.9 (d, 1H) 4.9 (m, 1H) 4.5 (s, 2H) 3.8 (m, 2H) 2.9 (m, 5H) 1.6 (m, 2H) 1.4 (s, 9H).

Compound 36: N-(3-Amino-propyl)-N-(3-{2-[2-(3-bromo-4-hydroxy-phenyl)-ethylamino]-pyrimidin-4-yl}-benzyl)-methanesulfonamide: Compound 35 was deprotected following procedure G. LC-MS showed the product had the expected M+H$^+$ of 534. $^1$H NMR (Varian 300 MHz, DMSO-d$_6$, shifts relative to the solvent peak at 2.49 ppm) δ 8.4 (d, 1H) 8.1 (m, 2H) 7.8 (m, 2H) 7.6 (m, 2H) 7.4 (s, 1H) 7.3 (m, 1H) 7.1 (d, 1H) 6.9 (d, 1H) 4.4 (s, 2H) 3.4 (m, 2H) 3.2 (m, 2H) 3.0 (s, 3H) 2.8 (m, 2H) 2.7 (m, 2H) 1.7 (m, 2H).

Intermediate 5: 2-Chloro-4-(3-nitro-phenyl)-pyrimidine: 2,4 dichloropyrimidine was coupled to 3-nitrophenyl boronic acid following procedure A. The workup and purification protocol was modified as follows: The THF was removed from the reaction mixture by rotary evaporation and the residue taken up in ethyl acetate. The solution was washed with water followed by sat. NaCl and the organic layer concentrated by rotary evaporation until the product started to precipitate, at which point the flask was placed in an ice bath for two hours. The product was collected by filtration in a Buchner funnel. The yield was 60%. Product was >95% pure by LC-MS and showed the expected M+H$^+$ of 236.

Intermediate 6: 3-(2-Chloro-pyrimidin-4-yl)-phenylamine: Intermediate 5 was dissolved in ethanol along with 5 mol % of 5% Pt/C. The mixture was stirred under an atmosphere of H$_2$ for 24 hours and then filtered through a pad of Celite to remove catalyst. Removal of the solvent gave product in 90% yield. LC-MS showed purity >95% and the expected M+H$^+$ of 206.

Intermediate 7: 4-[3-(2-Chloro-pyrimidin-4-yl)-phenylamino]-piperidine-1-carboxylic acid tert-butyl ester: Intermediate 6 was coupled with 4-oxo-piperidine-1-carboxylic acid tert-butyl ester by procedure J. The product was purified on silica (1:1 ethyl acetate:hexanes.) Yield: 80%. LC-MS showed purity >95% and the expected M+H$^+$ of 389.

Compound 37: 4-(3-{2-[2-(4-Hydroxy-phenyl)-ethylamino]-pyrimidin-4-yl}-phenylamino)-piperidine-1-carboxylic acid tert-butyl ester: Intermediate 7 was coupled with tyramine following procedure F. LC-MS showed the product had the expected M+H$^+$ of 490. $^1$H NMR (Varian 300 MHz, CDCl$_3$, shifts relative to the solvent peak at 7.24 ppm) δ 8.28 (d, 1H) 7.25 (m, 3H) 7.05 (m, 2H) 6.92 (d, 1H) 6.7 (m, 3H) 5.45 (m, 1H) 4.0 (m, 2H) 3.7 (m, 4H) 3.49 (m, 1H) 2.85 (m, 4H) 2.45 (t, 2H) 1.5 (s, 9H).

Compound 38: 4-(2-{4-[3-(Piperidin-4-ylamino)-phenyl]-pyrimidin-2-ylamino}-ethyl)-phenol: Compound 37 was deprotected by procedure G. LC-MS showed the product had the expected M+H$^+$ of 390. $^1$H NMR (Varian 300 MHz, DMSO-d$_6$, shifts relative to the solvent peak at 2.49 ppm) δ 8.2 (d, 1H) 7.3-7.5 (m, 3H) 6.95-7.25 (m, 4H) 6.7 (m, 2H) 5.45 (m, 1H) 3.6-3.9 (m, 3H) 3.45 (m, 2H) 3.0-3.25 (m, 4H) 2.9 (m, 2H) 2.4 (m, 2H) 1.95 (m, 2H).

Compound 39: 4-(3-{2-[2-(4-Hydroxy-3-methoxy-phenyl)-ethylamino]-pyrimidin-4-yl}-phenylamino)-piperidine-1-carboxylic acid tert-butyl ester: Intermediate 7 was coupled with 4-(2-Amino-ethyl)-2-methoxy-phenol following procedure F. LC-MS showed the product had the expected M+H$^+$ of 520. $^1$H NMR (Varian 300 MHz, CDCl$_3$, shifts relative to the solvent peak at 7.24 ppm) δ 8.30 (d, 1H) 7.25-7.4 (m, 3H) 6.8-7.0 (m, 2H) 6.65-6.78 (m, 3H) 5.45 (m, 1H) 4.0 (m, 2H) 3.82 (s, 3H) 3.7 (m, 4H) 3.49 (m, 1H) 2.85 (m, 4H) 2.0 (m, 2H) 1.5 (s, 9H).

Compound 40: 2-Methoxy-4-(2-{4-[3-(piperidin-4-ylamino)-phenyl]-pyrimidin-2-ylamino}-ethyl)-phenol: Compound 39 was deprotected by procedure G. LC-MS showed the product had the expected M+H$^+$ of 420. $^1$H NMR (Varian 300 MHz, DMSO-d$_6$, shifts relative to the solvent peak at 2.49 ppm) δ 8.2 (d, 1H) 7.3-7.5 (m, 3H) 7.1-7.25 (m, 3H) 7.0 (m, 1H) 6.7 (s, 1H) 4.85 (m, 1H) 3.8 (s, 3H) 3.6-3.9 (m, 3H) 3.45 (m, 2H) 3.3 (m, 2H) 3.15-3.25 (m, 2H) 2.9 (m, 2H) 2.28 (m, 2H) 1.7 (m, 2H).

Compound 41: {4-[3-(Piperidin-4-ylamino)-phenyl]-pyrimidin-2-yl}-(2-thiophen-2-yl-ethyl)-amine: Intermediate 7 was coupled with 2-thiophen-2-yl-ethylamine by procedure F and the resulting product deprotected by procedure G. LC-MS showed the product had the expected M+H$^+$ of 380. $^1$H NMR (Varian 300 MHz, CD$_3$OD, shifts relative to the solvent peak at 3.3 ppm) δ 8.28 (d, 1H) 6.8-7.5 (m, 8H) 4.85 (m, 1H) 3.9 (m, 2H) 3.7 (m, 2H) 3.1-3.5 (m, 4H) 2.2-2.3 (m, 2H) 2.28 (m, 2H) 1.6-1.8 (m, 2H).

Compound 42: Naphthalen-1-ylmethyl-{4-[3-(piperidin-4-ylamino)-phenyl]-pyrimidin-2-yl}-amine: Intermediate 7 was coupled with naphthalen-1-yl-methylamine following procedure F and the resulting product deprotected by procedure G. LC-MS showed the product had the expected M+H$^+$ of 410. $^1$H NMR (Varian 300 MHz, CD$_3$OD, shifts relative to the solvent peak at 3.3 ppm) δ 8.3 (d, 1H) 8.18 (d, 1H) 7.8-8.0 (m, 2H) 7.4-7.7 (m, 7H) 7.32 (m, 1H) 7.0 (m, 1H) 5.32 (s, 2H) 4.95 (m, 1 h) 3.58 (m, 1H) 3.2-3.4 (m, 3H) 2.8-3.1 (m, 2H) 2.1 (m, 2H) 1.65 (m, 2H).

Compound 43: 2-Methoxy-5-(2-{4-[3-(piperidin-4-ylamino)-phenyl]-pyrimidin-2-ylamino}-ethyl)-phenol: Intermediate 7 was coupled with 5-(2-Amino-ethyl)-2-methoxy-phenol following procedure F and the resulting product deprotected following procedure G. LC-MS showed the product had the expected M+H$^+$ of 420. $^1$H NMR (Varian 300 MHz, CD$_3$OD, shifts relative to the solvent peak at 3.3 ppm) δ 8.3 (d, 1H) 7.0-7.6 (m, 8H) 4.95 (m, 1H) 3.89 (m, 1H) 3.7 (m, 1H) 3.4 (m, 2H) 2.9-3.3 (m, 5H) 2.2-2.3 (m, 2H) 1.95 (m, 2H) 1.6-1.8 (m, 2H).

Compound 44: 443-{2-[2-(3-Chloro-4-hydroxy-phenyl)-ethylamino]-pyrimidin-4-yl}-phenylamino)-piperidine-1-carboxylic acid tert-butyl ester: Intermediate 7 was coupled with intermediate 71 following procedure F. LC-MS showed the product had the expected M+H$^+$ of 523. $^1$H NMR (Varian 300 MHz, CDCl$_3$, shifts relative to the solvent peak at 7.24 ppm) δ 6.6-7.4 (m, 9H) 5.5 (m, 1H) 4.05 (m, 2H) 3.7 (m, 4H) 3.5 (m, 1H) 2.8-3.0 (m, 5H) 1.5 (s, 9H) 1.4 (m, 2H).

Compound 45: 2-Chloro-4-(2-{4-[3-(piperidin-4-ylamino)-phenyl]-pyrimidin-2-ylamino}-ethyl)-phenol: Compound 44 was deprotected following procedure G. LC- MS showed the product had the expected M+H+ of 424. ¹H NMR (Varian 300 MHz, CD₃OD, shifts relative to the solvent peak at 3.3 ppm) δ 8.2 (d, 1H) 6.95-7.5 (m, 9H), 6.8 (m, 1H) 4.9 (m, 1H) 3.85 (m, 1H) 3.72 (m, 1H) 3.4-3.5 (m, 2H) 3.05-3.2 (m, 3H) 2.9 (m, 2H) 2.25 (m, 2H) 1.6-1.8 (m, 2H).

Compound 46: (2-Benzo[1,3]dioxol-5-yl-ethyl)-{4-[3-(piperidin-4-ylamino)-phenyl]-pyrimidin-2-yl}-amine: Intermediate was coupled with 2-benzo[1,3]dioxol-5-yl-ethylamine following procedure F and the resulting product deprotected following procedure G. LC-MS showed the product had the expected M+H+ of 418. ¹H NMR (Varian 300 MHz, CD₃OD, shifts relative to the solvent peak at 3.3 ppm) δ 8.2 (d, 1H) (6.95-7.5 (m, 7H) 6.68 (m, 2H) 5.8 (s, 2H) 4.95 (m, 1H) 3.6-3.9 (m, 4H) 3.4 (m, 2H) 3.15 (m, 2H) 2.25 (m, 3H) 1.7 (m, 2H).

Compound 47: [2-(3-Fluoro-phenyl)-ethyl]-{4-[3-(piperidin-4-ylamino)-phenyl]-pyrimidin-2-yl}-amine: Intermediate 7 was coupled with 2-(3-fluoro-phenyl)-ethylamine following procedure F and the resulting product deprotected following procedure G. LC-MS showed the product had the expected M+H+ of 393. ¹H NMR (Varian 300 MHz, CD₃OD, shifts relative to the solvent peak at 3.3 ppm) δ 8.2 (d, 1H) 6.95-7.6 (m, 8H) 6.9 (m, 1H) 4.95 (m, 1H) 3.6-4.0 (m, 3H) 3.4 (m, 3H) 3.15 (m, 2H) 3.0 (m, 2H) 2.25 (m, 2H) 1.7 (m, 2H).

Compound 48: 2,6-Dichloro-4-(2-{4-[3-(piperidin-4-ylamino)-phenyl]-pyrimidin-2-ylamino}-ethyl)-phenol: Intermediate 7 was coupled with 4-(2-Amino-ethyl)-2,6-dichloro-phenol following procedure F and the resulting product deprotected following procedure G. LC-MS showed the product had the expected M+H+ of 458. ¹H NMR (Varian 300 MHz, CD₃OD, shifts relative to the solvent peak at 3.3 ppm) δ 8.2 (d, 1H) 7.05-7.6 (m, 6H) 7.0 (m, 1H) 4.95 (m, 1H) 3.6-4.0 (m, 3H) 3.4 (m, 2H) 3.1-3.2 (m, 2H) 2.8-2.95 (m, 2H) 2.25 (m, 3H) 1.7 (m, 2H).

Compound 49: 3-(2-{4-[3-(Piperidin-4-ylamino)-phenyl]-pyrimidin-2-ylamino}-ethyl)-phenol: Intermediate 7 was coupled with 3-(2-amino-ethyl)-phenol following procedure F and the resulting product deprotected following procedure G. LC-MS showed the product had the expected M+H+ of 390. ¹H NMR (Varian 300 MHz, DMSO-d₆, shifts relative to the solvent peak at 2.49 ppm) δ 8.8 (m, 5H) 8.4 (d, 1H) 7.4 (m, 2H) 7.3 (m, 1H) 7.0 (d, 1H) 6.9 (m, 1H) 3.7 (m, 2H) 3.4 (m, 1H) 3.1 (m, 2H) 2.9 (m, 3H) 2.1 (m, 1H) 1.8 (m, 2H) 1.5 (m, 2H).

Compound 50: 2-Bromo-4-(2-{4-[3-(piperidin-4-ylamino)-phenyl]-pyrimidin-2-ylamino}-ethyl)-phenol: Intermediate 7 was coupled with 4-(2-Amino-ethyl)-2-bromo-phenol following procedure F and the resulting product deprotected following procedure G. LC-MS showed the product had the expected M+H+ of 468. ¹H NMR (Varian 300 MHz, DMSO-d₆, shifts relative to the solvent peak at 2.49 ppm) δ 8.8 (m, 5H) 8.4 (d, 1H) 7.4 (m, 2H) 7.3 (m, 1H) 7.0 (d, 1H) 6.9 (m, 1H) 3.7 (m, 2H) 3.4 (m, 1H) 3.1 (m, 2H) 2.9 (m, 3H) 2.1 (m, 1H) 1.8 (m, 2H) 1.5 (m, 2H).

Compound 51: (6-Fluoro-4H-benzo[1,3]dioxin-8-ylm-ethyl)-{4-[3-(piperidin-4-ylamino)-phenyl]-pyrimidin-2-yl}-amine: Intermediate 7 was coupled with C-(6-fluoro-4H-benzo[1,3]dioxin-8-yl)-methylamine following procedure F and the resulting intermediate 4eprotected following procedure G. LC-MS showed the product had the expected M+H+ of 436. ¹H NMR (Varian 300 MHz, DMSO-d₆, shifts relative to the solvent peak at 2.49 ppm) δ 8.6 (s, 1H) 8.4 (d, 1H) 8.3 (d, 1H) 7.8 (t, 1H) 7.4 (d, 1H), 7.2 (d, 1H), 7.1 (d, 2H), 6.6 (d, 2H), 3.4 (d, 2H), 2.8 (d, 2H).

Compound 52: 4-{2-[4-(3-Nitro-phenyl)-pyrimidin-2-ylamino]-ethyl}-phenol: Intermediate 5 was coupled with tyramine following procedure F. LC-MS showed the product had the expected M+H+ of 337. ¹H NMR (Varian 300 MHz, DMSO-d₆, shifts relative to the solvent peak at 2.49 ppm) (d, 1H) 7.6-6.6 (m, 7H) 6.0 (d, 2H) 4.85 (s, 2H) 4.40 (d, 2H) 3.0 (m, 1H), 2.0 (m, 4H), 1.6 (m, 4H).

Intermediate 8: 3-[3-(2-Chloro-pyrimidin-4-yl)-phenyl-amino]-piperidine-1-carboxylic acid tert-butyl ester: Intermediate 6 was coupled with 3-oxo-piperidine-1-carboxylic acid tert-butyl ester by procedure J. The product was purified on silica (1:1 ethyl acetate:hexanes) Yield: 65%. LC-MS showed the product had the expected M+H+ of 389.

Compound 53: 4-(2-{4-[3-(Piperidin-3-ylamino)-phenyl]-pyrimidin-2-ylamino}-ethyl)-phenol: Intermediate 8 was coupled with tyramine following procedure F and the resulting product deprotected by procedure G. LC-MS showed the product had the expected M+H+ of 390. ¹H NMR (Varian 300 MHz, CD₃OD, shifts relative to the solvent peak at 3.3 ppm) δ 8.2 (d, 1H) 6.95-7.6 (m, 8H) 6.7 (m, 2H) 4.95 (m, 1H) 3.7-3.9 (m, 2H) 3.5 (m, 1H) 2.8-3.2 (m, 5H) 1.6-2.4 (m, 5H).

Compound 54: 2-Chloro-4-(2-{4-[3-(piperidin-3-ylamino)-phenyl]-pyrimidin-2-ylamino}-ethyl)-phenol: Intermediate 8 was coupled with intermediate 71 following procedure F and the resulting product deprotected following procedure G. LC-MS showed the product had the expected M+H+ of 424. ¹H NMR (Varian 300 MHz, CD₃OD, shifts relative to the solvent peak at 3.3 ppm) δ 8.2 (d, 1H) 6.95-7.6 (m, 8H) 6.8 (d, 1H) 4.95 (m, 1H) 3.7-3.9 (m, 2H) 3.5 (m, 1H) 2.8-3.2 (m, 5H) 1.6-2.3 (m, 5H).

Intermediate 8b: 3-[3-(2-Chloro-pyrimidin-4-yl)-phenyl-amino]-pyrrolidine-1-carboxylic acid tert-butyl ester: Intermediate 6 was coupled with 3-oxo-pyrrolidine-1-carboxylic acid tert-butyl ester following procedure J. The product was purified on silica gel using 1:1 ethyl acetate:hexanes as eluent. Yield: 70%. LC-MS showed the product had the expected M+H+ of 375.

Compound 55: 4-(2-{4-[3-(Pyrrolidin-3-ylamino)-phenyl]-pyrimidin-2-ylamino}-ethyl)-phenol: Intermediate 8b was coupled with tyramine following procedure F and the resulting product deprotected following procedure G. LC-MS showed the product had the expected M+H+ of 376. ¹H NMR (Varian 300 MHz, CD₃OD, shifts relative to the solvent peak at 3.3 ppm) δ 8.2 (d, 1H) 7.0-7.5 (m, 4H) 6.9 (d, 1H) 6.68 (d, 2H) 5.05 (m, 1H) 4.28 (m, 1H) 3.8 (m, 2H) 3.2-3.6 (m, 4H) 2.9 (m, 2H) 2.0-2.6 (m, 2H).

Compound 56: N-{3-[(3-{2-[2-(4-Hydroxy-phenyl)-ethyl-amino]-pyrimidin-4-yl}-benzyl)-methanesulfonyl-amino]-propyl}-benzamide: Compound 2 was coupled with benzoic acid by procedure K. LC-MS showed the product had the expected M+H+ of 560. ¹H NMR (Varian 300 MHz, CD₃OD, shifts relative to the solvent peak at 3.35 ppm) 8.5 (d, 1H) 8.2 (d, 1H) 8.1 (s, 1H) 8.0 (d, 2H) 7.6 (d, 2H), 7.4 (m, 5H), 7.1 (m, 2H), 6.7 (d, 2H), 4.4 (s, 2H), 3.6 (t, 2H), 3.23 (d, 2H), 2.9 (s, 3H), 2.8 (t, 2H), 1.8 (m, 2H).

Compound 57: N-{3-[(3-{2-[2-(4-Hydroxy-phenyl)-ethyl-amino]-pyrimidin-4-yl}-benzyl)-methanesulfonyl-amino]-propyl}-2-methyl-benzamide: Compound 2 was coupled with 2-methylbenzoic acid by procedure K. LC-MS showed the product had the expected M+H+ of 574. ¹H NMR (Varian 300 MHz, CD₃OD, shifts relative to the solvent peak at 3.3 ppm) δ 8.3 (d, 1H) 8.2 (s, 1H) 8.0 (d, 1H) 7.6 (m, 2H) 7.3 (m, 7H), 6.8 (d, 2H), 4.4 (s, 2H), 3.7 (t, 2H), 3.3 (d, 2H), 3.2 (d, 2H) 184 (s, 3H), 2.3 (s, 3H), 1.8 (m, 2H).

Compound 58: 4-Chloro-N-{3-[(3-{2-[2-(4-hydroxy-phe-nyl)-ethylamino]-pyrimidin-4-yl}-benzyl)-methanesulfo-nyl-amino]-propyl}-benzamide: Compound 2 was coupled with 4-chlorobenzoic acid following procedure K. LC-MS showed the product had the expected M+H+ of 594. ¹H NMR (Varian 300 MHz, CD₃OD, shifts relative to the solvent peak at 3.3 ppm) δ 8.23 (d, 1H) 8.1 (d, 1H) 7.6 (d, 2H) 7.5 (d, 2H) 7.4 (m, 2H), 7.3 (d, 2H), 7.1 (d, 2H), 7.0 (d, 2H), 6.7 (d, 2H), 4.5 (s, 2H) 3.6 (t, 2H), 3.1 (d, 2H), δ 3.0 (s, 3H), 2.8 (t, 2H), δ 1.8 (m, 2H).

Compound 59: N-{3-[(3-{2-[2-(4-Hydroxy-phenyl)-ethylamino]-pyrimidin-4-yl}-benzyl)-methanesulfonyl-amino]-propyl}-4-methyl-benzamide: Compound 2 was coupled with 4-methylbenzoic acid following procedure K. LC-MS showed the product had the expected M+H$^+$ of 574. $^1$H NMR (Varian 300 MHz, DMSO-d$_6$, shifts relative to the solvent peak at 2.49 ppm) δ 8.0 (d, 2H) 7.65 (d, 2H) 7.50 (d, 2H) 7.2 (m, 3H) 7.0 (m, 3H), 6.7 (d, 2H), 4.4 (s, 2H), 3.45 (t, 2H), 3.2 (d, 4H), 3.0 (s, 3H) 2.7 (t, 2H), 2.45 (s, 3H), 1.8 (m, 2H).

Compound 60: Pyridine-2-carboxylic acid {3-[(3-{2-[2-(4-hydroxy-phenyl)-ethylamino]-pyrimidin-4-yl}-benzyl)-methanesulfonyl-amino]-propyl)-amide: Compound 2 was coupled with pyridine-2-carboxylic acid following procedure K. LC-MS showed the product had the expected M+H$^+$ of 561. $^1$H NMR (Varian 300 MHz, DMSO-D6, shifts relative to the solvent peak at 2.49 ppm) δ 8.7 (d, 1H) 8.6 (t, 1H) 8.3 (d, 1H) 8.0 (s, 1H) 7.9 (t, 1H), 7.5 (m, 3H), 7.2 (t, 1H), 7.0 (m, 3H), 6.6 (d, 2H), 4.4 (s, 2H), δ 3.4 (t, 2H), 3.2 (m, 4H), 3.0 (s, 3H), 2.7 (t, 2H), δ 1.7 (m, 2H).

Compound 61: 3-Chloro-N-{3-[(3-{2-[2-(4-hydroxy-phenyl)-ethylamino]-pyrimidin-4-yl}-benzyl)-methanesulfonyl-amino]-propyl}-benzamide: Compound 2 was coupled with 3-chlorobenzoic acid following procedure K. LC-MS showed the product had the expected M+H$^+$ of 594. $^1$H NMR (Varian 300 MHz, CDCl$_3$, shifts relative to the solvent peak at 7.24 ppm) δ 8.3 (d, 1H) 7.82 (s, 1H) 7.7 (d, 1H) 7.55 (d, 2H) 7.2 (m, 2H), 7.3 (m, 2H), 6.9 (m, 2H), 6.8 (d, 2H), 6.71 (d, 1H), 6.5 (d, 2H), δ 4.2 (s, 2H), 3.49 (t, 2H), 3.2 (d, 2H), 3.5 (t, 2H), δ 2.6 (s, 3H), δ 1.4 (m, 2H).

Compound 62: 3-Chloro-N-{3-[(3-{2-[2-(4-hydroxy-phenyl)-ethylamino]-pyrimidin-4-yl}-benzyl)-methanesulfonyl-amino]-propyl}-benzamide: Compound 2 was coupled with 2-methyl nicotinic acid following procedure K. LC-MS showed the product had the expected M+H$^+$ of 575. $^1$H NMR (Varian 300 MHz, CD$_3$OD, shifts relative to the solvent peak at 3.3 ppm) δ 8.4 (d, 1H) 8.3 (d, 1H) 8.0 (d, 1H) 7.62 (m, 2H) 7.5 (t, 1H), 7.2 (d, 1H), 7.0 (m, 4H), 6.7 (d, 2H), 4.5 (s, 2H), 3.6 (t, 2H), δ 3.3 (d, 4H), 3.0 (s, 3H), 2.8 (t, 2H), 2.4 (s, 3H), δ 2.8 (t, 2H).

Compound 63: N-{3-[(3-{2-[2-(4-Hydroxy-phenyl)-ethylamino]-pyrimidin-4-yl}-benzyl)-methanesulfonyl-amino]-propyl}-2-methoxy-benzamide: Compound 2, was coupled with 2-methoxybenzoic acid following procedure K. LC-MS showed the product had the expected M+H$^+$ of 590. $^1$H NMR (Varian 300 MHz, CDCl$_3$, shifts relative to the solvent peak at 7.24 ppm) δ 8.2 (d, 1H) 8.0 (s, 1H) 7.9 (s, 1H) 7.7 (t, 1H) 7.5 (m, 5H), 7.1 (d, 1H), 6.9 (d, 2H), 6.8 (d, 2H), 4.5 (s, 2H), 3.8 (s, 3H), δ 3.7 (t, 2H), 3.5 (t, 2H), 3.3 (t, 2H), 2.9 (t, 2H), δ 2.8 (s, 3H), δ 1.8 (m, 2H).

Compound 64: N-{3-[(3-{2-[2-(4-Hydroxy-phenyl)-ethylamino]-pyrimidin-4-yl}-benzyl)-methanesulfonyl-amino]-propyl}-C-phenyl-methanesulfonamide: Compound 2 was coupled with phenyl-methanesulfonyl chloride following procedure D. LC-MS showed the product had the expected M+H$^+$ of 610. $^1$H NMR (Varian 300 MHz, CD$_3$OD, shifts relative to the solvent peak at 3.3 ppm) δ 8.3 (d, 1H), 8.0 (d, 1H) 7.5 (m, 3H) 7.3 (d, 2H), 7.2 (m, 4H), 6.7 (d, 4H), 4.4 (s, 2H), 4.2 (s, 2H), 3.6 (t, 2H), 3.2 (t, 2H), δ 2.9 (s, 3H), 2.7 (t, 2H), 2.7 (t, 2H), δ 1.6 (m, 2H).

Compound 65: N-{3-[(3-{2-[2-(4-Hydroxy-phenyl)-ethylamino]-pyrimidin-4-yl}-benzyl)-methanesulfonyl-amino]-propyl}-benzenesulfonamide: Compound 2 was coupled with benzenesulfonyl chloride following procedure D. LC-MS showed the product had the expected M+H$^+$ of 596. $^1$H NMR (Varian 300 MHz, CD$_3$OD, shifts relative to the solvent peak at 3.3 ppm) δ 8.3 (d, 1H), 8.0 (d, 1H) 7.5 (m, 3H) 7.3 (d, 2H), 7.2 (m, 4H), 6.7 (d, 4H), 4.4 (s, 2H), 4.2 (s, 2H), 3.6 (t, 2H), 3.2 (t, 2H), δ 2.9 (s, 3H), 2.7 (t, 2H), 2.7 (t, 2H), δ 1.6 (m, 2H).

Intermediate 8c: 3-(2-Chloro-pyrimidin-4-yl)-benzoic acid ethyl ester: 2,4 dichloropyrimidine was coupled to 3-carboethoxyphenylboronic acid following procedure A. LC-MS showed the product to be >95% pure and to have the expected M+H$^+$ of 195.

Compound 66: 3-{2-[2-(4-Hydroxy-phenyl)-ethylamino]-pyrimidin-4-yl}-benzoic acid ethyl ester: Intermediate 8c was coupled with tyramine following procedure F. LC-MS showed the product had the expected M+H$^+$ of 364. $^1$H NMR (Varian 300 MHz, DMSO-d$_6$, shifts relative to the solvent peak at 2.49 ppm) δ 9.15 (s, 1H) 8.72 (br s, 8.35 (m, 2H) 8.07 (d, 1H) 7.65 (m, 1H) 7.18 (m, 1H) 7.05 (m, 2H) 6.68 (d, 2H) 4.35 (q, 2H) 3.5 (m, 2H) 2.78 (m, 2H) 1.35 (t, 3H).

Intermediate 9: 3-{2-[2-(4-Hydroxy-phenyl)-ethylamino]-pyrimidin-4-yl}-benzoic acid: Compound 66 (2.4 g) was treated with 20 equivalents of sodium hydroxide in methanol. The mixture was heated at 50 C for 2 hours and the solvent removed by rotary evaporation. The residue was taken up in water and brought to pH 7 by addition of 1N HCl. The solvent was again removed by rotary evaporation. LC-MS showed the product had the expected M+H$^+$ of 336. The crude product containing NaCl was used without purification in the next step.

Compound 67: 3-{2-[2-(4-Hydroxy-phenyl)-ethylamino]-pyrimidin-4-yl}-N-pyrrolidin-3-ylmethyl-benzamide: Intermediate 9 (2.2 mmol) was coupled with 3-aminomethyl-pyrrolidine-1-carboxylic acid tert-butyl ester (5 mmol) using EDC (3 mmol) in DMF (20 mL). The DMF was removed by rotary evaporation and the residue purified by flash chromatography on silica gel (ethyl acetate as eluent.) The resulting product was deprotected following procedure G. LC-MS showed the product had the expected M+H$^+$ of 418. $^1$H NMR (Varian 300 MHz, DMSO-d$_6$, shifts relative to the solvent peak at 2.49 ppm) δ 8.9 (s, 1H) 8.5-8.75 (m, 2H) 8.3 (m, 1H) 8.0 (d, 1H) 7.65 (m, 1H) 7.3 (m, 1H) 7.05 (m, 2H) 6.68 (d, 2H) 3.6 (m, 2H) 3.4 (m, 2H) 3.2-3.4 (m, 2H) 2.48 (m, 3H) 2.0 (m, 2H) 1.7 (m, 2H).

Compound 68: N-(3-Amino-propyl)-3-{2-[2-(4-hydroxyphenyl)-ethylamino]-pyrimidin-4-yl}-benzamide: Intermediate 9 (1 mmol) was coupled with (3-Amino-propyl)-carbamic acid tert-butyl ester (3 mmol) using EDC (2 mmol) in DMF (10 mL). The DMF was removed by rotary evaporation and the residue purified by flash chromatography on silica gel (ethyl acetate as eluent.) The resulting product was deprotected following procedure G. LC-MS showed the product had the expected M+H$^+$ of 392. $^1$H NMR (Varian 300 MHz, CD$_3$OD, shifts relative to the solvent peak at 3.3 ppm) δ 8.68 (s, 1H) 8.35-8.5 (m, 3H) 8.1 (d, 1H) 7.7 (m, 1H) 7.48 (d, 1H) 7.2 (d, 2H) 6.68 (d, 2H) 3.8 (m, 2H) 3.55 (m, 2H) 3.05 (m, 2H) 2.9 (m, 4H) 2.0 (t, 2H).

Compound 69: 3-{2-[2-(4-Hydroxy-phenyl)-ethylamino]-pyrimidin-4-yl}-N-piperidin-2-ylmethyl-benzamide: Intermediate 9 (1 mmol) was coupled with 2-aminomethyl-piperidine-1-carboxylic acid tert-butyl ester (3 mmol) using EDC (2 mmol) in DMF (10 mL). The DMF was removed by rotary evaporation and the residue purified by flash chromatography on silica gel (ethyl acetate as eluent). The resulting product was deprotected following procedure G. LC-MS showed the product had the expected M+H$^+$ of 432. $^1$H NMR (Varian 300 MHz, DMSO-d$_6$, shifts relative to the solvent peak at 2.49 ppm) δ 8.5-8.65 (m, 2H) 8.38 (m, 1H) 8.22 (m, 1H) 7.95 (m, 1H) 7.55 (m, 1H) 7.28 (m, 1H) 7.20 (d, 1H) 7.05 (d, 2H) 6.68 (d, 2H) 3.5 (m, 2H) 3.3 (m, 2H) 2.95 (m, 1H) 2.6-2.85 (m, 3H) 2.48 (m, 1H) 1.0-1.7 (m, 6H).

Intermediate 10: [3-(2-Chloro-pyrimidin-4-yl)-benzyl]-pyridin-2-ylmethyl-amine: Intermediate 1 was coupled with pyridin-2-yl-methylamine following procedure B. LC-MS showed the product had the expected M+H+ of 311.

Intermediate 11: N-[3-(2-Chloro-pyrimidin-4-yl)-benzyl]-N-pyridin-2-ylmethyl-methanesulfonamide: Intermediate 10 was coupled with methanesulfonyl chloride following procedure D. LC-MS showed the product had the expected M+H+ of 389.

Compound 70: N-(3-{2-[2-(4-Hydroxy-phenyl)-ethylamino]-pyrimidin-4-yl}-benzyl)-N-pyridin-2-ylmethyl-methanesulfonamide: Intermediate 11 was coupled with tyramine following procedure F. LC-MS showed the product had the expected M+H+ of 490. $^1$H NMR (Varian 300 MHz, CDCl$_3$, shifts relative to the solvent peak at 7.24 ppm) δ 8.6 (d, 1H) 8.3 (d, 1H) 7.9 (s, 2H) 7.6 (m, 1H) 7.4 (m, 2H) 7.3 (m, 2H) 7.2 (m, 1H) 7.0 (d, 2H) 6.9 (d, 1H) 6.7 (d, 2H) 5.5 (m, 1H) 4.5 (d, 4H) 3.7 (m, 2H) 3.0 (s, 3H) 2.9 (m, 2H).

Intermediate 12: [3-(2-Chloro-pyrimidin-4-yl)-benzyl]-pyridin-3-ylmethyl-amine: Intermediate 1 was coupled with pyridin-3-yl-methylamine following procedure B. LC-MS showed the product had the expected M+H+ of 311.

Intermediate 13: N-[3-(2-Chloro-pyrimidin-4-yl)-benzyl]-N-pyridin-3-ylmethyl-methanesulfonamide: Intermediate 12 was coupled with methanesulfonyl chloride following procedure D. LC-MS showed the product had the expected M+H+ of 389.

Compound 71: N-(3-{2-[2-(4-Hydroxy-phenyl)-ethylamino]-pyrimidin-4-yl}-benzyl)-N-pyridin-3-ylmethyl-methanesulfonamide: Intermediate 13 was coupled with tyramine following procedure F. LC-MS showed the product had the expected M+H+ of 490. $^1$H NMR (Varian 300 MHz, CDCl$_3$, shifts relative to the solvent peak at 7.24 ppm) δ 8.5 (d, 2H) 8.4 (s, 1H) 8.3 (d, 1H) 7.9 (m, 4H) 7.4 (d, 2H) 7.3 (m, 1H) 7.1 (d, 2H) 6.9 (d, 1H) 6.7 (d, 1H) 5.6 (m, 1H) 4.4 (d, 4H) 3.7 (m, 2H) 2.9 (m, 5H).

Intermediate 14: [3-(2-Chloro-pyrimidin-4-yl)-benzyl]-pyridin-4-ylmethyl-amine: Intermediate 1 was coupled with pyridin-4-yl-methylamine following procedure B. LC-MS showed the product had the expected M+H+ of 311.

Intermediate 15: N-[3-(2-Chloro-pyrimidin-4-yl)-benzyl]-N-pyridin-4-ylmethyl-methanesulfonamide: Intermediate 14 was coupled with methanesulfonyl chloride following procedure D. LC-MS showed the product had the expected M+H+ of 389.

Compound 72: N-(3-{2-[2-(4-Hydroxy-phenyl)-ethylamino]-pyrimidin-4-yl}-benzyl)-N-pyridin-4-ylmethyl-methanesulfonamide: Intermediate 15 was coupled with tyramine following procedure F. LC-MS showed the product had the expected M+H+ of 490. $^1$H NMR (Varian 300 MHz, CDCl$_3$, shifts relative to the solvent peak at 7.24 ppm) δ 8.4 (d, 2H) 8.2 (d, 1H) 7.9 (m, 2H) 7.4 (m, 2H) 7.2 (d, 2H) 7.0 (d, 2H) 6.9 (d, 1H) 6.7 (d, 2H) 4.4 (s, 2H) 4.3 (s, 2H) 3.6 (m, 2H) 2.9 (m, 5H).

Intermediate 16: [3-(2-Chloro-pyrimidin-4-yl)-benzyl]-(2-pyridin-2-yl-ethyl)-amine: Intermediate 1 was coupled with 2-pyridin-2-yl-ethylamine following procedure B. LC-MS showed the product had the expected M+H+ of 325.

Intermediate 17: N-[3-(2-Chloro-pyrimidin-4-yl)-benzyl]-N-(2-pyridin-2-yl-ethyl)-methanesulfonamide: Intermediate 16 was coupled with methanesulfonyl chloride following procedure D. LC-MS showed the product had the expected M+H+ of 403.

Compound 73: N-(3-{2-[2-(4-hydroxy-phenyl)-ethylamino]-pyrimidin-4-yl}-benzyl)-N-(2-pyridin-2-yl-ethyl)-methanesulfonamide: Intermediate 17 was coupled with tyramine following procedure F. LC-MS showed the product had the expected M+H+ of 504. $^1$H NMR (Varian 300 MHz, CDCl$_3$, shifts relative to the solvent peak at 7.24 ppm) δ 8.5 (d, 1H) 8.3 (d, 1H) 7.9 (m, 2H) 7.6 (m, 1H) 7.4 (m, 2H) 7.2 (m, 2H) 7.0 (d, 2H) 6.9 (d, 1H) 6.7 (d, 2H) 5.4 (s, br, 1H) 4.4 (s, 2H) 3.7 (m, 2H) 3.6 (m, 2H) 3.0 (m, 2H) 2.8 (m, 2H) 2.8 (s, 3H).

Intermediate 18: [3-(2-Chloro-pyrimidin-4-yl)-benzyl]-(2-pyridin-3-yl-ethyl)-amine: Intermediate 1 was coupled with 2-pyridin-3-yl-ethylamine following procedure B. LC-MS showed the product had the expected M+H+ of 325.

Intermediate 19: N-[3-(2-Chloro-pyrimidin-4-yl)-benzyl]-N-(2-pyridin-3-yl-ethyl)-methanesulfonamide: Intermediate 18 was coupled with methanesulfonyl chloride following procedure D. LC-MS showed the product had the expected M+H+ of 403.

Compound 74: N-(3-{2-[2-(4-hydroxy-phenyl)-ethylamino]-pyrimidin-4-yl}-benzyl)-N-(2-pyridin-3-yl-ethyl)-methanesulfonamide: Intermediate 19 was coupled with tyramine following procedure F. LC-MS showed the product had the expected M+H+ of 504. $^1$H NMR (Varian 300 MHz, CDCl$_3$, shifts relative to the solvent peak at 7.24 ppm) δ 8.4 (d, 1H) 8.3 (s, 2H) 8.0 (s, 1H) 7.9 (d, 1H) 7.5 (m, 3H) 7.2 (m, 1H) 7.0 (d, 2H) 6.9 (d, 1H) 6.7 (d, 2H) 5.5 (m, 1H) 4.4 (s, 2H) 3.7 (m, 2H) 3.4 (m, 2H) 2.8 (m, 7H).

Intermediate 20: [3-(2-Chloro-pyrimidin-4-yl)-benzyl]-(2-pyridin-4-yl-ethyl)-amine: Intermediate 1 was coupled with 2-pyridin-4-yl-ethylamine following procedure B. LC-MS showed the product had the expected M+H+ of 325.

Intermediate 21: N-[3-(2-chloro-pyrimidin-4-yl)-benzyl]-N-(2-pyridin-4-yl-ethyl)-methanesulfonamide: Intermediate 20 was coupled with methanesulfonyl chloride following procedure D. LC-MS showed the product had the expected M+H+ of 403.

Compound 75: N-(3-{2-[2-(4-hydroxy-phenyl)-ethylamino]-pyrimidin-4-yl}-benzyl)-N-(2-pyridin-4-yl-ethyl)-methanesulfonamide: Intermediate 21 was coupled with tyramine following procedure F. LC-MS showed the product had the expected M+H+ of 504. $^1$H NMR (Varian 300 MHz, CDCl$_3$, shifts relative to the solvent peak at 7.24 ppm) δ 8.4 (d, 2H) 8.3 (d, 1H) 8.0 (s, 1H) 7.9 (m, 1H) 7.5 (m, 2H) 7.0 (m, 4H) 6.9 (d, 1H) 6.7 (d, 2H) 5.5 (m, 1H) 4.4 (s, 2H) 3.7 (m, 2H) 3.5 (, 2H) 2.8 (m, 7H).

Intermediate 22: [3-(2-chloro-pyrimidin-4-yl)-benzyl]-ethyl-amine: Intermediate 1 was coupled with ethylamine following procedure B. LC-MS showed the product had the expected M+H+ of 248.

Intermediate 23: [3-(2-chloro-pyrimidin-4-yl)-benzyl]-ethyl-pyridin-3-ylmethyl-amine: Intermediate 22 was coupled with pyridine-3-carboxaldehyde following procedure E. LC-MS showed the product had the expected M+H+ of 339.

Compound 76: 4-[2-(4-{3-[(Ethyl-pyridin-3-ylmethyl-amino)-methyl]-phenyl}-pyrimidin-2-ylamino)-ethyl]-phenol: Intermediate 23 was coupled with tyramine following procedure F. LC-MS showed the product had the expected M+H+ of 440. $^1$H NMR (Varian 300 MHz, CDCl$_3$, shifts relative to the solvent peak at 7.24 ppm) δ 8.63 (s, 1H) 8.49 (m, 1H) 8.26 (m, 1H) 8.15 (s, 1H) 8.05 (s, 1H) 7.45 (m, 2H) 7.25 (m, 1H) 7.05 (m, 3H) 6.99 (d, 1H) 6.75 (m, 4H) 3.4-3.8 (m, 4H) 2.88 (t, 2H) 2.75 (t, 2H) 2.55 (m, 2H) 1.05 (t, 3H).

Intermediate 24: 4-{2-[4-(3-Amino-phenyl)-pyrimidin-2-ylamino]-ethyl}-phenol: Compound 52 was reduced by procedure I. LC-MS showed the product had the expected M+H+ of 307. ¹H NMR (Varian 300 MHz, DMSO-d₆, shifts relative to the solvent peak at 2.49 ppm) δ 9.2 (d, 1H) 8.8 (t, 1H) 8.3 (d, 1H) 7.9 (d, 1H) 7.4-6.9 (m 4H), 6.7 (d, 1H), 3.4 (t, 2H), 2.8 (t 2H).

Compound 77: 3-Amino-N-(3-{2-[2-(4-hydroxy-phenyl)-ethylamino]-pyrimidin-4-yl}-phenyl)-propionamide: Intermediate 24 was coupled to 3-tert-butoxycarbonylamino-propionic acid by procedure K. The resulting product was deprotected by procedure G. LC-MS showed the product had the expected M+H⁺ of 377. ¹H NMR (Varian 300 MHz, CD₃OD, shifts relative to the solvent peak at 3.3 ppm) δ 8.6 (d, 1H) 8.4 (d, 1H) 8.1 (s, 1H) 7.8 (d, 1H) 7.5 (t 3H), 7.2 (d, 1H), 7.1 (d, 2H), 6.7 (d 2H), 3.6 (d, 2H), 3.1 (d, 2H), 2.8 (d, 2H), 2.5 (d, 2H).

Compound 78: N-(3-{2-[2-(4-Hydroxy-phenyl)-ethylamino]-pyrimidin-4-yl}-phenyl)-3-pyridin-3-yl-propionamide: Intermediate 24 was coupled to 3-Pyridin-3-yl-propionic acid following procedure K. LC-MS showed the product had the expected M+H⁺ of 440. ¹H NMR (Varian 300 MHz, DMSO-d₆, shifts relative to the solvent peak at 2.49 ppm) δ 9.1 (s, 1H), 8.5 (d, 1H) 8.3 (d, 1H) 7.7 (m, 3H), 7.4 (t, 1H), 7.3 (t, 1H), 7.2 (d, 1H), 7.1 (d, 1H), 7.0 (d, 2H), 6.7 (d, 2H), δ 3.5 (t, 2H), 2.9 (t, 2H), 2.8 (t, 2H), δ 2.7 (t, 2H).

Compound 79: N-(3-{2-[2-(4-Hydroxy-phenyl)-ethylamino]-pyrimidin-4-yl}-phenyl)-C-phenyl-methanesulfonamide: Intermediate 24 was coupled with phenyl-methylsulfonyl chloride following procedure D. LC-MS showed the product had the expected M+H⁺ of 461. ¹H NMR (Varian 300 MHz, DMSO-d₆, shifts relative to the solvent peak at 2.49 ppm) δ 8.4 (d, 1H), 8.0 (d, 1H) 7.8 (d, 1H) 7.5 (t, 2H), 7.3 (m, 4H), 7.1 (d, 2H), 7.0 (d, 2H), 6.9 (d, 2H), 4.5 (s, 2H), 3.5 (t, 2H), δ 2.8 (t, 2H).

Intermediate 25: 4-[2-(4-{3-[(Pyridin-3-ylmethyl)-amino]-phenyl}-pyrimidin-2-ylamino)-ethyl]-phenol: Intermediate 24 was coupled with pyridine 3-carboxaldehyde following procedure E. LC-MS showed the product had the expected M+H⁺ of 398. ¹H NMR (Varian 300 MHz, CD₃OD, shifts relative to the solvent peak at 3.3 ppm) δ 8.6 (s, 1H), 8.4 (d, 1H) 8.2 (d, 1H) 7.8 (d, 1H), 7.4-7.3 (m, 3H), 7.2 (t, 1H), 7.1 (d, 2H), 6.9 (d, 2H), 6.8 (d, 1H), 6.7 (d, 1H), δ 4.4 (s, 2H), δ 3.6 (t, 2H), 2.8 (t, 2H).

Compound 80: 4-(2-{4-[3-(Ethyl-pyridin-3-ylmethyl-amino)-phenyl]-pyrimidin-2-ylamino}-ethyl)-phenol: Intermediate 25 was coupled with acetaldehyde following procedure E. LC-MS showed the product had the expected M+H⁺ of 426. ¹H NMR (Varian 300 MHz, CD₃OD, shifts relative to the solvent peak at 3.3 ppm) δ 8.4 (s, 1H) 8.39 (d, 1H) 8.2 (d, 1H) 7.6 (d, 1H) 7.5 (s, 1H), 7.3 (m, 3H), 7.0 (m, 1H), 6.9 (d 1H), 6.8 (d, 2H), 6.5 (d, 2H), 4.6 (s, 2H), 3.6 (m, 4H), 2.8 (t, 2H), 1.2 (d, 3H).

Intermediate 26: 2-Chloro-4-(3-dimethoxymethyl-phenyl)-pyrimidine: Intermediate 1 (3.69 g) was refluxed for two hours in trimethylorthoformate containing 10 mL of 4N HCl/dioxane. The solvent was removed by rotary evaporation to give product, which showed the expected M+H⁺ of 265 by LC-MS.

Intermediate 27: 4-{2-[4-(3-Dimethoxymethyl-phenyl)-pyrimidin-2-ylamino]-ethyl}-phenol: Intermediate 26 was coupled with tyramine following procedure F. The product was purified by flash chromatography using 99:1 CH₂Cl₂: MeOH as eluent. Yield: 35%. LC-MS showed the product had the expected M+H⁺ of 366.

Intermediate 28: 3-{2-[2-(4-Hydroxy-phenyl)-ethylamino]-pyrimidin-4-yl}-benzaldehyde: Intermediate 27 (2.2 g) was treated with 30 mL of 3N HCl in 60 mL of CH₃CN at room temperature overnight. The solvent was removed by rotary evaporation and the residue partitioned between ethyl acetate/sat. NaHCO₃. Yield: 1.9 g, 99%. LC-MS showed the product had the expected M+H⁺ of 320.

Compound 81: 4-(2-{4-[3-(4-Methyl-piperazin-1-ylmethyl)-phenyl]-pyrimidin-2-ylamino}-ethyl)-phenol: Intermediate 28 was coupled with N-methyl piperazine following procedure F. LC-MS showed the product had the expected M+H⁺ of 404. ¹H NMR (Varian 300 MHz, CDCl₃, shifts relative to the solvent peak at 7.24 ppm) δ 8.3 (d, 1H) 7.9 (m, 2H) 7.4 (m, 2H) 7.1 (d, 2H) 7.0 (d, 1H) 6.7 (d, 2H) 5.2 (m, 1H) 3.7 (m, 2H) 3.6 (s, 2H) 2.9 (m, 2H) 2.7 (s, 8H) 2.4 (s, 3H).

Compound 82: 4-(3-{2-[2-(4-Hydroxy-phenyl)-ethylamino]-pyrimidin-4-yl}-benzyl)-3-(S) methyl-piperazine-1-carboxylic acid tert-butyl ester: Intermediate 28 was coupled with 3-(S) methyl-piperazine-1-carboxylic acid tert-butyl ester following procedure B. LC-MS showed the product had the expected M+H⁺ of 504. ¹H NMR (Varian 300 MHz, CDCl₃, shifts relative to the solvent peak at 7.24 ppm) δ 8.3 (d, 1H) 8.1 (s, 1H) 7.9 (d, 1H) 7.5 (m, 2H) 7.1 (d, 2H) 7.0 (d, 1H) 6.7 (d, 2H) 5.5 (s, br, 1H) 4.1 (m, 1H) 3.7 (m, 6H) 3.1-3.5 (m, 2H) 2.9 (m, 2H) 2.6-2.8 (m, 2H) 1.5 (s, 9H) 1.3 (m, 3H).

Compound 83: 4-(3-{2-[2-(4-Hydroxy-phenyl)-ethylamino]-pyrimidin-4-yl}-benzyl)-3-(R) methyl-piperazine-1-carboxylic acid tert-butyl ester: Intermediate 28 was coupled with 3-(R) methyl-piperazine-1-carboxylic acid tert-butyl ester following procedure B. LC-MS showed the product had the expected M+H⁺ of 504. ¹H NMR (Varian 300 MHz, CDCl₃, shifts relative to the solvent peak at 7.24 ppm) δ8.3 (d, 1H) 8.1 (s, 1H) 7.9 (d, 1H) 7.5 (m, 2H) 7.1 (d, 2H) 7.0 (d, 1H) 6.7 (d, 2H) 5.5 (s, br, 1H) 4.1 (m, 1H) 3.7 (m, 6H) 3.1-3.5 (m, 2H) 2.9 (m, 2H) 2.6-2.8 (m, 2H) 1.5 (s, 9H) 1.3 (m, 3H).

Compound 84: 4-(2-{4-[3-(2(S)-Methyl-piperazin-1-ylmethyl)-phenyl]-pyrimidin-2-ylamino}-ethyl)-phenol: Compound 83 was deprotected following procedure G2. LC-MS showed the product had the expected M+H⁺ of 404. ¹H NMR (Varian 300 MHz, DMSO-d₆, shifts relative to the solvent peak at 2.49 ppm) δ 9.2 (s, 1H) 8.9 (s, br, 1H) 8.3 (d, 1H) 8.0 (d, 2H) 7.5 (s, 2H) 7.3 (m, 1H) 7.1 (d, 1H) 7.0 (d, 2H) 6.7 (d, 2H) 4.1 (d, 1H) 3.5 (d, 2H) 3.3 (m, 3H) 3.1 (m, 2H) 2.7 (m, 4H) 2.3 (m, 1H) 1.2 (d, 3H).

Compound 85: 4-(2-{4-[3-(2(R)-Methyl-piperazin-1-ylmethyl)-phenyl]-pyrimidin-2-ylamino}-ethyl)-phenol: Compound 83 was deprotected following procedure G2. LC-MS showed the product had the expected M+H⁺ of 404. ¹H NMR (Varian 300 MHz, DMSO-d₆, shifts relative to the solvent peak at 2.49 ppm) δ 9.2 (s, 1H) 8.9 (s, br, 1H) 8.3 (d, 1H) 8.0 (d, 2H) 7.5 (s, 2H) 7.3 (m, 1H) 7.1 (d, 1H) 7.0 (d, 2H) 6.7 (d, 2H) 4.1 (d, 1H) 3.5 (d, 2H) 3.3 (m, 3H) 3.1 (m, 2H) 2.7 (m, 4H) 2.3 (m, 1H) 1.2 (d, 3H).

Intermediate 29: 4-[3-(2-Chloro-pyrimidin-4-yl)-benzylamino]-piperidine-1-carboxylic acid tert-butyl ester: Intermediate 1 was coupled with 4-Amino-piperidine-1-carboxylic acid tert-butyl ester following procedure B. LC-MS showed the product had the expected M+H⁺ of 403.

Intermediate 30: 4-{[3-(2-Chloro-pyrimidin-4-yl)-benzyl]-methanesulfonyl-amino}-piperidine-1-carboxylic acid tert-butyl ester: Intermediate 29 was coupled with methanesulfonyl chloride following procedure D. LC-MS showed the product had the expected M+H⁺ of 481. ¹H NMR (Varian 300 MHz, CD₃OD, shifts relative to the solvent peak at 3.3 ppm) δ 8.4 (s, 1H) 8.39 (d, 1H) 8.2 (d, 1H) 7.6 (d, 1H) 7.5 (s, 1H), 7.3 (m, 3H), 7.0 (d, 1H), 6.9 (d 1H), 6.8 (d, 2H), 6.5 (d, 2H), 4.6 (s, 2H), 3.6 (m, 4H), 2.8 (t, 2H), 1.2 (d, 3H).

Compound 86: N-(3-{2-[2-(4-Hydroxy-phenyl)-ethylamino]-pyrimidin-4-yl}-benzyl)-N-piperidin-4-yl-methanesulfonamide: Intermediate 30 was coupled with tyramine following procedure F. The resulting product was deprotected following procedure G. LC-MS showed the product had the expected M+H$^+$ of 482. $^1$H NMR (Varian 300 MHz, CD$_3$OD, shifts relative to the solvent peak at 3.3 ppm) δ 8.4 (d, 1H), δ 8.2 (s, 1H) 8.0 (d, 1H) 7.6 (d, 1H), 7.5 (t, 1H), 7.1 (m, 3H), 6.8 (d, 2H), 4.5 (s, 2H), 3.6 (t, 2H), δ 3.0 (s, 3H), 2.9 (m, 5H), δ 2.8 (t, 2H), 2.0 (m, 4H).

Compound 87: N-(3-{2-[2-(3-Fluoro-phenyl)-ethylamino]-pyrimidin-4-yl}-benzyl)-N-piperidin-4-yl-methanesulfonamide: Intermediate 30 was coupled with 2-(3-fluoro-phenyl)-ethylamine following procedure F and the resulting product deprotected following procedure G. LC-MS showed the product had the expected M+H$^+$ of 484. $^1$H NMR (Varian 300 MHz, CD$_3$OD, shifts relative to the solvent peak at 3.3 ppm) δ 8.4 (s, 1H), 8.3 (d, 1H) 8.1 (d, 1H) 7.7 (d, 1H), 7.5 (m, 1H), 7.3 (m, 2H), 7.1 (m, 2H), 6.9 (t, 1H), 4.6 (s, 2H), δ 3.4 (t, 2H), 3.09 (s, 3H), δ 3.05 (m, 5H), 3.04 (t, 2H), 2.08 (m, 4H).

Compound 88: N-[3-(2-Phenethylamino-pyrimidin-4-yl)-benzyl]-N-piperidin-4-yl-methanesulfonamide: Intermediate 30 was coupled with phenethylamine following procedure F. The resulting product was deprotected following procedure G. LC-MS showed the product had the expected M+H$^+$ of 466. $^1$H NMR (Varian 300 MHz, CD$_3$OD, shifts relative to the solvent peak at 3.3 ppm) δ 8.3 (d, 1H), 8.1 (d, 2H) 7.7 (d, 2H) 7.5 (t, 2H), 7.2 (m, 3H), 7.1 (d, 1H), 4.6 (s, 2H), δ 3.4 (t, 2H), 3.09 (s, 3H), δ 3.05 (m, 7H), 2.0 (m, 4H).

Compound 89: N-(3-{2-[2-(3-Chloro-phenyl)-ethylamino]-pyrimidin-4-yl}-benzyl)-N-piperidin-4-yl-methanesulfonamide: Intermediate 30 was coupled with 2-(3-chloro-phenyl)-ethylamine following procedure F and the resulting product deprotected following procedure G. LC-MS showed the product had the expected M+H$^+$ of 500. $^1$H NMR (Varian 300 MHz, CD$_3$OD, shifts relative to the solvent peak at 3.3 ppm) δ 8.3 (d, 1H), 8.1 (d, 1H) 7.7 (d, 1H) 7.5 (t, 1H), 7.3 (m, 2H), 7.25 (m, 3H), 7.20 (d, 1H), δ 4.6 (s, 2H), δ 3.3 (t, 2H), 3.09 (s, 3H), δ 3.04 (m, 7H), 2.0 (m, 4H).

Compound 90: N-(3-{2-[2-(4-Hydroxy-3-methoxy-phenyl)-ethylamino]-pyrimidin-4-yl}-benzyl)-N-piperidin-4-yl-methanesulfonamide: Intermediate 30 was coupled with 4-(2-amino-ethyl)-2-methoxy-phenol following procedure F. The resulting product was deprotected following procedure G. LC-MS showed the product had the expected M+H$^+$ of 512. $^1$H NMR (Varian 300 MHz, CD$_3$OD, shifts relative to the solvent peak at 3.3 ppm) δ 8.3 (d, 1H), 8.0 (d, 2H) 7.6 (m, 2H), 7.5 (t, 1H), 7.2 (d, 1H), 6.8 (d, 1H), δ 6.7 (s, 1H), 4.5 (d, 2H), δ 3.8 (s, 3H), 3.3 (t, 2H), δ 3.0 (s, 3H), 2.9 (m, 5H), δ 2.8 (t, 2H), δ 2.0 (m, 4H).

Intermediate 31: 3-[3-(2-Chloro-pyrimidin-4-yl)-benzylamino]-piperidine-1-carboxylic acid tert-butyl ester: Intermediate 1 was coupled with 3-Amino-piperidine-1-carboxylic acid tert-butyl ester following procedure B. LC-MS showed the product had the expected M+H$^+$ of 403.

Intermediate 32: 3-{[3-(2-Chloro-pyrimidin-4-yl)-benzyl]-methanesulfonyl-amino}-piperidine-1-carboxylic acid tert-butyl ester: Intermediate 30 was coupled with methanesulfonyl chloride following procedure D. LC-MS showed the product had the expected M+H$^+$ of 481.

Compound 91: N-(3-{2-[2-(4-Hydroxy-phenyl)-ethylamino]-pyrimidin-4-yl}-benzyl)-N-piperidin-4-yl-methanesulfonamide: Intermediate 31 was coupled with tyramine following procedure F. The resulting product was deprotected following procedure G. LC-MS showed the product had the expected M+H$^+$ of 482. $^1$H NMR (Varian 300 MHz, CD$_3$OD, shifts relative to the solvent peak at 3.3 ppm) δ 8.2 (d, 1H), 8.32 (d, 1H), 8.31 (s, 1H) 7.7 (d, 2H), 7.6 (t, 1H), 7.3 (d, 2H), 7.1 (d, 1H), δ 6.7 (d, 2H), 4.6 (d, 2H), δ 3.3 (t, 2H), 3.1 (s, 3H), δ 2.9 (m, 5H), 2.7 (t, 2H), δ 2.1-1.7 (m, 4H).

Compound 92: N-(3-{2-[2-(4-Hydroxy-3-methoxy-phenyl)-ethylamino]-pyrimidin-4-yl}-benzyl)-N-piperidin-3-yl-methanesulfonamide: Intermediate 31 was coupled with 4-(2-Amino-ethyl)-2-methoxy-phenol following procedure F. The resulting product was deprotected following procedure G. LC-MS showed the product had the expected M+H$^+$ of 512. $^1$H NMR (Varian 300 MHz, CD$_3$OD, shifts relative to the solvent peak at 3.3 ppm) δ 8.2 (d, 1H), 8.1 (d, 2H) 7.6 (d, 1H) 7.5 (t, 1H), 7.3 (d, 1H), 6.8 (d, 1H), 6.7 (s, 1H), δ 4.6 (s, 2H), 3.8 (s, 3H), δ 3.2 (t, 2H), 3.1 (s, 3H), δ 2.9-2.7 (m, 7H), δ 2.1-1.7 (m, 4H).

Intermediate 33: 4-{[3-(2-Chloro-pyrimidin-4-yl)-benzylamino]-methyl}-piperidine-1-carboxylic acid tert-butyl ester: Intermediate 1 was coupled with 4-Aminomethyl-piperidine-1-carboxylic acid tert-butyl ester following procedure B. LC-MS showed the product had the expected M+H$^+$ of 417.

Intermediate 34: 4-({[3-(2-Chloro-pyrimidin-4-yl)-benzyl]-methanesulfonyl-amino}-methyl)-piperidine-1-carboxylic acid tert-butyl ester: Intermediate 33 was coupled with methane sulfonyl chloride following procedure D. LC-MS showed the product had the expected M+H$^+$ of 495.

Compound 93: N-(3-{2-[2-(4-Hydroxy-phenyl)-ethylamino]-pyrimidin-4-yl}-benzyl)-N-piperidin-4-ylmethyl-methanesulfonamide: Intermediate 34 was coupled with tyramine following procedure F. The resulting product was deprotected following procedure G. LC-MS showed the product had the expected M+H$^+$ of 496. $^1$H NMR (Varian 300 MHz, CD$_3$OD, shifts relative to the solvent peak at 3.3 ppm) δ 8.3 (d, 2H), 8.1 (d, 1H) 7.6 (d, 1H) 7.5 (t, 1H), 7.3 (d, 1H), 7.1 (d, 2H), 6.7 (d, 2H), δ 4.5 (s, 2H), 3.3-3.2 (m, 6H), δ 3.0 (s, 3H), 2.9 (t, 2H), δ 2.7 (t, 2H), δ 1.6 (m, 1H), δ 1.2 (m, 4H).

Intermediate 35: 3-[3-(2-Chloro-pyrimidin-4-yl)-benzylamino]-pyrrolidine-1-carboxylic acid tert-butyl ester: Intermediate 1 was coupled with 3-Amino-pyrrolidine-1-carboxylic acid tert-butyl ester following procedure B. LC-MS showed the product had the expected M+H$^+$ of 389.

Intermediate 36: 3-{[3-(2-Chloro-pyrimidin-4-yl)-benzyl]-methanesulfonyl-amino}-pyrrolidine-1-carboxylic acid tert-butyl ester: Intermediate 35 was coupled with methanesulfonyl chloride following procedure D. LC-MS showed the product had the expected M+H$^+$ of 467.

Compound 94: 3-[(3-{2-[2-(4-Hydroxy-phenyl)-ethylamino]-pyrimidin-4-yl}-benzyl)-methanesulfonyl-amino]-pyrrolidine-1-carboxylic acid tert-butyl ester: Intermediate 36 was coupled with tyramine following procedure F. The resulting product was deprotected following procedure G. LC-MS showed the product had the expected M+H$^+$ of 468. $^1$H NMR (Varian 300 MHz, CD$_3$OD, shifts relative to the solvent peak at 3.3 ppm) δ 8.2 (d, 2H), 8.0 (d, 1H) 7.6 (d, 1H) 7.5 (t, 1H), 7.2 (d, 1H), 7.1 (d, 2H), 6.7 (d, 2H), δ 4.6 (s, 2H), 3.5-3.4 (m, 6H), δ 3.2-3.1 (m, 1H), 3.0 (s, 3H), δ 2.9 (t, 2H), δ 2.2-2.0 (m, 2H).

Intermediate 37: [3-(2-Chloro-pyrimidin-4-yl)-benzyl]-ethyl-carbamic acid tert-butyl ester: Intermediate 22 (2.46 g) was treated with di-tert butyl dicarbonate (2.62 g) and diisopropylethylamine (2.6 mL) in methylene chloride (100 mL). The mixture was stirred at room temperature for 1 hour, washed with water (3×100 mL), dried over MgSO$_4$, and the solvent removed to give 2.15 g of product. LC-MS showed the product had the expected M+H$^+$ of 348.

Compound 95: 2-Chloro-4-{2-[4-(3-ethylaminomethyl-phenyl)-pyrimidin-2-ylamino]-ethyl}-phenol: Intermediate 37 was coupled with intermediate 71 following procedure F and the resulting product deprotected following procedure G.

LC-MS showed the product had the expected M+H⁺ of 383. ¹H NMR (Varian 300 MHz, DMSO-d₆, shifts relative to the solvent peak at 2.49 ppm) δ 9.5 (s, 2H) 8.5 (m, 3H) 8.2 (d, 1H) 7.8 (d, 1H) 7.6 (m, 1H) 7.5 (m, 1H) 7.3 (s, 1H) 7.0 (d, 1H) 6.9 (d, 1H) 4.2 (s, 2H) 4.0 (m, 2H) 3.0 (m, 2H) 2.8 (m, 2H) 1.3 (m, 3H).

Compound 96: [4-(3-Ethylaminomethyl-phenyl)-pyrimidin-2-yl]-[2-(3-fluoro-phenyl)-ethyl]-amine: Intermediate 37 was coupled with 2-(3-fluoro-phenyl)-ethylamine following procedure F and the resulting product deprotected following procedure G. LC-MS showed the product had the expected M+H⁺ of 351. ¹H NMR (Varian 300 MHz, DMSO-d₆, shifts relative to the solvent peak at 2.49 ppm) δ 9.5 (s, 2H) 8.5 (m, 2H) 8.2 (d, 1H) 7.8 (d, 1H) 7.6 (m, 1H) 7.5 (ms, 1H) 7.3 (m, 1H) 7.1 (m, 2H) 7.0 (m, 1H) 4.2 (s, 2H) 3.8 (m, 2H) 2.9 (m, 4H) 1.2 (m, 3H).

Compound 97: N-(3-{2-[2-(3-Chloro-4-hydroxy-phenyl)-ethylamino]-pyrimidin-4-yl}-benzyl)-N-ethyl-methanesulfonamide: Compound 94 was coupled with methanesulfonyl chloride following procedure D. LC-MS showed the product had the expected M+H⁺ of 461. ¹H NMR (Varian 300 MHz, DMSO-d₆, shifts relative to the solvent peak at 2.49 ppm) δ 8.3 (d, 1H) 8.1 (s, 1H) 8.0 (s, 1H) 7.5 (d, 2H) 7.3 (m, 1H) 7.2 (s, 1H) 7.1 (d, 1H) 7.0 (d, 1H) 6.9 (d, 1H) 4.4 (s, 2H) 3.5 (m, 2H) 3.2 (m, 2H) 3.0 (s, 3H) 2.8 (m, 2H) 1.0 (m, 3H).

Compound 98: 2-Chloro-4-[2-(4-{3-[(ethyl-isopropyl-amino)-methyl]-phenyl}-pyrimidin-2-ylamino)-ethyl]-phenol: Compound 94 was coupled with acetone following procedure E. LC-MS showed the product had the expected M+H⁺ of 425. ¹H NMR (Varian 300 MHz, CD₃OD, shifts relative to the solvent peak at 3.3 ppm) δ 8.3 (d, 1H) 8.2 (s, 1H) 8.1 (m, 1H) 7.5 (m, 2H) 7.2 (d, 1H) 7.1 (d, 1H) 7.0 (m, 1H) 6.8 (d, 1H) 4.1 (s, 2H) 3.6 (m, 2H) 3.4 (m, 1H) 2.9 (m, 4H) 1.3 (d, 6H) 1.2 (m, 3H).

Compound 99: 2-Chloro-4-{2-[4-(3-{[ethyl-(3-methyl-butyl)-amino]-methyl}-phenyl)-pyrimidin-2-ylamino]-ethyl}-phenol: Compound 94 was coupled with 3-Methyl-butyraldehyde following procedure E. LC-MS showed the product had the expected M+H⁺ of 453. ¹H NMR (Varian 300 MHz, CD₃OD, shifts relative to the solvent peak at 3.3 ppm) δ 8.3 (d, 1H) 8.2 (s, 1H) 8.1 (m, 1H) 7.5 (m, 2H) 7.2 (d, 1H) 7.1 (d, 1H) 7.0 (m, 1H) 6.8 (d, 1H) 4.0 (s, 2H) 3.6 (m, 2H) 2.8 (m, 6H) 1.5 (m, 3H) 1.2 (m, 3H) 0.9 (d, 6H).

Compound 100: 2-Chloro-4-{2-[4-{3-[(ethyl-isobutyl-amino)-methyl]-phenyl}-pyrimidin-2-ylamino)-ethyl]-phenol: Compound 94 was coupled with 2-Methyl-propionaldehyde following procedure E. LC-MS showed the product had the expected M+H⁺ of 439. ¹H NMR (Varian 300 MHz, CD₃OD, shifts relative to the solvent peak at 3.3 ppm) δ 8.3 (d, 1H) 8.2 (s, 1H) 8.0 (m, 1H) 7.5 (m, 2H) 7.2 (d, 1H) 7.1 (d, 1H) 7.0 (m, 1H) 6.8 (d, 1H) 3.8 (s, 2H) 3.6 (m, 2H) 2.8 (m, 2H) 2.7 (m, 2H) 2.4 (d, 2H) 1.9 (m, 1H) 1.1 (m, 3H) 0.9 (m, 6H).

Compound 101: 2-Chloro-4-{2-[4-(3-diethylaminomethyl-phenyl)-pyrimidin-2-ylamino]ethyl}-phenol: Compound 94 was coupled with acetaldehyde following procedure E. LC-MS showed the product had the expected M+H⁺ of 425. ¹H NMR (Varian 300 MHz, CD₃OD, shifts relative to the solvent peak at 3.3 ppm) δ 8.3 (d, 1H) 8.2 (s, 1H) 8.0 (m, 1H) 7.5 (m, 2H) 7.2 (d, 1H) 7.1 (d, 1H) 7.0 (m, 1H) 6.8 (d, 1H) 3.9 (s, 2H) 3.7 (m, 2H) 2.8 (m, 4H) 2.7 (m, 2H) 1.6 (m, 2H) 1.2 (m, 3H) 0.9 (m, 3H).

Intermediate 38: 1-[3-(2-Chloro-pyrimidin-4-yl)-phenyl]-ethanone: 2,4 dichloropyrimidine was coupled with 3-acetylphenylboronic acid following procedure A. LC-MS showed the product had the expected M+H⁺ of 234.

Intermediate 39: 1-(3-{2-[2-(4-Methoxy-phenyl)-ethylamino]-pyrimidin-4-yl}-phenyl)-ethanone: Intermediate 38 was coupled with 2-(4-Methoxy-phenyl)-ethylamine following procedure F. LC-MS showed the product had the expected M+H⁺ of 348.

Intermediate 40: N1-[1-(3-{2-[2-(4-Methoxy-phenyl)-ethylamino]-pyrimidin-4-yl}-phenyl)-ethyl]-propane-1,3-diamine: Intermediate 39 was coupled with (3-Amino-propyl)-carbamic acid tert-butyl ester following procedure C. LC-MS showed the product had the expected M+H⁺ of 506.

Compound 102: Intermediate 40 was deprotected following procedure G. LC-MS showed the product had the expected M+H⁺ of 406. ¹H NMR (Varian 300 MHz, CD₃OD, shifts relative to the solvent peak at 3.3 ppm) δ 8.4 (m, 3H) 7.6-7.9 (m, 2H) 7.48 (d, 1H) 7.2 (m, 3H) 6.8 (d, 2H) 4.55 (q, 1H) 3.85 (m, 1H) 3.68 (s, 3H) 3.15 (m, 1H) 2.95 (m, 6H) 2.08 (m, 2H) 1.78 (d, 3H).

Compound 103: Intermediate 40 was coupled with methanesulfonyl chloride following procedure D. The resulting product was deprotected following procedure G. LC-MS showed the product had the expected M+H⁺ of 484. ¹H NMR (Varian 300 MHz, CD₃OD, shifts relative to the solvent peak at 3.3 ppm) δ 8.3 (br s, 1H) 8.2 (d, 1H) 7.78 (d, 1H) 7.6 (m, 1H) 7.38 (m, 1H) 7.2 (d, 2H) 6.8 (d, 2H) 5.3 (q, 1H) 3.8 (br s, 2H) 3.75 (s, 3H) 3.2-3.4 (m, 2H) 3.05-3.1 (m, 2H) 2.95 (s, 3H) 2.78 (m, 2H) 1.77 (d, 3H) 1.6 (m, 2H).

Compound 104: Compound 103 (0.1 g) was treated with BBr₃ (0.1 mL) in CH₂Cl₂ (10 mL) at 0 C for ½ hour. The solvent was evaporated and the crude mixture subjected to HPLC purification. LC-MS showed the product had the expected M+H⁺ of 470. ¹H NMR (Varian 300 MHz, CD₃OD, shifts relative to the solvent peak at 3.3 ppm) δ 8.5 (br s, 1H) 8.2-8.35 (m, 3H) 8.05 (d, 1H) 7.65 (d, 1H) 7.52 (m, 1H) 7.1 (d, 2H) 6.7 (d, 2H) 5.25 (q, 1H) 3.63 (t, 2H) 3.2-3.4 (m, 2H) 2.96 (s, 3H) 2.85 (m, 2H) 2.7 (m, 2H) 1.72 (d, 3H) 1.6 (m, 2H).

Intermediate 41: (3-Benzoylamino-propyl)-carbamic acid tert-butyl ester: (3-Amino-propyl)-carbamic acid tert-butyl ester (1.6 g) was treated with benzoyl chloride (1.1 eq.) and triethylamine (1.5 eq) in methylene chloride (50 mL). The reaction mixture was washed with 1 N HCl, sat, NaHCO3, and sat NaCl and the solvent removed to give product. LC-MS showed the product had the expected M+H⁺ of 279.

Intermediate 42: N-(3-Amino-propyl)-benzamide: Intermediate 41 was deprotected by procedure G. LC-MS showed the product had the expected M+H⁺ of 179.

Intermediate 43: N-{3-[3-(2-Chloro-pyrimidin-4-yl)-benzylamino]-propyl}-benzamide: Intermediate 42 was coupled with intermediate 1 following procedure B. LC-MS showed the product had the expected M+H⁺ of 381.

Intermediate 44: N-(3-{[3-(2-Chloro-pyrimidin-4-yl)-benzyl]-ethyl-amino}-propyl)-benzamide: Intermediate 43 was coupled with acetaldehyde following procedure E. LC-MS showed the product had the expected M+H⁺ of 409.

Compound 105: N-{3-[Ethyl-(3-{2-{2-(4-hydroxy-phenyl)-ethylamino]-pyrimidin-4-yl}-benzyl)-amino}-propyl}-benzamide: Intermediate 44 was coupled with tyramine following procedure F. LC-MS showed the product had the expected M+H⁺ of 510.

Intermediate 45: 2-Chloro-4-(3-isopropoxy-phenyl)-pyrimidine: 2,4 dichlorpyrimidine was coupled with 3-isopropoxyphenylboronic acid following procedure A. LC-MS showed the product had the expected M+H⁺ of 249.

Compound 106: 4-{2-[4-(3-Isopropoxy-phenyl)-pyrimidin-2-ylamino]-ethyl}-phenol: Intermediate 45 was coupled with tyramine following procedure F. LC-MS showed the product had the expected M+H⁺ of 350. ¹H NMR (Varian 300 MHz, CDCl₃, shifts relative to the solvent peak at 7.24 ppm)

δ 8.28 (m, 1H) 7.6 (m, 2H) 7.35 (m, 1H) 7.0 (m, 4H) 6.68 (m, 2H) 5.5 (m, 1H) 4.62 (m, 1H) 3.71 (m, 2H) 2.85 (m, 2H) 1.32 (d, 6H).

Compound 107: 4-{2-[4-(3-Isopropoxy-phenyl)-pyrimidin-2-ylamino]-ethyl}-2-methoxy-phenol: Intermediate 45 was coupled with 4-(2-Amino-ethyl)-2-methoxy-phenol following procedure F. LC-MS showed the product had the expected M+H$^+$ of 380. $^1$H NMR (Varian 300 MHz, CDCl$_3$, shifts relative to the solvent peak at 7.24 ppm) δ 8.3 (m, 1H) 7.6 (m, 2H) 7.36 (m, 1H) 6.9 (m, 2H) 6.83 (m, 1H) 6.72 (m, 2H) 5.5 (m, 1H) 4.62 (m, 1H) 3.75 (s, 3H) 3.7 (m, 2H) 2.88 (m, 2H) 1.32 (d, 6H).

Intermediate 46: 4-(3-Butoxy-phenyl)-2-chloro-pyrimidine: 2,4 dichloropyrimidine was coupled with 3-butoxyphenylboronic acid following procedure A. LC-MS showed the product had the expected M+H$^+$ of 263.

Compound 108: 4-{2-[4-(3-Butoxy-phenyl)-pyrimidin-2-ylamino]-ethyl}-phenol: Intermediate 46 was coupled with tyramine following procedure F. LC-MS showed the product had the expected M+H$^+$ of 364. $^1$H NMR (Varian 300 MHz, CDCl$_3$, shifts relative to the solvent peak at 7.24 ppm) δ 8.28 (m, 1H) 7.6 (m, 2H) 7.35 (m, 1H) 7.0 (m, 4H) 6.7 (d, 2H) 5.49 (br s, 1H) 4.0 (t, 2H) 3.7 (d, 2H) 2.85 (t, 2H) 1.78 (d, 2H) 1.5 (d, 2H) (t, 3H).

Compound 109: 4-{2-[4-(3-Butoxy-phenyl)-pyrimidin-2-ylamino]-ethyl}-2-methoxy-phenol: Intermediate 46 was coupled with 4-(2-Amino-ethyl)-2-methoxy-phenol following procedure F. LC-MS showed the product had the expected M+H$^+$ of 394. $^1$H NMR (Varian 300 MHz, CDCl$_3$, shifts relative to the solvent peak at 7.24 ppm) δ 8.3 (m, 1H) 7.6 (m, 2H) 7.35 (m, 1H) 7.0 (m, 2H) 6.85 (m, 1H) 672 (m, 2H) 5.51 (br s, 1H) 4.0 (t, 2H) 3.75 (s, 3H) 3.7 (m, 2H) 2.89 (t, 2H) 1.78 (d, 2H) 1.5 (d, 2H) (t, 3H).

Intermediate 47: 4-(4-ethoxy-phenyl)-2-chloro-pyrimidine: 2,4 dichloropyrimidine was coupled with 3-ethoxyphenylboronic acid following procedure A. LC-MS showed the product had the expected M+H$^+$ of 235.

Compound 110: 4-{2-[4-(4-ethoxy-phenyl)-pyrimidin-2-ylamino]-ethyl}-phenol: Intermediate 47 was coupled with tyramine following procedure F. LC-MS showed the product had the expected M+H$^+$ of 336. $^1$H NMR (Varian 300 MHz, DMSO-d$_6$, shifts relative to the solvent peak at 2.49 ppm) δ 8.2 (d, 1H), 8.0 (d, 2H) 7.0 (m, 4H) 6.6 (d, 3H), δ 4.0 (q, 2H), 3.4 (t, 2H), δ 2.7 (t, 2H), 1.3 (t, 3H).

Compound 111: 4-{2-[4-(4-ethoxy-phenyl)-pyrimidin-2-ylamino]-ethyl}-2-methoxy-phenol: Intermediate 47 was coupled with 4-(2-Amino-ethyl)-2-methoxy-phenol following procedure F. LC-MS showed the product had the expected M+H$^+$ of 366. $^1$H NMR (Varian 300 MHz, DMSO-d$_6$, shifts relative to the solvent peak at 2.49 ppm) δ 8.0 (d, 1H), 7.1-7.0 (m, 4H) 6.8 (s, 1H), δ 6.7-6.6 (m, 3H), δ 4.0 (q, 2H), δ 3.7 (s, 3H), 3.5 (t, 2H), δ 2.7 (t, 2H), 1.3 (t, 3H).

Intermediate 48: [4-(2-Chloro-pyrimidin-4-yl)-phenyl]-carbamic acid benzyl ester: 2,4 dichloropyrimidine was coupled with 4-carbobenzyloxyphenylboronic acid following procedure A. LC-MS showed the product had the expected M+H$^+$ of 340.

Compound 112: (4-{2-[2-(4-Hydroxy-3-methoxy-phenyl)-ethylamino]-pyrimidin-4-yl}-phenyl)-carbamic acid benzyl ester: Intermediate 48 was coupled with 4-(2-Amino-ethyl)-2-methoxy-phenol following procedure F. LC-MS showed the product had the expected M+H$^+$ of 471. $^1$H NMR (Varian 300 MHz, CDCl$_3$, shifts relative to the solvent peak at 7.24 ppm) δ 8.28 (m, 1H) 8.0 (d, 2H) 7.5 (d, 2H) 7.4 (m, 4H) 7.05 (s, 1H) 6.9 (d, 1H) 6.83 (m, 1H) 6.7 (m, 2H) 5.55 (br s, 1H) 5.21 (s, 2H) 3.81 (s, 3H) 3.7 (t, 2H) 2.9 (t, 2H).

Intermediate 49: 2-Chloro-4-(4-isobutyl-phenyl)-pyrimidine: 2,4 dichloropyrimidine was coupled with 4-isobutylphenylboronic acid following procedure A. LC-MS showed the product had the expected M+H$^+$ of 247.

Compound 113: 4-{2-[4-(4-Isobutyl-phenyl)-pyrimidin-2-ylamino]-ethyl}-2-methoxy-phenol: Intermediate 49 was coupled with 4-(2-Amino-ethyl)-2-methoxy-phenol following procedure F. LC-MS showed the product had the expected M+H$^+$ of 378. $^1$H NMR (Varian 300 MHz, CDCl$_3$, shifts relative to the solvent peak at 7.24 ppm) δ 8.3 (m, 1H) 7.99 (d, 2H) 7.25 (d, 2H) 6.95 (d, 1H) 6.85 (m, 1H) 6.74 (m, 2H) 5.5 (br s, 1H) 3.8 (s, 3H) 3.75 (m, 2H) 2.87 (t, 2H) 2.52 (t, 2H) 1.88 (m, 1H) 0.9 (d, 6H).

Intermediate 50: 2-Chloro-4-(4-propoxy-phenyl)-pyrimidine: 2,4 dichloropyrimidine was coupled with 4-propoxyphenylboronic acid following procedure A. LC-MS showed the product had the expected M+H$^+$ of 249.

Compound 114: 2-Methoxy-4-{2-[4-(4-propoxy-phenyl)-pyrimidin-2-ylamino]-ethyl}-phenol: Intermediate 50 was coupled with 4-(2-Amino-ethyl)-2-methoxy-phenol following procedure F. LC-MS showed the product had the expected M+H$^+$ of 380. $^1$H NMR (Varian 300 MHz, DMSO-d$_6$, shifts relative to the solvent peak at 2.49 ppm) δ 8.0 (d, 1H), 7.1-7.0 (m, 4H) 6.8 (s, 1H), δ 6.7-6.6 (m, 3H), δ 4.0 (t, 2H), δ 3.7 (s, 3H), 3.5 (t, 2H), δ 2.7 (t, 2H), δ 1.8-1.7 (m, 2H), 0.9 (t, 3H).

Intermediate 51: 3-[3-(2-Chloro-pyrimidin-4-yl)-benzylamino]-piperidine-1-carboxylic acid tert-butyl ester: Intermediate 1 was coupled with 3-Amino-piperidine-1-carboxylic acid tert-butyl ester following procedure B. LC-MS showed the product had the expected M+H$^+$ of 403.

Intermediate 52: 3-{[3-(2-Chloro-pyrimidin-4-yl)-benzyl]-methanesulfonyl-amino}-piperidine-1-carboxylic acid tert-butyl ester: Intermediate 51 was coupled with methanesulfonyl chloride following procedure D. LC-MS showed the product had the expected M+H$^+$ of 481.

Compound 115: N-(3-{2-[2-(3-Chloro-4-hydroxy-phenyl)-ethylamino]-pyrimidin-4-yl}-benzyl)-N-piperidin-3-yl-methanesulfonamide: Intermediate 52 was coupled with intermediate 71 following procedure F. The resulting product was deprotected following procedure G. LC-MS showed the product had the expected M+H$^+$ of 516. $^1$H NMR (Varian 300 MHz, CD$_3$OD, shifts relative to the solvent peak at 3.3 ppm) δ 8.3 (d, 1H), δ 8.1 (d, 1H), δ 7.6 (d, 1H), 7.5 (t, 1H), 7.3 (d, 1H) 7.2 (d, 1H), δ 7.1 (d, 1H), δ 7.0 (d, 1H), 6.8 (d, 1H), δ 4.6 (s, 2H), δ 3.7 (t, 2H), δ 3.2 (t, 2H), 3.1 (s, 3H), δ 2.9-2.8 (m, 4H), δ 2.8-2.7 (m, 1H), δ 2.1-1.7 (m, 4H).

Intermediate 53: 3-[3-(2-Chloro-pyrimidin-4-yl)-benzylamino]-pyrrolidine-1-carboxylic acid tert-butyl ester: Intermediate 1 was coupled with 3-Amino-piperidine-1-carboxylic acid tert-butyl ester following procedure B. LC-MS showed the product had the expected M+H$^+$ of 389.

Intermediate 54: 3-{[3-(2-Chloro-pyrimidin-4-yl)-benzyl]-methanesulfonyl-amino}-pyrrolidine-1-carboxylic acid tert-butyl ester: Intermediate 53 was coupled with methanesulfonyl chloride following procedure D. LC-MS showed the product had the expected M+H$^+$ of 467.

Compound 116: N-(3-{2-[2-(3-Chloro-4-hydroxy-phenyl)-ethylamino]-pyrimidin-4-yl}-benzyl)-N-pyrrolidin-3-yl-methanesulfonamide: Intermediate 54 was coupled with intermediate 71 following procedure F. The resulting product was deprotected following procedure G. LC-MS showed the product had the expected M+H$^+$ of 502. $^1$H NMR (Varian 300 MHz, CD$_3$OD, shifts relative to the solvent peak at 3.3 ppm) δ 8.3 (d, 1H), δ 8.2 (s, 1H), 8.0 (d, 1H) 7.6 (d, 1H) 7.5 (t, 1H), 7.2 (d, 1H), 7.1 (d, 1H), δ 7.0 (d, 1H), 6.8, d, 1H), δ 4.6 (s, 2H), m, 6H δ 3.2-3.1 (m, 1H), 3.1 (s, 3H), δ 2.9 (t, 2H), δ 2.3-2.1 (m, 2H).

Intermediate 55: 4-{[3-(2-Chloro-pyrimidin-4-yl)-benzylamino]-methyl}-piperidine-1-carboxylic acid tert-butyl ester: Intermediate 1 was coupled with 4-Aminomethyl-piperidine-1-carboxylic acid tert-butyl ester following procedure B. LC-MS showed the product had the expected M+H$^+$ of 417.

Intermediate 56: 4-({[3-(2-Chloro-pyrimidin-4-yl)-benzyl]-methanesulfonyl-amino}-methyl)-piperidine-1-carboxylic acid tert-butyl ester: Intermediate 55 was coupled with methanesulfonyl chloride following procedure D. LC-MS showed the product had the expected M+H$^+$ of 495.

Compound 117: N-(3-{2-[2-(3-Chloro-4-hydroxy-phenyl)-ethylamino]-pyrimidin-4-yl}-benzyl)-N-piperidin-4-ylmethyl-methanesulfonamide: Intermediate 56 was coupled with intermediate 71 following procedure F. The resulting product was deprotected following procedure G. LC-MS showed the product had the expected M+H$^+$ of 530. $^1$H NMR (Varian 300 MHz, CD$_3$OD, shifts relative to the solvent peak at 3.3 ppm) δ 8.3 (d, 1H), 8.1 (d, 1H) 7.6 (d, 1H) 7.5 (t, 1H), 7.3 (s, 1H), 7.2 (d, 1H), 7.1 (d, 1H), δ 7.0 (d, 1H), δ 6.8 (d, 1H), δ 4.5 (s, 2H), 3.3-3.2 (m, 6H), δ 3.0 (s, 3H), δ 2.9 (t, 2H), δ 2.7 (t, 2H), δ 1.7-1.6 (m, 1H), δ 1.3-1.2 (m, 4H).

Intermediate 57: 2-{2-[3-(2-Chloro-pyrimidin-4-yl)-benzylamino]-ethyl}-piperidine-1-carboxylic acid tert-butyl ester: Intermediate 1 was coupled with 2-(2-Amino-ethyl)-piperidine-1-carboxylic acid tert-butyl ester following procedure B. LC-MS showed the product had the expected M+H$^+$ of 431.

Intermediate 58: 2-(2-{[3-(2-Chloro-pyrimidin-4-yl)-benzyl]-methanesulfonyl-amino}-ethyl)-piperidine-1-carboxylic acid tert-butyl ester: Intermediate 57 was coupled with methanesulfonyl chloride following procedure D. LC-MS showed the product had the expected M+H$^+$ of 509.

Compound 118: N-(3-{2-[2-(3-Chloro-4-hydroxy-phenyl)-ethylamino]-pyrimidin-4-yl}-benzyl)-N-(2-piperidin-2-yl-ethyl)-methanesulfonamide: Intermediate 58 was coupled with intermediate 71 following procedure F. The resulting product was deprotected following procedure G. LC-MS showed the product had the expected M+H$^+$ of 544. $^1$H NMR (Varian 300 MHz, CD$_3$OD, shifts relative to the solvent peak at 3.3 ppm) δ 8.3 (d, 1H), 8.1 (d, 1H) 7.7 (d, 1H) 7.6 (t, 1H), 7.3 (d, 1H), 7.2 (d, 1H), 7.1 (d, 1H), δ 7.0 (d, 1H), δ 6.8 (d, 1H), δ 4.5 (s, 2H), 3.5-3.4 (m, 5H), δ 3.2 (t, 2H), δ 3.0 (s, 3H), δ 2.9 (t, 2H), δ 1.8-1.7 (m, 4H), δ 1.6-1.5 (m, 2H), δ 1.4-1.2 (m, 2H).

Compound 119: N1-Ethyl-N1-(3-{2-[2-(4-methoxy-3-methyl-phenyl)-ethylamino]-pyrimidin-4-yl}-benzyl)-propane-1,3-diamine: Intermediate 3 was coupled with 2-(4-Methoxy-3-methyl-phenyl)-ethylamine following procedure F. The resulting product was deprotected by procedure G. LC-MS showed the product had the expected M+H$^+$ of 434. $^1$H NMR (Varian 300 MHz, CD$_3$OD, shifts relative to the solvent peak at 3.3 ppm) δ 8.4 (m, 2H) 8.0 (s, 1H) 7.6-7.8 (m, 2H) 7.47 (d, 1H) 6.82 (d, 1H) 6.67 (m, 2H) 4.5 (s, 2H) 3.81 (s, 3H) 3.4 (m, 4H) 3.28 (m, 4H) 3.03 (t, 2H) 2.68 (t, 2H) 2.16 (m, 2H) 1.4 (t, 3H).

Intermediate 59: 3-{[3-(2-Chloro-pyrimidin-4-yl)-benzylamino]-methyl}-pyrrolidine-1-carboxylic acid tert-butyl ester: Intermediate 1 was coupled with 3-Aminomethyl-pyrrolidine-1-carboxylic acid tert-butyl ester following procedure B. LC-MS showed the product had the expected M+H$^+$ of 403.

Intermediate 60: 3-({Acetyl-[3-(2-chloro-pyrimidin-4-yl)-benzyl]-amino}-methyl)-pyrrolidine-1-carboxylic acid tert-butyl ester: Intermediate 59 was coupled with acetyl chloride following procedure D. LC-MS showed the product had the expected M+H$^+$ of 445.

Compound 120: N-(3-{2-[2-(4-Hydroxy-phenyl)-ethylamino]-pyrimidin-4-yl}-benzyl)-N-pyrrolidin-3-ylmethyl-acetamide: Intermediate 60 was coupled with tyramine following procedure F. The resulting product was deprotected following procedure G. LC-MS showed the product had the expected M+H$^+$ of 446.

Intermediate 61: 4-[2-(4-Chloro-pyrimidin-2-ylamino)-ethyl]-phenol: 2,4 dichloropyrimidine (1.49 g) was dissolved in DMF along with diisopropylethylmine (1.29 g) and tyramine (1.37 g.) The mixture was stirred at room temperature overnight. The mixture was partitioned between ethyl acetate and water and the organic layer washed with 1 N HCl followed by saturated NaHCO$_3$ and brine. The solvent was removed and the residue subjected to flash chromatography (ethyl acetate as eluent.) 4-[2-(4-Chloro-pyrimidin-2-ylamino)-ethyl]-phenol eluted first and was isolate as a minor product (15% yield.) LC-MS showed the product had the expected M+H$^+$ of 250.

Intermediate 62: 1-(3-{2-[2-(4-Hydroxy-phenyl)-ethylamino]-pyrimidin-4-yl}-phenyl)-ethanone: Intermediate 61 was coupled with 3-acetyl phenylboronic acid following procedure A. LC-MS showed the product had the expected M+H$^+$ of 334.

Compound 121: 4-(2-{4-[3-(1-Hydroxy-ethyl)-phenyl]-pyrimidin-2-ylamino}-ethyl)-phenol: Intermediate 62 (0.96 g) was dissolved in methanol (30 mL) and treated with 0.5 g of sodium borohydride. The solvent was removed and the residue partitioned between ethyl acetate and water. The residue was purified by HPLC. LC-MS showed the product had the expected M+H$^+$ of 336. $^1$H NMR (Varian 300 MHz, CDCl$_3$, shifts relative to the solvent peak at 7.24 ppm) δ 8.31 (m, 1H) 8.05 (s, 1H) 7.4-7.6 (m, 3H) 7.09 (d, 2H) 6.99 (d, 1H) 6.72 (d, 2H) 5.29 (t, 1H) δ 5.0 (q, 1H) 3.73 (q, 2H) 2.9 (t, 2H) 1.52 (d, 3H).

Compound 122: 4-(2-{4-[3-(Pyrazin-2-ylaminomethyl)-phenyl]-pyrimidin-2-ylamino}-ethyl)-phenol: Intermediate 28 was coupled with 2-aminopyrazine following procedure B. LC-MS showed the product had the expected M+H$^+$ of 399. $^1$H NMR (Varian 300 MHz, CDCl$_3$, shifts relative to the solvent peak at 7.24 ppm) δ 8.3 (m, 2H), 8.1 (m, 1H), 8.0 (m, 3H), 7.7 (m, 2H), 7.5 (m, 3H), 7.1 (m, 2H), 6.7 (m, 2H), 4.6 (m, 2H), 3.6 (m, 2H), 2.8 (m, 2H).

Intermediate 63: [3-(2-Chloro-pyrimidin-4-yl)-benzyl]-pyridin-3-yl-amine: Intermediate 1 was coupled with 3-aminopyridine following procedure B. LC-MS showed the product had the expected M+H$^+$ of 297.

Compound 123: 4-(2-{4-[3-(Pyridin-3-ylaminomethyl)-phenyl]-pyrimidin-2-ylamino}-ethyl)-phenol: Intermediate 63 was coupled with tyramine following procedure F. LC-MS showed the product had the expected M+H$^+$ of 398. $^1$H NMR (Varian 300 MHz, CDCl$_3$, shifts relative to the solvent peak at 7.24 ppm) δ 9.2 (m, 1H), 8.3 (s, 1H), 8.2 (m, 2H), 8.1 (m, 2H), 8.0 (m, 3H), 7.7 (s, 1H), 7.5 (d, 2H), 7.1 (m, 4H), 6.6 (m, 2H), 4.2 (m, 1H), 3.2 (m, 2H), 2.7 (m, 2H).

Compound 124: (2-Morpholin-4-yl-ethyl)-{4-[3-(pyridin-3-ylaminomethyl)-phenyl]-pyrimidin-2-yl}-amine: Intermediate 63 was coupled with (2-Morpholin-4-yl-ethyl)-{4-[3-(pyridin-3-ylaminomethyl)-phenyl]-pyrimidin-2-yl}-amine following procedure F. LC-MS showed the product had the expected M+H$^+$ of 398. $^1$H NMR (Varian 300 MHz, CDCl$_3$, shifts relative to the solvent peak at 7.24 ppm) δ 8.3 (m, 2H), 8.1 (s, 1H), 7.9 (d, 1H), 7.5 (m, 2H), 7.1 (m, 5H), 6.2 (d, 2H), 6.5 (m, 1H), 6.3 (m, 1H), 4.2 (m, 2H), 3.5 (m, 4H), 3.4 (m, 2H), 2.4 (m, 4H).

Intermediate 64: N'-[3-(2-Chloro-pyrimidin-4-yl)-benzyl]-N,N-diethyl-propane-1,3-diamine: Intermediate 1 was coupled with N,N diethylpropanediamine following procedure B. LC-MS showed the product had the expected M+H$^+$ of 333.

Compound 125: 4-[2-(4-{3-[(3-Diethylamino-propylamino)-methyl]-phenyl}-pyrimidin-2-ylamino)-ethyl]-phenol: Intermediate 64 was coupled with tyramine following procedure F. LC-MS showed the product had the expected M+H$^+$ of 434. $^1$H NMR (Varian 300 MHz, CDCl$_3$, shifts relative to the solvent peak at 7.24 ppm) δ 8.4 (d, 1H), 8.2 (m, 2H), 8.1 (m, 1H), 8.0 (m, 1H), 7.5 (m, 3H), 7.2 (m, 1H), 7.1 (m, 4H), 6.6 (m, 2H), 4.2 (m, 1H), 3.5 (m, 2H), 2.7 (m, 3H), 2.6 (m, 6H), 1.7 (m, 2H), 1.0 (m, 6H).

Compound 126: 4-{2-[4-(3-{[(3-Diethylamino-propyl)-ethyl-amino]-methyl}-phenyl)-pyrimidin-2-ylamino]-ethyl}-phenol: Compound 125 was coupled with acetaldehyde following procedure E. LC-MS showed the product had the expected M+H$^+$ of 462. $^1$H NMR (Varian 300 MHz, CDCl$_3$, shifts relative to the solvent peak at 7.24 ppm) δ 8.3 (m, 1), 8.1 (m, 1), 8.0 (m, 2H), 7.5 (m, 2H), 71 (m, 3H), 6.7 (m, 2H), 4.9 (s, 1H), 3.8 (s, 1H), 3.6 (m, 3H), 3.0 (m, 6H), 2.8 (m, 3H), 2.6 (m, 4H), 1.8 (m, 2H), 1.2 (m, 9H).

Intermediate 65: [3-(2-Chloro-pyrimidin-4-yl)-benzyl]-isopropyl-amine: Intermediate 2 was coupled with isopropylamine following procedure B. LC-MS showed the product had the expected M+H$^+$ of 262.

Compound 127: 4-(2-{4-[3-(Isopropylamino-methyl)-phenyl]-pyrimidin-2-ylamino}-ethyl)-phenol: Intermediate 65 was coupled with tyramine following procedure F. The product was purified by HPLC. LC-MS showed the product had the expected M+H$^+$ of 363. $^1$H NMR (Varian 300 MHz, CDCl$_3$, shifts relative to the solvent peak at 7.24 ppm) δ 8.3 (m, 1H), 8.2 (m, 2H), 8.1 (m, 2H), 7.5 (d, 2H), 7.2 (m, 2H), 7.1 (d, 1H), 7.0 (d, 2H), 6.7 (d, 2H), 3.8 (m, 1H), 3.3 (m, 4H), 2.7 (m, 1H), 1.1 (m, 6H).

Intermediate 66: 3-(R)-[Ethyl-(3-{2-[2-(3-fluoro-phenyl)-ethylamino]-pyrimidin-4-yl}-benzyl)-carbamoyl]-piperidine-1-carboxylic acid tert-butyl ester: compound 96 was coupled with (R)-(−)-N-boc-nipecotic acid following procedure K and purified by chromatography on silica gel using MeOH:methylene chloride (2:98) as eluent. LC-MS showed the product had the expected M+H$^+$ of 562. $^1$H NMR (Varian 300 MHz, CDCl$_3$, shifts relative to the solvent peak at 7.24 ppm) δ 8.3 (m, 1H), 7.9 (m, 2H) 7.4 (m, 2H) 7.3 (m, 1H) 7.0 (m, 4H) 4.7 (m, 1H) 4.2 (m, 2H) 3.8 (m, 2H) 3.4 (m, 2H) 3.0 (m, 4H) 2.7 (m, 2H) 1.8 (m, 4H) 1.5 (s, 6H) 1.4 (s, 3H) 1.2 (m, 3H).

Compound 128: Piperidine-3-(R)-carboxylic acid ethyl-(3-{2-[2-(3-fluoro-phenyl)-ethylamino]-pyrimidin-4-yl}-benzyl)-amide: Intermediate 66 was deprotected following procedure G2. LC-MS showed the product had the expected M+H$^+$ of 462. $^1$H NMR (Varian 300 MHz, CD$_3$OD shifts relative to the solvent peak at 3.3 ppm) δ 8.3 (m, 1H), 8.2 (s, 2H) 7.6 (m, 3H) 7.3 (m, 1H) 7.1 (m, 2H) 6.9 (m, 1H) 4.7 (m, 1H) 4.0 (m, 2H) 3.7 (m, 2H) 3.2 (m, 4H) 3.1 (m, 4H) 1.9 (m, 4H) 1.3 (m, 3H).

Intermediate 67: 3-(S)-[Ethyl-(3-{2-[2-(3-fluoro-phenyl)-ethylamino]-pyrimidin-4-yl}-benzyl)-carbamoyl]-piperidine-1-carboxylic acid tert-butyl ester: compound 96 was coupled with (S)-(+)-N-boc-nipecotic acid following procedure K and purified by chromatography on silica gel using MeOH:methylene chloride (2:98) as eluent. LC-MS showed the product had the expected M+H$^+$ of 562. $^1$H NMR (Varian 300 MHz, CDCl$_3$, shifts relative to the solvent peak at 7.24 ppm) δ 8.3 (m, 1H), 7.9 (m, 2H) 7.4 (m, 2H) 7.3 (m, 1H) 7.0 (m, 4H) 4.7 (m, 1H) 4.2 (m, 2H) 3.8 (m, 2H) 3.4 (m, 2H) 3.0 (m, 4H) 2.7 (m, 2H) 1.8 (m, 4H) 1.5 (s, 6H) 1.4 (s, 3H) 1.2 (m, 3H).

Compound 129: Piperidine-3-(S)-carboxylic acid ethyl-(3-{2-[2-(3-fluoro-phenyl)-ethylamino]-pyrimidin-4-yl}-benzyl)-amide: Intermediate 67 was deprotected following procedure G2. LC-MS showed the product had the expected M+H$^+$ of 462. $^1$H NMR (Varian 300 MHz, CD$_3$OD shifts relative to the solvent peak at 3.3 ppm) δ 8.3 (m, 1H), 8.2 (s, 2H) 7.6 (m, 3H) 7.3 (m, 1H) 7.1 (m, 2H) 6.9 (m, 1H) 4.7 (m, 1H) 4.0 (m, 2H) 3.7 (m, 2H) 3.2 (m, 4H) 3.1 (m, 4H) 1.9 (m, 4H) 1.3 (m, 3H).

Intermediate 68: 4-[3-(2-Chloro-pyrimidin-4-yl)-benzyl]-3-(S)-methyl-piperazine-1-carboxylic acid tert-butyl ester: Intermediate 1 was coupled with 4-boc-2-(S)-methyl-piperazine following procedure B. LC-MS showed the product had the expected M+H$^+$ of 403. $^1$H NMR (Varian 300 MHz, CDCl$_3$, shifts relative to the solvent peak at 7.24 ppm) δ 8.6 (d, 1H) 8.0 (m, 2H) 7.6 (d, 1H) 7.5 (m, 2H) 4.8 (d, 1H) 4.1 (m, 1H) 3.6 (m, 2H) 3.3 (m, 1H) 3.0 (m, 2H) 2.5 (m, 2H) 1.4 (s, 9H) 1.1 (m, 3H).

Intermediate 69: 4-(3-{2-[2-(3-Fluoro-phenyl)-ethylamino]-pyrimidin-4-yl}-benzyl)-3-(S)-methyl-piperazine-1-carboxylic acid tert-butyl ester: Intermediate 68 was coupled with 3-fluorophenethylamine following procedure F. LC-MS showed the product had the expected M+H$^+$ of 506. $^1$H NMR (Varian 300 MHz, CDCl$_3$, shifts relative to the solvent peak at 7.24 ppm) δ 8.4 (m, 2H) 8.0 (m, 1H) 7.7 (m, 1H) 7.5 (m, 2H) 7.0 (m, 4H) 5.3 (m, 1H) 3.9 (m, 4H) 3.7 (m, 4H) 3.0 (m, 4H) 1.6 (m, 3H) 1.4 (s, 9H).

Compound 130: [2-(3-Fluoro-phenyl)-ethyl]-{4-[3-(2-(S)-methyl-piperazin-1-ylmethyl)-phenyl]-pyrimidin-2-yl}-amine: Intermediate 69 was deprotected following procedure G2. LC-MS showed the product had the expected M+H$^+$ of 406. $^1$H NMR (Varian 300 MHz, CD$_3$OD shifts relative to the solvent peak at 3.3 ppm) δ 8.7 (s, 1H) 8.4 (m, 2H) 7.9 (d, 1H) 7.7 (m, 2H) 7.3 (m, 1H) 7.1 (d, 2H) 6.9 (m, 1H) 5.1 (m, 1H) 4.4 (m, 1H) 4.0 (m, 2H) 3.7 (m, 5H) 3.5 (m, 2H) 3.1 (m, 2H) 1.7 (d, 3H).

Compound 131: 4-{2-[4-(3-Ethylaminomethyl-phenyl)-pyrimidin-2-ylamino]-ethyl}-phenol; Intermediate 28 was coupled with ethylamine following procedure B. LC-MS showed the product had the expected M+H$^+$ of 349. $^1$H NMR (Varian 300 MHz, CDCl$_3$, shifts relative to the solvent peak at 7.24 ppm) δ 8.3 (d, 1H) 7.9 (m, 2H) 7.4 (m, 2H) 7.0 (d, 2H) 6.9 (d, 1H) 6.7 (d, 2H) 5.2 (m, 1H) 3.9 (s, 2H) 3.7 (m, 2H) 2.8 (m, 2H) 2.7 (m, 2H) 1.2 (m, 3H).

Intermediate 70: [3-(2-Chloro-pyrimidin-4-yl)-benzyl]-isopropyl-carbamic acid tert-butyl ester: Intermediate 63 was treated with 1.3 eq. of di-tert-butyl dicarbonate and 1.5 eq. of N,N-diisopropylethylamine in methylene chloride for 5 hours. The mixture was washed with water, brine, dried with anhydrous Na$_2$SO$_4$, and purified by chromatography (EtOAc:Hexane=10:90). LC-MS showed the product had the expected M+H$^+$ of 362. $^1$H NMR (Varian 300 MHz, CDCl$_3$, shifts relative to the solvent peak at 7.24 ppm) δ 8.6 (d, 1H) 8.0 (s, 1H) 7.9 (d, 1H) 7.6 (d, 1H) 7.4 (m, 2H) 4.4 (s, 2H) 1.4 (s, br, 10H) 1.1 (d, 6H).

Intermediate 71: 4-(2-Amino-ethyl)-2-chloro-phenol: 0.1 mol of 2-(4-Methoxy-phenyl)-ethylamine was dissolved in 200 ml of acetic acid, followed by addition of 1.5 eq. of sulfuryl chloride at 0° to 5° C. The solution was stirred at room temperature for 1 hour. 250 ml of ether was added and the resulted solid was collected by filtration. The solid was heated in 48% aqueous HBr at 135° C. for 4 hours, cooled to 0° C., and the crystal was collected by filtration and washed with small amount of methanol then with ethyl acetate. LC-MS showed the product as HBr salt had the expected M+H$^+$ of 186. $^1$H NMR (Varian 300 MHz, CD$_3$OD shifts relative to the solvent peak at 3.3 ppm) δ 7.2 (d, 1H) 7.0 (m, 1H) 6.9 (d, 1H) 3.1 (m, 2H) 2.9 (m, 2H).

Intermediate 72: (3-{2-[2-(3-Chloro-4-hydroxy-phenyl)-ethylamino]-pyrimidin-4-yl}-benzyl)-isopropyl-carbamic acid tert-butyl ester: Intermediate 70 was coupled with Intermediate 71 following procedure F. LC-MS showed the product had the expected M+H$^+$ of 497. $^1$H NMR (Varian 300 MHz, CDCl$_3$, shifts relative to the solvent peak at 7.24 ppm) δ 8.3 (d, 1H) 7.9 (m, 2H) 7.4 (m, 2H) 7.2 (m, 2H) 7.0 (m, 3H) 4.4 (s, 2H) 3.7 (m, 2H) 2.8 (m, 2H) 1.4 (s, br, 10H) 1.0 (d, 6H).

Compound 132: 2-Chloro-4-(2-{4-[3-(isopropylamino-methyl)-phenyl]-pyrimidin-2-ylamino}-ethyl)-phenol: Intermediate 72 was deprotected following procedure G2. LC-MS showed the product had the expected M+H$^+$ of 397. $^1$H NMR (Varian 300 MHz, CD$_3$OD shifts relative to the solvent peak at 3.3 ppm) δ 8.4 (s, 1H) 8.3 (m, 2H) 7.8 (d, 1H) 7.7 (m, 1H) 7.6 (d, 1H) 7.3 (d, 1H) 7.1 (d, 1H) 6.8 (d, 1H) 4.4 (s, 2H) 3.8 (m, 2H) 3.6 (m, 1H) 3.0 (m, 2H) 1.4 (d, 6H).

Intermediate 73: 2-(S)-[3-(2-Chloro-pyrimidin-4-yl)-benzylamino]-propan-1-ol: Intermediate 1 was coupled with 2-(S)-amino-propan-1-ol following procedure B. LC-MS showed the product had the expected M+H$^+$ of 278. $^1$H NMR (Varian 300 MHz, CDCl$_3$, shifts relative to the solvent peak at 7.24 ppm) δ 8.4 (m, 1H) 7.8 (s, 1H) 7.7 (m, 1H) 7.5 (m, 1H) 7.3 (m, 1H) 7.0 (m, 1H) 3.8 (m, 1H) 3.6 (m, 1H) 3.4 (m, 1H) 3.1 (m, 1H) 2.6 (m, 1H) 0.9 (m, 3H).

Intermediate 74: {[[3-(2-Chloro-pyrimidin-4-yl)-benzyl]-(2-hydroxy-1-methyl-ethyl)-carbamoyl]-methyl}-methyl-carbamic acid tert-butyl ester: Intermediate 73 was coupled with (tert-butoxycarbonyl-methyl-amino)-acetic acid following procedure K. LC-MS showed the product had the expected M+H$^+$ of 449. $^1$H NMR (Varian 300 MHz, CDCl$_3$, shifts relative to the solvent peak at 7.24 ppm) δ 8.6 (m, 1H) 8.1 (m, 1H) 8.0 (m, 1H) 7.7 (m, 1H) 7.5 (m, 2H) 4.6 (m, 2H) 4.3 (m, 2H) 4.0 (m, 1H) 3.7 (s, 1H) 3.5 (s, 1H) 3.0 (m, 4H) 1.4 (m, 9H) 1.2 (m, 3H).

Intermediate 75: N-[3-(2-Chloro-pyrimidin-4-yl)-benzyl]-N-(2-hydroxy-1-methyl-ethyl)-2-methylamino-acetamide: Intermediate 73 was deprotected following procedure G2. LC-MS showed the product had the expected M+H$^+$ of 349. $^1$H NMR (Varian 300 MHz, CD$_3$OD shifts relative to the solvent peak at 3.3 ppm) δ 8.7 (m, 1H) 8.1 (m, 3H) 7.6 (m, 2H) 4.7 (m, 2H) 4.4 (m, 1H) 3.8 (m, 1H) 3.7 (m, 3H) 2.8 (m, 2H) 2.1 (m, 1H) 1.6 (m, 1H) 1.3 (m, 1H) 1.2 (m, 1H).

Intermediate 76: 1-[3-(2-Chloro-pyrimidin-4-yl)-benzyl]-4,6-dimethyl-piperazin-2-one: Intermediate 75 was cyclized following procedure L. LC-MS showed the product had the expected M+H$^+$ of 331. $^1$H NMR (Varian 300 MHz, CDCl$_3$, shifts relative to the solvent peak at 7.24 ppm) δ 8.6 (m, 1H) 8.0 (m, 2H) 7.5 (m, 3H) 5.3 (m, 1H) 4.3 (m, 1H) 3.4 (m, 2H) 3.1 (m, 1H) 2.5 (m, 2H) 2.3 (s, 3H) 1.2 (d, 3H).

Compound 133: 1-(3-{2-[2-(3-Chloro-4-hydroxy-phenyl)-ethylamino]-pyrimidin-4-yl}-benzyl)-4,6-dimethyl-piperazin-2-one: Intermediate 76 was coupled with intermediate 71 following procedure F. LC-MS showed the product had the expected M+H$^+$ of 466. $^1$H NMR (Varian 300 MHz, CDCl$_3$, shifts relative to the solvent peak at 7.24 ppm) δ 8.3 (m, 1H) 7.9 (m, 2H) 7.4 (m, 2H) 7.2 (m, 1H) 7.0 (m, 3H) 5.6 (m, 1H) 5.3 (m, 1H) 4.1 (d, 1H) 3.7 (m, 2H) 3.5 (m, 1H) 3.3 (d, 1H) 3.1 (d, 1H) 2.8 (m, 2H) 2.5 (m, 2H) 2.3 (s, 3H) 1.3 (d, 3H).

Intermediate 77: 4-{[3-(2-Chloro-5-fluoro-pyrimidin-4-yl)-benzyl]-methanesulfonyl-amino}-piperidine-1-carboxylic acid tert-butyl ester: Made by procedure O. LC-MS showed the product had the expected M+H$^+$ of 499.

Compound 134: N-(3-{5-Fluoro-2-[2-(4-hydroxy-phenyl)-ethylamino]-pyrimidin-4-yl}-benzyl)-N-piperidin-4-yl-methanesulfonamide: Intermediate 77 was coupled with tyramine following procedure Q. The resulting product was deprotected following procedure R. LC-MS showed the product had the expected M+H$^+$ of 500. $^1$H NMR (Varian 300 MHz, CD$_3$OD, shifts relative to the solvent peak at 3.3 ppm) δ 8.23 (d, 1H), 8.16 (s, 1H), 7.96 (d, 1H), 7.48 (m, 2H), 7.05 (d, 2H), 6.69 (d, 2H), 4.54 (s, 2H), 3.90 (m, 1H), 3.56 (t, 2H), 3.34 (m, 2H), 3.00 (s, 3H), 2.91 (m, 2H), 2.80 (t, 2H), 1.84 (m, 4H).

Compound 135: 4-[(3-{5-Fluoro-2-[2-(3-fluoro-4-hydroxy-phenyl)-ethylamino]-pyrimidin-4-yl}-benzyl)-methanesulfonyl-amino]-piperidine-1-carboxylic acid tert-butyl ester: Intermediate 77 was coupled with intermediate 83 following procedure Q. LC-MS showed the product had the expected M+H$^+$ of 618. $^1$H NMR (Varian 300 MHz, CDCl$_3$, shifts relative to the solvent peak at 7.24 ppm) δ 8.19 (d, 1H), 8.01 (s, 1H), 7.93 (d, 1H), 7.43 (m, 2H), 6.84 (m, 3H), 5.77 (s, 1H), 5.07 (t, 1H), 4.44 (s, 2H), 4.02 (m, 2H), 3.84 (m, 1H), 3.63 (q, 2H), 2.87 (m, 2H), 2.83 (s, 3H), 2.64 (t, 2H), 1.59 (m, 4H), 1.39 (s, 9H).

Compound 136: N-(3-{5-Fluoro-2-[2-(3-fluoro-4-hydroxy-phenyl)-ethylamino]-pyrimidin-4-yl}-benzyl)-N-piperidin-4-yl-methanesulfonamide: Compound 135 was deprotected following procedure R. LC-MS showed the product had the expected M+H$^+$ of 518. $^1$H NMR (Varian 300 MHz, CD$_3$OD, shifts relative to the solvent peak at 3.3 ppm) δ 8.26 (d, 1H), 8.18 (s, 1H), 7.97 (d, 1H), 7.48 (m, 2H), 7.08 (m, 2H), 6.78 (m, 1H), 4.54 (s, 2H), 3.92 (m, 1H), 3.60 (t, 2H), 3.32 (m, 2H), 3.03 (s, 3H), 2.95 (m, 2H), 2.80 (t, 2H), 1.88 (m, 4H).

Compound 137: N-(3-{5-Fluoro-2-[2-(3-fluoro-phenyl)-ethylamino]-pyrimidin-4-yl}-benzyl)-N-piperidin-4-yl-methanesulfonamide: Intermediate 77 was coupled with 2-(3-fluoro-phenyl)-ethylamine following procedure Q. The resulting product was deprotected following procedure R. LC-MS showed the product had the expected M+H$^+$ of 502. $^1$H NMR (Varian 300 MHz, CD$_3$OD, shifts relative to the solvent peak at 3.3 ppm) δ 8.26 (d, 1H), 8.19 (s, 1H), 7.98 (d, 1H), 7.49 (m, 2H), 7.08 (m, 3H), 6.87 (m, 1H), 4.55 (s, 2H), 3.91 (m, 1H), 3.64 (t, 2H), 3.34 (m, 2H), 3.03 (s, 3H), 3.00 (m, 2H), 2.92 (t, 2H), 1.91 (m, 4H).

Compound 138: N-(3-{5-Fluoro-2-[2-(4-hydroxy-3-methoxy-phenyl)-ethylamino]-pyrimidin-4-yl}-benzyl)-N-piperidin-4-yl-methanesulfonamide: Intermediate 77 was coupled with 4-(2-amino-ethyl)-2-methoxy-phenol following procedure Q. The resulting product was deprotected following procedure R. LC-MS showed the product had the expected M+H$^+$ of 530. $^1$H NMR (Varian 300 MHz, CD$_3$OD, shifts relative to the solvent peak at 3.3 ppm) δ 8.25 (d, 1H), 8.14 (s, 1H), 7.97 (d, 1H), 7.48 (m, 2H), 6.82 (s, 1H), 6.69 (s, 2H), 4.54 (s, 2H), 3.91 (m, 1H), 3.80 (s, 3H) 3.60 (t, 2H), 3.32 (m, 2H), 3.03 (s, 3H), 2.94 (m, 2H), 2.81 (t, 2H), 1.87 (m, 4H).

Compound 139: N-(3-{2-[2-(3-Chloro-phenyl)-ethylamino]-5-fluoro-pyrimidin-4-yl}-benzyl)-N-piperidin-4-yl-methanesulfonamide: Intermediate 77 was coupled with 2-(3-chloro-phenyl)-ethylamine following procedure Q. The resulting product was deprotected following procedure R. LC-MS showed the product had the expected M+H$^+$ of 518. $^1$H NMR (Varian 300 MHz, CD$_3$OD, shifts relative to the solvent peak at 3.3 ppm) δ 8.25 (d, 1H), 8.18 (s, 1H), 7.97 (d, 1H), 7.49 (m, 2H), 7.15 (m, 4H), 4.56 (s, 2H), 3.93 (m, 1H), 3.64 (t, 2H), 3.33 (m, 2H), 3.04 (s, 3H), 2.98 (m, 2H), 2.91 (t, 2H), 1.91 (m, 4H).

Compound 140: N-[3-(5-Fluoro-2-phenethylamino-pyrimidin-4-yl)-benzyl]-N-piperidin-4-yl-methanesulfonamide: Intermediate 77 was coupled with phenethylamine following procedure Q. The resulting product was deprotected following procedure R. LC-MS showed the product had the expected M+H+ of 484. ¹H NMR (Varian 300 MHz, CD₃OD, shifts relative to the solvent peak at 3.3 ppm) δ 8.25 (d, 1H), 8.17 (s, 1H), 7.98 (d, 1H), 7.49 (m, 2H), 7.26 (m, 5H), 4.55 (s, 2H), 3.89 (m, 1H), 3.62 (t, 2H), 333 (m, 2H), 3.03 (s, 3H), 2.98 (m, 2H), 2.90 (t, 2H), 1.89 (m, 4H).

Compound 141: 4-[(3-{2-[2-(3-Chloro-4-hydroxy-phenyl)-ethylamino]-5-fluoro-pyrimidin-4-yl}-benzyl)-methanesulfonyl-amino]-piperidine-1-carboxylic acid tert-butyl ester: Intermediate 77 was coupled with intermediate 71 following procedure Q. LC-MS showed the product had the expected M+H+ of 634. ¹H NMR (Varian 300 MHz, CDCl₃, shifts relative to the solvent peak at 7.24 ppm) δ 8.20 (d, 1H), 8.03 (s, 1H), 7.94 (d, 1H), 7.43 (m, 2H), 7.19 (s, 1H), 6.89 (m, 2H), 5.71 (s, 1H), 5.08 (t, 1H), 4.45 (s, 2H), 4.02 (m, 2H), 3.81 (m, 1H), 3.63 (q, 2H), 2.83 (s, 3H), 2.81 (m, 2H), 2.63 (t, 2H), 1.51 (m, 4H), 1.39 (s, 9H).

Compound 142: N-(3-{2-[2-(3-Chloro-4-hydroxy-phenyl)-ethylamino]-5-fluoro-pyrimidin-4-yl}-benzyl)-N-piperidin-4-yl-methanesulfonamide: Compound 141 was deprotected following procedure R. LC-MS showed the product had the expected M+H+ of 534. 1H NMR (Varian 300 MHz, CD₃OD, shifts relative to the solvent peak at 3.3 ppm) δ 8.25 (d, 1H), 8.17 (s, 1H), 7.97 (d, 1H), 7.49 (m, 2H), 7.18 (d, 1H), 6.99 (d, 1H), 6.79 (d, 1H), 4.55 (s, 2H), 3.91 (m, 1H), 3.58 (t, 2H), 3.34 (m, 2H), 3.03 (s, 3H), 2.95 (m, 2H), 2.80 (t, 2H), 1.87 (m, 4H).

Intermediate 78: (3-{[3-(2-Chloro-5-fluoro-pyrimidin-4-yl)-benzyl]-ethyl-amino}-propyl)-carbamic acid tert-butyl ester: Made by procedure P. LC-MS showed the product had the expected M+H+ of 423.

Compound 143: 4-{2-[4-(3-{[(3-Amino-propyl)-ethyl-amino]-methyl}-phenyl)-5-fluoro-pyrimidin-2-ylamino]-ethyl}-2-fluoro-phenol: Intermediate 78 was coupled with intermediate 83 following procedure Q. The resulting product was deprotected following procedure R. LC-MS showed the product had the expected M+H+ of 442. ¹H NMR (Varian 300 MHz, CD₃OD, shifts relative to the solvent peak at 3.3 ppm) δ 8.29 (d, 1H), 8.18 (s, 2H), 7.66 (m, 2H), 6.77 (m, 3H), 4.49 (s, 2H), 3.59 (t, 2H), 3.24 (m, 4H), 2.98 (t, 2H), 2.80 (t, 2H), 2.07 (m, 2H), 1.36 (t, 3H).

Compound 144: N1-Ethyl-N1-(3-{5-fluoro-2-[2-(3-fluoro-phenyl)-ethylamino]-pyrimidin-4-yl}-benzyl)-propane-1,3-diamine: Intermediate 78 was coupled with 2-(3-fluoro-phenyl)-ethylamine following procedure Q. The resulting product was deprotected following procedure R. LC-MS showed the product had the expected M+H+ of 426. ¹H NMR (Varian 300 MHz, CD₃OD, shifts relative to the solvent peak at 3.3 ppm) δ 8.29 (d, 1H), 8.19 (s, 2H), 7.66 (m, 2H), 6.97 (m, 4H), 4.49 (s, 2H), 3.64 (t, 2H), 3.24 (m, 4H), 2.97 (t, 2H), 2.92 (t, 2H), 2.07 (m, 2H), 1.36 (t, 3H).

Compound 145: N1-(3-{2-[2-(3-Chloro-phenyl)-ethylamino]-5-fluoro-pyrimidin-4-yl}-benzyl)-N1-ethyl-propane-1,3-diamine: Intermediate 78 was coupled with 2-(3-chloro-phenyl)-ethylamine following procedure Q. The resulting product was deprotected following procedure R. LC-MS showed the product had the expected M+H+ of 442. ¹H NMR (Varian 300 MHz, CD₃OD, shifts relative to the solvent peak at 3.3 ppm) δ 8.30 (d, 1H), 8.18 (s, 2H), 7.66 (m, 2H), 7.12 (m, 4H), 4.49 (s, 2H), 3.63 (t, 2H), 3.24 (m, 4H), 2.98 (t, 2H), 2.90 (t, 2H), 2.08 (m, 2H), 1.36 (t, 3H).

Compound 146: 4-{2-[4-(3-{[(3-Amino-propyl)-ethyl-amino]-methyl}-phenyl)-5-fluoro-pyrimidin-2-ylamino]-ethyl}-phenol: Intermediate 78 was coupled with tyramine following procedure Q. The resulting product was deprotected following procedure R. LC-MS showed the product had the expected M+H+ of 424. ¹H NMR (Varian 300 MHz, CD₃OD, shifts relative to the solvent peak at 3.3 ppm) δ 8.29 (d, 1H), 8.19 (s, 2H), 7.66 (m, 2H), 7.05 (d, 2H), 6.68 (d, 2H), 4.49 (s, 2H), 3.58 (t, 2H), 3.24 (m, 4H), 2.98 (t, 2H), 2.80 (t, 2H), 2.07 (m, 2H), 1.36 (t, 3H).

Compound 147: 4-{2-[4-(3-{[(3-Amino-propyl)-ethyl-amino]-methyl}-phenyl)-5-fluoro-pyrimidin-2-ylamino]-ethyl}-2-chloro-phenol: Intermediate 78 was coupled with 4-(2-amino-ethyl)-2-chloro-phenol following procedure Q. The resulting product was deprotected following procedure R. LC-MS showed the product had the expected M+H+ of 458. ¹H NMR (Varian 300 MHz, CD₃OD, shifts relative to the solvent peak at 3.3 ppm) δ 8.28 (d, 1H), 8.17 (s, 2H), 7.66 (m, 2H), 7.17 (d, 1H), 6.97 (d, 1H), 6.78 (d, 1H), 4.48 (s, 2H), 3.59 (t, 2H), 3.24 (m, 4H), 2.98 (t, 2H), 2.79 (t, 2H), 2.06 (m, 2H), 1.36 (t, 3H).

Intermediate 79: 4-[2-(3-{5-Fluoro-2-[2-(4-hydroxy-phenyl)-ethylamino]-pyrimidin-4-yl}-phenyl)-ethyl]-piperidine-1-carboxylic acid tert-butyl ester: Made by procedure U. LC-MS showed the product had the expected M+H+ of 521.

Compound 148: 4-(2-{5-Fluoro-4-[3-(2-piperidin-4-yl-ethyl)-phenyl]-pyrimidin-2-ylamino}-ethyl)-phenol: Intermediate 79 was coupled with tyramine following procedure I. The resulting product was deprotected following procedure J. LC-MS showed the product had the expected M+H+ of 421. ¹H NMR (Varian 300 MHz, CD₃OD, shifts relative to the solvent peak at 3.3 ppm) δ 8.23 (d, 1H), 7.91 (s, 1H), 7.85 (d, 1H), 7.32 (m, 2H), 7.06 (d, 2H), 6.68 (d, 2H), 3.54 (t, 2H), 3.35 (m, 2H), 2.89 (t, 2H), 2.73 (m, 4H), 1.97 (d, 2H), 1.61 (m, 3H), 1.32 (m, 2H).

Compound 149: 2-Chloro-4-(2-{5-fluoro-4-[3-(2-piperidin-4-yl-ethyl)-phenyl]-pyrimidin-2-ylamino}-ethyl)-phenol: Intermediate 79 was coupled with 4-(2-amino-ethyl)-2-chloro-phenol following procedure I. The resulting product was deprotected following procedure J. LC-MS showed the product had the expected M+H+ of 455. ¹H NMR (Varian 300 MHz, CD₃OD, shifts relative to the solvent peak at 3.3 ppm) δ 8.23 (d, 1H), 7.90 (s, 1H), 7.85 (d, 1H), 7.35 (m, 2H), 7.20 (s, 1H), 6.99 (d, 1H), 6.80 (d, 1H), 3.56 (t, 2H), 3.34 (m, 2H), 2.89 (t, 2H), 2.72 (m, 4H), 1.97 (d, 2H), 1.60 (m, 3H), 1.32 (m, 2H).

Intermediate 80: 2-(3,5-Difluoro-phenyl)-ethylamine: 3,5 difluorophenylacetonitrile (5 g) was dissolved in TI-IF (100 mL) and a solution of BH3 in THF (200 mL of 1 M) was added dropwise. The mixture was refluxed overnight, cooled in an ice bath, and the reaction quenched with methanol (20 mL). The solvent was removed by rotary evaporation and the residue partitioned between ethyl acetate and water. The organic layer was washed with sat NaCl and the solvent again removed to give product, which was used in the next step without purification.

Compound 150: [2-(3,5-Difluoro-phenyl)-ethyl]-{4-[3-(piperidin-4-ylamino)-phenyl]-pyrimidin-2-yl}-amine: Intermediate 7 was coupled with intermediate 80 following procedure F. The resulting product was deprotected following procedure G. LC-MS showed the product had the expected M+H+ of 408. ¹H NMR (Varian 300 MHz, CD₃OD, shifts relative to the solvent peak at 3.30 ppm) δ 8.5 (m, 1H) 7.3-7.6 (m, 6H) 7.05 (m, 1H) 6.92 (m, 1H) 6.75 (m, 1H) 3.9 (br s, 2H) 3.75 (m, 1H) 3.45 (m, 3H) 3.18 (m, 2H) 3.05 (m, 2H) 2.27 (m, 3H) 1.77 (m, 2H).

Intermediate 81: 2-Fluoro-1-methoxy-4-(2-nitro-vinyl)-benzene: 3-Fluoro-4-methoxy-benzaldehyde (10 g) was dissolved in 100 mL of nitromethane along with 5 g of ammonium acetate. The mixture was refluxed for 2 hours. The nitromethane was removed by rotary evaporation and the residue recrystallized from ethanol to give 7.6 g of the expected product. LC-MS showed the product had the expected M+H$^+$ of 198.

Intermediate 82: 2-(3-Fluoro-4-methoxy-phenyl)-ethylamine: Lithium aluminum hydride (200 mL of 1 M in diethyl ether) was placed in a 1 L round bottomed flask along with 300 mL of diethyl ether. Intermediate 81 was placed in the thimble of a soxhlet extractor atop this flask and the mixture refluxed for 24 hours. The mixture was cooled to 0° C. and 50 mL of ethyl acetate added dropwise. After stirring for 1 hour, the mixture was quenched with 100 mL of 1 N KHSO$_4$. The Organic layer was separated washed with sat. NaHCO$_3$, sat. NaCl, and dried over MgSO$_4$. Removal of the solvent gave product. LC-MS showed the product had the expected M+H$^+$ of 170. It was used in the next step without purification.

Intermediate 83: 4-(2-Amino-ethyl)-2-fluoro-phenol: Intermediate 82 was dissolved in 200 mL of 48% aqueous HBr and the mixture heated to reflux for 2 hours. The Solvent was removed by rotary evaporation. The residue was taken up in 100 mL of ethanol and the solvent again removed. This was repeated twice more to remove residual water. LC-MS showed the product was >90% pure had the expected M+H$^+$ of 156.

Compound 151: 2-Fluoro-4-(2-{4-[3-(piperidin-4-ylamino)-phenyl]-pyrimidin-2-ylamino}-ethyl)-phenol: Intermediate 7 was coupled with intermediate 83 following procedure F. The resulting product was deprotected following procedure G. LC-MS showed the product had the expected M+H$^+$ of 408.

Intermediate 84: 4-{[3-(2-Chloro-pyrimidin-4-yl)-benzyl]-ethyl-amino}-piperidine-1-carboxylic acid tert-butyl ester: Intermediate 1 was coupled with 4-Amino-piperidine-1-carboxylic acid tert-butyl ester following procedure B. When the starting aldehyde had been consumed, 2 equivalents each of acetaldehyde and sodium triacetoxyborohydride were added and the mixture stirred for another two hours. The organic layer was washed with, water followed by sat. NaCl. The solvent was removed to give product LC-MS showed the product was >90% pure and had the expected M+H$^+$ of 403, and it was used in the following reactions without purification.

Compound 152: [2-(3,5-Difluoro-phenyl)-ethyl]-(4-{3-[(ethyl-piperidin-4-yl-amino)-methyl]-phenyl}-pyrimidin-2-yl)-amine: Intermediate 84 was coupled with intermediate 80 following procedure F. The resulting product was deprotected following procedure G. LC-MS showed the product had the expected M+H$^+$ of 452. $^1$H NMR (Varian 300 MHz, CD$_3$OD, shifts relative to the solvent peak at 3.30 ppm) δ 8.3-8.4 (m, 3H), 7.6-7.9 (m, 2H) 7.45 (d, 1H) 7.2 (m, 1H) 6.92 (m, 2H) 6.75 (m, 1H) 4.56 (br s, 2H) 3.88 (m, 3H) 3.62 (m, 2H) 3.15 (m, 1H) 3.05 (m, 2H) 2.47 (m, 2H) 2.2 (m, 2H) 1.33 (t, 3H).

Compound 153: 2-Chloro-4-(2-{4-[3-(2-(S) methyl-piperazin-1-ylmethyl)-phenyl]-pyrimidin-2-ylamino}-ethyl)-phenol Intermediate 68 was coupled with intermediate 71 following procedure F. The resulting product was deprotected following procedure G. LC-MS showed the product had the expected M+H$^+$ of 438. $^1$H NMR (Varian 300 MHz, CD$_3$OD, shifts relative to the solvent peak at 3.30 ppm) δ 8.55 (s, 1H) 8.28 (d, 1H) 8.1 (s, 1H) 7.99 (d, 1H) 7.5 (m, 2H) 7.29 d, 1H) 7.1 (d, 1H) 7.0 (m, 1H) 6.82 (m, 1H) 4.2 (d, 1H) 3.62 (t, 1H) 3.38 (m, 4H) 3.2 (m, 1H) 3.0 (m, 1H) 2.85 (m, 3H) 2.7 (m, 1H) 2.35 (m, 1H) 1.28 (d, 3H).

Compound 154: [2-(3,5-Difluoro-phenyl)-ethyl]-{4-[3-(2-(S) methyl-piperazin-1-ylmethyl)-phenyl]-pyrimidin-2-yl}-amine: Intermediate 68 was coupled with intermediate 80 following procedure F. The resulting product was deprotected following procedure G. LC-MS showed the product had the expected M+H$^+$ of 424. $^1$H NMR (Varian 300 MHz, CD$_3$OD, shifts relative to the solvent peak at 3.30 ppm) δ 8.38 (m, 2H) 8.36 (d, 2H) 7.8 (m, 1H) 7.68 (m, 1H) 7.5 (d, 1H) 6.95 (m, 2) 6.75 (m, 1H) 4.75 (d, 1H) 4.02 (d, 1H) 3.9 (br s, 2H) 3.4-3.65 (m, 3H) 3.2-3.4 (m, 4H) 3.05 (m, 3H) 1.55 (d, 3H).

Compound 155: (4-{3-[(Ethyl-piperidin-4-yl-amino)-methyl]-phenyl}-pyrimidin-2-yl)-[2-(3-fluoro-phenyl)-ethyl]-amine: Intermediate 84 was coupled with 3-fluoro phenethylamine following procedure F. The resulting product was deprotected following procedure G. The product was purified by HPLC. LC-MS showed the product had the expected M+H$^+$ of 434. $^1$H NMR (Varian 300 MHz, DMSO, shifts relative to the solvent peak at 2.50 ppm) δ 8.3 (d, 1H), 8.0 (s, 1H), 7.9 (d, 1H), 7.4 (m, 2H), 7.3 (m, 2H), 7.1 (d, 2H), 7.0 (d, 1H), 3.6 (s, 2H), 3.2 (m, 2H), 2.9 (m, 6H), 2.7 (q, 2H), 1.8-1.7 (m, 5H), 0.96 (t, 3H).

Compound 156: (N-(3-{2-[2-(3-Chloro-4-hydroxy-phenyl)-ethylamino]-pyrimidin-4-yl}-benzyl)-N-(1-ethyl-piperidin-4-yl)methanesulfonamide: Compound 169 was coupled with acetaldehyde following procedure E. The product was purified by HPLC. LC-MS showed the product had the expected M+H$^+$ of 544. $^1$H NMR (Varian 300 MHz, DMSO, shifts relative to the solvent peak at 2.50 ppm) δ 8.3 (d, 1H), 8.1 (d, 1H), 7.5-7.4 (m, 3H), 7.2 (d, 1H), 7.1 (d, 1H), 7.0 (d, 1H), 6.8 (d, 1H), 4.4 (s, 2H), 3.6 (d, 2H), 3.5 (d, 2H), 3.0 (s, 3H), 2.8 (q, 2H), 2.2 (m, 1H), 1.8 (m, 4H), 1.6 (m, 4H), 0.96 (t, 3H).

Compound 157: (N-(3-{2-[2-(3-Chloro-4-hydroxy-phenyl)-ethylamino]-pyrimidin-4-yl}-benzyl)-N-(1-propyl-piperidin-4-yl)methanesulfonamide: Compound 169 was coupled with propionaldehyde following procedure E. The product was purified by HPLC. LC-MS showed the product had the expected M+H$^+$ of 558. $^1$H NMR (Varian 300 MHz, DMSO, shifts relative to the solvent peak at 2.50 ppm) δ 8.3 (d, 1H), 8.1 (d, 1H), 7.5-7.4 (m, 3H), 7.2 (d, 1H), 7.1 (d, 1H), 7.0 (d, 1H), 6.8 (d, 1H), 4.4 (s, 2H), 3.6 (d, 2H), 3.5 (d, 2H), 3.0 (s, 3H), 2.7 (m, 1H), 2.1 (t, 2H), 1.8 (m, 4H), 1.6 (m, 4H), 1.3 (q, 2H), 0.76 (t, 3H).

Intermediate 85: 2-Chloro-4-[2-(4-{3-[(ethyl-piperidin-4-yl-amino)-methyl]-phenyl}-pyrimidin-2-ylamino)-ethyl]-phenol: Intermediate 84 was coupled with intermediate 71 following procedure F. The resulting product was deprotected by procedure G. LC-MS showed the product had the expected M+H$^+$ of 466.

Compound 158: 2-Chloro-4-{2-[4-(3-{[ethyl-(-ethyl-piperidin-4-yl)-amino}-methyl]-phenyl)-pyrimidin-2-ylamino]-ethyl}-phenol: Intermediate 85 was coupled with acetaldehyde following procedure E. The product was purified by HPLC. LC-MS showed the product had the expected M+H$^+$ of 494. $^1$H NMR (Varian 300 MHz, DMSO, shifts relative to the solvent peak at 2.50 ppm) δ 8.3 (d, 1H), 7.9 (d, 1H), 7.5-7.4 (m, 3H), 7.2 (d, 1H), 7.1 (d, 1H), 7.0 (d, 1H), 6.8 (d, 1H), 3.6 (s, 2H), 3.5 (d, 2H), 3.1 (d, 2H), 2.7 (q, 2H), 2.6 (m, 3H), 2.3 (m, 4H), 1.7-1.6 (m, 4H), 1.0 (t, 3H), 0.94 (t, 3H).

Compound 159: 2-Chloro-4-{2-[4-(3-{[ethyl-(1-propyl-piperidin-4-yl)-amino]-methyl}-phenyl)-pyrimidin-2-ylamino]-ethyl}-phenol: Intermediate 85 was coupled with propionaldehyde following procedure E. The product was purified by HPLC. LC-MS showed the product had the expected M+H$^+$ of 508. $^1$H NMR (Varian 300 MHz, DMSO, shifts relative to the solvent peak at 2.50 ppm) δ 8.3 (d, 1H), 7.9 (d, 1H), 7.5-7.4 (m, 3H), 7.2 (d, 1H), 7.1 (d, 1H), 7.0 (d, 1H), 6.8 (d, 1H), 3.6 (s, 2H), 3.5 (d, 2H), 3.1 (d, 2H), 2.7 (q, 2H), 2.6 (m, 3H), 2.3 (m, 4H), 1.7-1.6 (m, 4H), 1.5-1.4 (m, 2H), 0.94 (t, 3H), 0.80 (t, 3H).

Compound 160: 2-Chloro-4-{2-[4-(3-{[ethyl-(1-pyridin-4-ylmethyl-piperidin-4-yl)-amino]-methyl}-phenyl)-pyrimidin-2-ylamino]-ethyl}-phenol: Intermediate 85 was coupled with pyridine 4-carboxaldehyde following procedure E. The product was purified by HPLC. LC-MS showed the product had the expected M+H⁺ of 557. ¹H NMR (Varian 300 MHz, DMSO, shifts relative to the solvent peak at 2.50 ppm) δ 8.4 (d, 2H), 8.2 (d, 1H), 8.1 (s, 1H), 7.8 (d, 1H), 7.4-7.3 (m, 2H), 7.2-7.1 (m, 3H), 7.0 (d, 1H), 6.9 (d, 1H), 6.8 (d, 1H), 3.6 (s, 4H), 3.4 (d, 2H), 3.1 (d, 2H), 2.7 (m, 3H), 1.9-1.8 (m, 4H), 1.6-1.4 (m, 4H), 0.94 (t, 3H).

Intermediate 86: 5-(2-Chloro-pyrimidin-4-yl)-2-methoxy-benzaldehyde: 2,4 dichloropyrimidine and 3-formyl 4-methoxy phenyl boronic acid were coupled following procedure A. LC-MS showed the product was >95% pure and had the expected M+H⁺ of 249.

Intermediate 87: 4-[5-(2-Chloro-pyrimidin-4-yl)-2-methoxy-benzylamino]-piperidine-1-carboxylic acid tert-butyl ester: Intermediate 86 was coupled with 4-Amino-piperidine-1-carboxylic acid tert-butyl ester following procedure B. LC-MS showed the product was >95% pure and had the expected M+H⁺ of 433.

Intermediate 88: 4-{[5-(2-Chloro-pyrimidin-4-yl)-2-methoxy-benzyl]-methanesulfonyl-amino}-piperidine-1-carboxylic acid tert-butyl ester: Intermediate 88 was coupled with methanesulfonyl chloride following procedure D. LC-MS showed the product was >95% pure and had the expected M+H⁺ of 511.

Compound 161: N-(5-{2-[2-(3-Fluoro-phenyl)-ethylamino]-pyrimidin-4-yl}-2-methoxy-benzyl)-N-piperidin-4-yl-methanesulfonamide: Intermediate 88 was coupled with 3-fluorophenethylamine following procedure F. The resulting product was deprotected following procedure G. The product was purified by HPLC. LC-MS showed the product had the expected M+H⁺ of 514. ¹H NMR (Varian 300 MHz, DMSO, shifts relative to the solvent peak at 2.50 ppm) δ 7.9 (d, 1H), 7.3 (m, 2H), 7.1 (t, 1H), 7.0 (m, 3H), 6.8 (d, 2H), 4.3 (s, 2H), 3.9 (s, 3H), 3.5 (d, 2H), 3.0 (s, 3H), 2.9 (m, 6H), 2.6 (m, 1H), 1.8-1.6 (m, 4H).

Compound 162: (N-[2-Methoxy-5-(2-phenylethylamino-pyrimidin-4-yl)-benzyl]-N-piperidin-4-yl-methanesulfonamide: Intermediate 88 was coupled with phenethylamine. The product was purified by HPLC. LC-MS showed the product had the expected M+H⁺ of 496. ¹H NMR (Varian 300 MHz, DMSO, shifts relative to the solvent peak at 2.50 ppm) δ 7.9 (d, 1H), 7.3-7.2 (m, 4H), 7.2-7.0 (m, 3H), 6.9 (d, 2H), 4.3 (s, 2H), 3.9 (s, 3H), 3.5 (d, 2H), 3.0 (s, 3H), 2.8 (m, 6H), 2.6 (m, 1H), 1.7-1.5 (m, 4H).

Compound 163: (N-(5-{2-[2-(3-Fluoro-4-hydroxy-phenyl)-ethylamino]-pyrimidin-4-yl}-2-methoxy-benzyl)-N-piperidin-4-yl-methanesulfonamide: Intermediate 88 was coupled with intermediate 83 following procedure F. The resulting product was deprotected following procedure G. The product was purified by HPLC. LC-MS showed the product had the expected M+H⁺ of 530. ¹H NMR (Varian 300 MHz, DMSO, shifts relative to the solvent peak at 2.50 ppm) δ 7.9 (d, 1H), 7.0 (m, 2H), 7.0 (m, 3H), 6.8 (m, 2H), 4.3 (s, 2H), 3.9 (s, 3H), 3.5 (d, 2H), 3.0 (s, 3H), 2.7 (m, 6H), 2.6 (m, 1H), 1.7-1.5 (m, 4H).

Intermediate 89: 5-(2-Chloro-pyrimidin-4-yl)-2-fluoro-benzaldehyde: 2,4 dichloropyrimidine and 3-formyl 4-fluorophenyl boronic acid were coupled following procedure A. LC-MS showed the product was >95% pure and had the expected M+H⁺ of 237.

Intermediate 90: 4-[5-(2-Chloro-pyrimidin-4-yl)-2-fluoro-benzylamino]-piperidine-1-carboxylic acid tert-butyl ester: Intermediate 89 was coupled with 4-Amino-piperidine-1-carboxylic acid tert-butyl ester following procedure B. LC-MS showed the product was >95% pure and had the expected M+H⁺ of 421.

Intermediate 91: 4-{[5-(2-Chloro-pyrimidin-4-yl)-2-fluoro-benzyl]-methanesulfonyl-amino}-piperidine-1-carboxylic acid tert-butyl ester: Intermediate 90 was coupled with methanesulfonyl chloride following procedure D LC-MS showed the product was >95% pure and had the expected M+H⁺ of 499.

Compound 164: N-(2-Fluoro-5-{2-[2-(3-fluoro-phenyl)-ethylamino]-pyrimidin-4-yl}-benzyl)-N-piperidin-4-yl-methanesulfonamide: Intermediate 91 was coupled with 3-fluorophenethylamine following procedure F. The resulting product was deprotected following procedure G. The product was purified by HPLC. LC-MS showed the product had the expected M+H⁺ of 502. ¹H NMR (Varian 300 MHz, DMSO, shifts relative to the solvent peak at 2.50 ppm) δ 8.0 (d, 1H), 7.3-7.2 (m, 3H), 7.1-6.9 (m, 5H), 4.4 (s, 2H), 3.6 (d, 2H), 3.0 (s, 3H), 2.9 (m, 6H), 2.7 (m, 1H), 1.7 (m, 4H).

Compound 165: (N-(2-Fluoro-5-{2-[2-(3-Fluoro-4-hydroxy-phenyl)-ethylamino]-pyrimidin-4-yl}-2-methoxy-benzyl)-N-piperidin-4-yl-methanesulfonamide: Intermediate 91 was coupled with intermediate 83 following procedure F. The resulting product was deprotected following procedure G. The product was purified by HPLC. LC-MS showed the product had the expected M+H⁺ of 518. ¹H NMR (Varian 300 MHz, DMSO, shifts relative to the solvent peak at 2.50 ppm) δ 8.0 (d, 1H), 7.3-7.2 (m, 2H), 7.0 (m, 2H), 6.8 (m, 3H), 4.4 (s, 2H), 3.5 (d, 2H), 3.0 (s, 3H), 2.8-2.6 (m, 7H), 1.7 (m, 4H).

Intermediate 92: 4-[2-(4-{3-[(Ethyl-piperidin-4-yl-amino)-methyl]-phenyl}-pyrimidin-2-ylamino)-ethyl]-2-fluoro-phenol: Intermediate 84 was coupled with intermediate 83 following procedure F. The resulting product was deprotected following procedure G. LC-MS showed the product had the expected M+H⁺ of 450.

Compound 166: 4-{2-[4-(3-{[Ethyl-(1-propyl-piperidin-4-yl)-amino]-methyl}-phenyl)-pyrimidin-2-ylamino]-ethyl}-2-fluoro-phenol: Intermediate 92 was coupled with propionaldehyde following procedure E. The product was purified by HPLC. LC-MS showed the product had the expected M+H⁺ of 492. ¹H NMR (Varian 300 MHz, DMSO, shifts relative to the solvent peak at 2.50 ppm) δ 7.9 (d, 1H), 7.4-7.3 (m, 2H), 7.2 (t, 1H), 7.0-6.9 (m, 2H), 6.8 (m, 3H), 3.6 (s, 2H), 3.5 (d, 2H), 3.1 (m, 3H), 2.7 (q, 2H), 2.6 (m, 4H), 2.2 (t, 2H), 1.7-1.6 (m, 4H), 1.5-1.4 (m, 2H), 0.94 (t, 3H), 0.80 (t, 3H).

Compound 167: 4-{2-[4-(3-{[Ethyl-(1-pyridin-4-ylmethyl-piperidin-4-yl)-amino]-methyl}-phenyl)-pyrimidin-2-ylamino]-ethyl}-2-fluoro-phenol: Intermediate 92 was coupled with pyridine-4-carboxaldehyde following procedure E. The product was purified by HPLC. LC-MS showed the product had the expected M+H⁺ of 541. ¹H NMR (Varian 300 MHz, DMSO, shifts relative to the solvent peak at 2.50 ppm) δ 8.4 (d, 2H), 8.3 (d, 1H), 7.9 (d, 1H), 7.4 (m, 2H), 7.2 (m, 3H), 7.0 (m, 2H), 6.8 (m, 2H), 3.6 (s, 2H), 3.5 (d, 2H), 3.4 (s, 2H), 2.7 (m, 4H), 2.5 (q, 2H), 1.9 (m, 1H), 1.7-1.4 (m, 4H), 0.9 (t, 3H).

Compound 168: (N-(3-{2-[2-(3-Fluoro-4-hydroxy-phenyl)-ethylamino]-pyrimidin-4-yl}-benzyl)-N-piperidin-4-yl-methanesulfonamide: Intermediate 30 was coupled with intermediate 83 following procedure F. The resulting product was deprotected following procedure G. The product was purified by HPLC. LC-MS showed the product had the expected M+H⁺ of 500. ¹H NMR (Varian 300 MHz, DMSO, shifts relative to the solvent peak at 2.50 ppm) δ 8.1 (d, 1H), 7.9 (d, 1H), 7.5 (m, 2H), 7.2 (t, 1H), 7.0 (m, 2H), 6.8 (d, 2H), 4.4 (s, 2H), 3.8 (d, 2H), 3.5 (d, 2H), 3.0 (s, 3H), 2.7 (m, 4H), 2.6 (m, 1H), 1.7 (m, 4H).

Compound 169: (N-(3-{2-[2-(3-Chloro-4-hydroxy-phenyl)-ethylamino]-pyrimidin-4-yl}-benzyl)-N-piperidin-4-yl)methanesulfonamide: Intermediate 30 was coupled with intermediate 71 following procedure F. The resulting product was deprotected following procedure G. The product was purified by HPLC. LC-MS showed the product had the expected M+H+ of 516. $^1$H NMR (Varian 300 MHz, DMSO, shifts relative to the solvent peak at 2.50 ppm) δ 8.3 (d, 1H), 7.9 (d, 1H), 7.4 (m, 2H), 7.2 (m, 2H), 7.0 (d, 1H), 6.9 (d, 1H), 6.8 (d, 1H), 4.4 (s, 2H), 3.8 (d, 2H), 3.5 (d, 2H), 3.0 (s, 3H), 2.7 (m, 4H), 2.6 (m, 1H), 1.6 (m, 4H).

Intermediate 93: 4-{[3-(2-Chloro-pyrimidin-4-yl)-benzyl]-propyl-amino}-piperidine-1-carboxylic acid tert-butyl ester: Intermediate 29 was coupled with propionaldehyde following procedure E. LC-MS showed the product had the expected M+H+ of 445.

Compound 170: 2-Fluoro-4-[2-(4-{3-[(piperidin-4-yl)-propyl-amino)-methyl]-phenyl}-pyrimidin-2-ylamino)-ethyl]-phenol: Intermediate 93 was coupled with intermediate 83 following procedure F. The resulting product was deprotected following procedure G. The product was purified by HPLC. LC-MS showed the product had the expected M+H+ of 464. $^1$H NMR (Varian 300 MHz, DMSO, shifts relative to the solvent peak at 2.50 ppm) δ 8.3 (d, 1H), 7.9 (d, 1H), 7.4 (m, 2H), 7.2 (t, 1H), 7.0 (d, 2H), 6.9 (d, 1H), 6.8 (d, 1H), 3.6 (s, 2H), 3.5 (d, 2H), 3.2 (d, 2H), 2.7 (m, 5H), 2.4 (t, 2H), 1.8 (m, 4H), 1.3 (q, 2H), 0.96 (t, 3H).

Compound 171: 2-Chloro-4-[2-(4-{3-[(piperidin-4-yl)-propyl-amino)-methyl]-phenyl}-pyrimidin-2-ylamino]-ethyl]-phenol: Intermediate 93 was coupled with intermediate 71 following procedure F. The resulting product was deprotected following procedure G. The product was purified by HPLC. LC-MS showed the product had the expected M+H+ of 480. $^1$H NMR (Varian 300 MHz, DMSO, shifts relative to the solvent peak at 2.50 ppm) δ 8.3 (d, 1H), 7.9 (d, 1H), 7.4 (m, 2H), 7.2 (m, 2H), 7.0 (d, 1H), 6.9 (d, 1H), 6.8 (d, 1H), 3.6 (s, 2H), 3.5 (d, 2H), 3.2 (d, 2H), 2.7 (m, 5H), 2.4 (t, 2H), 1.8 (m, 4H), 1.3 (m, 2H), 0.7 (t, 3H).

Compound 172: [2-(3-Fluoro-phenyl)-ethyl-(4-{3-[(piperidin-4-yl-propyl-amino)-methyl]-phenyl}-pyrimidin-2-yl)-amine: Intermediate 93 was coupled with 3-fluorophenethylamine following procedure F. The resulting product was deprotected following procedure G. The product was purified by HPLC. LC-MS showed the product had the expected M+H+ of 448. $^1$H NMR (Varian 300 MHz, DMSO, shifts relative to the solvent peak at 2.50 ppm) δ 8.3 (d, 1H), 8.0 (s, 1H), 7.9 (d, 1H), 7.4 (m, 2H), 7.3 (m, 2H), 7.1 (d, 2H), 7.0 (d, 1H), 3.6 (s, 2H), 3.5 (d, 2H), 3.2 (d, 2H), 2.9 (m, 4H), 2.8 (m, 1H), 2.5 (d, 2H), 1.8 (m, 4H), 1.3 (m, 2H), 0.96 (t, 3H).

Intermediate 94: 4-{2-[3-(2-Chloro-pyrimidin-4-yl)-phenyl]-ethyl}-piperidine-1-carboxylic acid tert-butyl ester: Made by Procedure U. LC-MS showed the product had the expected M+H+ of 402.

Compound 173: 2-Chloro-4-(2-{4-[3-(2-piperidin-4-yl-ethyl)-phenyl]-pyrimidin-2-ylamino}-ethyl)-phenol: Intermediate 94 was coupled with 4-(2-amino-ethyl)-2-chloro-phenol following procedure Q. The resulting product was deprotected following procedure G2. LC-MS showed the product had the expected M+H+ of 437. $^1$H NMR (Varian 300 MHz, CD$_3$OD, shifts relative to the solvent peak at 3.3 ppm) δ 8.27 (d, 1H), 8.05 (s, 1H), 7.99 (m, 1H), 7.46 (d, 2H), 7.35 (d, 1H), 7.24 (d, 1H), 7.03 (d, 1H), 6.80 (d, 1H), 3.70 (m, 2H), 3.35 (m, 2H), 2.78 (m, 6H), 1.99 (d, 2H), 1.66 (m, 3H), 1.37 (m, 2H).

Compound 174: 2-Chloro-4-[2-(4-{3-[(ethyl-piperidin-4-yl-amino)-methyl]-phenyl}-pyrimidin-2-ylamino)-ethyl]-phenol: Intermediate 84 was coupled with 4-(2-amino-ethyl)-2-chloro-phenol following procedure F. The resulting product was deprotected following procedure G2. LC-MS showed the product had the expected M+H+ of 467. $^1$H NMR (Varian 300 MHz, CD$_3$OD, shifts relative to the solvent peak at 3.3 ppm) δ 8.27 (m, 2H), 7.69 (m, 2H), 7.26 (d, 1H), 7.19 (m, 1H), 7.04 (s, 1H), 7.01 (d, 1H), 6.80 (d, 1H), 4.48 (m, 2H), 3.53 (m, 4H), 3.09 (m, 4H), 2.85 (t, 2H), 2.39 (d, 2H), 2.03 (m, 3H), 1.32 (t, 3H).

Intermediate 95: 3-({[3-(2-Chloro-pyrimidin-4-yl)-benzyl]-ethyl-amino}-methyl)-piperidine-1-carboxylic acid tert-butyl ester: Intermediate 1 was coupled with 3-aminomethyl-piperidine-1-carboxylic acid tert-butyl ester following procedure B. The crude product was coupled with acetaldehyde following procedure E. LC-MS showed the product had the expected M+H+ of 444.

Compound 175: 4-[2-(4-{3-[(Ethyl-piperidin-3(S)-ylmethyl-amino)-methyl]-phenyl}-pyrimidin-2-ylamino)-ethyl]-phenol: Intermediate 95 was coupled with tyramine following procedure F. The resulting product was deprotected following procedure G2. LC-MS showed the product had the expected M+H+ of 447. $^1$H NMR (Varian 300 MHz, CD$_3$OD, shifts relative to the solvent peak at 3.3 ppm) δ 8.66 (s, 1H), 8.38 (d, 1H), 8.35 (s, 1H), 7.94 (d, 1H), 7.75 (t, 1H), 7.67 (d, 1H), 7.11 (d, 2H), 6.68 (d, 2H), 4.57 (s, 2H), 3.94 (s, 2H), 3.13 (m, 2H), 2.82 (m, 6H), 2.65 (t, 1H), 2.34 (m, 2H), 1.74 (m, 4H), 1.24 (t, 3H).

Intermediate 96: 5-(2-Chloro-pyrimidin-4-yl)-thiophene-2-carboxaldehyde: was made by procedure V. LC-MS showed the product had the expected M+H+ of 225.

Intermediate 97: 4-{[5-(2-Chloro-pyrimidin-4-yl)-thiophen-2-ylmethyl]-amino}-piperidine-1-carboxylic acid tert-butyl ester was made from intermediate 96 by procedure B. LC-MS showed the product had the expected M+H+ of 409.

Intermediate 98: 4-{[5-(2-Chloro-pyrimidin-4-yl)-thiophen-2-ylmethyl]-propyl-amino}-piperidine-1-carboxylic acid tert-butyl ester was made from intermediate 97 by procedure E. LC-MS showed the product had the expected M+H+ of 451.

Compound 176: 2-Chloro-4-[2-(4-{5-[(piperidin-4-yl-propyl-amino)-methyl]-thiophen-2-yl}-pyrimidin-2-ylamino)-ethyl]-phenol: Intermediate 98 was coupled with 4-(2-amino-ethyl)-2-chloro-phenol following procedure F. The resulting product was deprotected following procedure G2. LC-MS showed the product had the expected M+H+ of 487. $^1$H NMR (Varian 300 MHz, CD$_3$OD, shifts relative to the solvent peak at 3.3 ppm) δ 8.18 (d, 1H), 7.98 (d, 1H), 7.37 (d, 1H), 7.26 (s, 1H), 7.23 (d, 1H), 7.01 (d, 1H), 6.80 (d, 1H), 4.49 (s, 2H), 3.70 (s, 2H), 3.44 (m, 3H), 2.97 (m, 4H), 2.85 (t, 2H), 2.27 (d, 2H), 1.93 (m, 2H), 1.66 (m, 2H), 0.94 (t, 3H).

Intermediate 99: 4-[5-(2-Chloro-pyrimidin-4-yl)-thiophen-2-ylmethyl]-piperazine-1-carboxylic acid tert-butyl ester was made from 97 by procedure B. LC-MS showed the product had the expected M+H+ of 395.

Compound 177: (S)-2-Chloro-4-(2-{4-[5-(2(S)-methyl-piperazin-1-ylmethyl)-thiophen-2-yl]-pyrimidin-2-ylamino}-ethyl)-phenol: Intermediate 99 was coupled with 4-(2-amino-ethyl)-2-chloro-phenol following procedure F. The resulting product was deprotected following procedure G2. LC-MS showed the product had the expected M-Fir of 445. $^1$H NMR (Varian 300 MHz, CD$_3$OD, shifts relative to the solvent peak at 3.3 ppm) δ 8.12 (d, 1H), 7.98 (d, 1H), 7.30 (s, 1H), 7.26 (d, 1H), 7.18 (d, 1H), 7.02 (d, 1H), 6.80 (d, 1H), 4.28 (d, 1H), 3.78 (d, 1H), 3.68 (s, 2H), 3.29 (m, 3H), 3.16 (m, 2H), 2.84 (m, 3H), 2.50 (m, 1H), 1.28 (t, 3H).

Compound 178: 4-[2-(4-{3-[(Ethyl-piperidin-4-yl-amino)-methyl]-phenyl}-pyrimidin-2-ylamino)-ethyl]-2-methyl-phenol: Intermediate 84 was coupled with 4-(2-amino-ethyl)-2-methyl-phenol following procedure F. The resulting product was deprotected following procedure G2. LC-MS showed the product had the expected M-Fir of 446. $^1$H NMR (Varian 300 MHz, CD$_3$OD, shifts relative to the solvent peak at 3.3 ppm) δ 8.30 (s, 2H), 7.68 (m, 2H), 7.32 (d, 1H), 7.19 (m, 1H), 6.98 (s, 1H), 6.89 (d, 1H), 6.63 (d, 1H), 4.53 (s, 2H), 3.78 (m, 2H), 3.60 (m, 3H), 3.08 (m, 4H), 2.84 (t, 2H), 2.41 (d, 2H), 2.17 (m, 2H), 2.10 (s, 3H), 1.32 (t, 3H).

Intermediate 100: 4-{[5-(2-Chloro-pyrimidin-4-yl)-thiophen-2-ylmethyl]-ethyl-amino}-piperidine-1-carboxylic acid tert-butyl ester was made from 97 by procedure E. LC-MS showed the product had the expected M+H$^+$ of 437.

Compound 179: 2-Chloro-4-[2-(4-{5-[(ethyl-piperidin-4-yl-amino)-methyl]-thiophen-2-yl}-pyrimidin-2-ylamino)-ethyl]-phenol: Intermediate 100 was coupled with 4-(2-amino-ethyl)-2-chloro-phenol following procedure F. The resulting product was deprotected following procedure G2. LC-MS showed the product had the expected M+H$^+$ of 473. $^1$H NMR (Varian 300 MHz, CD$_3$OD, shifts relative to the solvent peak at 3.3 ppm) δ 8.19 (d, 1H), 7.95 (d, 1H), 7.38 (d, 1H), 7.21 (d, 2H), 7.02 (d, 1H), 6.80 (d, 1H), 4.54 (s, 2H), 3.68 (s, 2H), 3.54 (m, 3H), 3.06 (m, 4H), 2.85 (t, 2H), 2.34 (d, 2H), 1.98 (m, 2H), 1.30 (t, 3H).

Intermediate 101: 4-[3-(2-Chloro-pyrimidin-4-yl)-benzyl]-3-isopropyl-piperazine-1-carboxylic acid tert-butyl ester was made by procedure B from intermediate 1 and 3-Isopropyl-piperazine-1-carboxylic acid tert-butyl ester. LC-MS showed the product had the expected M+H$^+$ of 431.

Compound 180: 2-Chloro-4-(2-{4-[3-(2-isopropyl-piperazin-1-ylmethyl)-phenyl]-pyrimidin-2-ylamino}-ethyl)-phenol: Intermediate 101 was coupled with 4-(2-amino-ethyl)-2-chloro-phenol following procedure F. The resulting product was deprotected following procedure G2. LC-MS showed the product had the expected M+H$^+$ of 467. $^1$H NMR (Varian 300 MHz, CD$_3$OD, shifts relative to the solvent peak at 3.3 ppm) δ 8.28 (d, 2H), 8.19 (d, 1H), 7.74 (d, 1H), 7.61 (t, 1H), 7.47 (d, 1H), 7.23 (s, 1H), 7.01 (d, 1H), 6.77 (d, 1H), 4.55 (d, 1H), 3.86 (s, 2H), 3.70 (d, 1H), 3.49 (d, 1H), 3.38 (m, 1H), 3.14 (m, 3H), 2.89 (m, 3H), 2.74 (t, 1H), 2.55 (m, 1H), 1.05 (t, 6H).

Intermediate 102: 3-(2-Chloro-5-fluoro-pyrimidin-4-yl)-benzaldehyde was made by procedure A. LC-MS showed the product had the expected M+H$^+$ of 237.

Intermediate 103: (3-{[3-(2-Chloro-5-fluoro-pyrimidin-4-yl)-benzyl]-methanesulfonyl-amino}-propyl)-carbamic acid tert-butyl ester was made from intermediate 102 by procedure B followed by procedure D using methansulfonyl chloride. LC-MS showed the product had the expected M+H$^+$ of 473.

Compound 181: N-(3-Amino-propyl)-N-(3-{2-[2-(3-chloro-4-hydroxy-phenyl)-ethylamino]-5-fluoro-pyrimidin-4-yl}-benzyl)-methanesulfonamide: Intermediate 103 was coupled with 4-(2-amino-ethyl)-2-chloro-phenol following procedure F. The resulting product was deprotected following procedure G2. LC-MS showed the product had the expected M+H$^+$ of 509. $^1$H NMR (Varian 300 MHz, CD$_3$OD, shifts relative to the solvent peak at 3.3 ppm) δ 8.26 (d, 1H), 8.14 (s, 1H), 8.02 (d, 1H), 7.53 (m, 2H), 7.19 (d, 1H), 7.01 (d, 1H), 6.80 (d, 1H), 4.50 (s, 2H), 3.59 (t, 2H), 3.38 (m, 2H), 2.97 (s, 3H), 2.81 (t, 4H), 1.68 (m, 2H).

Compound 182: 2-Methyl-4-(2-{4-[3-(2(S)-methyl-piperazin-1-ylmethyl)-phenyl]-pyrimidin-2-ylamino}-ethyl)-phenol: Intermediate 68 was coupled with 4-(2-amino-ethyl)-2-methyl-phenol following procedure F. The resulting product was deprotected following procedure G2. LC-MS showed the product had the expected M+H$^+$ of 418. $^1$H NMR (Varian 300 MHz, CD$_3$OD, shifts relative to the solvent peak at 3.3 ppm) δ 8.32 (s, 1H), 8.26 (d, 1H), 7.78 (d, 1H), 7.64 (t, 1H), 7.45 (d, 1H), 7.13 (d, 1H), 6.98 (s, 1H), 6.88 (d, 1H), 6.60 (d, 1H), 4.71 (d, 1H), 3.99 (d, 1H), 3.84 (s, 2H), 3.45 (m, 3H), 3.23 (m, 3H), 3.02 (t, 1H), 2.86 (t, 2H), 2.07 (s, 3H), 1.54 (d, 3H).

Intermediate 104: 3-[3-(2-Chloro-pyrimidin-4-yl)-benzylamino]-azetidine-1-carboxylic acid tert-butyl ester: Intermediate 1 was coupled with 3-Amino-azetidine-1-carboxylic acid tert-butyl ester following procedure B. LC-MS showed the product had the expected M+H$^+$ of 375.

Intermediate 105: 3-{[3-(2-Chloro-pyrimidin-4-yl)-benzyl]-ethyl-amino}-azetidine-1-carboxylic acid tert-butyl ester: Intermediate 104 was coupled with acetaldehyde following procedure E. LC-MS showed the product had the expected M+H$^+$ of 403.

Compound 183: 4-[2-(4-{3-[(Azetidin-3-yl-ethyl-amino)-methyl]-phenyl}-pyrimidin-2-ylamino)-ethyl]-phenol: Intermediate 105 was coupled with tyramine following procedure F. The resulting product was deprotected following procedure G2. LC-MS showed the product had the expected M+H$^+$ of 405. $^1$H NMR (Varian 300 MHz, CD$_3$OD, shifts relative to the solvent peak at 3.3 ppm) δ 8.69 (s, 1H), 8.40 (d, 1H), 8.34 (s, 1H), 7.96 (d, 1H), 7.72 (t, 1H), 7.68 (d, 1H), 7.11 (d, 2H), 6.67 (d, 2H), 4.56 (m, 5H), 3.78 (m, 4H), 3.21 (q, 2H), 2.93 (t, 2H), 1.39 (t, 3H).

Compound 184: 4-(2-{4-[3-(2-Isopropyl-piperazin-1-yl-methyl)-phenyl]-pyrimidin-2-ylamino}-ethyl)-phenol: Intermediate 101 was coupled with tyramine following procedure F. The resulting product was deprotected following procedure G2. LC-MS showed the product had the expected M+H$^+$ of 432. $^1$H NMR (Varian 300 MHz, CD$_3$OD, shifts relative to the solvent peak at 3.3 ppm) δ 8.30 (s, 1H), 826 (d, 1H), 8.20 (d, 1H), 7.74 (d, 1H), 7.60 (t, 1H), 7.47 (d, 1H), 7.08 (d, 2H), 6.66 (d, 2H), 4.54 (d, 1H), 3.82 (m, 2H), 3.71 (d, 1H), 3.49 (d, 1H), 3.33 (m, 1H), 3.14 (m, 3H), 2.98 (m, 1H), 2.89 (t, 2H), 2.76 (t, 1H), 2.57 (m, 1H), 1.05 (t, 6H).

Compound 185: 442-{4-[3-(2-Isopropyl-piperazin-1-ylmethyl)-phenyl]-pyrimidin-2-ylamino}-ethyl)-phenol: Intermediate 84 was coupled with 4-(2-Amino-ethyl)-naphthalen-1-ol following procedure F. The resulting product was deprotected following procedure G2. LC-MS showed the product had the expected M+H$^+$ of 483. $^1$H NMR (Varian 300 MHz, CD$_3$OD, shifts relative to the solvent peak at 3.3 ppm) δ 8.22 (d, 1H), 8.07 (m, 2H), 7.78 (d, 1H), 7.57 (t, 1H), 7.46 (t, 1H), 7.35 (t, 2H), 7.10 (m, 3H), 6.63 (d, 1H), 4.47 (s, 2H), 4.01 (s, 2H), 3.75 (t, 1H), 3.58 (d, 2H), 3.46 (t, 2H), 3.24 (m, 2H), 3.10 (t, 2H), 2.38 (d, 2H), 2.11 (m, 2H), 1.27 (t, 3H).

Intermediate 106: 2-{2-[3-(2-Chloro-pyrimidin-4-yl)-benzylamino]-ethyl}-pyrrolidine-1-carboxylic acid tert-butyl ester: 2-ethyl-pyrrolidine-1-carboxylic acid tert-butyl ester was coupled with intermediate 1 following procedure B. LC-MS showed the product had the expected M+H$^+$ of 417.

Intermediate 107: 2-(2-{[3-(2-Chloro-pyrimidin-4-yl)-benzyl]-ethyl-amino}-ethyl)-pyrrolidine-1-carboxylic acid tert-butyl ester: Intermediate 106 was coupled with acetaldehyde following procedure E. LC-MS showed the product had the expected M+H$^+$ of 445.

Compound 186: 4-{2-[4-(3-{[Ethyl-(2(S)-pyrrolidin-2-yl-ethyl)-amino]-methyl}-phenyl)-pyrimidin-2-ylamino]-ethyl}-phenol: Intermediate 107 was coupled with tyramine following procedure F. The resulting product was deprotected following procedure G2. LC-MS showed the product had the expected M+H$^+$ of 447. $^1$H NMR (Varian 300 MHz, CD$_3$OD, shifts relative to the solvent peak at 3.3 ppm) δ 8.62 (s, 1H), 8.37 (d, 1H), 8.34 (m, 1H), 7.93 (d, 1H), 7.72 (t, 1H), 7.66 (d, 1H), 7.11 (d, 2H), 6.67 (d, 2H), 4.52 (m, 2H), 3.95 (m, 2H), 3.58 (m, 2H), 3.27 (m, 4H), 2.93 (t, 2H), 2.24 (m, 4H), 1.99 (m, 2H), 1.70 (m, 1H), 1.40 (t, 3H).

Intermediate 108: 2-Chloro-4-[3-(2-methyl-piperidin-1-ylmethyl)-phenyl]-pyrimidine: 2-Methylpiperidine was coupled with intermediate 1 following procedure B. LC-MS showed the product had the expected M+H$^+$ of 302.

Compound 187: 2-Chloro-4-(2-{4-[3-(2(S)-methyl-piperidin-1-ylmethyl)-phenyl]-pyrimidin-2-ylamino}-ethyl)-phenol: Intermediate 108 was coupled with 4-(2-aminoethyl)-2-chloro-phenol following procedure F. The resulting product was deprotected following procedure G2. LC-MS showed the product had the expected M+H$^+$ of 438. $^1$H NMR (Varian 300 MHz, CD$_3$OD, shifts relative to the solvent peak at 3.3 ppm) δ 8.29 (d, 1H), 8.24 (s, 1H), 8.00 (d, 1H), 7.61 (d, 1H), 7.44 (t, 1H), 7.15 (s, 1H), 7.08 (d, 1H), 6.93 (d, 1H), 6.84 (d, 1H), 5.37 (t, 1H), 4.36 (d, 1H), 3.75 (d, 1H), 3.66 (m, 2H), 2.93 (m, 2H), 2.80 (t, 2H), 2.42 (s, 1H), 1.75 (m, 5H), 1.38 (m, 4H).

Intermediate 109: 4-[3-(2-Chloro-pyrimidin-4-yl)-benzyl]-2-(1H-indol-3-ylmethyl)-piperazine-1-carboxylic acid tert-butyl ester: Intermediate 1 was coupled with 2-(1H-Indol-3-ylmethyl)-piperazine-1-carboxylic acid tert-butyl ester following procedure B. LC-MS showed the product had the expected M+H$^+$ of 518.

Compound 188: 4-[2-(4-{3-[3(S)-(1H-Indol-3-ylmethyl)-piperazin-1-ylmethyl]-phenyl}-pyrimidin-2-ylamino)-ethyl]-phenol: Intermediate 109 was coupled with tyramine following procedure F. The resulting product was deprotected following procedure G2. LC-MS showed the product had the expected M+H$^+$ of 520. $^1$H NMR (Varian 300 MHz, CD$_3$OD, shifts relative to the solvent peak at 3.3 ppm) δ 8.51 (s, 1H), 8.29 (d, 2H), 7.81 (d, 1H), 7.55 (m, 3H), 7.34 (d, 1H), 7.25 (s, 1H), 7.02 (m, 4H), 6.69 (s, 2H), 4.54 (m, 2H), 4.08 (m, 1H), 3.90 (m, 2H), 3.61 (m, 4H), 3.25 (m, 4H), 2.92 (t, 2H).

Intermediate 110: 2-Benzyl-4-[3-(2-chloro-pyrimidin-4-yl)-benzyl]-piperazine-1-carboxylic acid tert-butyl ester: Intermediate 1 was coupled with 2-Benzyl-piperazine-1-carboxylic acid tert-butyl ester following procedure B. LC-MS showed the product had the expected M+H$^+$ of 479.

Compound 189: 4-(2-{4-[3-(3(R)-Benzyl-piperazin-1-ylmethyl)-phenyl]-pyrimidin-2-ylamino}-ethyl)-phenol: Intermediate 110 was coupled with tyramine following procedure F. The resulting product was deprotected following procedure G2. LC-MS showed the product had the expected M+H$^+$ of 481. $^1$H NMR (Varian 300 MHz, CD$_3$OD, shifts relative to the solvent peak at 3.3 ppm) δ 8.59 (s, 1H), 8.33 (d, 2H), 7.90 (d, 1H), 7.67 (t, 1H), 7.61 (d, 1H), 7.28 (m, 5H), 7.11 d, 2H), 6.68 (s, 2H), 4.64 (d, 2H), 4.16 (m, 1H), 3.91 (m, 2H), 3.56 (m, 6H), 3.30 (m, 2H), 2.92 (t, 2H).

Compound 190: 3-{2-[4-(3-{[Ethyl-(2(S)-pyrrolidin-2-yl-ethyl)-amino]-methyl}-phenyl)-pyrimidin-2-ylamino]-ethyl}-phenol: Intermediate 107 was coupled with 3-(2-Amino-ethyl)-phenol following procedure F. The resulting product was deprotected following procedure G2. LC-MS showed the product had the expected M+H$^+$ of 447. $^1$H NMR (Varian 300 MHz, CD$_3$OD, shifts relative to the solvent peak at 3.3 ppm) δ 8.62 (s, 1H), 8.36 (d, 2H), 7.94 (d, 1H), 7.72 (t, 1H), 7.66 (d, 1H), 7.05 (t, 1H), 6.78 (s, 2H), 6.59 (d, 1H), 4.53 (m, 2H), 3.90 (m, 2H), 3.58 (m, 2H), 3.32 (m, 5H), 3.00 (t, 2H), 2.22 (m, 3H), 2.02 (m, 2H), 1.71 (m, 1H), 1.40 (t, 3H).

Intermediate 111: 4-[3-(2-Chloro-pyrimidin-4-yl)-benzyl]-3-methyl-piperazine-1-carboxylic acid tert-butyl ester: Intermediate 1 was coupled with 3-(R)Methyl-piperazine-1-carboxylic acid tert-butyl ester following procedure B. LC-MS showed the product had the expected M+H$^+$ of 403.

Compound 191: [2-(3,5-Difluoro-phenyl)-ethyl]-{4-[3-(2(R)-methyl-piperazin-1-ylmethyl)-phenyl]-pyrimidin-2-yl]-amine: Intermediate 111 was coupled with 2-(3,5-difluoro-phenyl)-ethylamine following procedure F. The resulting product was deprotected following procedure G2. LC-MS showed the product had the expected M+H$^+$ of 425. $^1$H NMR (Varian 300 MHz, CD$_3$OD, shifts relative to the solvent peak at 3.3 ppm) δ 8.72 (s, 1H), 8.36 (t, 2H), 7.97 (d, 1H), 7.73 (d, 1H), 7.69 (d, 1H), 7.01 (d, 2H), 6.72 (s, 1H), 4.43 (d, 1H), 4.05 (m, 3H), 3.55 (m, 6H), 3.39 (m, 1H), 3.06 (t, 2H), 1.77 (d, 3H).

Compound 192: N-(3-Amino-propyl)-N-(3-{5-fluoro-2-[2-(3-fluoro-phenyl)-ethylamino]-pyrimidin-4-yl}-benzyl)-methanesulfonamide: Intermediate 103 was coupled with 2-(3-fluoro-phenyl)-ethylamine following procedure F. The resulting product was deprotected following procedure G2. LC-MS showed the product had the expected M+H$^+$ of 477. $^1$H NMR (Varian 300 MHz, CD$_3$OD, shifts relative to the solvent peak at 3.3 ppm) δ 8.27 (d, 1H), 8.16 (s, 1H), 8.03 (d, 1H), 7.53 (m, 2H), 7.24 (m, 1H), 7.07 (d, 1H), 7.00 (d, 1H), 6.87 (t, 1H), 4.50 (s, 2H), 3.65 (t, 2H), 3.36 (t, 2H), 2.93 (m, 5H), 2.81 (t, 2H), 1.66 (m, 2H).

Intermediate 112: 4-[3-(2-Chloro-pyrimidin-4-yl)-benzyl]-3-ethyl-piperazine-1-carboxylic acid tert-butyl ester: Intermediate 1 was coupled with 3-Ethyl-piperazine-1-carboxylic acid tert-butyl ester following procedure B. LC-MS showed the product had the expected M+H$^+$ of 417.

Compound 193: [2-(3,5-Difluoro-phenyl)-ethyl]-{4-[3-(2(S)-ethyl-piperazin-1-ylmethyl)-phenyl]-pyrimidin-2-yl}-amine: Intermediate 112 was coupled with 2-(3,5-difluoro-phenyl)-ethylamine following procedure F. The enantiomers of this product were separated by chiral HPLC, with compound 195 coming from the first peak to elute. The resulting product was deprotected following procedure G2. LC-MS showed the product had the expected M+H$^+$ of 439. $^1$H NMR (Varian 300 MHz, CD$_3$OD, shifts relative to the solvent peak at 3.3 ppm) δ 8.74 (s, 1H), 8.38 (d, 2H), 7.97 (d, 1H), 7.71 (m, 2H), 7.00 (d, 2H), 6.74 (s, 1H), 4.58 (m, 6H), 4.07 (m, 4H), 3.25 (m, 3H), 3.07 (t, 2H), 1.39 (t, 3H).

Compound 194: N-(3-Amino-propyl)-N-(3-{5-fluoro-2-[2-(3-fluoro-phenyl)-ethylamino]-pyrimidin-4-yl}-benzyl)-methanesulfonamide: Intermediate 113 was coupled with phenethylamine following procedure F. The resulting product was deprotected following procedure G2. LC-MS showed the product had the expected M+H$^+$ of 477. $^1$H NMR (Varian 300 MHz, CD$_3$OD, shifts relative to the solvent peak at 3.3 ppm) δ 8.27 (d, 1H), 8.15 (s, 1H), 8.03 (d, 1H), 7.55 (m, 2H), 7.26 (m, 4H), 7.17 (m, 1H), 4.50 (s, 2H), 3.63 (t, 2H), 3.34 (m, 2H), 3.08 (m, 1H), 2.91 (m, 4H), 2.79 (t, 2H), 1.65 (m, 2H).

Compound 195: The second peak to elute in the synthesis of compound 193, above, was isolated and deprotected following procedure G2. LC-MS showed the product had the expected M+H$^+$ of 439. $^1$H NMR (Varian 300 MHz, CD$_3$OD, shifts relative to the solvent peak at 3.3 ppm) δ 8.74 (s, 1H), 8.38 (d, 2H), 7.97 (d, 1H), 7.71 (m, 2H), 7.00 (d, 2H), 6.74 (s, 1H), 4.58 (m, 6H), 4.07 (m, 4H), 3.25 (m, 3H), 3.07 (t, 2H), 1.39 (t, 3H).

Intermediate 113: 4-[3-(2-Chloro-pyrimidin-4-yl)-benzyl]-2-isobutyl-piperazine-1-carboxylic acid tert-butyl ester: Intermediate 1 was coupled with 2-Isobutyl-piperazine-1-carboxylic acid tert-butyl ester following procedure B. LC-MS showed the product had the expected M+H$^+$ of 445.

Compound 196: 4-(2-{4-[3-(3 (S)-Isobutyl-piperazin-1-ylmethyl)-phenyl]-pyrimidin-2-ylamino}-ethyl)-phenol: Intermediate 113 was coupled with tyramine following procedure F. The resulting product was deprotected following procedure G2. LC-MS showed the product had the expected M+H$^+$ of 447. $^1$H NMR (Varian 300 MHz, CD$_3$OD, shifts relative to the solvent peak at 3.3 ppm) δ 8.65 (s, 1H), 8.36 (d, 1H), 8.32 (s, 1H), 7.95 (d, 1H), 7.71 (t, 1H), 7.65 (d, 1H), 7.11 (d, 1H), 6.68 (s, 1H), 4.70 (d, 1H), 4.57 (d, 1H), 3.96 (m, 2H), 3.81 (m, 2H), 3.58 (m, 4H), 3.40 (t, 1H), 2.92 (t, 2H), 1.75 (m, 1H), 1.62 (t, 2H), 1.00 (d, 3H), 0.98 (d, 3H).

Compound 197: [2-(3-Fluoro-phenyl)-ethyl]-{4-[3-(2-piperidin-4-yl-ethyl)-phenyl]-pyrimidin-2-yl}-amine: Intermediate 92 was coupled with 2-(3-fluoro-phenyl)-ethylamine following procedure F. The resulting product was deprotected following procedure G2. LC-MS showed the product had the expected M+H$^+$ of 406. $^1$H NMR (Varian 300 MHz, CD$_3$OD, shifts relative to the solvent peak at 3.3 ppm) δ 8.27 (d, 1H), 8.04 (s, 1H), 7.96 (m, 1H), 7.47 (d, 2H), 7.25 (m, 2H), 7.09 (d, 1H), 7.04 (d, 1H), 6.89 (t, 1H), 3.80 (m, 2H), 3.36 (m, 2H), 2.91 (m, 4H), 2.77 (t, 2H), 2.00 (d, 2H), 1.67 (m, 3H), 1.36 (m, 2H).

Intermediate 114: 4-[3-(2-Chloro-pyrimidin-4-yl)-benzyl]-3,5-dimethyl-piperazine-1-carboxylic acid tert-butyl ester: Intermediate 1 was coupled with 3,5-Dimethyl-piperazine-1-carboxylic acid tert-butyl ester following procedure B. LC-MS showed the product had the expected M+H$^+$ of 417.

Compound 198: [2-(3,5-Difluoro-phenyl)-ethyl]-{4-[3-(2 (S),6(R)-dimethyl-piperazin-1-ylmethyl)-phenyl]-pyrimidin-2-yl}-amine: Intermediate 114 was coupled with 2-(3,5-difluoro-phenyl)-ethylamine following procedure F. The resulting product was deprotected following procedure G2. LC-MS showed the product had the expected M+H$^+$ of 439. $^1$H NMR (Varian 300 MHz, CD$_3$OD, shifts relative to the solvent peak at 3.3 ppm) δ 8.57 (s, 1H), 8.36 (t, 2H), 7.94 (d, 1H), 7.74 (m, 2H), 6.99 (d, 2H), 6.75 (t, 1H), 3.77 (m, 5H), 3.64 (m, 5H), 3.07 (t, 2H), 1.69 (d, 6H).

Compound 199: N-(3-Amino-propyl)-N-(3-{2-[2-(3-chloro-phenyl)-ethylamino]-5-fluoro-pyrimidin-4-yl}-benzyl)-methanesulfonamide: Intermediate 113 was coupled with 2-(3-chloro-phenyl)-ethylamine following procedure F. The resulting product was deprotected following procedure G2. LC-MS showed the product had the expected M+H$^+$ of 493. $^1$H NMR (Varian 300 MHz, CD$_3$OD, shifts relative to the solvent peak at 3.3 ppm) δ 8.27 (d, 1H), 8.15 (s, 1H), 8.02 (d, 1H), 7.53 (m, 2H), 7.17 (m, 4H), 4.51 (s, 2H), 3.64 (t, 2H), 3.38 (t, 2H), 2.97 (m, 5H), 2.81 (t, 2H), 1.66 (m, 2H).

Intermediate 115: 2-(3,5-Difluoro-phenyl)-2,2 dideuteroethyl amine: (3,5-Difluoro-phenyl)-acetonitrile (10 g) was refluxed in THF (200 mL) containing 20% D$_2$0 and 10 g K$_2$CO$_3$ for 30 minutes. The solvent was removed and the process repeated. NMR showed complete exchange of hydrogen for deuterium in the benzylic position. The resulting deuterated nitrile was reduced to the phenethylamine as follows: The nitrile was dissolved in THF (200 mL) and sodium borohydride (5 eq) and trifluoroacetic acid (15 eq.). The mixture was heated to reflux for 5 hours. After cooling, the reaction was quenched with methanol. The solvent was removed by rotary evaporation and the residue partitioned between ethyl acetate and sat. Sodium bicarbonate. Removal of the solvent gave the expected product. LC-MS showed a single peak with the expected M+H$^+$ of 160.

Compound 200: [2-(3,5-Difluoro-phenyl)-2,2 dideuteroethyl]-{4-[3-(2(S)-methyl-piperazin-1-ylmethyl)-phenyl]-pyrimidin-2-yl}-amine: Intermediate 66 was coupled with 2-(3, 5-difluoro-phenyl)-2,2 dideutero-ethylamine following procedure F. The resulting product was deprotected following procedure G2. LC-MS showed the product had the expected M+H$^+$ of 427. $^1$H NMR (Varian 300 MHz, CD$_3$OD, shifts relative to the solvent peak at 3.3 ppm) δ 8.68 (s, 1H), 8.35 (d, 2H), 7.91 (d, 1H), 7.71 (t, 1H), 7.67 (d, 1H), 6.98 (d, 2H), 6.74 (m, 1H), 4.29 (m, 1H), 3.85 (m, 3H), 3.57 (m, 5H), 3.40 (m, 2H), 1.72 (d, 3H).

Compound 201: (4-{3-[(Azetidin-3-yl-ethyl-amino)-methyl]-phenyl}-pyrimidin-2-yl)-[2-(3,5-difluoro-phenyl)-ethyl]-amine: Intermediate 114 was coupled with 2-(3,5-difluoro-phenyl)-ethylamine following procedure F. The resulting product was deprotected following procedure G2. LC-MS showed the product had the expected M+H$^+$ of 425. $^1$H NMR (Varian 300 MHz, CD$_3$OD, shifts relative to the solvent peak at 3.3 ppm) δ 8.74 (s, 1H), 8.38 (d, 2H), 7.97 (d, 1H), 7.71 (m, 2H), 7.90 (d, 2H), 6.74 (s, 1H), 4.58 (m, 5H), 4.07 (m, 4H), 3.25 (q, 2H), 3.07 (t, 2H), 1.39 (t, 3H).

Compound 202: [2-(3,5-Difluoro-phenyl)-ethyl]-{4-[3-(2-isopropyl-piperazin-1-ylmethyl)-phenyl]-pyrimidin-2-yl}-amine: Intermediate 101 was coupled with 2-(3,5-difluoro-phenyl)-ethylamine following procedure F. The resulting product was deprotected following procedure G2. LC-MS showed the product had the expected M+H$^+$ of 452. $^1$H NMR (Varian 300 MHz, CD$_3$OD, shifts relative to the solvent peak at 3.3 ppm) δ 8.31 (d, 1H), 8.27 (s, 1H), 8.18 (d, 1H), 7.72 (d, 1H), 7.59 (t, 1H), 7.48 (d, 1H), 6.92 (d, 2H), 6.72 (t, 1H), 4.47 (d, 1H), 3.91 (s, 2H), 3.59 (d, 1H), 3.44 (d, 1H), 3.33 (m, 1H), 3.02 (m, 5H), 2.81 (m, 1H), 2.63 (t, 1H), 2.51 (m, 1H), 1.06 (t, 6H).

Compound 203: 4-(2-{4-[3-(2(S)-Methyl-piperidin-1-ylmethyl)-phenyl]-pyrimidin-2-ylamino}-ethyl)-phenol: Intermediate 108 was coupled with tyramine following procedure F. The resulting product was deprotected following procedure G2. LC-MS showed the product had the expected M+H$^+$ of 404. $^1$H NMR (Varian 300 MHz, CD$_3$OD, shifts relative to the solvent peak at 3.3 ppm) δ 8.26 (d, 1H), 7.93 (s, 1H), 7.86 (d, 1H), 7.36 (m, 2H), 6.99 (d, 2H), 6.92 (d, 1H), 6.63 (d, 2H), 5.26 (t, 1H), 4.05 (d, 1H), 3.70 (d, 2H), 3.28 (d, 1H), 2.75 (m, 4H), 2.37 (s, 1H), 1.63 (m, 2H), 1.39 (m, 3H), 1.20 (m, 4H).

Compound 204: (4-{3-[(Ethyl-piperidin-4-yl-amino)-methyl]-phenyl}-pyrimidin-2-yl)-[2-(3-trifluoromethyl-phenyl)-ethyl]-amine: Intermediate 84 was coupled with 2-(3-trifluoromethyl-phenyl)-ethylamine following procedure F. The resulting product was deprotected following procedure G2. LC-MS showed the product had the expected M+H$^+$ of 485. $^1$H NMR (Varian 300 MHz, CD$_3$OD, shifts relative to the solvent peak at 3.3 ppm) δ 8.24 (m, 3H), 7.77 (t, 1H), 7.67 (t, 1H), 7.55 (m, 2H), 7.35 (m, 3H), 4.54 (s, 2H), 3.79 (m, 4H), 3.60 (d, 2H), 3.08 (m, 5H), 2.42 (d, 2H), 2.12 (m, 2H), 1.30 (t, 3H).

Compound 205: (4-{3-[(Ethyl-piperidin-3(S)-ylmethyl-amino)-methyl]-phenyl}-pyrimidin-2-yl)-(2-thiophen-2-yl-ethyl)-amine: Intermediate 105 was coupled with 2-thiophen-2-yl-ethylamine following procedure F. The resulting product was deprotected following procedure G2. LC-MS showed the product had the expected M+H$^+$ of 437. $^1$H NMR (Varian 300 MHz, CD$_3$OD, shifts relative to the solvent peak at 3.3 ppm) δ 8.71 (s, 1H), 8.40 (d, 2H), 7.98 (d, 1H), 7.75 (s, 2H), 7.21 (d, 1H), 6.93 (d, 2H), 4.61 (s, 2H), 4.03 (s, 2H), 3.13 (m, 6H), 2.85 (t, 2H), 2.67 (t, 1H), 2.39 (m, 2H), 1.81 (m, 4H), 1.29 (t, 3H).

Compound 206: [2-(3-Chloro-phenyl)-ethyl]-{5-fluoro-4-[3-(2-piperidin-4-yl-ethyl)-phenyl]-pyrimidin-2-yl}-amine: Intermediate 79 was coupled with 2-(3-chloro-phenyl)-ethylamine following procedure F. The resulting product was deprotected following procedure G2. LC-MS showed the product had the expected M+H$^+$ of 440. $^1$H NMR (Varian 300

MHz, CD₃OD, shifts relative to the solvent peak at 3.3 ppm) δ 8.24 (d, 1H), 7.86 (d, 2H), 7.37 (m, 2H), 7.18 (m, 4H), 3.63 (t, 2H), 3.32 (d, 2H), 3.91 (m, 4H), 2.76 (t, 2H), 1.99 (d, 2H), 1.67 (m, 3H), 1.36 (m, 2H).

Compound 207: [2-(3-Fluoro-phenyl)-ethyl]-{5-fluoro-4-[3-(2-piperidin-4-yl-ethyl)-phenyl]-pyrimidin-2-yl}-amine: Intermediate 79 was coupled with 2-(3-fluoro-phenyl)-ethylamine following procedure F. The resulting product was deprotected following procedure G2. LC-MS showed the product had the expected M+H⁺ of 424. ¹H NMR (Varian 300 MHz, CD₃OD, shifts relative to the solvent peak at 3.3 ppm) δ 8.25 (d, 1H), 7.86 (d, 2H), 7.37 (m, 2H), 7.25 (q, 1H), 7.00 (m, 2H), 6.88 (t, 1H), 3.64 (t, 2H), 3.35 (d, 2H), 2.91 (m, 4H), 2.76 (t, 2H), 1.99 (d, 2H), 1.63 (m, 3H), 1.35 (m, 2H).

Compound 208: [2-(3,5-Difluoro-phenyl)-ethyl]-(4-{3-[3(S)-(1H-indol-3-ylmethyl)-piperazin-1-ylmethyl]-phenyl}-pyrimidin-2-yl)-amine: Intermediate 109 was coupled with 2-(3,5-difluoro-phenyl)-ethylamine following procedure F. The resulting product was deprotected following procedure G2. LC-MS showed the product had the expected M+H⁺ of 540. ¹H NMR (Varian 300 MHz, CD₃OD, shifts relative to the solvent peak at 3.3 ppm) δ 8.59 (s, 1H), 8.34 (d, 1H), 8.29 (d, 1H), 7.84 (d, 1H), 7.60 (m, 3H), 7.33 (d, 1H), 7.26 (s, 1H), 6.98 (m, 4H), 6.72 (s, 1H), 4.63 (s, 2H), 4.16 (m, 1H), 4.04 (s, 2H), 3.49 (m, 4H), 3.26 (m, 4H), 3.05 (t, 2H).

Compound 209: {5-Fluoro-4-[3-(2-piperidin-4-yl-ethyl)-phenyl]-pyrimidin-2-yl}-phenethyl-amine: Intermediate 79 was coupled with phenethylamine following procedure F. The resulting product was deprotected following procedure G2. LC-MS showed the product had the expected M+H⁺ of 406. ¹H NMR (Varian 300 MHz, CD₃OD, shifts relative to the solvent peak at 3.3 ppm) δ 8.25 (d, 1H), 7.91 (s, 1H), 7.87 (d, 1H), 7.37 (m, 2H), 7.27 (m, 4H), 7.15 (m, 1H), 3.62 (t, 2H), 3.34 (d, 2H), 2.91 (m, 4H), 2.76 (t, 2H), 1.99 (d, 2H), 1.62 (m, 3H), 1.34 (m, 2H).

Compound 210: (4-{3-[(Azetidin-3-yl-ethyl-amino)-methyl]-phenyl}-pyrimidin-2-yl)-[2-(3-fluoro-phenyl)-ethyl]-amine: Intermediate 104 was coupled with 2-(3-fluoro-phenyl)-ethylamine following procedure F. The resulting product was deprotected following procedure G2. LC-MS showed the product had the expected M+H⁺ of 407. ¹H NMR (Varian 300 MHz, CD₃OD, shifts relative to the solvent peak at 3.3 ppm) δ 8.72 (s, 1H), 8.36 (m, 2H), 7.97 (m, 1H), 7.70 (m, 2H), 7.27 (d, 1H), 7.13 (d, 2H), 6.90 (s, 1H), 4.58 (m, 5H), 3.96 (m, 4H), 3.22 (q, 2H), 3.06 (t, 2H), 1.38 (t, 3H).

Compound 211: [2-(3-Fluoro-phenyl)-ethyl]-{4-[3-(2-isopropyl-piperazin-1-ylmethyl)-phenyl]-pyrimidin-2-yl}-amine: Intermediate 101 was coupled with 2-(3-fluoro-phenyl)-ethylamine following procedure F. The resulting product was deprotected following procedure G2. LC-MS showed the product had the expected M+H⁺ of 435. ¹H NMR (Varian 300 MHz, CD₃OD, shifts relative to the solvent peak at 3.3 ppm) δ 8.30 (d, 1H), 8.29 (s, 1H), 8.19 (d, 1H), 7.73 (d, 1H), 7.60 (t, 1H), 7.49 (d, 1H), 7.24 (q, 1H), 7.05 (m, 2H), 6.87 (t, 1H), 4.51 (d, 1H), 3.90 (s, 2H), 3.65 (d, 1H), 3.47 (d, 1H), 3.35 (m, 1H), 3.11 (m, 3H), 3.02 (t, 2H), 2.90 (m, 1H), 2.71 (t, 1H), 2.52 (m, 1H), 1.05 (t, 6H).

Compound 212: (4-{3-[(Ethyl-piperidin-3(S)-ylmethyl-amino)-methyl]-phenyl}-pyrimidin-2-yl)-[2-(3-fluoro-phenyl)-ethyl]-amine: Intermediate 95 was coupled with 2-(3-fluoro-phenyl)-ethylamine following procedure F. The resulting product was deprotected following procedure G2. LC-MS showed the product had the expected M+H⁺ of 449. ¹H NMR (Varian 300 MHz, CD₃OD, shifts relative to the solvent peak at 3.3 ppm) δ 8.71 (s, 1H), 8.36 (t, 2H), 7.96 (d, 1H), 7.70 (m, 2H), 7.30 (s, 1H), 7.12 (d, 2H), 6.91 (s, 1H), 4.60 (s, 2H), 3.99 (s, 2H), 3.06 (m, 6H), 2.84 (m, 2H), 2.65 (t, 1H), 2.34 (m, 2H), 1.87 (m, 4H), 1.45 (t, 3H).

Compound 213: {4-[3-(2-Isopropyl-piperazin-1-ylmethyl)-phenyl]-pyrimidin-2-yl}-(2-pyridin-4-yl-ethyl)-amine: Intermediate 101 was coupled with 2-pyridin-4-yl-ethylamine following procedure F. The resulting product was deprotected following procedure G2. LC-MS showed the product had the expected M+H⁺ of 417. ¹H NMR (Varian 300 MHz, CD₃OD, shifts relative to the solvent peak at 3.3 ppm) δ 8.70 (d, 2H), 8.34 (d, 1H), 8.20 (s, 1H), 8.15 (d, 1H), 8.02 (d, 2H), 7.68 (d, 1H), 7.56 (t, 1H), 7.40 (d, 1H), 4.47 (d, 1H), 4.03 (s, 1H), 3.59 (d, 1H), 3.45 (d, 1H), 3.34 (t, 2H), 3.09 (m, 4H), 2.85 (m, 1H), 2.65 (t, 1H), 2.52 (m, 1H), 1.07 (d, 3H), 1.05 (d, 3H).

Compound 214: [2-(3,5-Difluoro-phenyl)-ethyl]-{4-[3-(2-ethyl-4-methyl-piperazin-1-ylmethyl)-phenyl]-pyrimidin-2-yl}-amine: Compound 193 was coupled with formaldehyde following procedure E. LC-MS showed the product had the expected M+H⁺ of 452. ¹H NMR (Varian 300 MHz, CD₃OD, shifts relative to the solvent peak at 3.3 ppm) δ 8.68 (s, 1H), 8.36 (d, 2H), 7.92 (d, 1H), 7.67 (m, 2H), 6.99 (d, 2H), 6.72 (s, 1H), 5.07 (d, 1H), 4.36 (s, 1H), 3.43 (m, 7H), 3.04 (m, 4H), 2.36 (s, 1H), 2.05 (m, 1H), 2.00 (s, 3H), 1.15 (t, 3H).

Intermediate 116: (2R)-tert-butyl 4-(3-(2-chloropyrimidin-4-yl)benzyl)-2-phenylpiperazine-1-carboxylate: Intermediate 1 was coupled with 2-phenyl-piperazine-1-carboxylic acid tert-butyl ester following procedure B. LC-MS showed the product had the expected M+H⁺ of 465.

Compound 215: 4-(2-{4-[3-(3(R)-Phenyl-piperazin-1-ylmethyl)-phenyl]-pyrimidin-2-ylamino}-ethyl)-phenol: Intermediate 116 was coupled with 2-(3-fluoro-phenyl)-ethylamine following procedure F. The resulting product was deprotected following procedure G2. LC-MS showed the product had the expected M+H⁺ of 467. ¹H NMR (Varian 300 MHz, CD₃OD, shifts relative to the solvent peak at 3.3 ppm) δ 8.66 (s, 1H), 8.34 (d, 1H), 8.32 (s, 1H), 7.96 (d, 1H), 7.62 (m, 4H), 7.53 (m, 3H), 7.10 (d, 2H), 6.67 (s, 2H), 5.04 (d, 1H), 4.66 (m, 2H), 3.71 (m, 8H), 2.91 (t, 2H).

Compound 216: [2-(3,5-Difluoro-phenyl)-ethyl]-{4-[3-(4-ethyl-2(S)-methyl-piperazin-1-ylmethyl)-phenyl]-pyrimidin-2-yl}-amine: Compound 154 was coupled with formaldehyde following procedure E. LC-MS showed the product had the expected M+H⁺ of 453. ¹H NMR (Varian 300 MHz, CD₃OD, shifts relative to the solvent peak at 3.3 ppm) δ 8.33 (d, 1H), 8.30 (s, 1H), 7.93 (s, 2H), 7.41 (m, 2H), 6.97 (d, 2H), 6.76 (d, 1H), 6.62 (m, 1H), 5.44 (s, 1H), 4.20 (d, 1H), 3.72 (q, 2H), 3.19 (m, 3H), 2.81 (m, 6H), 2.41 (m, 4H), 1.28 (t, 3H), 1.24 (d, 2H).

Intermediate 117: tert-Butyl-[3-(2-chloro-pyrimidin-4-yl)-benzyl]-amine: 3-(2-Chloro-pyrimidin-4-yl)-benzaldehyde (intermediate 1) and tert butylamine were coupled by procedure B. The yield was 97%. LC-MS showed the product had the expected M+H⁺ of 276. ¹H NMR (Varian 300 MHz, CDCl₃, shifts relative to the solvent peak at 7.24 ppm) 8.6 (d, 1H) 8.1 (s, 1H) 7.9 (d, 1H) 7.6 (d, 1H) 7.5 (m, 2H) 1.2 (s, 9H).

Intermediate 118: (Alloc protection) tert-Butyl-[3-(2-chloro-pyrimidin-4-yl)-benzyl]-carbamic acid allyl ester: tert-Butyl-[3-(2-chloro-pyrimidin-4-yl)-benzyl]-amine from the above reaction (1.33 g, 4.84 mmol) was treated with allyl chloroformate (0.77 mL) in methylene chloride (15 mL) with diisopropyl ethylamine (1.7 mL) at room temperature for 3 hours. The mixture was diluted with methylene chloride (50 mL), washed with water (2×), brine, dried over Na₂SO₄, filtered. Removal of the solvent followed by chromatography on silica gel (1:4 ethyl acetate:hexane eluent) afforded product in 61% yield. LC-MS showed the product had the expected M+H⁺ of 360. ¹H NMR (Varian 300 MHz, CDCl₃, shifts relative to the solvent peak at 7.24 ppm) 8.6 (d, 1H) 7.9 (d, 2H) 7.6 (d, 1H) 7.4 (m, 2H) 5.9 (m, 1H) 5.2 (m, 2H) 4.7 (s, 2H) 4.6 (d, 2H) 1.4 (s, 9H).

Intermediate 119: tert-Butyl-(3-{2-[2-(4-hydroxy-phenyl)-ethylamino]-pyrimidin-4-yl}benzyl)-carbamic acid allyl ester: tert-Butyl-[3-(2-chloro-pyrimidin-4-yl)-benzyl]-carbamic acid allyl ester from the above reaction was coupled with tyramine following procedure F to give the title product in 91% yield. LC-MS showed the product had the expected M+H$^+$ of 461. $^1$H NMR (Varian 300 MHz, CDCl$_3$, shifts relative to the solvent peak at 7.24 ppm) 8.3 (d, 1H)) 7.9 (m, 2H) 7.4 (m, 1H) 7.3 (m, 1H) 7.0 (d, 2H) 6.9 (d, 1H) 6.7 (d, 2H) 5.9 (m, 1H) 5.3 (m, 2H) 5.1 (m, 2H) 4.7 (s, 2H) 4.6 (d, 2H) 3.7 (m, 2H) 2.9 (m, 2H) 1.41 (s, 9H).

Intermediate 120: tert-Butyl-(3-{2-[2-(3-chloro-4-hydroxy-phenyl)-ethylamino]pyrimidin-4-yl}-benzyl)-carbamic acid allyl ester: tert-Butyl-[3-(2-chloro-pyrimidin-4-yl)-benzyl]-carbamic acid allyl ester was coupled with 4-(2-amino-ethyl)-2-chloro-phenol hydrobromide salt (intermediate 71) following procedure F to give the title product in 79% yield. LC-MS showed the product had the expected M+H$^+$ of 495. $^1$H NMR (Varian 300 MHz, CDCl$_3$, shifts relative to the solvent peak at 7.24 ppm) 8.3 (d, 1H)) 7.9 (m, 2H) 7.4 (m, 1H) 7.3 (m, 1H) 7.2 (s, 1H) 7.0 (d, 1H) 6.9 (m, 2H) 5.9 (m, 1H) 5.2 (m, 2H) 5.1 (m, 2H) 4.7 (s, 2H) 4.6 (d, 2H) 3.7 (m, 2H) 2.9 (m, 2H) 1.41 (s, 9H).

Compound 217: 4-(2-{4-[3-(tert-Butylamino-methyl)-phenyl]-pyrimidin-2-ylamino}-ethyl)-phenol: tert-Butyl-(3-{2-[2-(4-hydroxy-phenyl)-ethylamino]-pyrimidin-4-yl}benzyl)-carbamic acid allyl ester (intermediate 118, 176 mg) was dissolved in methylene chloride (5 mL), followed by addition of diisopropylethylamine (0.11 mL), 1,3-dimethylbarbituric acid (78 mg) then Pd(PPh$_3$)$_4$ (50 mg). The mixture was stirred at room temperature overnight. The mixture was washed with saturated NaHCO$_3$, brine, dried over Na$_2$SO$_4$, filtered and chromatographed on silica gel with methylene chloride:methanol (95:5) to afford 112 mg of product in 78% yield. LC-MS showed the product had the expected M+H$^+$ of 377. $^1$H NMR (Varian 300 MHz, CD$_3$OD, shifts relative to the solvent peak at 3.31 ppm) δ 8.3 (d, 1H) 8.1 (s, 1H) 8.0 (d, 1H) 7.5 (m, 2H) 7.1 (m, 3H) 6.7 (m, 2H) 3.8 (s, 2H) 3.6 (m, 2H) 2.8 (m, 2H) 1.2 (s, 9H).

Compound 218: 4-(2-{4-[3-(tert-Butylamino-methyl)-phenyl]-pyrimidin-2-ylamino}-ethyl)-2-chloro-phenol: tert-Butyl-(3-{2-[2-(3-chloro-4-hydroxy-phenyl)-ethylamino] pyrimidin-4-yl}-benzyl)-carbamic acid allyl ester (Intermediate 120, 168 mg) was dissolved in methylene chloride (5 mL), followed by addition of diisopropylethylamine (0.11 mL), 1,3-dimethylbarbituric acid (78 mg) then Pd(PPh$_3$)$_4$ (50 mg). The mixture was stirred at room temperature overnight. The mixture was washed with saturated NaHCO$_3$, brine, dried over Na$_2$SO$_4$, filtered and chromatographed on silica gel with methyl chloride:methanol (95:5) to afford 120 mg of product in 86% yield. LC-MS showed the product had the expected M+H$^+$ of 411. $^1$H NMR (Varian 300 MHz, CD$_3$OD, shifts relative to the solvent peak at 3.31 ppm) δ 8.3 (d, 1H) 8.1 (s, 1H) 8.0 (d, 1H) 7.5 (m, 2H) 7.2 (d, 1H) 7.1 (d, 1H) 7.0 (m, 1H) 6.8 (d, 1H) 3.9 (s, 2H) 3.7 (m, 2H) 2.8 (m, 2H) 1.3 (s, 9H).

Intermediate 121: 4-Aminomethyl-2-chloro-phenol hydrobromide salt: To a solution of 4-methoxybenzylamine (13.7 g) in acetic acid (150 mL) at 0° C. was dropwise added sulfuryl chloride (18.9 g). The suspension was stirred at 10°-20° C. for 4 hours. Ether (300 mL) was added and the solid was collected by filtration and washed with ether to afforded 16.9 g of white solid intermediate upon dried under vacuum overnight. The intermediate (11.43 g) was heated at 133° C. in 48% aqueous HBr (80 mL) for 4 hours then cooled with ice bath. The resulted solid was collected by filtration, washed with methanol (8 mL) then ethyl acetate (20 mL) to give 12.16 g of the title product. LC-MS showed the product had the expected M+H$^+$ of 158. $^1$H NMR (Varian 300 MHz, DMSO-d6, shifts relative to the solvent peak at 2.49 ppm) δ 8.2 (s, br, 2H) 7.5 (s, 1H) 7.52 (m, 1H) 7.0 (d, 1H) 3.9 (s, 2H) 3.3 (s, 1H).

Compound 219: 2-Chloro-4-({4-[3-(isopropylamino-methyl)-phenyl]-pyrimidin-2-ylamino}-methyl)-phenol: [3-(2-Chloro-pyrimidin-4-yl)-benzyl]-isopropyl-carbamic acid tert-butyl ester (intermediate 70) was coupled with 4-Aminomethyl-2-chloro-phenol hydrobromide salt (Intermediate 121) following procedure F then deprotected by procedure G. LC-MS showed the product had the expected M+H$^+$ of 383. $^1$H NMR (Varian 300 MHz, CD$_3$OD, shifts relative to the solvent peak at 3.31 ppm) δ 8.5 (s, 1H) 8.4 (d, 1H) 8.3 (d, 1H) 7.8 (d, 1H) 7.7 (m, 1H) 7.6 (d, 1H) 7.4 (s, 1H) 7.2 (d, 1H) 6.9 (d, 1H) 4.3 (s, 1H) 3.6 (m, 2H) 3.5 (m, 1H) 1.4 (d, 6H)

Intermediate 122: 2-(2H-Tetrazol-5-yl)-ethylamine HCl salt: 3-Amino-propionitrile (14.0 g) was treated with (Boc)$_2$O (45.7 g) and NaHCO$_3$ (42.4 g) in tetrahydrofuran-water (120 mL/200 mL) at room temperature for 3 days. The organic layer was separated and aqueous layer was extracted with ethyl acetate. The combined organic layer was washed with water, brine and dried over Na$_2$SO$_4$, concentrated under reduced pressure. The residue was washed with 5% ethyl acetate in hexane to give 18.65 g of solid intermediate in 55% yield. This intermediate (8.5 g) was treated with sodium azide (3.74 g) and NH$_4$Cl (3.1 g) in DMF (180 mL) at 90° C. for 4 days. The solvent was removed under reduced pressure and the residue was basified with 1 N NaOH, washed with ether (3×). The aqueous solution then was acidified with 1 N citric acid to pH 3~4, extracted with ethyl acetate (3×) and methylene chloride (3×). The combined organic layer was dried over Na$_2$SO$_4$, filtered and concentrated under reduced pressure to give an oily product [2-(2H-tetrazol-5-yl)-ethyl]-carbamic acid tert-butyl ester (4.96 g) in 35% yield. Deprotection of the material (2.72 g) with 6 N aqueous HCl (50 mL) at room temperature for 5 hours, followed by concentration and azeotroped with methanol in rotary evaporator gave the title product as a solid (1.80 g, 1:1 mixture with DMF). LC-MS showed the product had the expected M+H$^+$ of 114. $^1$H NMR (Varian 300 MHz, CD$_3$OD, shifts relative to the solvent peak at 3.31 ppm) δ 8.1 (s, 1H) 3.4 (d, 2H) 3.3 (m, 2H) 3.0 (s, 3H) 2.9 (s, 3H).

Compound 220: {4-[3-(2-S-Methyl-piperazin-1-ylmethyl)-phenyl]pyrimidin-2-yl}-[2-(2H-tetrazol-5-yl)-ethyl]-amine: 4-[3-(2-Chloro-pyrimidin-4-yl)-benzyl]-3-(S)-methyl-piperazine-1-carboxylic acid tert-butyl ester (intermediate 68) was coupled with 2-(2H-tetrazol-5-yl)-ethylamine HCl salt (Intermediate 122) following procedure F then deprotection by procedure G2. LC-MS showed the product had the expected M+H$^+$ of 380. $^1$H NMR (Varian 300 MHz, CD$_3$OD, shifts relative to the solvent peak at 3.31 ppm) δ 8.7 (s, 1H) 8.4 (s, 1H) 8.3 (d, 1H) 7.9 (d, 1H) 7.7 (d, 2H) 5.1 (s, br, 1H) 4.4 (s, br, 1H) 4.2 (s, br, 2H) 3.9 (s, br, 1H) 3.6 (m, 5H) 3.4 (m, 3H) 1.8 (d, 3H).

Compound 221: [2-(3-Chloro-4-methoxy-phenyl)-ethyl]-{4-[3-(2-S-methyl-piperazin-1-ylmethyl)-phenyl]-pyrimidin-2-yl}-amine: Following procedure F 4-[3-(2-Chloro-pyrimidin-4-yl)-benzyl]-3-(S)-methyl-piperazine-1-carboxylic acid tert-butyl ester (intermediate 68) was coupled with 2-(3-Chloro-4-methoxy-phenyl)-ethylamine HCl salt prepared in a procedure described in preparation of Intermediate 121. Deprotection by procedure G2 gave the title product. LC-MS showed the product had the expected M+H$^+$ of 452. $^1$H NMR (Varian 300 MHz, CD$_3$OD, shifts relative to the solvent peak at 3.31 ppm) δ 8.6 (s, 1H) 8.3 (d, 2H) 7.9 (d, 1H) 7.7 (m, 1H) 7.6 (m, 1H) 7.4 (s, 1H) 7.2 (d, 1H) 6.9 (s, 1H) 5.0 (s, br, 1H) 4.3 (s, br, 1H) 4.0 (s, br, 1H) 3.7 (m, 6H) 3.6 (m, 3H) 3.4 (s, br, 2H) 3.0 (m, 2H) 1.7 (d, 3H).

Intermediate 123: 4-(2-Amino-ethyl)-2-chloro-phenylamine 2HCl salt: To a solution of 2-(4-aminophenyl)ethylamine (6.81 g) in methylene chloride (160 mL) with diisopropylethylamine (10.4 mL) at 0° C. was added (Boc)$_2$O (8.72 g) over 10 min. The mixture was stirred at room temperature overnight. The reaction was worked up by washing with water, saturated NaHCO$_3$, brine and dried over Na$_2$SO$_4$. Removal of solvent afforded a solid (9.54 g). The Boc protected amine (2.35 g) was heated with acetic anhydride (10 mL) at 100° C. for 30 min, cooled to 0° C. Acetic acid (8 mL) was added, followed by NaOCl solution (4% Cl$_2$, 9 mL) dropwise and the mixture was stirred at room temperature overnight. Solvent was removed under reduced pressure and the residue was dissolved in ethyl acetate (250 mL), washed with saturated NaHCO$_3$, water, brine, dried over Na$_2$SO$_4$, concentrated and chromatographed on silica gel (ethyl acetate:hexane=1:9 to 3:7) to afford [2-(4-acetylamino-3-chloro-phenyl)-ethyl]-carbamic acid tert-butyl ester as a solid (0.82 g), which was deprotected with 4N HCl-dioxane (10 mL) in methanol (10 mL) at room temperature for 5 hours to give a solid title product (0.64 g) upon solvent removal. LC-MS showed the product had the expected M+H$^+$ of 171. $^1$H NMR (Varian 300 MHz, CD$_3$OD, shifts relative to the solvent peak at 3.31 ppm) δ 7.5 (d, 1H) 7.4 (m, 2H) 3.2 (m, 2H). 3.0 (m, 2H).

Compound 222: [2-(4-Amino-3-chloro-phenyl)-ethyl]-{4-[3-(2-S-methyl-piperazin-1-ylmethyl)-phenyl]-pyrimidin-2-yl}-amine: 4-[3-(2-Chloro-pyrimidin-4-yl)-benzyl]-3-(S)-methyl-piperazine-1-carboxylic acid tert-butyl ester (intermediate 68) was coupled with 4-(2-amino-ethyl)-2-chloro-phenylamine 2HCl salt (Intermediate 123) following procedure F then deprotection by procedure G2. LC-MS showed the product had the expected M+H$^+$ of 437. $^1$H NMR (Varian 300 MHz, CD$_3$OD, shifts relative to the solvent peak at 3.31 ppm) δ 8.7 (s, 1H) 8.4 (m, 2H) 7.9 (d, 1H) 7.7 (m, 3H) 7.4 (m, 2H) 5.0 (s, br, 1H) 4.4 (s, br, 1H) 4.0 (m, 2H) 3.7 (m, 5H) 3.4 (m, 2H) 3.1 (s, br, 2H) 1.7 (d, 3H).

Compound 223: N-(3-{2-[2-(3-Chloro-4-hydroxy-phenyl)-ethylamino]-pyrimidin-4-yl}-benzyl)-N-isopropyl-2-methyl-nicotinamide: 2-Chloro-4-(2-{4-[3-(isopropylamino-methyl)-phenyl]-pyrimidin-2-ylamino}-ethyl)-phenol (compound 132) was coupled with 2-methyl-nicotinic acid following procedure D2. LC-MS showed the product had the expected M+H$^+$ of 516. $^1$H NMR (Varian 300 MHz, CDCl$_3$, shifts relative to the solvent peak at 7.24 ppm) δ 8.7 (d, 1H)) 8.5 (m, 2H) 8.3 (d, 1H) 8.1 (s, 1H) 7.9 (m, 1H) 7.4 (m, 3H) 7.3 (m, 1H) 7.2 (m, 1H) 6.9 (d, 1H) 5.5 (s, br, 1H) 3.9 (s, 2H) 3.7 (m, 2H) 2.9 (m, 6H) 1.2 (d, 6H).

Compound 224: N-(3-{2-[2-(3-Chloro-4-hydroxy-phenyl)-ethylamino]-pyrimidin-4-yl}-benzyl)-N-isopropyl-4-methyl-nicotinamide: 2-Chloro-4-(2-{4-[3-(isopropylamino-methyl)-phenyl]-pyrimidin-2-ylamino}-ethyl)-phenol (compound 132) was coupled with 4-methyl-nicotinic acid following procedure D2. LC-MS showed the product had the expected M+H$^+$ of 516. $^1$H NMR (Varian 300 MHz, CDCl$_3$, shifts relative to the solvent peak at 7.24 ppm) δ 9.3 (s, 1H)) 8.6 (s, 1H) 8.5 (s, 1H) 8.3 (d, 1H) 8.1 (s, 1H) 7.9 (d, 1H) 7.5 (m, 1H) 7.4 (m, 2H) 7.2 (m, 3H) 6.9 (d, 1H) 5.6 (s, br, 1H) 3.9 (s, 2H) 3.7 (m, 2H) 3.0 (d, 1H) 2.9 (m, 2H) 2.7 (s, 3H) 1.2 (d, 6H).

Compound 225: N-(3-{2-[2-(3-Chloro-4-hydroxy-phenyl)-ethylamino]-pyrimidin-4-yl}-benzyl)-N-isopropyl-5-methyl-nicotinamide: 2-Chloro-4-(2-{4-[3-(isopropylamino-methyl)-phenyl]-pyrimidin-2-ylamino}-ethyl)-phenol (compound 132) was coupled with 5-methyl-nicotinic acid following procedure D2. LC-MS showed the product had the expected M+H$^+$ of 516. $^1$H NMR (Varian 300 MHz, CDCl$_3$, shifts relative to the solvent peak at 7.24 ppm) δ 9.2 (s, 1H)) 8.7 (s, 1H) 8.4 (s, 1H) 8.3 (m, 2H) 8.1 (s, 1H) 7.9 (d, 1H) 7.5 (m, 1H) 7.4 (m, 2H) 7.2 (s, 1H) 7.0 (d, 1H) 5.6 (s, br, 1H) 3.9 (s, 2H) 3.7 (m, 2H) 3.1 (m, 1H) 2.9 (m, 2H) 2.4 (s, 3H) 1.2 (d, 6H).

Compound 226: N-(3-{2-[2-(3-Chloro-4-hydroxy-phenyl)-ethylamino]-pyrimidin-4-yl}-benzyl)-N-isopropyl-6-methyl-nicotinamide: 2-Chloro-4-(2-{4-[3-(isopropylamino-methyl)-phenyl]-pyrimidin-2-ylamino}-ethyl)-phenol (compound 132) was coupled with 6-methyl-nicotinic acid following procedure D2. LC-MS showed the product had the expected M+H$^+$ of 516. $^1$H NMR (Varian 300 MHz, CDCl$_3$, shifts relative to the solvent peak at 7.24 ppm) δ 9.3 (s, 1H)) 8.3 (m, 2H) 8.2 (s, 1H) 8.0 (d, 2H) 7.6 (d, 1H) 7.4 (m, 2H) 7.3 (d, 1H) 7.2 (s, 1H) 7.0 (d, 1H) 5.4 (s, br, 1H) 3.9 (s, 2H) 3.7 (m, 2H) 3.1 (m, 1H) 2.9 (m, 2H) 2.7 (s, 3H) 1.3 (d, 6H).

Compound 227: N-(3-{2-[2-(3-Chloro-4-hydroxy-phenyl)-ethylamino]-pyrimidin-4-yl}-benzyl)-N-isopropyl-isonicotinamide: 2-Chloro-4-(2-{4-[3-isopropylamino-methyl)-phenyl]-pyrimidin-2-ylamino}-ethyl)-phenol (compound 132) was coupled with isonicotinic acid following procedure D2. LC-MS showed the product had the expected M+H$^+$ of 502. $^1$H NMR (Varian 300 MHz, CDCl$_3$, shifts relative to the solvent peak at 7.24 ppm) δ 8.9 (d, 2H)) 8.5 (s, 1H) 8.3 (d, 1H) 8.1 (s, 1H) 8.0 (d, 2H) 7.9 (m, 1H) 7.5 (d, 1H) 7.4 (m, 2H) 7.2 (s, 1H) 6.9 (d, 1H) 5.5 (s, br, 1H) 3.9 (s, 2H) 3.7 (m, 2H) 3.1 (m, 1H) 2.9 (m, 2H) 1.2 (d, 6H).

Compound 228: N-(3-{2-[2-(3-Chloro-4-hydroxy-phenyl)-ethylamino]pyrimidin-4-yl}-benzyl)-N-isopropyl-6-trifluoromethyl-nicotinamide: 2-Chloro-4-(2-{4-[3-(isopropylamino-methyl)-phenyl}-pyrimidin-2-ylamino]-ethyl)-phenol (compound 132) was coupled with 6-trifluoromethyl-nicotinic acid following procedure D2. LC-MS showed the product had the expected M+H$^+$ of 570. $^1$H NMR (Varian 300 MHz, CDCl$_3$, shifts relative to the solvent peak at 7.24 ppm) δ 9.5 (s, 1H)) 8.6 (d, 1H) 8.5 (s, 1H) 8.2 (d, 1H) 8.1 (s, 1H) 7.9 (m, 2H) 7.5 (m, 1H) 7.4 (m, 2H) 7.2 (s, 1H) 6.9 (d, 1H) 5.7 (s, br, 1H) 3.9 (s, 2H) 3.7 (m, 2H) 3.1 (m, 1H) 3.0 (m, 2H) 1.2 (d, 6H).

Compound 229: N-(3-{2-[2-(3-Chloro-4-hydroxy-phenyl)-ethylamino]pyrimidin-4-yl}-benzyl)-N-isopropyl-4-trifluoromethyl-nicotinamide: 2-Chloro-4-(2-{4-[3-(isopropylamino-methyl)-phenyl]-pyrimidin-2-ylamino}-ethyl)-phenol (compound 132) was coupled with 4-trifluoromethyl-nicotinic acid following procedure D2. LC-MS showed the product had the expected M+H$^+$ of 570. $^1$H NMR (Varian 300 MHz, CDCl$_3$, shifts relative to the solvent peak at 7.24 ppm) δ 9.4 (s, 1H)) 9.0 (d, 1H) 8.4 (s, 1H) 8.3 (d, 1H) 8.1 (s, 1H) 7.9 (d, 1H) 7.7 (d, 1H) 7.5 (m, 1H) 7.4 (m, 2H) 7.2 (s, 1H) 6.9 (d, 1H) 5.7 (s, br, 1H) 3.9 (s, 2H) 3.7 (m, 2H) 3.1 (m, 1H) 2.9 (m, 2H) 1.2 (d, 6H).

Compound 230: 5-Bromo-N-(3-{2-[2-(3-chloro-4-hydroxy-phenyl)-ethylamino]-pyrimidin-4-yl}-benzyl)-N-isopropyl-nicotinamide: 2-Chloro-4-(2-{4-[3-(isopropylamino-methyl)-phenyl]-pyrimidin-2-ylamino}-ethyl)-phenol (compound 132) was coupled with 5-bromo-nicotinic acid following procedure D2. LC-MS showed the product had the expected M+H$^+$ of 581. $^1$H NMR (Varian 300 MHz, CDCl$_3$, shifts relative to the solvent peak at 7.24 ppm) δ 9.3 (s, 1H), 8.9 (s, 1H) 8.6 (s, 1H) 8.4 (s, 1H) 8.2 (d, 1H) 8.1 (s, 1H) 7.9 (d, 1H) 7.5 (m, 1H) 7.4 (m, 2H) 7.2 (s, 1H) 6.9 (d, 1H) 5.8 (s, 1H) 3.9 (s, 2H) 3.7 (m, 2H) 3.1 (m, 1H) 2.9 (m, 2H) 1.2 (d, 6H).

Compound 231: 1-Methyl-piperidine-4-carboxylic acid (3-{2-[2-(3-chloro-4-hydroxy-phenyl)-ethylamino]-pyrimidin-4-yl}-benzyl)-isopropyl-amide: 2-Chloro-4-(2-{4-[3-(isopropylamino-methyl)-phenyl]-pyrimidin-2-ylamino}-ethyl)-phenol (compound 132) was coupled with 1-methyl-piperidine-4-carboxylic acid following procedure D2. LC-MS showed the product had the expected M+H+ of 522. $^1$H NMR (Varian 300 MHz, CDCl$_3$, shifts relative to the solvent peak at 7.24 ppm) δ 8.6 (s, 1H) 8.3 (m, 1H) 7.8 (m, 2H) 7.4 (m, 1H) 7.2 (s, 1H) 6.9 (m, 3H) 5.0 (s, br, 1H) 4.8 (m, 1H) 4.5 (d, 2H) 4.2 (m, 1H) 3.7 (m, 2H) 3.4 (s, 1H) 3.2 (m, 2H) 2.8 (m, 2H 2.5 (m, 5H) 2.0 (s, br, 2H) 1.9 (s, br, 1H) 1.2 (d, 3H) 1.0 (d, 3H).

Intermediate 124: 2-(1H-Indol-5-yl)-ethylamine: 5-Formyl indole (14.5 g) was refluxed with NH4OAc (10.0 g) in nitromethane ((100 mL) for 3 hours. The mixture was cooled and evaporated under reduced pressure. The residue was recrystallized from isopropanol to give the first portion of intermediate and the mother liquid was purified by chromatograph (EtOAc:hexane=1:4 to 2:3) to the second portion intermediate of 5-(2-nitro-vinyl)-1H-indole (2.09 g combined, in 11% yield), which was treated with NaBH4 (1.85 g) in methanol (150 mL) at room temperature for 35 min then quenched with acetic acid (4 mL), concentrated and followed by chromatography purification (EtOAc:hexane=1:9) to afford 5-(2-nitro-ethyl)-1H-indole (1.37 g) in 65% yield. This nitro compound was hydrogenated with Pd—C (10%) under atmosphere hydrogen in methanol overnight to afford 2-(1H-indol-5-yl)-ethylamine in 99% yield. LC-MS showed the product had the expected M+H+ of 161.

Compound 232: [2-(1H-Indol-5-yl)-ethyl]-{4-[3-(2-S-methyl-piperazin-1-ylmethyl)-phenyl]-pyrimidin-2-yl}-amine: 4-[3-(2-Chloro-pyrimidin-4-yl)-benzyl]-3-(S)-methyl-piperazine-1-carboxylic acid tert-butyl ester (intermediate 68) was coupled with 2-(1H-indol-5-yl)-ethylamine (Intermediate 124) following procedure F then deprotected following procedure G. LC-MS showed the product had the expected M+H+ of 427. $^1$H NMR (Varian 300 MHz, CD$_3$OD, shifts relative to the solvent peak at 3.31 ppm) δ 8.6 (m, 1H). 8.3 (m, 2H). 7.9 (m, 1H). 7.6 (m, 5H) 7.2 (m, 2H). 4.3 (m, 1H). 3.7 (m, 10H). 3.2 (m, 2H) 1.7 (d, 3H).

Compound 233: (4-{3-[(Ethyl-piperidin-4-yl-amino)-methyl]-phenyl}-pyrimidin-2-yl)-[2-(1H-indol-5-yl)-ethyl]-amine: 4-{[3-(2-Chloro-pyrimidin-4-yl)-benzyl]-ethyl-amino}-piperidine-1-carboxylic acid tert-butyl ester (intermediate 84) was coupled with 2-(1H-indol-5-yl)-ethylamine (intermediate 124) following procedure F then deprotected following procedure G. LC-MS showed the product had the expected M+H+ of 455. $^1$H NMR (Varian 300 MHz, CD$_3$OD, shifts relative to the solvent peak at 3.31 ppm) δ 8.7 (m, 1H) 8.4 (m, 3H) 7.9 (m, 1H) 7.6 (m, 4H) 7.4 (m, 1H) 7.2 (m, 1H) 4.4 (m, 1H) 3.9 (m, 2H) 3.7 (m, 7H) 3.2 (m, 3H) 2.5 (m, 2H) 2.3 (m, 2H) 1.3 (m, 3H).

Intermediate 125: Methanesulfonic acid 3-(2-chloro-pyrimidin-4-yl)-benzyl ester: To a suspension of 3-(2-chloro-pyrimidin-4-yl)-benzaldehyde (intermediate 1, 4.36 g) and NaBH$_4$ (0.3 g) in THF (70 mL) at room temperature was dropwise added methanol (5 mL). The mixture was stirred for 20 min and quenched with concentrated HCl (1 mL) with water bath cooling. Solvent was removed by rotary evaporation. The residue was dissolved in EtOAc, washed with saturated NaHCO$_3$, brine and dried over Na$_2$SO$_4$. Removal of solvent gave 4.15 g of solid alcohol intermediate in 91% yield. The alcohol intermediate (3.2 g) was treated with mathanesulfonic anhydride (3.05 g), diisopropylethylamine (3.8 mL) and DMAP (0.18 g) in methylene chloride (50 mL) at room temperature for 2 hours. The mixture was diluted with methylene chloride (150 mL), washed with water, brine, dried over Na$_2$SO$_4$ and purified by chromatograph (EtOAc:hexane=1:4 to 2:3) to give a solid product (3.5 g) in 81% yield. LC-MS showed the product had the expected M+H+ of 299. $^1$H NMR (Varian 300 MHz, CDCl$_3$, shifts relative to the solvent peak at 7.24 ppm) δ 8.6 (d, 1H) 8.1 (m, 2H) 7.7 (d, 1H) 7.6 (m, 2H) 5.3 (s, 1H) 3.0 (s, 3H).

Intermediate 126: 2-(S)-Methyl-piperazine-1-carboxylic acid tert-butyl ester: To the solution of (S)-(+)-2-methyl-piperazine (2.0 g) in methylene chloride (15 mL) at 0° C. was added benzylchloroformate (3.0 mL) dropwise. The mixture was stirred at 0° C. for one hour then at room temperature for 2 hours, cooled to 0° C. Diisopropylethylamine (4.5 mL) was added and followed by (Boc)$_2$O (4.8 g). The mixture was stirred at room temperature overnight then the solvent was removed by rotary evaporation. The residue was dissolved in EtOAc, washed with water, brine, dried over Na$_2$SO$_4$, chromatographed on silica gel (EtOAc:hexane=1:9) to give an oily intermediate (4.2 g) in 62% yield. Hydrogenation with Pd—C(10%) in methanol gave the title product (2.17 g) in 87% yield. LC-MS showed the product had the expected M+H+ of 201. $^1$H NMR (Varian 300 MHz, CDCl$_3$, shifts relative to the solvent peak at 7.24 ppm) δ 4.2 (s, br, 1H) 3.8 (m, 1H) 3.0 (m, 4H) 2.7 (m, 2H) 1.4 (s, 9H) 1.2 (d, 3H).

Intermediate 127: 2-(R)-Methyl-piperazine-1-carboxylic acid tert-butyl ester: To the solution of (R)-(−)-2-methyl-piperazine (1.68 g) in methylene chloride (15 mL) at 0° C. was added benzylchloroformate (2.5 mL) dropwise. The mixture was stirred at 0° C. for one hour then at room temperature for 2 hours, cooled to 0° C. Diisopropylethylamine (3.8 mL) was added and followed by (Boc)$_2$O (4.0 g). The mixture was stirred at room temperature overnight then the solvent was removed by rotary evaporation. The residue was dissolved in EtOAc, washed with water, brine, dried over Na$_2$SO$_4$, chromatographed on silica gel (EtOAc:hexane=1:9) to give an oily intermediate. Hydrogenation with Pd—C(10%) in methanol gave the title product (3.03 g) in 85% yield over two steps. LC-MS showed the product had the expected. M+H+ of 201. $^1$H NMR (Varian 300 MHz, CDCl$_3$, shifts relative to the solvent peak at 7.24 ppm) δ 4.2 (m, 1H) 3.8 (m, 1H) 3.0 (m, 4H) 2.7 (m, 2H) 1.4 (s, 9H) 1.2 (d, 3H).

Intermediate 128: 4-[3-(2-Chloro-pyrimidin-4-yl)-benzyl]-2-(S)-methyl-piperazine-1-carboxylic acid tert-butyl ester: Intermediate 125 Methanesulfonic acid 3-(2-chloro-pyrimidin-4-yl)-benzyl ester (0.70 g) and Intermediate 126 2-(S)-Methyl-piperazine-1-carboxylic acid tert-butyl ester (0.61 g) with diisopropylethylamine (0.70 mL) in ethylene glycol dimethyl ether (20 mL) was refluxed for 3 hours, cooled to room temperature, evaporated under reduced pressure and the residue was dissolved in dichloromethane, washed with water (3×), brine, dried over dried over Na$_2$SO$_4$, chromatographed on silica gel (dichloromethane:methanol=98:2) to give 0.60 g of oily product with yield 64%. LC-MS showed the product had the expected M+H+ of 403. $^1$H NMR (Varian 300 MHz, CDCl$_3$, shifts relative to the solvent peak at 7.24 ppm) δ 8.6 (s, 1H) 8.0 (s, 1H) 7.9 (d, 1H) 7.6 (d, 1H) 7.5 (m, 2H) 4.2 (S, 1 h) 3.8 (d, 1H) 3.4 (m, 2H) 3.0 (m, 1H) 2.7 (d, 1H). 2.6 (d, 1H) 2.1 (m, 2H) 1.5 (s, 9H) 1.2 (d, 3H).

Intermediate 129: 4-[3-(2-Chloro-pyrimidin-4-yl)-benzyl]-2-(R)-methyl-piperazine-1-carboxylic acid tert-butyl ester: Intermediate 125 Methanesulfonic acid 3-(2-chloro-pyrimidin-4-yl)-benzyl ester (0.70 g) and Intermediate 127 2-(R)-Methyl-piperazine-1-carboxylic acid tert-butyl ester (0.61 g) with diisopropylethylamine (0.70 mL) in ethylene glycol dimethyl ether (20 mL) was refluxed for 3 hours, cooled to room temperature, evaporated under reduced pressure and the residue was dissolved in dichloromethane, washed with water (3×), brine, dried over dried over Na$_2$SO$_4$, chromatographed on silica gel (dichloromethane:methanol=98:2) to give 0.50 g of oily product with yield 53%. LC-MS showed the product had the expected M+H$^+$ of 403. $^1$H NMR (Varian 300 MHz, CDCl$_3$, shifts relative to the solvent peak at 7.24 ppm) δ 8.6 (s, 1H) 8.0 (s, 1H) 7.9 (d, 1H) 7.6 (d, 1H) 7.5 (m, 2H) 4.2 (S, 1 h) 3.8 (d, 1H) 3.4 (m, 2H) 3.0 (m, 1H) 2.7 (d, 1H), 2.6 (d, 1H) 2.1 (m, 2H) 1.4 (s, 9H) 1.2 (d, 3H).

Compound 234: 442-{4-[3-(3-S-Methyl-piperazin-1-ylmethyl)-phenyl]-pyrimidin-2-ylamino}-ethyl)-phenol: Intermediate 128 4-[3-(2-Chloro-pyrimidin-4-yl)-benzyl]-2-(S)-methyl-piperazine-1-carboxylic acid tert-butyl ester was coupled with tyramine following procedure F then deprotected following procedure G. LC-MS showed the product had the expected M+H$^+$ of 404. $^1$H NMR (Varian 300 MHz, CD$_3$OD, shifts relative to the solvent peak at 3.30 ppm) δ 8.6 (s, 1H) 8.4 (m, 2H) 7.9 (s, 1H) 7.6 (d, 2H) 7.1 (s, 2H) 6.7 (a, 2H) 4.6 (S, 2H) 3.9 (s, 2H) 3.6 (m, 7H) 2.9 (s, 2H) 1.4 (s, 3H).

Compound 235: 4-(2-{4-[3-(3-R-Methyl-piperazin-1-ylmethyl)-phenyl]-pyrimidin-2-ylamino}-ethyl)-phenol: Intermediate 129 4-[3-(2-Chloro-pyrimidin-4-yl)-benzyl]-2-(R)-methyl-piperazine-1-carboxylic acid tert-butyl ester was coupled with tyramine following procedure F then deprotected following procedure G. LC-MS showed the product had the expected M+H$^+$ of 404. $^1$H NMR (Varian 300 MHz, CD$_3$OD, shifts relative to the solvent peak at 3.30 ppm) δ 8.6 (s, 1H) 8.4 (m, 2H) 7.9 (s, 1H) 7.6 (d, 2H) 7.1 (s, 2H) 6.7 (s, 2H) 4.6 (S, 2H) 3.9 (s, 2H) 3.6 (m, 7H) 2.9 (s, 2H) 1.4 (s, 3H).

Compound 236: [2-(3,5-Difluoro-phenyl)-ethyl]-{4-[3-(3-S-methyl-piperazin-1-ylmethyl)-phenyl]-pyrimidin-2-yl}-amine: Intermediate 130 4-[3-(2-Chloro-pyrimidin-4-yl)-benzyl]-2-(S)-methyl-piperazine-1-carboxylic acid tert-butyl ester was coupled with 2-(3,5-difluorophenyl) ethanamine following procedure F then deprotected following procedure G. LC-MS showed the product had the expected M+H$^+$ of 424. $^1$H NMR (Varian 300 MHz, CD$_3$OD, shifts relative to the solvent peak at 3.30 ppm) δ 8.7 (s, 1H) 8.4 (d, 2H) 7.9 (d, 1H) 7.7 (m, 2H) 7.0 (d, 2H) 6.7, (m, 1H) 4.6 (S, 2H) 4.0 (m, 2H) 3.7 (m, 7H) 3.1 (m, 2H) 1.4 (d, 3H).

Compound 237: [2-(3,5-Difluoro-phenyl)-ethyl]-{4-[3-(3-R-methyl-piperazin-1-ylmethyl)-phenyl]-pyrimidin-2-yl}-amine: Intermediate 131 4-[3-(2-Chloro-pyrimidin-4-yl)-benzyl]-2-(R)-methyl-piperazine-1-carboxylic acid tert-butyl ester was coupled with 2-(3,5-difluorophenyl) ethanamine following procedure F then deprotected following procedure G. LC-MS showed the product had the expected M+H$^+$ of 424. $^1$H NMR (Varian 300 MHz, CD$_3$OD, shifts relative to the solvent peak at 3.30 ppm) δ 8.6 (s, 1H) 8.4 (m, 2H) 7.9 (s, 1H) 7.6 (d, 2H) 7.1 (s, 2H) 6.7 (s, 2H) 4.6 (S, 2H) 3.9 (s, 2H) 3.6 (m, 7H) 2.9 (s, 2H) 1.4 (s, 3H).

Intermediate 130: 4-[3-(2-Chloro-pyrimidin-4-yl)-benzyl]-3-ethyl-piperazine-1-carboxylic acid tert-butyl ester: Intermediate 1 was coupled with 3-ethyl-piperazine-1-carboxylic acid tert-butyl ester following procedure B. LC-MS showed the product had the expected M+H$^+$ of 417.

Compound 238: 4-(2-{4-[3-(2-Ethyl-piperazin-1-ylmethyl)-phenyl]-pyrimidin-2-ylamino}-ethyl)-phenol: Intermediate 130 was coupled with tyramine following procedure F. The product was deprotected following procedure G2. LC-MS showed the product had the expected M+H$^+$ of 418. $^1$H NMR (Varian 300 MHz, CD$_3$OD, shifts relative to the solvent peak at 3.3 ppm) δ 8.35 (s, 1H) 8.29 (d, 2H) 8. 7.81 (d, 1H) 7.68 (t, 1H) 7.49 (d, 1H) 7.2-7.2 (m, 3H) 6.68 (d, 2H) 4.8 (d, 1H) 4.17 (d, 1H) 3.85 (br s, 2H) 3.68 (d, 1H) 3.1-3.6 (m, 6H) 2.9 (t, 2H) 2.2 (m, 1H) 1.9 (m, 1H) 1.1 (t, 3H).

Intermediate 131: 4-[3-(2-Chloro-pyrimidin-4-yl)-benzyl]-3-propyl-piperazine-1-carboxylic acid tert-butyl ester: Intermediate 1 was coupled with 3-propyl-piperazine-1-carboxylic acid tert-butyl ester following procedure B. LC-MS showed the product had the expected M+H$^+$ of 431.

Compound 239: 4-(2-{4-[3-(2-Propyl-piperazin-1-ylmethyl)-phenyl]-pyrimidin-2-ylamino}-ethyl)-phenol: Intermediate 131 was coupled with tyramine following procedure F. The product was deprotected following procedure G. LC-MS showed the product had the expected M+H$^+$ of 432. $^1$H NMR (Varian 300 MHz, CD$_3$OD, shifts relative to the solvent peak at 3.3 ppm) δ 8.35 (s, 1H) 8.29 (d, 2H) 8. 7.81 (d, 1H) 7.68 (t, 1H) 7.49 (d, 1H) 7.2-7.2 (m, 3H) 6.68 (d, 2H) 4.8 (d, 1H) 4.17 (d, 1H) 3.85 (br s, 2H) 3.68 (d, 1H) 3.1-3.6 (m, 6H) 2.9 (t, 2H) 2.2 (m, 1H) 1.9 (m, 1H) 1.38-1.65 (m, 1H) 1.05 (t, 3H).

Compound 240: (4-{3-[(Ethyl-piperidin-4-yl-amino)-methyl]-phenyl}-pyrimidin-2-yl)-(2-thiophen-2-yl-ethyl)-amine: Intermediate 84 was coupled with 2-thiophen-2-yl-ethylamine following procedure F. The product was deprotected following procedure G2. LC-MS showed the product had the expected M+H$^+$ of 422.

Intermediate 132: 4-[3-(2-Chloro-pyrimidin-4-yl)-benzyl]-piperazine-1,2-dicarboxylic acid 1-tert-butyl ester 2-methyl ester: Intermediate 1 was coupled with piperazine-1,2-dicarboxylic acid 1-tert-butyl ester 2-methyl ester following procedure B. LC-MS showed the product had the expected M+H$^+$ of 447.

Compound 241: 4-(3-{2-[2-(4-Hydroxy-phenyl)-ethylamino]-pyrimidin-4-yl}-benzyl)-piperazine-2-carboxylic acid methyl ester: Intermediate 132 was coupled with tyramine following procedure F. The product was deprotected following procedure G2. LC-MS showed the product had the expected M+H$^+$ of 448.

Compound 242: [2-(3-Chloro-phenyl)-ethyl]-(4-{3-[(ethyl-piperidin-4-yl-amino)-methyl]-phenyl}-pyrimidin-2-yl)-amine: Intermediate 84 was coupled with 2-(3-chlorophenyl)-ethylamine following procedure F. The resulting product was deprotected following procedure G2. LC-MS showed the product had the expected M+H$^+$ of 450. $^1$H NMR (Varian 300 MHz, CD$_3$OD, shifts relative to the solvent peak at 3.3 ppm) δ 8.7 (s, 1H) 8.36 (d, 2H) 7.95 (d, 1H) 7.68-7.8 (m, 2H) 7.4 (s, 1H) 7.25 (br s, 2H) 7.16 (s, 1H) 4.56 (br s, 2H) 3.88 (m, 3H) 3.62 (m, 2H) 3.15 (m, 1H) 3.05 (m, 2H) 2.47 (m, 2H) 2.2 (m, 2H) 1.33 (t, 3H).

Compound 243: Intermediate 68 was coupled with 2-thiophen-2-yl-ethylamine following procedure F. The resulting product was deprotected following procedure G2. LC-MS showed the product had the expected M+H$^+$ of 394. $^1$H NMR (Varian 300 MHz, CD$_3$OD, shifts relative to the solvent peak at 3.30 ppm) δ 8.7 (s, 1H) 8.4 (d, 2H) 7.85 (s, 1H) 7.72 (m, 2H) 7.22 (s, 1H) 6.95 (m, 2H) 4.75 (d, 1H) 4.02 (d, 1H) 3.9 (br s, 2H) 3.4-3.65 (m, 3H) 3.2-3.4 (m, 4H) 3.05 (m, 3H) 1.45 (d, 3H).

Compound 244: Intermediate 68 was coupled with 2,5 difluorophenethylamine following procedure F. The resulting product was deprotected following procedure G. LC-MS showed the product had the expected M+H$^+$ of 424. $^1$H NMR (Varian 300 MHz, CD$_3$OD, shifts relative to the solvent peak at 3.30 ppm) δ 8.7 (s, 1H) 8.5 (d, 2H) 8.0 (d, 1H) 7.72 (m, 2H) 7.22 (s, 1H) 6.9-7.05 (m, 2H) 4.75 (d, 1H) 4.02 (d, 1H) 3.9 (br s, 2H) 3.45-3.8 (m, 3H) 3.2-3.4 (m, 4H) 3.05 (m, 3H) 1.8 (d, 3H).

Intermediate 133: 3-(2-Fluoro-pyridin-4-yl)-benzaldehyde: 2 fluoro-4-iodo pyridine (5 g), 3 formylphenylboronic acid (4 g), and palladium tetrakis triphenylphosphine were suspended in 500 mL of THF. Potassium carbonate (7.42 g)

was added along with 50 mL of water. The flask was purged with nitrogen and the mixture heated to 65 C for 4 hours. The solvent was removed by rotary evaporation and the residue partitioned between ethyl acetate and water. Removal of the ethyl acetate gave a residue which was chromatographed on silica gel (1:1 ethyl acetate hexanes) to give the desired product. Yield: 1.42 g. LC-MS showed the product had the expected M+H$^+$ of 202.

Intermediate 134: (1.4 g) was dissolved in methylene chloride (30 mL) along with 0.78 g of 3-(S) Methyl-piperazine-1-carboxylic acid tert-butyl ester. Sodium triacetoxyborohydride (1.4 g) was added and the mixture stirred at room temperature for 2 hours. The mixture was partitioned between ethyl acetate and water. The organic layer was washed with a saturated solution of sodium chloride and the solvent removed. The residue was chromatographed on silica gel to give 1.14 g of the desired product. LC-MS showed the product had the expected M+H$^+$ of 386.

Compound 245: 4-(2-{4-[3-(2-Methyl-piperazin-1-ylmethyl)-phenyl]-pyridin-2-ylamino}-ethyl)-phenol: 134 (0.3 g) was dissolved in 4 mL of ethanol along with 300 mg of tyramine and 250 uL of diisopropylethylamine. The mixture was placed in a sealed tube and heated under microwave irradiation to 170 C for 12 hours. The solvent was removed and the residue chromatographed on silica gel (1:1 ethyl acetate hexanes as eluent.) The resulting material was further purified by reverse phase HPLC to give 23 mg of product. This was deprotected following procedure G2. LC-MS showed the product had the expected M+H$^+$ of 403. $^1$H NMR (Varian 300 MHz, CD$_3$OD, shifts relative to the solvent peak at 3.30 ppm) δ 8.27 (m, 1H) 7.8-7.9 (m, 2H) 7.58-7.8 (m, 4H) 7.28-7.38 (m, 2H) 7.25-7.35 (m, 2H) 7.15 (d, 2H) 6.7 (d, 1H) 4.75 (d, 1H) 4.02 (d, 1H) 3.9 (br s, 2H) 3.45-3.8 (m, 3H) 3.2-3.4 (m, 4H) 3.05 (m, 3H) 1.8 (d, 3H).

Compound 246: {4-[3-(2-Ethyl-piperazin-1-ylmethyl)-phenyl]-pyrimidin-2-yl}-[2-(3-fluoro-phenyl)-ethyl]-amine: Intermediate 130 was coupled with 3-fluorophenethylamine following procedure F. The resulting product was deprotected following procedure G2. LC-MS showed the product had the expected M+H$^+$ of 420. $^1$H NMR (Varian 300 MHz, CD$_3$OD, shifts relative to the solvent peak at 3.30 ppm) δ 8.25-8.4 (m, 2H) 7.8 (d, 1H) 7.7 (t, 1H) 7.5 (d, 1H) 7.18-7.35 (m, 2H) 7.05-7.15 (m, 2H) 6.9 (m, 1H) 4.72 (d, 1H) 4.1 (d, 1H) 3.92 (br s, 2H) 3.65 (m, 1H) 3.3-3.5 (m, 6H) 3.12 (m, 1H) 3.05 (m, 2H) 2.18 (m, 1H) 1.92 (m, 1H) 1.1 (t, 3H).

Compound 247: (4-{3-[(Ethyl-piperidin-4-yl-amino)-methyl]-phenyl}-pyrimidin-2-yl)-(2-pyridin-4-yl-ethyl)-amine: Intermediate 84 was coupled with 2-Pyridin-4-yl-ethylamine following procedure F. The resulting product was deprotected following procedure G. LC-MS showed the product had the expected M+H$^+$ of 417. $^1$H NMR (Varian 300 MHz, CD$_3$OD, shifts relative to the solvent peak at 3.30 ppm) δ 8.72 (d, 2H) 88.3-8.5 (m, 2H) 8.06 (d, 2H) 7.88 (d, 1H) 7.72 (m, 1H) 7.58 (d, 1H) 4.59 (d, 2H) 4.12 (br s, 2H) 3.85 (m, 1H) 3.62 (m, 2H) 3.1-3.45 (m, 6H) 2.48 (m, 2H) 2.18-2.24 (m, 2H) 1.35 (t, 3H).

Intermediate 135: 4-[3-(2-Chloro-pyrimidin-4-yl)-benzyl]-[1,4]diazepane-1-carboxylic acid tert-butyl ester: Intermediate 1 was coupled with [1,4]Diazepane-1-carboxylic acid tert-butyl ester following procedure B. LC-MS showed the product had the expected M+H$^+$ of 403.

Compound 248: [4-(3-[1,4]Diazepan-1-ylmethyl-phenyl)-pyrimidin-2-yl]-(2-thiophen-2-yl-ethyl)-amine: Intermediate 135 was coupled with 2-thiophen-2-yl-ethyl)-amine following procedure F. The resulting product was deprotected following procedure G2. LC-MS showed the product had the expected M+H$^+$ of 394. $^1$H NMR (Varian 300 MHz, CD$_3$OD, shifts relative to the solvent peak at 3.30 ppm) δ 8.38 (m, 3H) 7.85 (m, 1H) 7.71 (m, 1H) 7.53 (m, 1H) 7.1-7.3 (m, 2H) 6.85-7.0 (m, 2H) 4.59 (br s, 2H) 3.95 (br s, 2H) 3.68-3.83 (m, 3H) 3.55 (m, 2H) 3.45 (m, 2H) 3.2-3.45 (m, 3H).

Intermediate 136: 4(R)-[3-(2-Chloro-pyrimidin-4-yl)-benzylamino]-3(S)-methyl-piperidine-1-carboxylic acid benzyl ester: Intermediate 1 was coupled with 4(R)-amino-3(S)-methyl-piperidine-1-carboxylic acid benzyl ester (prepared according to literature procedure (ref 1)) following procedure B. LC-MS showed the product had the expected M+H$^+$ of 451.

Compound 249: 4-[2-(4-{3-[(3(S)-Methyl-piperidin-4(R)-ylamino)-methyl]-phenyl}-pyrimidin-2-ylamino)-ethyl]-phenol: Intermediate 136 was coupled with tyramine following procedure F. The resulting product was deprotected following procedure G3. LC-MS showed the product had the expected M+H$^+$ of 418. $^1$H NMR (Varian 300 MHz, CD$_3$OD, shifts relative to the solvent peak at 3.3 ppm) δ 8.63 (s, 1H) 8.36 (d, 2H) 7.95 (d, 1H) 7.75 (t, 1H) 7.67 (d, 1H) 7.15 (d, 2H) 6.71 (d, 2H) 4.50 (s, 2H) 3.96 (m, 1H) 3.80 (m, 1H) 3.72 (m, 1H) 3.56 (d, 1H) 3.34 (d, 1H) 3.20 (t, 2H) 2.96 (t, 2H) 2.80 (m, 1H) 2.38 (dd, 2H) 1.36 (d, 3H).

Compound 250: [2-(3,5-Difluoro-phenyl)-ethyl]-(4-{3-[(3(S)-methyl-piperidin-4(R)-ylamino)-methyl]-phenyl}-pyrimidin-2-yl)-amine: Intermediate 136 was coupled with 2-(3,5-difluoro-phenyl)-ethylamine following procedure F. The resulting product was deprotected following procedure G3. LC-MS showed the product had the expected M+H$^+$ of 418 LC-MS showed the product had the expected M+H$^+$ of 438. $^1$H NMR (Varian 300 MHz, CD$_3$OD, shifts relative to the solvent peak at 3.3 ppm) δ 8.70 (s, 1H) 8.39 (d, 2H) 7.97 (d, 1H)) 7.74 (d, 2H) 7.00 (d, 2H) 6.86 (d, 1H) 4.57 (s, 2H) 4.06 (m, 1H) 3.88 (m, 1H) 3.72 (m, 1H) 3.57 (m, 1H) 3.42 (d, 2H) 3.10 (t, 2H) 2.92 (m, 2H) 2.38 (m, 2H) 1.38 (d, 3H).

Compound 251: [2-(4-Bromo-phenyl)-ethyl]-(4-{3-[(3(S)-methyl-piperidin-4(R)-ylamino)-methyl]-phenyl}-pyrimidin-2-yl)-amine: Intermediate 136 was coupled with 2-(4-bromo-phenyl)-ethylamine following procedure F. The resulting product was deprotected following procedure G3. LC-MS showed the product had the expected M+H$^+$ of 481. $^1$H NMR (Varian 300 MHz, CD$_3$OD, shifts relative to the solvent peak at 3.3 ppm) δ 8.67 (s, 1H) 8.39 (d, 2H) 7.95 (d, 1H)) 7.69 (t, 1H) 7.40 (d, 2H) 7.28 (d, 2H) 4.50 (s, 2H) 4.00 (m, 1H) 3.84 (m, 1H) 3.72 (m, 1H) 3.57 (m, 1H) 3.42 (d, 1H) 3.36 (d, 1H) 3.20 (t, 2H) 3.04 (t, 2H) 2.30 (m, 2H) 1.30 (d, 3H).

Intermediate 137: 1-[3-(2-Chloro-pyrimidin-4-yl)-benzyl]-piperazine-2-carboxylic acid: Intermediate 1 was coupled with 4-[3-(2-chloro-pyrimidin-4-yl)-benzyl]-piperazine-1,3-dicarboxylic acid 1-tert-butyl ester following procedure B. LC-MS showed the product had the expected M+H$^+$ of 433.

Compound 252: 1-(3-{2-[2-(4-Hydroxy-phenyl)-ethylamino]-pyrimidin-4-yl}-benzyl)-piperazine-2-carboxylic acid: Intermediate 137 was coupled with tyramine following procedure F. The resulting product was deprotected following procedure G2. LC-MS showed the product had the expected M+H$^+$ of 434. $^1$H NMR (Varian 300 MHz, CD$_3$OD, shifts relative to the solvent peak at 3.3 ppm) δ 8.47 (s, 1H) 8.36 (d, 2H) 7.88 (d, 1H) 7.74 (t, 1H) 7.61 (d, 1H) 7.15 (d, 2H) 6.68 (d, 2H) 4.68 (dd, 1H) 4.39 (s, 2H) 3.96 (t, 2H) 3.84 (dd, 2H) 3.52 (t, 2H) 3.44 (t, 2H) 2.95 (t, 2H).

Compound 253: 1-(3-{2-[2-(3,5-Difluoro-phenyl)-ethylamino]-pyrimidin-4-yl}-benzyl)-piperazine-2-carboxylic acid: Intermediate 137 was coupled with 2-(3,5-difluoro-phenyl)-ethylamine following procedure F. The resulting product was deprotected following procedure G2. LC-MS showed the product had the expected M+H$^+$ of 454. $^1$H NMR (Varian 300

MHz, CD$_3$OD, shifts relative to the solvent peak at 3.3 ppm) δ 8.47 (s, 1H) 8.36 (d, 1H)) 8.33 (d, 1H) 7.87 (d, 1H) 7.71 (t, 1H) 7.65 (d, 1H) 7.00 (d, 2H) 6.77 (s, 1H) 4.63 (dd, 1H) 4.36 (s, 2H) 4.08 (t, 2H) 3.84 (dd, 2H) 3.65 (t, 2H) 3.47 (t, 2H) 3.09 (t, 2H).

Intermediate 158: 3-Carbamoyl-4-[3-(2-chloro-pyrimidin-4-yl)-benzyl]-piperazine-1-carboxylic acid tert-butyl ester: Intermediate 137 was converted to Intermediate 138 following literature procedure (ref 2). LC-MS showed the product had the expected M+H$^+$ of 432.

Compound 254: 1-(3-{2-[2-(4-Hydroxy-phenyl)-ethylamino]-pyrimidin-4-yl}-benzyl)-piperazine-2-carboxylic acid amide: Intermediate 138 was coupled with tyramine following procedure F. The resulting product was deprotected following procedure G2. LC-MS showed the product had the expected M+H$^+$ of 433. $^1$H NMR (Varian 300 MHz, CD$_3$OD, shifts relative to the solvent peak at 3.3 ppm) δ 8.15 (s, 1H) 8.11 (d, 1H) 8.07 (d, 1H) 7.77 (d, 1H) 7.58 (t, 1H) 7.50 (d, 1H) 7.15 (d, 2H) 6.70 (d, 2H) 4.00 (dd, 2H) 3.78 (dd, 1H) 3.65 (t, 2H) 3.35 (dd, 2H) 3.07 (t, 2H) 2.96 (t, 2H) 2.87 (t, 2H).

Compound 255: 1-(3-{2-[2-(3-Fluoro-phenyl)-ethylamino]-pyrimidin-4-yl}-benzyl)-piperazine-2-carboxylic acid amide: Intermediate 138 was coupled with 2-(3-fluoro-phenyl)-ethylamine following procedure F. The resulting product was deprotected following procedure G2. LC-MS showed the product had the expected M+H$^+$ of 435. $^1$H NMR (Varian 300 MHz, CD$_3$OD, shifts relative to the solvent peak at 3.3 ppm) δ 8.33 (d, 1H) 8.27 (s, 1H) 8.19 (d, 1H) 7.75 (d, 1H) 7.58 (t, 1H) 7.54 (d, 1H)) 7.30 (m, 1H) 7.13 (t, 2H) 6.92 (m, 1H) 3.98 (dd, 2H) 3.78 (dd, 1H) 3.40-3.60 (m, 6H) 3.24 (d, 2H) 3.08 (t, 2H).

Compound 256: 1-(3-{2-[2-(3,5-Difluoro-phenyl)-ethylamino]-pyrimidin-4-yl}-benzyl)-piperazine-2-carboxylic acid amide: Intermediate 138 was coupled with 2-(3,5-difluoro-phenyl)-ethylamine following procedure F. The resulting product was deprotected following procedure G2. LC-MS showed the product had the expected M+H$^+$ of 453. $^1$H NMR (Varian 300 MHz, CD$_3$OD, shifts relative to the solvent peak at 3.3 ppm) δ 8.44 (s, 1H) 8.38 (d, 1H) 8.33 (d, 1H) 7.86 (d, 1H) 7.68 (t, 1H) 7.63 (d, 1H)) 6.99 (d, 2H) 6.75 (m, 1H) 4.47 (d, 2H) 4.26 (dd, 1H) 4.22 (t, 2H) 3.80 (dd, 2H) 3.53 (t, 2H) 3.47 (t, 2H) 3.10 (t, 2H).

Intermediate 139: 4-[3-(2-Chloro-pyrimidin-4-yl)-benzyl]-3-cyano-piperazine-1-carboxylic acid tert-butyl ester: Intermediate 1 was coupled with 3-cyano-piperazine-1-carboxylic acid tert-butyl ester (generated according to literature procedure (ref 3)) following procedure B. LC-MS showed the product had the expected M+H$^+$ of 414.

Compound 257: 1-(3-{2-[2-(4-Hydroxy-phenyl)-ethylamino]-pyrimidin-4-yl}-benzyl)-piperazine-2-carbonitrile: Intermediate 139 was coupled with tyramine following procedure F. The resulting product was deprotected following procedure G2. LC-MS showed the product had the expected M+H$^+$—CN of 388. $^1$H NMR (Varian 300 MHz, CD$_3$OD, shifts relative to the solvent peak at 3.3 ppm) δ 8.32 (d, 1H) 8.27 (s, 1H) 8.23 (d, 1H) 7.75 (d, 1H) 7.62 (t, 1H) 7.55 (d, 1H) 7.14 (d, 2H) 6.71 (d, 2H) 4.38 (s, 2H) 3.92 (dd, 1H) 3.80 (d, 2H) 3.40 (t, 2H) 3.24 (t, 2H) 2.95 (t, 2H) 2.84 (t, 2H).

Intermediate 140: 4-[3-(2-Chloro-pyrimidin-4-yl)-benzyl]-2-cyano-piperazine-1-carboxylic acid benzyl ester: Intermediate 1 was coupled with 2-cyano-piperazine-1-carboxylic acid benzyl ester (generated according to literature procedure (ref 4)) following procedure B. LC-MS showed the product had the expected M+H$^+$ of 448.

Compound 258: 4-(3-{2-[2-(3,5-Difluoro-phenyl)-ethylamino]-pyrimidin-4-yl}-benzyl)-piperazine-2-carbonitrile: Intermediate 140 was coupled with 2-(3,5-difluoro-phenyl)-ethylamine following procedure F. The resulting product was deprotected following procedure G3. LC-MS showed the product had the expected M+H$_3$O$^+$ of 453. $^1$H NMR (Varian 300 MHz, CD$_3$OD, shifts relative to the solvent peak at 3.3 ppm) δ 8.37 (d, 1H) 8.19 (s, 1H) 8.15 (d, 1H) 7.68 (d, 1H) 7.60 (t, 1H) 7.37 (d, 1H) 6.94 (d, 2H) 6.85 (m, 1H) 4.60 (s, 2H) 4.05 (dd, 1H) 3.94 (t, 2H) 3.52 (dd, 2H) 3.24 (t, 2H) 3.03 (t, 2H) 2.58 (t, 2H).

Intermediate 141: 4-[3-(2-Chloro-pyrimidin-4-yl)-benzyl]-3,3-dimethyl-piperazine-1-carboxylic acid tert-butyl ester: Intermediate 1 was coupled with 3,3-dimethyl-piperazine-1-carboxylic acid tert-butyl ester following procedure B. LC-MS showed the product had the expected M+H$^+$ of 417.

Compound 259: {4-[3-(2,2-Dimethyl-piperazin-1-ylmethyl)-phenyl]-pyrimidin-2-yl}-[2-(3-fluoro-phenyl)-ethyl]-amine: Intermediate 141 was coupled with 2-(3-fluoro-phenyl)-ethylamine following procedure F. The resulting product was deprotected following procedure G2. LC-MS showed the product had the expected M+H$_3$O$^+$ of 438. $^1$H NMR (Varian 300 MHz, CD$_3$OD, shifts relative to the solvent peak at 3.3 ppm) δ 8.75 (s, 1H) 8.36 (d, 2H) 7.96 (d, 1H) 7.65 (m, 2H) 7.27 (m, 1H) 7.18 (m, 2H)) 6.92 (m, 1H) 4.54 (s, 2H) 3.96 (t, 2H) 3.72 (s, 2H) 3.59 (t, 2H) 3.35 (t, 2H) 3.08 (t, 2H) 1.74 (s, 6H).

Compound 260: [2-(3,5-Difluoro-phenyl)-ethyl]-{-4-[3-(2,2-dimethyl-piperazin-1-ylmethyl)-phenyl]-pyrimidin-2-yl}-amine: Intermediate 141 was coupled with 2-(3,5-difluoro-phenyl)-ethylamine following procedure F. The resulting product was deprotected following procedure G2. LC-MS showed the product had the expected M+H$_3$O$^+$ of 456. $^1$H NMR (Varian 300 MHz, CD$_3$OD, shifts relative to the solvent peak at 3.3 ppm) δ 8.76 (s, 1H) 8.36 (d, 1H) 8.33 (d, 1H) 7.97 (d, 1H) 7.70 (t, 2H) 7.03 (d, 2H) 6.76 (m, 1H) 4.54 (s, 2H) 3.98 (t, 2H) 3.72 (s, 2H) 3.35 (m, 4H) 3.10 (t, 2H) 1.74 (s, 6H).

Compound 261: 442-{4-[3-(2,2-Dimethyl-piperazin-1-ylmethyl)-phenyl]-pyrimidin-2-ylamino}-ethyl)-phenol: Intermediate 141 was coupled with tyramine following procedure F. The resulting product was deprotected following procedure G2. LC-MS showed the product had the expected M+H$_3$O$^+$ of 436. $^1$H NMR (Varian 300 MHz, CD$_3$OD, shifts relative to the solvent peak at 3.3 ppm) δ 8.72 (s, 1H) 8.34 (d, 2H) 7.95 (d, 1H) 7.68 (m, 2H) 7.17 (d, 2H) 6.72 (d, 2H) 4.54 (s, 2H) 3.96 (t, 2H) 3.71 (s, 2H) 3.35 (m, 4H) 2.96 (t, 2H) 1.76 (s, 6H).

Intermediate 142: 4-[3-(2-Chloro-pyrimidin-4-yl)-benzyl]-2,6-dimethyl-piperazine-1-carboxylic acid tert-butyl ester: Intermediate 1 was coupled with 2,6-dimethyl-piperazine-1-carboxylic acid tert-butyl ester following procedure B. LC-MS showed the product had the expected M+H$^+$ of 417.

Compound 262: 4-(2-{4-[3-(3,5-Dimethyl-piperazin-1-ylmethyl)-phenyl]-pyrimidin-2-ylamino}-ethyl)-phenol: Intermediate 142 was coupled with tyramine following procedure F. The resulting product was deprotected following procedure G2. LC-MS showed the product had the expected M+H$^+$ of 418. $^1$H NMR (Varian 300 MHz, CD$_3$OD, shifts relative to the solvent peak at 3.3 ppm) δ 8.67 (s, 1H) 8.56 (d, 1H)) 8.52 (d, 1H) 8.00 (d, 1H) 7.75 (t, 1H) 7.65 (d, 1H) 7.15 (d, 2H) 6.67 (d, 2H) 4.70 (s, 2H) 3.75 (d, 2H) 3.70 (d, 2H) 3.60-3.66 (m, 2H) 3.40 (t, 2H) 2.96 (t, 2H) 1.44 (d, 6H).

Compound 263: 2-Chloro-4-(2-{4-[3-(3,5-dimethyl-piperazin-1-ylmethyl)-phenyl]-pyrimidin-2-ylamino}-ethyl)-phenol: Intermediate 142 was coupled with 4-(2-amino-ethyl)-2-chloro-phenol following procedure F. The resulting product was deprotected following procedure G2. LC-MS showed the product had the expected M+H$^+$ of 452. $^1$H NMR (Varian 300 MHz, CD$_3$OD, shifts relative to the solvent peak at 3.3 ppm) δ 8.63 (s, 1H) 8.35 (d, 2H)) 7.93 (d, 1H) 7.74 (d, 1H) 7.62 (d, 1H) 7.17 (s, 1H) 7.07 (d, 1H) 6.74 (d, 1H) 4.60 (s, 2H) 3.60-3.70 (m, 6H) 3.35 (t, 2H) 2.92 (t, 2H) 1.44 (d, 6H).

Compound 264: [2-(3,5-Difluoro-phenyl)-ethyl]-{-4-[3-(3,5-dimethyl-piperazin-1-ylmethyl)-phenyl]-pyrimidin-2-yl}-amine: Intermediate 142 was coupled with 2-(3,5-difluoro-phenyl)-ethylamine following procedure F. The resulting product was deprotected following procedure G2. LC-MS showed the product had the expected M+H⁺ of 438. ¹H NMR (Varian 300 MHz, CD₃OD, shifts relative to the solvent peak at 3.3 ppm) δ 8.32 (s, 1H) 8.12 (d, 1H)) 7.98 (d, 1H) 7.47 (m, 2H) 7.12 (d, 1H) 6.90 (d, 2H) 6.75 (d, 1H) 3.75 (t, 2H) 3.60 (m, 4H) 3.47 (t, 2H) 2.98 (t, 2H) 2.90 (t, 2H) 1.04 (d, 6H).

Intermediate 143: 5-[3-(2-Chloro-pyrimidin-4-yl)-benzyl]-2,5-diaza-bicyclo[2.2.1]heptane-2-carboxylic acid tert-butyl ester: Intermediate 1 was coupled with 2,5-diaza-bicyclo[2.2.1]heptane-2-carboxylic acid tert-butyl ester following procedure B. LC-MS showed the product had the expected M+H⁺ of 401.

Compound 265: 2-Chloro-4-(2-{4-[3-(2,5-diaza-bicyclo[2.2.1]hept-2-ylmethyl)-phenyl]-pyrimidin-2-ylamino}-ethyl)-phenol: Intermediate 143 was coupled with 4-(2-amino-ethyl)-2-chloro-phenol following procedure F. The resulting product was deprotected following procedure G2. LC-MS showed the product had the expected M+H⁺ of 436. ¹H NMR (Varian 300 MHz, CD₃OD, shifts relative to the solvent peak at 3.3 ppm) δ 8.38 (s, 1H) 8.26 (d, 2H) 7.87 (d, 1H) 7.72 (m, 1H) 7.48 (d, 1H) 7.20 (s, 1H) 7.00 (d, 1H) 6.79 (d, 1H) 4.62 (s, 2H) 3.92 (d, 2H) 3.74 (d, 2H) 3.61 (t, 2H) 3.24 (t, 2H) 2.88 (t, 2H) 2.76 (d, 1H) 2.37 (d, 1H).

Compound 266: 4-(2-{4-[3-(2,5-Diaza-bicyclo[2.2.1]hept-2-ylmethyl)-phenyl]-pyrimidin-2-ylamino}-ethyl)-phenol: Intermediate 142 was coupled with tyramine following procedure F. The resulting product was deprotected following procedure G2. LC-MS showed the product had the expected M+H⁺ of 402. ¹H NMR (Varian 300 MHz, CD₃OD, shifts relative to the solvent peak at 3.3 ppm) δ 8.43 (s, 1H) 8.37 (d, 1H) 8.34 (d, 1H) 8.04 (d, 1H) 7.73 (t 1H) 7.65 (d, 1H) 7.17 (d, 2H) 6.69 (d, 2H) 4.62 (s, 2H) 4.19 (d, 2H) 3.92 (d, 2H) 3.63 (t, 2H) 3.23 (d, 2H) 2.94 (t, 2H) 2.61 (d, 1H) 2.37 (d, 1H).

Compound 267: {4-[3-(2,5-Diaza-bicyclo[2.2.1]hept-2-ylmethyl)-phenyl]-pyrimidin-2-yl}-[2-(3-fluoro-phenyl)-ethyl]-amine: Intermediate 142 was coupled with 2-(3-fluoro-phenyl)-ethylamine following procedure F. The resulting product was deprotected following procedure G2. LC-MS showed the product had the expected M+H⁺ of 404. ¹H NMR (Varian 300 MHz, CD₃OD, shifts relative to the solvent peak at 3.3 ppm) δ 8.45 (s, 1H) 8.36 (d, 2H) 7.89 (d, 1H) 7.73 (t, 1H) 7.54 (d, 1H) 7.27 (q, 1H) 7.10 (m, 2H) 6.91 (t, 1H) 4.63 (q, 2H) 4.61 (d, 2H) 3.92 (m, 3H) 3.78 (d, 1H) 3.59 (t, 2H) 3.07 (t, 2H) 2.76 (d, 1H) 2.33 (d, 1H).

Compound 268: {4-[3-(2,5-Diaza-bicyclo[2.2.1]hept-2-ylmethyl)-phenyl]-pyrimidin-2-yl}-[2-(3,5-difluoro-phenyl)-ethyl]-amine: Intermediate 142 was coupled with 2-(3,5-difluoro-phenyl)-ethylamine following procedure F. The resulting product was deprotected following procedure G2. LC-MS showed the product had the expected M+H⁺ of 422. ¹H NMR (Varian 300 MHz, CD₃OD, shifts relative to the solvent peak at 3.3 ppm) δ 8.78 (s, 1H) 8.38 (d, 2H) 8.00 (d, 1H) 7.77 (t, 1H) 7.68 (d, 1H) 7.00 (d, 2H) 6.75 (t, 1H) 4.84 (d, 1H) 4.65 (s, 2H) 4.60 (d, 1H) 4.24 (d, 1H) 4.10 (d, 1H) 3.89 (d, 1H) 3.68 (d, 1H) 3.63 (t, 2H) 3.07 (t, 2H) 2.86 (d, 1H) 2.37 (d, 1H).

Compound 269: {4-[3-(2,5-Diaza-bicyclo[2.2.1]hept-2-ylmethyl)-phenyl]-pyrimidin-2-yl}-[2,2,2-(dideutero-3,5-difluoro-phenyl)-ethyl]-amine: Intermediate 142 was coupled 115 following procedure F. The resulting product was deprotected following procedure G2. LC-MS showed the product had the expected M+H⁺ of 424. ¹H NMR (Varian 300 MHz, CD₃OD, shifts relative to the solvent peak at 3.3 ppm) δ 8.60 (s, 1H) 8.37 (d, 2H) 7.93 (d, 1H) 7.71 (t, 1H) 7.59 (d, 1H) 7.00 (d, 2H) 6.75 (t, 1H) 4.74 (d, 1H) 4.65 (s, 2H) 4.60 (d, 1H) 4.06 (d, 2H) 3.85 (d, 1H) 3.65 (d, 2H) 3.63 (d, 1H) 2.78 (d, 1H) 2.37 (d, 1H).

Intermediate 144: 2-[3-(2-Chloro-pyrimidin-4-yl)-benzyl]-1,1-dioxo-1λ⁶-[1,2,5]thiadiazepane-5-carboxylic acid tert-butyl ester: To a suspension of Intermediate 1 (10 g, 42 mmol) in methanol (150 mL) cooled to 0° C. (ice bath) add sodium borohydride (1.9 g, 1.2 equiv). Remove the ice bath and stir for 2-3 hr. Quench the reaction mixture with sodium bicarbonate (saturated solution, 50 mL) and concentrate on the rotovap to remove most of the methanol. Dilute with ethyl acetate (400 mL) and wash with brine. Dry the ethyl acetate layer with (MgSO₄), filter and concentrate on the rotovap. Purify the crude material on silica gel (30-60% ethyl acetate/hexanes) to obtain the alcohol as a white solid. Yields are typically 60-80%.

To a suspension of the alcohol prepared from the reduction of Intermediate 1 (10 g, 42 mmol) in CH₂Cl₂ (300 mL) add Hunig's base (11.2 mL, 1.5 equiv) and methanesulfonic anhydride (8.8 g, 50 mmol, 1.2 equiv). Stir the solution for 2-3 hr and poured over water (100 mL). Extract the water layer with CH₂Cl₂, dry (MgSO₄), filter and concentrate. Purify the crude material on silica gel (30-60% ethyl acetate/hexanes) to obtain the mesylate a white solid. Yields are typically 50-70%.

To a solution of 1.2 g (3.4 mmol) of the mesylate and 1.0 g (4.0 mmol) of 1,1-dioxo-1λ⁶-[1,2,5]thiadiazepane-5-carboxylic acid tert-butyl ester (prepared according to literature procedure[4]) in 40 mL of THF add 0.23 g (10 mmol) of sodium hydride and stir at rt overnight. Quench with 50 mL of water and extract the reaction mixture 3× with ethyl acetate. Dry the combined organic layers (Na₂SO₄), filter and concentrate on the rotavap. Purify the crude material on silica gel (70% ethyl acetate/hexanes) to obtain the intermediate as a white solid (62% yield). LC-MS showed the product had the expected M+H⁺ of 453.

Compound 270: 4-(2-{4-[3-(1,1-Dioxo-1λ⁶-[1,2,5]thiadiazepan-2-ylmethyl)-phenyl]-pyrimidin-2-ylamino}-ethyl)-phenol: Intermediate 144 was coupled with tyramine following procedure F. The resulting product was deprotected following procedure G2. LC-MS showed the product had the expected M+H⁺ of 454. ¹H NMR (Varian 300 MHz, CD₃OD, shifts relative to the solvent peak at 3.3 ppm) δ 8.36 (s, 1H) 8.30 (d, 1H) 8.20 (d, 1H) 7.73 (d, 1H) 7.64 (t 1H) 7.53 (d, 1H) 7.14 (d, 2H) 6.68 (d, 2H) 4.70 (s, 2H) 3.80 (t, 2H) 3.67 (m, 4H) 3.56 (t, 2H) 3.36 (t, 2H) 2.95 (t, 2H).

Intermediate 145: 3-(2-chloropyrimidin-4-yl)-4-methoxybenzaldehyde: 2,4 dichloropyrimidine and 5-formyl-2-methoxyphenylboronic acid was coupled following procedure A. The yield was 70%. LC-MS showed the product was >95% pure and had the expected M+H⁺ of 249. ¹H NMR (Varian 300 MHz, MeOD-d₆, shifts relative to the solvent peak at 3.33 ppm) δ 9.9 (s, 1H) 8.7 (d, 1H) 8.4 (s, 1H) 8.0 (d, 2H) 7.4 (d, 1H) 3.9 (s, 3H).

Intermediate 146: (3S)-tert-butyl 4-(3-(2-chloropyrimidin-4-yl)-4-methoxybenzyl)-3-methylpiperazine-1-carboxylate: The product from the above reaction and (S)-tert-butyl 3-methylpiperazine-1-carboxylate was coupled by procedure B. The yield was 84%. LC-MS showed the product had the expected M+H⁺ of 433.

Compound 271: 4-(2-(4-(2-methoxy-5(((S)-2-methylpiperazin-1-yl)methy 1)phenyl)pyrimidin-2-ylamino)ethyl)

phenol: Intermediate 146 from above was coupled with tyramine following procedure F. The product was deprotected by procedure G2. LC-MS showed the product had the expected M+H+ of 434. ¹H NMR (Varian 300 MHz, DMSO-d₆, shifts relative to the solvent peak at 2.49 ppm) δ 8.4 (d, 1H) 7.8 (s, 1H) 7.3 (d, 1H) 7.1 (m, 3H), 6.6 (m, 3H), 3.9 (s, 3H) 3.6 (m, 4H) 3.5 (d, 2H) 3.43-3.37 (m, 2H) 3.2 (m, 2H) 2.8 (t, 2H), 1.5 (d, 3H).

Compound 272: 2-chloro-4-(2-(4-(2-methoxy-5-(((S)-2-methylpiperazin-1-yl)methyl)phenyl)pyrimidin-2-ylamino)ethyl)phenol: Intermediate 146 from above was coupled with 4-(2-aminoethyl)-2-chlorophenol following procedure F. The product was deprotected by procedure G2. LC-MS showed the product had the expected M+H+ of 468. ¹H NMR (Varian 300 MHz, DMSO-d₆, shifts relative to the solvent peak at 2.49 ppm) δ 8.4 (d, 1H) 7.8 (d, 1H) 7.4-7.2 (m, 3H) 7.1 (m, 2H), 6.1 (d, 1H), 3.9 (s, 3H) 3.7-3.6 (m, 4H) 3.5 (d, 2H) 3.4-3.3 (m, 4H), 3.2 (m, 1H), 2.8 (t, 2H), 1.6 (d, 3H).

Intermediate 147: 5-(2-chloropyrimidin-4-yl)nicotinaldehdye: 2,4 dichloropyrimidine and 5-(4,4,5,5-tetramethyl-1,3,2-dioxaborolan-2-yl)nicotinaldehyde was coupled following procedure A. The yield was 34%. LC-MS showed the product was >95% pure and had the expected M+H+ of 220.

Intermediate 148: (3S)-tert-butyl 445-(2-chloropyrimidin-4-yl)pyridine-3-yl)methyl)-3-methylpiperazine-1-carboxylate: Intermediate 147 from the above reaction and (S)-tert-butyl 3-methylpiperazine-1-carboxylate was coupled by procedure B. The yield was 60%. LC-MS showed the product had the expected M+H+ of 404.

Compound 273: 2-chloro-4-(2-(4-(5-(((S)-2-methylpiperazin-1-yl)methyl)pyridine-3-yl)pyrimidin-2-ylamino)ethyl)phenol: Intermediate 148 from above was coupled with 4-(2-aminoethyl)-2-chlorophenol following procedure F. The product was deprotected by procedure G2. LC-MS showed the product had the expected M+H+ of 439. ¹H NMR (Varian 300 MHz, DMSO-d₆, shifts relative to the solvent peak at 2.49 ppm) δ 9.4 (s, 1H) 9.1 (m, 2H) 8.5 (d, 1H) 7.5 (s, 1H), 7.2 (d, 1H) 7.0 (d, 1H) 6.8 (d, 1H), 3.7-3.5 (m, 5H) 3.4-3.2 (m, 6H), 2.8 (t, 2H), 1.5 (d, 3H).

Compound 274: 4-(2-(4-(5-(((S)-2-methylpiperazin-1-yl)methyl)pyridine-3-yl)pyrimidin-2-ylamino)ethylphenol: Intermediate 148 from above was coupled with tyramine following procedure F. The product was deprotected by procedure G2. LC-MS showed the product had the expected M+H+ of 405. ¹H NMR (Varian 300 MHz, DMSO-d₆, shifts relative to the solvent peak at 2.49 ppm) δ 9.4 (s, 1H) 9.0 (m, 2H) 8.5 (d, 1H) 7.5 (s, 1H), 7.0 (d, 2H), 6.6 (d, 2H), 3.7-3.5 (m, 5H) 3.4-3.3 (m, 6H), 2.8 (t, 2H), 1.6 (d, 3H).

Compound 275: N-(3-fluorophenethyl)-4-(5-(((S)-2-methylpiperazin-1-yl)methyl)pyridine-3-yl)pyrimidin-2-amine: Intermediate 148 from above was coupled with 2-(3-fluorophenyl)ethanamine following procedure F. The product was deprotected by procedure G2. LC-MS showed the product had the expected M+H+ of 407. ¹H NMR (Varian 300 MHz, DMSO-d₆, shifts relative to the solvent peak at 2.49 ppm) δ 9.4 (s, 1H) 9.0 (m, 2H) 8.5 (d, 1H) 7.4 (s, 1H), 7.2 (t, 1H), 7.1 (m, 2H), 6.9 (d, 1H), 3.71-3.65 (m, 4H) 3.57 (d, 2H), 3.47-3.44 (m, 1H), 3.39-3.31 (m, 4H), 2.9 (t, 2H), 1.6 (d, 3H).

Intermediate 149: 3-(2-chloro-6-methylpyrimidin-4-yl)benzaldhye: 2,4-dichloro-6-methylpyrimidine and 3-formyl phenyl boronic acid was coupled following procedure A. The yield was 69%. LC-MS showed the product was >95% pure and had the expected M+H+ of 233. ¹H NMR (Varian 300 MHz, CDCl₃, shifts relative to the solvent peak at 7.24 ppm) δ 10.1 (s, 1H) 8.6 (s, 1H), 8.4 (d, 1H), 8.1 (d, 1H), 7.7 (t, 1H), 7.5 (s, 1H) 2.6 (s, 3H).

Intermediate 150: (3S)-tert-butyl 4-(3-(2-chloro-6-methylpyrimdin-4-yl)benzyl)-3-methylpiperazine-1-carboxylate: Intermediate 149 from the above reaction and (S)-tert-butyl 3-methylpiperazine-1-carboxylate was coupled by procedure B. The yield was 77%. LC-MS showed the product had the expected M+H+ of 417

Compound 276: 2-chloro-4-(2-(4-methyl-6-(3-(((S)-2-methylpiperazin-1-yl)methyl)phenyl)pyrimidin-2-ylamino)ethyl)phenol: Intermediate 150 from above was coupled with 4-(2-aminoethyl)-2-chlorophenol following procedure F. The product was deprotected by procedure G2. LC-MS showed the product had the expected M+H+ of 452. ¹H NMR (Varian 300 MHz, DMSO-d₆, shifts relative to the solvent peak at 2.49 ppm) δ 8.6 (d, 1H) 8.3 (d, 1H) 7.9 (d, 1H) 7.7 (t, 1H), 7.5 (s, 1H), 7.2 (s, 1H), 7.0 (d, 1H), 6.8 (d, 1H), 4.12-3.9 (m, 5H) 3.8-3.47 (m, 6H), 2.9 (t, 2H), 2.6 (s, 3H), 1.6 (d, 3H).

Intermediate 151: (S)-tert-butyl 4-(3-bromophenylsulfonyl)-3-methylpiperazine-1-carboxylate: 3-bromobenzene-1-sulfonyl chloride and (S)-tert-butyl 3-methylpiperazine-1-carboxylate was coupled following as follows: Dissolve 1 g (5 mmol) of the amine in 10 mL of methylene chloride. Add 2.0 eq. of diisopropyl ethylamine. Cool to 0° C. and add 1.5 equivalents of bromobenzene sulfonyl chloride dropwise (ca. 1 min) and stir for 5 min. Warm to rt and stir for an additional 16 h. Work up by adding a saturated solution of NaHCO₃ and extracting with EtOAc. Wash the organic layer with HCl (1 N) followed by NaHCO₃ and brine. Remove the solvent to afford crude, yellow oil. Purification of the sulfonamide derivative by Biotage on silica gel (99% MeOH/DCM) affords the desired product as a yellow oil. The yield was 55%. LC-MS showed the product was >95% pure and had the expected M+H+ of 420. ¹H NMR (Varian 300 MHz, CDCl₃, shifts relative to the solvent peak at 7.24 ppm) δ 7.9 (d, 1H) 7.72-7.65 (m, 2H) 7.4 (t, 1H), 3.7 (m, 2H) 3.6 (m, 1H), 3.13-3.0 (m, 2H) 2.92-2.77 (m, 2H), 1.4 (s, 12H) 1.0 (d, 3H).

Intermediate 152: (S)-tert-butyl 3-methyl-4-(3-(4,4,5,5-tetramethyl-1,3,2-dioxaborolan-2-yl)phenylsulfonyl)piperazine-1-carboxy late: (S)-tert-butyl 4-(3-bromophenylsulfonyl)-3-methylpiperazine-1-carboxylate was cross-coupled to 4,4,5,5-tetramethyl-2-(4,4,5,5-tetramethyl-1,3,2-dioxaborolan-2-yl)-1,3,2-dioxaborolane as follows: Charge a round bottom flask with 1.1 equivalents 4,4,5,5-tetramethyl-2-(4,4,5,5-tetramethyl-1,3,2-dioxaborolan-2-yl)-1,3,2-dioxaborolane, 3 mol % PdCl₂(dppf), and 3 equivalents potassium acetate. Purge with argon and add DMSO (2-mL) followed by 1.0 equivalent bromobenzene sulfonamide. Heat the mixture to 80° C., overnight, under argon. Add H₂O (2 mL) and extract with ethyl acetate (20 mL). Wash organic layer with H₂O and brine. Remove the solvent and purify the product by ISCO on silica gel (ethyl acetate as eluent). The yield was 93%. LC-MS showed the product was >95% pure and had the expected M+H+ of 467.

Intermediate 153: (3S)-tert-butyl 4-(3-(2-chloropyrimidin-4-yl)phenylsulfonyl)-3-methylpiperazine-1-carboxylate: 2,4-dichloropyrimidine and (S)-tert-butyl 3-methyl-4-(3-(4,4,5,5-tetramethyl-1,3,2-dioxaborolan-2-yl)phenylsulfonyl)piperazine-1-carboxylate was coupled following procedure A. The yield was 90%. LC-MS showed the product was >95% pure and had the expected M+H+ of 453.

Compound 277: N-(3,5-difluorophenethyl)-4-(3-((S)-2-methylpiperazin-1-ylsulfonyl)phenyl)pyrimidin-2-amine: Intermediate 153 from above was coupled with 2-(3,5-difluorophenyl)ethanamine following procedure F. The product was deprotected by procedure G2. LC-MS showed the product had the expected M+H+ of 474. ¹H NMR (Varian 300 MHz, MeOD-d₆, shifts relative to the solvent peak at 3.33 ppm) δ 8.7 (d, 1H) 8.5 (d, 1H) 8.4 (d, 1H) 8.1 (d, 1H), 7.8 (t, 1H), 7.6 (d, 1H), 6.9 (d, 2H), 6.7 (s, 1H), 3.52-3.34 (m, 4H) 3.26-3.15 (m, 2H), 3.11-3.01 (m, 5H), 1.2 (d, 3H).

Compound 278: 2-Chloro-4-(2-(4-(3-(((S)-2-methylpiperazin-1-ylsulfonyl)phenyl)pyrimidin-2-ylamino)ethylphenol: Intermediate 153 from above was coupled with 4-(2-aminoethyl)-2-chlorophenol following procedure F. The product was deprotected by procedure G2. LC-MS showed the product had the expected M+H$^+$ of 489. $^1$H NMR (Varian 300 MHz, DMSO-d$_6$, shifts relative to the solvent peak at 2.49 ppm) δ 8.6 (d, 1H) 8.4 (m, 2H) 8.0 (d, 1H), 7.8 (t, 1H), 7.3 (s, 1H), 7.2 (d, 1H), 7.0 (d, 1H), 6.8 (d, 1H) 3.5 (m, 3H), 3.3 (m, 3H), 3.1 (m, 2H), 2.9 (m, 1H), 2.7 (t, 2H), 1.1 (d, 3H).

Compound 279: N-(3-fluorophenethyl)-4-(3-(((S)-2-methylpiperazin-1-ylsulfonyl)phenyl)pyrimidin-2-amine: Intermediate 153 from, above was coupled with 2-(3-fluorophenyl)ethanamine following procedure F. The product was deprotected by procedure G2. LC-MS showed the product had the expected M+H$^+$ of 456. $^1$H NMR (Varian 300 MHz, MeOD-d$_6$, shifts relative to the solvent peak at 3.31 ppm) δ 8.6 (d, 1H) 8.5 (d, 1H) 8.4 (d, 1H), 8.1 (d, 1H), 7.8 (t, 1H), 7.6 (d, 1H), 7.2 (t, 1H), 7.1 (d, 1H), 7.0 (d, 1H), 6.8 (d, 1H), 3.9 (m, 3H), 3.4 (m, 1H), 3.3 (m, 2H), 3.2 (m, 2H), 3.1 (m, 1H), 3.0 (t, 2H), 1.2 (d, 3H).

Compound 280: 4-(2-(4-(3-((S)-2-methylpiperazin-1-ylsulfonyl)phenyl)pyrimidin-2-ylamino)ethyl)phenol: Intermediate 153 from above was coupled with tyramine following procedure F. The product was deprotected by procedure G2. LC-MS showed the product had the expected M+H$^+$ of 454. $^1$H NMR (Varian 300 MHz, MeOD-d$_6$, shifts relative to the solvent peak at 3.31 ppm) δ 8.6 (d, 1H) 8.5 (d, 1H) 8.3 (d, 1H), 8.1 (d, 1H), 7.8 (t, 1H), 7.6 (d, 1H), 7.1 (d, 2H), 6.6 (d, 2H), 3.9-3.8 (m, 3H), 3.4-3.3 (m, 2H), 3.2-3.1 (m, 3H), 3.0-2.9 (m, 3H), 1.2 (d, 3H).

Intermediate 154: (3-bromo-4-methylphenyl)methanol: Ethyl 3-bromo-4-methylbenzoate was reduced follows: 2 equivalents lithium aluminium hydride (LAH) in THF was cooled to 0° C. Ethyl 3-bromo-4-methylbenzoate in anhydrous THF (10 mL) was added slowly to the cooled solution of LAH over 10 minutes, while stirring. The mixture was stirred at room temperature for 1 hour. The reaction was cooled to 0° C. and poured into ether (100 mL). The mixture was acidified by adding 1N HCl (aqueous) dropwise over 10 minutes. Separate fractions and wash aqueous phase with ether (50 mL). The fractions were combined and dried over magnesium sulfate. Solvent removal left a clear oil. The yield was 90%. $^1$H NMR (Varian 300 MHz, CDCl$_3$, shifts relative to the solvent peak at 7.24 ppm) δ 7.5 (s, 1H) 7.2 (d, 1H) 7.1 (d, 1H), 4.6 (s, 2H) 2.3 (s, 3H).

Intermediate 155: 3-bromo-4-methylbenzaldehyde: (3-bromo-4-methylphenyl)methanol was oxidized as follows: To the primary alcohol (15 mmol) in methylene chloride (30 mL) was added 10 equivalents of activated manganese oxide (IV). The mixture was stirred at room temperature for 24 hours, the filtered through a bed of celite. Removal of the solvent left a yellow solid. Product was used crude in next step without further purification. The yield was 89%. $^1$H NMR (Varian 300 MHz CDCl$_3$, shifts relative to the solvent peak at 7.24 ppm) δ 9.8 (s, 1H) 8.0 (s, 1H) 7.7 (d, 1H), 7.2 (d, 1H), 2.3 (s, 3H).

Intermediate 156: 4-methyl-3-(4,4,5,5-tetramethyl-1,3,2-dioxaborolan-2-yl)benzaldehyde: 3-bromo-4-methylbenzaldehyde was cross-coupled to 4,4,5,5-tetramethyl-2-(4,4,5,5-tetramethyl-1,3,2-dioxaborolan-2-yl)-1,3,2-dioxaborolane as follows: Charge a round bottom flask with 1.1 equivalents 4,4,5,5-tetramethyl-2-(4,4,5,5-tetramethyl-1,3,2-dioxaborolan-2-yl)-1,3,2-dioxaborolane, 3 mol % PdCl$_2$(dppf), and 3 equivalents potassium acetate. Purge with argon and add DMSO (2-mL) followed by 1.0 equivalent bromobenzene sulfonamide. Heat the mixture to 80° C., overnight, under argon. Add H$_2$O (2 mL) and extract with ethyl acetate (20 mL). Wash organic layer with H$_2$O and brine. Remove the solvent and purify the product by ISCO on silica gel (ethyl acetate as eluent). The yield was 60%. LC-MS showed the product was >95% pure and had the expected M+H$^+$ of 246. $^1$H NMR (Varian 300 MHz, CDCl$_3$, shifts relative to the solvent peak at 7.24 ppm) δ 9.9 (s, 1H), 8.2 (s, 1H) 7.7 (d, 1H), 7.3 (d, 1H), 2.5 (s, 3H), 1.3 (s, 12H).

Intermediate 157: 3-(2-chloropyrimidin-4-yl)-4-methylbenzaldehyde: 2,4 dichloropyrimidine and 4-methyl-3-(4,4,5,5-tetramethyl-1,3,2-dioxaborolan-2-yl)benzaldehyde was coupled following procedure A. The yield was 80%. LC-MS showed the product was >95% pure and had the expected M+H$^+$ of 233. $^1$H NMR (Varian 300 MHz, CDCl$_3$, shifts relative to the solvent peak at 7.24 ppm) δ 10.0 (s, 1H) 8.7 (s, 1H) 7.9 (d, 2H) 7.5 (d, 2H), 2.5 (s, 3H).

Intermediate 158: (3S)-tert-butyl 4-(3-(2-chloropyrimidin-4-yl)-4-methylbenzyl)-3-methylpiperazine-1-carboxylate: The product from the above reaction and (S)-tert-butyl 3-methylpiperazine-1-carboxylate was coupled by procedure B. The yield was 60%. LC-MS showed the product had the expected M+H$^+$ of 417.

Compound 281: 4-(2-(4-(2-methyl-5-(((S)-2-methylpiperazin-1-yl)methyl)phenyl)pyrimidin-2-ylamino)ethyl)phenol: Intermediate 158 from above was coupled with tyramine following procedure F. The product was deprotected by procedure G2. LC-MS showed the product had the expected M+H$^+$ of 418. $^1$H NMR (Varian 300 MHz, MeOD-d$_6$, shifts relative to the solvent peak at 3.31 ppm) δ 8.3 (d, 1H) 8.0 (d, 1H) 7.7 (d, 1H) 7.5 (d, 1H), 7.3 (d, 1H), 7.0 (d, 2H) 6.7 (d, 2H) 4.0 (t, 2H) 3.7 (m, 3H) 3.6-3.4 (m, 6H) 2.8 (t, 2H), 2.5 (s, 3H), 1.7 (d, 3H).

Compound 283: N-(3,5-difluorophenethyl)-4-(2-methyl-5-(((S)-2-methylpiperazin-1-yl)methyl)phenyl)pyrimidin-2-amine: Intermediate 158 from above was coupled with 2-(3,5-difluorophenyl)ethanamine following procedure F. The product was deprotected by procedure G2. LC-MS showed the product had the expected M+H$^+$ of 438. $^1$H NMR (Varian 300 MHz, MeOD-d$_6$, shifts relative to the solvent peak at 3.31 ppm) δ 8.4 (d, 1H) 8.0 (d, 1H) 7.7 (d, 1H) 7.5 (d, 1H), 7.4 (d, 1H), 6.9 (d, 2H) 6.7 (t, 1H), 3.9-3.8 (m, 3H) 3.7-3.6 (m, 6H) 3.5-3.4 (m, 2H) 3.0 (t, 2H), 2.5 (s, 3H), 1.7 (d, 3H).

Intermediate 159: 2-Chloro-4-(3-nitro-phenyl)-pyrimidine: 2,4 dichloropyrimidine was coupled to 3-nitrophenyl boronic acid following procedure A. The workup and purification protocol was modified as follows: The THF was removed from the reaction mixture by rotary evaporation and the residue taken up in ethyl acetate. The solution was washed with water followed by sat. NaCl and the organic layer concentrated by rotary evaporation until the product started to precipitate, at which point the flask was placed in an ice bath for two hours. The product was collected by filtration in a Buchner funnel. The yield was 60%. Product was >95% pure by LC-MS and showed the expected M+H$^+$ of 236.

Intermediate 160: (3-bromo-2-methylphenyl)methanol: Ethyl 3-bromo-2-methylbenzoic acid was reduced as follows: Add 5 equivalents of borane tetrahydrofuran complex, via syringe, to 10 mmol ethyl 3-bromo-2-methylbenzoic acid in tetrahydrofuran (5 mL). The mixture was refluxed for two hours, then cooled in an ice bath. Methanol (10 mL) was added dropwise, followed by 1 N HCl (50 mL). The solvent was removed and the mixture partitioned between ethyl acetate and water. The yield was 90%. $^1$H NMR (Varian 300

MHz, CDCl$_3$, shifts relative to the solvent peak at 7.24 ppm) δ7.5 (d, 1H) 7.2 (d, 1H) 7.1 (t, 1H), 4.6 (s, 2H) 2.3 (s, 3H).

Intermediate 161: 3-bromo-2-methylbenzaldehyde: (3-bromo-2-methylphenyl)methanol was oxidized as follows: The alcohol (15 mmol) was dissolved in methylene chloride (30 mL). 10 equivalents of activated manganese oxide (IV) was added and the mixture stirred at room temperature for 24 hours. The mixture was filtered through a bed of celite and the solvent removed in-vacuo to leave yellow solid. Product was used crude in next step without further purification. The yield was 93%. $^1$H NMR (Varian 300 MHz, CDCl$_3$, shifts relative to the solvent peak at 7.24 ppm) δ 9.8 (s, 1H) 8.1 (d, 1H) 7.7 (d, 1H), 7.2 (t, 1H), 2.4 (s, 3H).

Intermediate 162: 2-methyl-3-(4,4,5,5-tetramethyl-1,3,2-dioxaborolan-2-yl)benzaldehyde: 3-bromo-2-methylbenzaldehyde was cross-coupled to 4,4,5,5-tetramethyl-2-(4,4,5,5-tetramethyl-1,3,2-dioxaborolan-2-yl)-1,3,2-dioxaborolane as follows: A round bottom flask was charged with 1.1 equivalents 4,4,5,5-tetramethyl-2-(4,4,5,5-tetramethyl-1,3,2-dioxaborolan-2-yl)-1,3,2-dioxaborolane, 3 mol % PdCl$_2$(dppf), and 3 equivalents potassium acetate. The flask was purged with argon and DMSO (2-mL) added followed by 1.0 equivalent bromobenzene sulfonamide. The mixture was heated to 80° C., overnight, under argon. H$_2$O (2 mL) was added and the mixture extracted with ethyl acetate (20 mL). The organic layer was washed with H$_2$O and brine. Removal of the solvent was followed and purification of the product by ISCO on silica gel (ethyl acetate as eluent). The yield was 65%. LC-MS showed the product was >95% pure and had the expected M+H$^+$ of 246.

Intermediate 163: 3-(2-chloropyrimidin-4-yl)-2-methylbenzaldehyde: 2,4 dichloropyrimidine and 2-methyl-3-(4,4,5,5-tetramethyl-1,3,2-dioxaborolan-2-yl)benzaldehyde was coupled following procedure A. The yield was 50%. LC-MS showed the product was >95% pure and had the expected M+H$^+$ of 233. $^1$H NMR (Varian 300 MHz, CDCl$_3$, shifts relative to the solvent peak at 7.24 ppm) δ 9.9 (s, 1H) 8.6 (s, 1H) 7.5 (d, 2H) 7.4 (t, 1H), 7.2 (d, 1H), 2.5 (s, 3H).

Intermediate 164: (3S)-tert-butyl 4-(3-(2-chloropyrimidin-4-yl)-2-methylbenzyl)-3-methylpiperazine-1-carboxylate: The product from the above reaction and (S)-tert-butyl 3-methylpiperazine-1-carboxylate was coupled by procedure B. The yield was 60%. LC-MS showed the product had the expected M+H$^+$ of 417.

Compound 284: 4-(2-(4-(2-methyl-3-(((S)-2-methylpiperazin-1-yl)methyl)phenyl)pyrimidin-2-ylamino)ethyl)phenol: Intermediate 164 from above was coupled with tyramine following procedure F. The product was deprotected by procedure G2. LC-MS showed the product had the expected M+H$^+$ of 418. $^1$H NMR (Varian 300 MHz, MeOD-d$_6$, shifts relative to the solvent peak at 3.31 ppm) δ 8.3 (d, 1H) 8.0 (d, 1H) 7.7 (d, 1H) 7.5 (d, 1H), 7.3 (t, 1H), 7.0 (d, 2H) 6.6 (d, 2H), 3.9 (t, 2H) 3.8-3.7 (m, 3H) 3.6-3.4 (m, 6H) 2.8 (t, 2H) 2.5 (s, 3H), 1.7 (d, 3H).

Intermediate 165: 5-(2-chloropyrimidin-4-yl) 2-fluorobenzaldehyde: 2,4 dichloropyrimidine and 4-fluoro-3-formylphenylboronic acid was coupled following procedure A. The yield was 40%. LC-MS showed the product was >95% pure and had the expected M+H$^+$ of 237.

Intermediate 166: (3S)-tert-butyl 4-(5-(2-chloropyrimidin-4-yl)-2-fluorobenzyl)-3-methylpiperazine-1-carboxylate: The product from the above reaction and (S)-tert-butyl 3-methylpiperazine-1-carboxylate was coupled by procedure B. The yield was 50%. LC-MS showed the product had the expected M+H$^+$ of 421.

Compound 285 N-(3,5-difluorophenethyl)-4-(4-fluoro-3-(((S)-2-methylpiperazin-1-yl)methyl)phenyl)pyrimidin-2-amine: Intermediate 166 from above was coupled with 2-(3,5-difluorophenyl)ethanamine following procedure F. The product was deprotected by procedure G2. LC-MS showed the product had the expected M+H$^+$ of 442. $^1$H NMR (Varian 300 MHz, MeOD-d$_6$, shifts relative to the solvent peak at 3.31 ppm) δ 8.8 (d, 1H) 8.4 (d, 1H) 8.3 (d, 1H) 7.7 (d, 1H), 7.5 (t, 1H), 7.0 (d, 2H) 6.7 (d, 1H), 3.8-3.7 (m, 3H) 3.6-3.5 (m, 8H), 3.0 (t, 2H), 1.7 (d, 3H).

Compound 286: 4-(2-(4-(4-fluoro-3-(((S)-2-methylpiperazin-1-yl)methyl)phenyl)pyrimidin-2-ylamino)ethyl)phenol: Intermediate 166 from above was coupled with tyramine following procedure F. The product was deprotected by procedure G2. LC-MS showed the product had the expected M+H$^+$ of 422. $^1$H NMR (Varian 300 MHz, MeOD-d$_6$, shifts relative to the solvent peak at 3.31 ppm) δ 8.7 (d, 1H) 8.4 (d, 1H) 8.3 (d, 1H) 7.6 (d, 1H), 7.5 (t, 1H), 7.1 (d, 2H) 6.6 (d, 1H), 3.9-3.7 (m, 3H) 3.69-3.57 (m, 8H), 2.9 (t, 2H), 1.7 (d, 3H).

Compound 287: N-(3-fluorophenethyl)-4-(4-fluoro-3-(((S)-2-methylpiperazin-1-yl)methyl)phenyl)pyrimidin-2-amine: Intermediate 166 from above was coupled with 2-(3-fluorophenyl)ethanamine following procedure F. The product was deprotected by procedure G2. LC-MS showed the product had the expected M+H$^+$ of 424. $^1$H NMR (Varian 300 MHz, MeOD-d$_6$, shifts relative to the solvent peak at 3.31 ppm) δ 8.8 (d, 1H) 8.4 (d, 1H) 8.3 (d, 1H) 7.6 (d, 1H), 7.5 (t, 1H), 7.2 (d, 1H) 7.1 (d, 2H), 6.8 (d, 1H), 3.8-3.7 (m, 3H) 3.69-3.62 (m, 8H), 3.0 (t, 2H), 1.7 (d, 3H).

Intermediate 167: 5-(2-chloropyrimidin-4-yl-1H-indole: 2,4 dichloropyrimidine and 1H-indol-5-ylboronic acid was coupled following procedure A. The yield was 78%. LC-MS showed the product was >95% pure and had the expected M+H$^+$ of 230. $^1$H NMR (Varian 300 MHz, DMSO-d$_6$, shifts relative to the solvent peak at 2.49 ppm) δ 8.6 (d, 1H) 8.4 (s, 1H) 8.0 (d, 1H) 7.9 (d, 1H), 7.5 (d, 2H), 6.5 (d, 1H).

Compound 288: 4-(2-(4-(1H-indol-5-yl)pyrimidin-2-ylamino)ethyl)-2-chlorophenol: Intermediate 167 from above was coupled with 4-(2-aminoethyl)-2-chlorophenol following procedure F. LC-MS showed the product had the expected M+H$^+$ of 365. $^1$H NMR (Varian 300 MHz, MeOD-d$_6$, shifts relative to the solvent peak at 3.31 ppm) δ 8.3 (d, 1H) 8.1 (s, 1H) 7.9 (d, 1H) 7.4 (d, 1H), 7.3 (d, 1H), 7.2 (s, 1H) 7.1 (d, 1H), 7.0 (d, 1H), 6.8 (d, 1H) 6.5 (d, 1H), 3.6 (t, 2H), 2.8 (t, 2H).

Intermediate 168: 3-(2-Chloro-pyrimidin-4-yl)-benzaldehyde: 2,4 dichloropyrimidine and 3-formyl phenyl boronic acid were coupled following procedure A. The yield was 60%. LC-MS showed the product was >95% pure and had the expected M+H$^+$ of 219. $^1$H NMR (Varian 300 MHz, CDCl$_3$, shifts relative to the solvent peak at 7.24 ppm) 10.1 (s, 1H) 8.7 (d, 1H) 8.6 (m, 1H) 8.4 (m, 1H) 8.1 (m, 1H) 7.7 (m, 2H).

Intermediate 169: tert-butyl 2-(2-(3-(2-chloropyrimidin-4-yl)benzylamino)ethyl)piperidine-1-carboxylate: The product from the above reaction and tert-butyl 2-(2-aminoethyl)piperidine-1-carboxylate were coupled by procedure B. The yield was 40%. LC-MS showed the product had the expected M+H$^+$ of 431.

Intermediate 170: tert-butyl 2-(2-((3-(2-chloropyrimidin-4-yl)benzyl)(ethyl)amino)ethylpiperidine-1-carboxylate: The product from the above reaction was coupled with acetaldehyde by procedure C. The yield was 90%. LC-MS showed the product had the expected M+H$^+$ of 460.

Compound 289: 2-chloro-4-(2-(4-(3-((ethyl(2-(piperidin-2-yl)ethyl)amino)methyl)phenyl)pyrimidin-2-ylamino)ethyl)phenol: Intermediate 170 from above was coupled with 4-(2-aminoethyl)-2-chlorophenol following procedure F. The product was deprotected by procedure G2. LC-MS showed the product had the expected M+H+ of 495. ¹H NMR (Varian 300 MHz, MeOD-d$_6$, shifts relative to the solvent peak at 3.31 ppm) δ 8.4 (d, 1H) 8.2 (d, 1H) 8.1 (s, 1H), 7.5 (d, 2H), 7.2 (t, 1H) 7.1 (d, 1H), 7.0 (d, 1H), 6.8 (d, 1H) 3.7 (d, 2H), 3.6 (t, 2H), 2.98-2.92 (m, 1H), 2.90-2.68 (m, 8H), 1.98-1.87 (m, 1H), 1.79-1.64 (m, 4H), 1.61-1.51 (m, 1H), 1.45-1.29 (m, 2H), 1.2 (t, 3H).

Compound 290: 4-(3-((ethyl(2-(piperidin-2-yl)ethyl)amino)methyl)phenyl)-N-(2-(thiophen-2-yl)ethyl)pyrimidin-2-amine: Intermediate 170 from above was coupled with 2-(thiophen-2-yl)ethanamine following procedure F. The product was deprotected by procedure G2. LC-MS showed the product had the expected M+H+ of 450 ¹H NMR (Varian 300 MHz, MeOD-d$_6$, shifts relative to the solvent peak at 3.31 ppm) δ 8.4 (d, 1H) 8.3 (d, 1H) 8.1 (s, 1H), 7.5 (d, 2H), 7.19 (t, 1H) 7.13 (d, 1H), 6.9 (m, 2H), 3.9 (d, 2H) 3.75-3.61 (m, 3H), 3.1 t 2H), 2.9 (m, 1H), 2.84-2.62 (m, 5H), 1.92-1.85 (m, 1H), 1.78-1.51 (m, 5H), 1.44-1.26 (m, 2H), 1.1 (t, 3H).

Compound 291: N-(3-fluorophenethyl)-4-(3-((ethyl(2-(piperidin-2-yl)ethyl)amino)methyl)phenyl)pyrimidin-2-amine: Intermediate 170 from above was coupled with 2-(3-fluorophenyl)ethanamine following procedure F. The product was deprotected by procedure G2. LC-MS showed the product had the expected M+H+ of 462. ¹H NMR (Varian 300 MHz, MeOD-d$_6$, shifts relative to the solvent peak at 3.31 ppm) δ 8.4 (d, 1H) 8.2 (d, 1H) 8.1 (s, 1H), 7.5 (d, 2H), 7.32-7.24 (m, 1H) 7.13-7.01 (m, 3H), 6.9 (t, 1H), 3.9 (d, 2H) 3.70 (t, 2H), 2.9 (t, 2H), 2.86-2.63 (m, 8H), 1.97-1.85 (m, 1H), 1.79-1.51 (m, 4H), 1.41-1.28 (m, 2H), 1.2 (t, 3H).

Intermediate 171: N-(3-(2-chloropyrimidin-4-yl)benzyl)-2-(pyridine-2-yl)ethanamine: Intermediate 25 from above and 2-(pyridine-2-yl)ethanamine was coupled following procedure A. The yield was 60%. LC-MS showed the product was >95% pure and had the expected M+H+ of 325.

Compound 292: 2-chloro-4-(2-(4-(3-((2-(pyridinyl-2-yl)ethylamino)methyl)phenyl)pyrimidin-2-ylamino)ethyl)phenol: Intermediate 171 from above was coupled with 4-(2-aminoethyl)-2-chlorophenol following procedure F. LC-MS showed the product had the expected M+H+ of 460. ¹H NMR (Varian 300 MHz, MeOD-d$_6$, shifts relative to the solvent peak at 3.31 ppm) δ 8.8 (d, 1H) 8.5 (t, 2H) 8.3 (d, 2H), 8.1 (d, 1H), 8.0 (t, 1H) 7.9 (d, 1H), 7.7 (t, 1H), 7.6 (d, 1H) 7.2 (d, 1H), 7.0 (d, 1H), 6.7 (d, 1H), 4.4 (s, 2H), 3.6 (m, 4H), 2.9 (t, 2H), 1.9 (t, 2H).

Intermediate 172: N-(3-(2-chloropyrimidin-4-yl)benzyl)-2-(pyridine-3-yl)ethanamine: Intermediate 25 from above and 2-(pyridine-3-yl)ethanamine was coupled following procedure A. The yield was 55%. LC-MS showed the product was >95% pure and had the expected M+H+ of 325.

Compound 293: 2-chloro-4-(2-(4-(3-((2(pyridine-3-yl)ethylamino)methyl)phenyl)pyrimidin-2-ylamino)ethyl)phenol: Intermediate 172 from above was coupled with 4-(2-aminoethyl)2-chlorophenol following procedure F. LC-MS showed the product had the expected M+H+ of 460 ¹H NMR (Varian 300 MHz, MeOD-d$_6$, shifts relative to the solvent peak at 3.31 ppm) δ 8.50-8.43 (m, 2H) 8.29 (d, 1H) 8.21 (s, 1H), 8.1 (d, 1H), 7.7 (d, 1H) 7.63-7.55 (m, 2H), 7.42-7.38 (m, 1H), 7.19 (d, 1H) 7.09 (d, 1H), 6.99 (d, 1H), 6.8 (d, 1H), 4.2 (s, 2H), 3.6 (t, 2H), 3.3 (t, 2H), 3.0 (t, 2H), 2.8 (t, 2H).

Intermediate 173: N-(3-(2-chloropyrimidin-4-yl)benzyl)-2-(pyridine-4-yl)ethanamine: Intermediate 25 from above and 2-(pyridine-3-yl)ethanamine was coupled following procedure A. The yield was 60%. LC-MS showed the product was >95% pure and had the expected M+H+ of 325.

Compound 294: 2-chloro-4-(2-(4-(3-((2-(pyridine-4-yl)ethylamino)methyl)phenyl)pyrimidin-2-ylamino)ethyl)phenol: Intermediate 173 from above was coupled with 4-(2-aminoethyl)-2-chlorophenol following procedure F. LC-MS showed the product had the expected M+H+ of 460. ¹H NMR (Varian 300 MHz, MeOD-d$_6$, shifts relative to the solvent peak at 3.31 ppm) δ 8.4 (d, 2H) 8.4 (s, 1H) 8.29 (d, 1H), 8.25 (s, 1H), 8.15 (d, 1H) 7.66-7.56 (m, 2H), 7.36 (d, 1H), 7.20 (d, 1H) 7.10 (d, 1H), 7.0 (d, 1H), 6.8 (d, 1H), 4.3 (s, 2H), 3.6 (t, 2H), 3.3 (t, 2H), 3.0 (t, 2H), 2.8 (t, 2H).

The following references are cited in the experimentals:
1. WO2004058736 page 73
2. Synlett 2001, 11, 1811-1812
3. EP0754686 page 9
4. WO 2002030931 page 62-63

An in vitro assay for detecting and measuring inhibition activity against PKC-theta isoform by candidate pharmacological agents is useful for evaluating and selecting a compound that modulates PKC-theta isoform. An IC$_{50}$ value can be calculated after running the assay. Following is an assay protocol for measuring PKC-theta isoform.

Testing Assay

Per well of a 384 well plate, compounds at various concentrations in 5 µL of 20% DMSO were pre-incubated for about 30 minutes at about 25° C. with 15 µL of full length PKC θ (Panvera Corporation) at 27 pM in an assay buffer (25 mM Hepes, pH 7.5, 5 mM DTT, 10 mM MgCl$_2$, 10 mM 2-glycerophosphate, 12.5 µg/mL 1,2-dioleoyl-rac-glycerol, 10 µg/mL L-α-phosphatidyl-L-serine, 0.1% Bovine Serum Albumin). 10 µL of peptide substrate (biotin-(CH$_2$)$_6$—RFARKGSLRQKNV—CONH$_2$) at 300 nM+3 µM ATP were added to each well and incubated for about 1 hour before quenching with 10 µL of 250 mM EDTA. 40 µL of detection buffer (25 mM Hepes, pH 7.5, 100 mM KF, 0.1% Bovine Serum Albumin, 0.01% Tween20) containing 2 nM anti-phospho antibody 2B9 (MBL International) labeled with europium cryptate (Cis-Bio International) and 0.0064 µg/mL streptavidin-allophycocyanin (Prozyme) was added to each well and incubated for two hours. Signal was then read on a Discovery HTRF (Packard). The ratio of emission from the europium cryptate at 615 nM and the streptavidin-allophycocyanin at 665 nM has previously been shown to be linear with enzyme concentration and time and was used to determine the inhibition activity of candidate pharmacological agents.

A compound can be run through this assay and its corresponding IC$_{50}$ inhibition value can be calculated from the assay data. Compounds having the formula I can exhibit PKC-theta isoform inhibitor activities of varying degrees. The PKC-theta isoform inhibition average IC$_{50}$ values for the compounds of formula I generally range from >0 nM to about 1000 nM, preferably, from about 0.01 nM to about 500 nM, more preferably, from about 0.01 nM to about 100 nM, even more preferably, from >0 nM to about 25 nM, and yet even more preferably, from >0 nM to about 10 nM. In preferred embodiments, the inventive compounds are both potent and selective (e.g., 50%, 2×, 5×, etc., more selective over other PKC isoforms) inhibitors of the PKC-theta isoform. In some embodiments, the following compounds have IC$_{50}$ values less than 100 nM: 1, 2, 5, 6, 8, 22, 24, 26, 29, 36, 38, 40, 45, 48, 49, 50, 53, 54, 55, 60, 62, 64, 65, 67, 68, 70-75, 77, 80, 81, 84-95, 97-101, 104, 107, 115-118, 120, 121, 125, 126, 130, 131, 132, 134, 136-138, 142, 143, 146-149, 151-161, 163-196, 200, 218, 223-231, 233-235, 238-244, 249, 254, 258-259, 261-263, 265, 266, 268-274, 278, 280-282, 284, 286, 289, 292, and 295-372.

While we have described a number of embodiments of this invention, it is apparent that our basic examples may be altered to provide other embodiments, which utilize the compounds and methods of this invention. Therefore, it will be

The invention claimed is:
1. A compound of formula I-A-i:

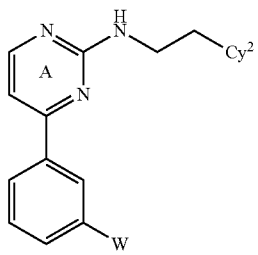

I-A-i or a pharmaceutically acceptable salt thereof, wherein:
Cy' is phenyl optionally substituted by one to three independent occurrences of $R^9$;
each occurrence of $R^9$ is independently selected from $-OR^B$, $-N(R^B)C(O)R^A$, $-N(R^B)_2$, halo, $C_{1-4}$ aliphatic optionally substituted by halo, $NO_2$, $-OS(O)_2R^C$, $-S(O)R^C$, $-N(R^B)SO_2R^A$, or $-S(O)_2N(R^B)_2$;
each occurrence of $R^A$ is independently H, $C_{1-3}$ alkyl or $C_{3-5}$ cycloalkyl;
each occurrence of $R^B$ is independently H or $C_{14}$ aliphatic; or two $R^B$ on the same nitrogen atom taken together with the nitrogen atom form a 5-8 membered aromatic or non-aromatic ring having in addition to the nitrogen atom 0-2 ring heteroatoms selected from N, O or S; and each occurrence of $R^C$ is independently $C_{1-4}$ aliphatic;
ring A is optionally substituted with 1 or 2 independent occurrences of $R^5$, wherein $R^5$ on ring A, when present, is selected from F, Cl, Br, or methyl;
W is $L_1-R^7$,
$L_1$ is an optionally substituted $C_{1-6}$ alkylene chain;
$R^7$ is H, halo, $-OH$, $-N(R^F)_2$, $-CN$, $-OR^G$, $-C(O)R^G$, $-CO_2H$, $-CO_2R^G$, $-SR^G$, $-S(O)R^G$, $-S(O)_2R^G$, $-N(R^E)C(O)R^G$, $-N(R^E)CO_2R^G$, $-N(R^E)SO_2R^G$, $-C(O)N(R^F)_2$, $-SO_2N(R^F)_2$, $-N(R^E)C(O)N(R^F)_2$, $-OC(O)R^F$ or an optionally substituted group selected from $C_{1-10}$ aliphatic, $C_{6-10}$ aryl, 3-14 membered heterocyclyl or 5-14 membered heteroaryl, wherein each occurrence of $R^F$ is independently H, $C_{1-6}$ aliphatic, $C_{6-10}$ aryl, 3-14 membered heterocyclyl, 5-14 membered heteroaryl, $-C(=O)R^B$, $-C(O)OR^B$ or $-SO_2R^B$; or two $R^F$ on the same nitrogen atom taken together with the nitrogen atom form an optionally substituted 5-8 membered aromatic or non-aromatic ring having in addition to the nitrogen atom 0-2 ring heteroatoms selected from N, O or S; and each occurrence of $R^G$ is $C_{1-6}$ aliphatic, $C_{6-10}$ aryl, 3-14 membered heterocyclyl, or 5-14 membered heteroaryl.

2. The compound of claim 1, wherein $Cy^2$ is optionally substituted with one, two or three occurrences of $R^9$, wherein each occurrence of $R^9$ is independently selected from halo or $-OH$.

3. The compound of claim 1, wherein $R^7$ is selected from $-NH_2$, $-NH(C_{1-5}alkyl)$, $-N(C_{1-5}alkyl)_2$, $-NHCO_2(C_{1-6}alkyl)$, $-NHCO(C_{1-6}alkyl)$, $-NHCO$(optionally substituted phenyl), $-NHSO_2(C_{1-6}alkyl)$, or an optionally substituted group selected from $C_{1-6}$alkyl, phenyl, pyridyl, piperidinyl, piperazinyl, pyrrolidinyl, or azetidinyl.

4. The compound of claim 1, wherein the optionally substituted group in $R^7$ is optionally substituted at one or more carbon atoms with one, two or three independent occurrences of $R^{11}$, and at one or more substitutable nitrogen atoms with $R^{12}$, wherein each occurrence of $R^{11}$ is independently selected from optionally substituted $C_{1-6}$aliphatic, optionally substituted 6-10-membered aryl, optionally substituted 5-10-membered heteroaryl, $-N(R^B)_2$, $=O$, halo, $NO_2$, $-CN$, $-OR^B$, $-C(O)R^A$, $-CO_2R^A$, $-SR^C$, $-S(O)R^C$, $-S(O)_2R^C$, $-OS(O)_2R^C$, $-N(R^B)C(O)R^A$, $-N(R^B)SO_2R^A$, $-N(R^B)SO_2R^A$, $-C(O)N(R^B)_2$, $-SO_2N(R^B)_2$, $-N(R^B)C(O)N(R^B)_2$, or $-OC(O)R^A$, and each occurrence of $R^{12}$ is independently selected from H, optionally substituted $C_{1-6}$ aliphatic, optionally substituted 6-10-membered aryl, optionally substituted 5-10-membered heteroaryl, $-C(=O)R^B$, $-C(O)OR^B$ or $-SO_2R^B$.

5. The compound of claim 1 wherein $R^7$ is piperidinyl.

6. The compound of claim 1, wherein $L_1$ is an optionally substituted $C_1-C_4$ alkylene.

7. The compound of claim 1, wherein $L_1$ is $-(CH_2)_n$, where n is 1-2, and wherein one hydrogen atom on any methylene unit is optionally substituted with $C_{1-3}$alkyl, $-OH$, $-O(C_{1-3}alkyl)$, $-COOH$, or $-COO(C_{1-3}alkyl)$.

8. The compound of claim 1, wherein ring A is optionally substituted with 1 occurrence of $R^5$, wherein $R^5$ on ring A, when present is F.

9. The compound of claim 1, wherein the compound is:

121

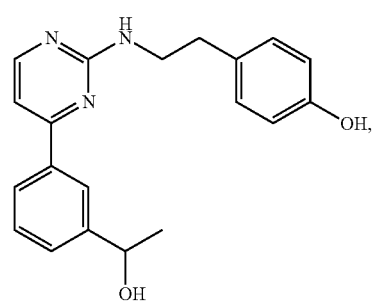

148

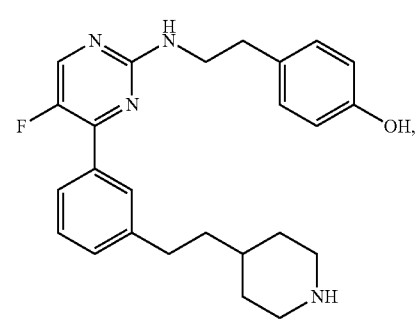

149

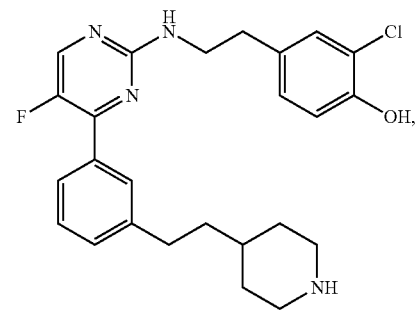

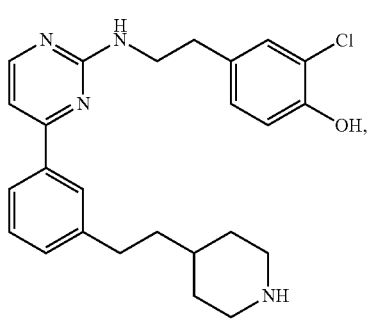

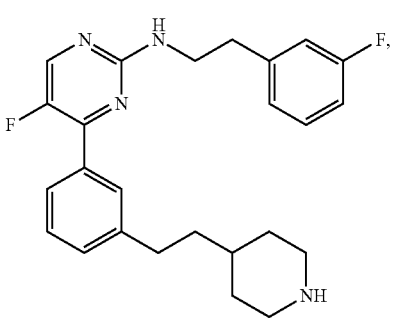

10. A pharmaceutical composition comprising the compound or pharmaceutically acceptable salt according to claim 1 and a pharmaceutically acceptable excipient or carrier.

11. A pharmaceutical composition comprising:
a) the compound or pharmaceutically acceptable salt according to claim 1,
b) methotrexate or a pharmaceutically acceptable salt thereof, and
c) a pharmaceutically acceptable excipient or carrier.

* * * * *